US012329983B2

(12) United States Patent
Williams et al.

(10) Patent No.: US 12,329,983 B2
(45) Date of Patent: Jun. 17, 2025

(54) DISTRIBUTED PHOTOBIOMODULATION THERAPY SYSTEM WITH INTELLIGENT LED PAD

(71) Applicant: Applied BioPhotonics Ltd., Hong Kong (CN)

(72) Inventors: Richard K. Williams, Cupertino, CA (US); Keng-Hung Lin, Chupei (TW); Laura E. Williams, Cupertino, CA (US)

(73) Assignee: Applied BioPhotonics Ltd., Hong Kong (CN)

( * ) Notice: Subject to any disclaimer, the term of this patent is extended or adjusted under 35 U.S.C. 154(b) by 59 days.

(21) Appl. No.: 16/377,192

(22) Filed: Apr. 6, 2019

(65) Prior Publication Data

US 2019/0335551 A1    Oct. 31, 2019

Related U.S. Application Data

(60) Continuation-in-part of application No. 15/857,002, filed on Dec. 28, 2017, now Pat. No. 11,006,488, which is a division of application No. 14/073,371, filed on Nov. 6, 2013, now Pat. No. 9,877,361.

(60) Provisional application No. 62/653,855, filed on Apr. 6, 2018, provisional application No. 61/723,950, filed on Nov. 8, 2012.

(51) Int. Cl.
*A61N 5/00* (2006.01)
*A61N 5/06* (2006.01)
*H05B 45/24* (2020.01)
*H05B 45/46* (2020.01)
*H05B 47/105* (2020.01)
(Continued)

(52) U.S. Cl.
CPC ............. *A61N 5/06* (2013.01); *H05B 45/24* (2020.01); *H05B 45/46* (2020.01); *H05B 47/105* (2020.01); *A61N 2005/0626* (2013.01); *A61N 2005/0651* (2013.01); *H05B 45/325* (2020.01); *H05B 45/375* (2020.01)

(58) Field of Classification Search
None
See application file for complete search history.

(56) References Cited

U.S. PATENT DOCUMENTS

2001/0028227 A1* 10/2001 Lys .................. H05B 45/46
                                                        315/317
2003/0187486 A1* 10/2003 Savage, Jr. .......... A61N 5/0618
                                                        607/89

(Continued)

*Primary Examiner* — Sana Sahand
(74) *Attorney, Agent, or Firm* — Patentability Associates

(57) ABSTRACT

In a photobiomodulation therapy (PBT) process, defined patterns (e.g., sequences of square-wave pulses, sine waves, or combinations thereof) of electromagnetic radiation (EMR) having one or more wavelengths, or spectral bands of wavelengths, are introduced into a living organism (e.g. a human being or animal) using a distributed system comprising two or more distributed components or "nodes" communicating using a bus or transceiver to send instructions or files between or among the constituent components. The distributed PBT system prevents intentional usurpation of system control (hacking), thwarts unauthorized monitoring of data (surveillance), and reduces the likelihood and severity of accidental system malfunction arising from corrupted command and control packets or ambient EMI.

21 Claims, 150 Drawing Sheets

(51) Int. Cl.
   *H05B 45/325*   (2020.01)
   *H05B 45/375*   (2020.01)

(56) References Cited

U.S. PATENT DOCUMENTS

| | | | |
|---|---|---|---|
| 2007/0293918 A1* | 12/2007 | Thompson | A61N 1/36034 607/72 |
| 2009/0026966 A1* | 1/2009 | Budde | H05B 47/19 315/152 |
| 2009/0076844 A1* | 3/2009 | Koegen | G16H 40/67 705/2 |
| 2012/0165716 A1* | 6/2012 | Reuben | A61N 5/0616 602/56 |
| 2014/0052199 A1* | 2/2014 | Mohn | A61N 1/37235 607/3 |
| 2018/0225230 A1* | 8/2018 | Litichever | G06F 21/82 |
| 2019/0083809 A1* | 3/2019 | Zhang | A61N 5/0616 |

* cited by examiner

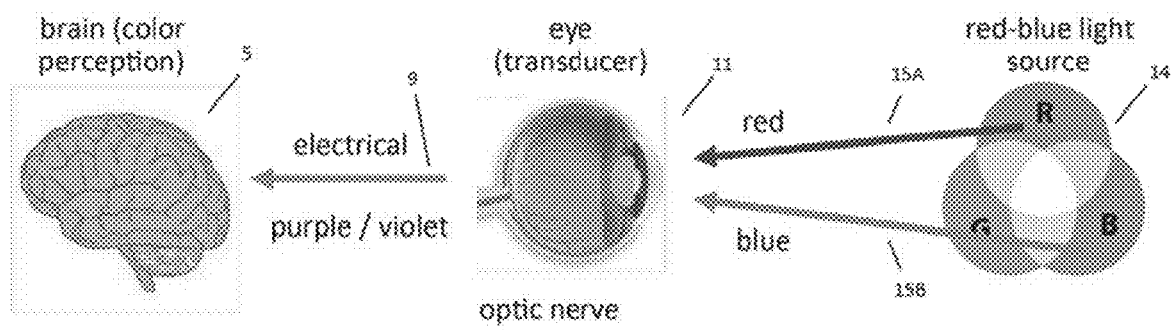
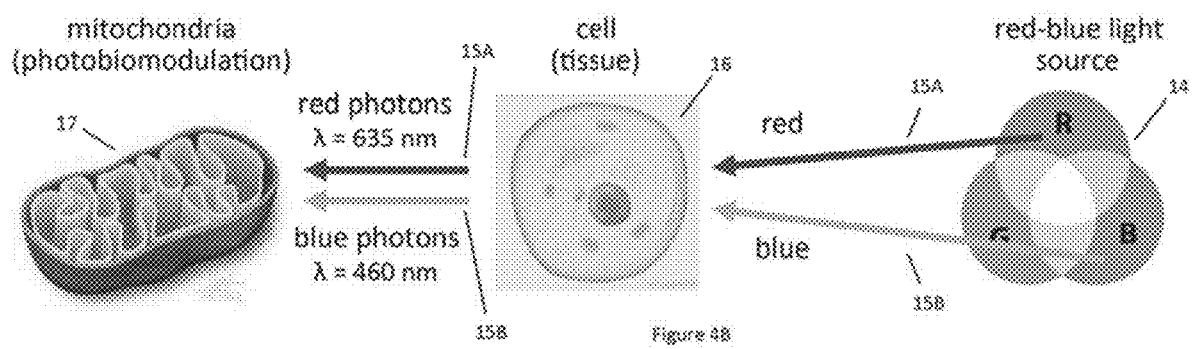
Figure 4B

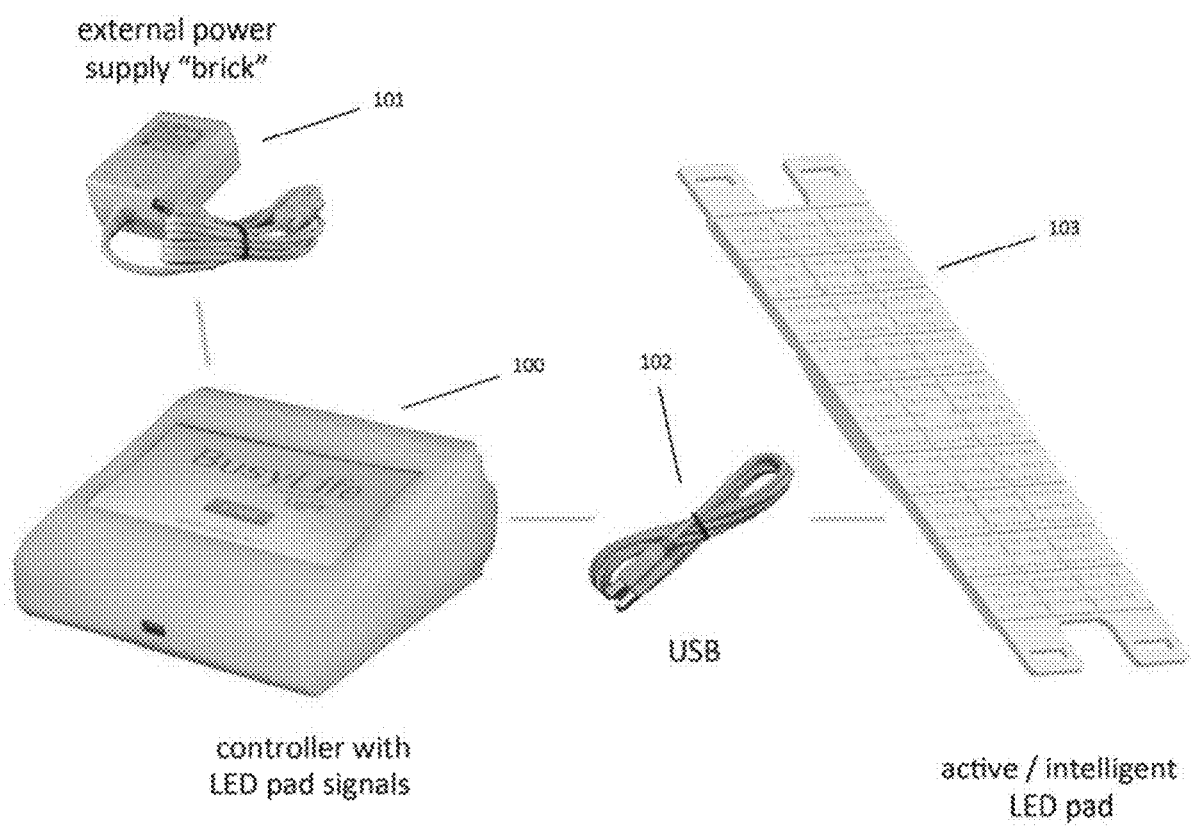

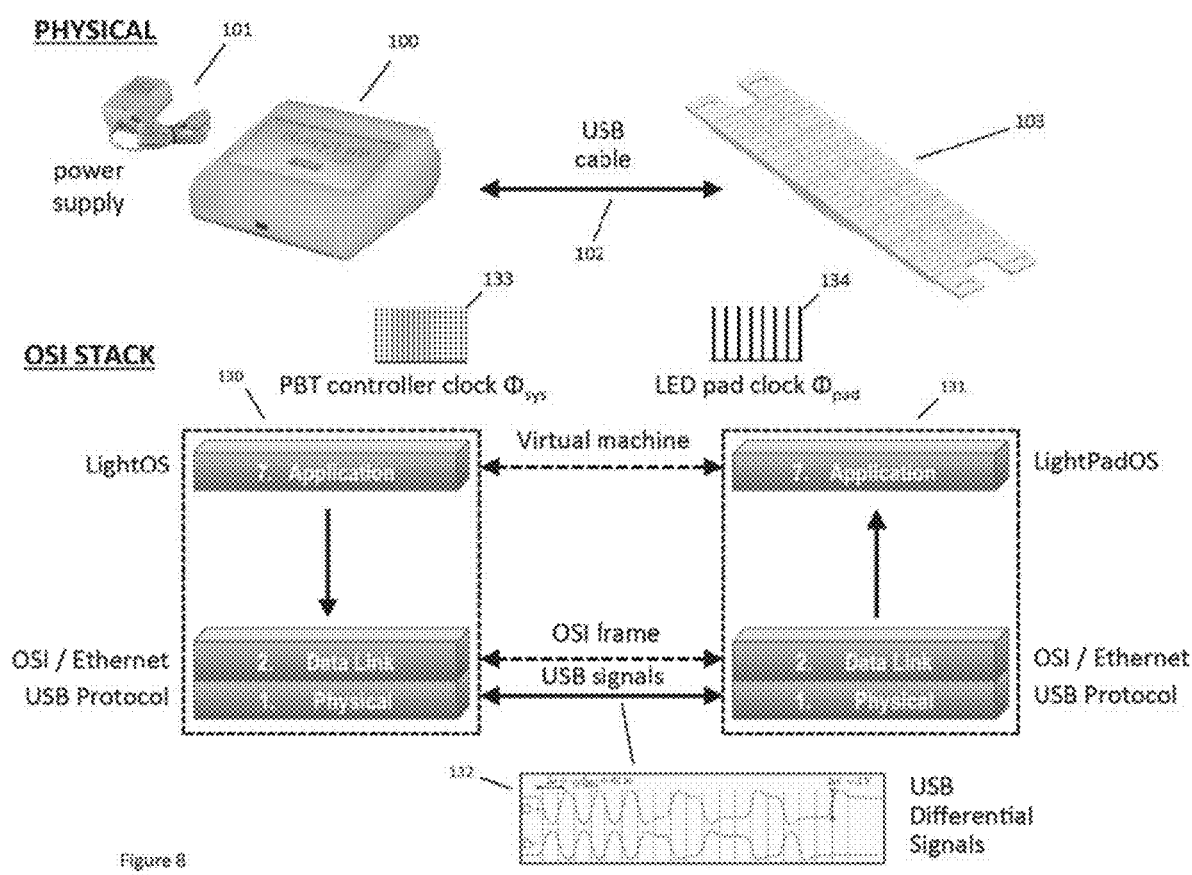

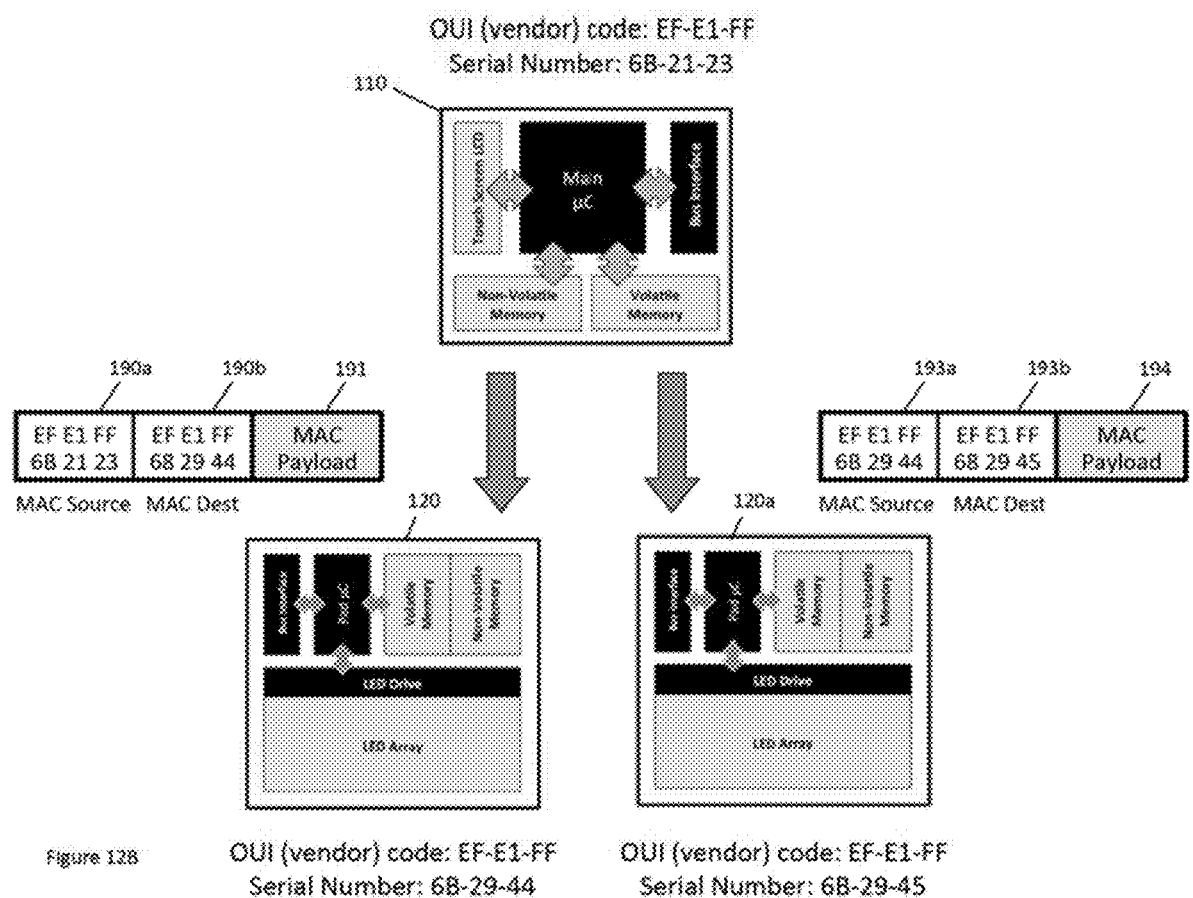

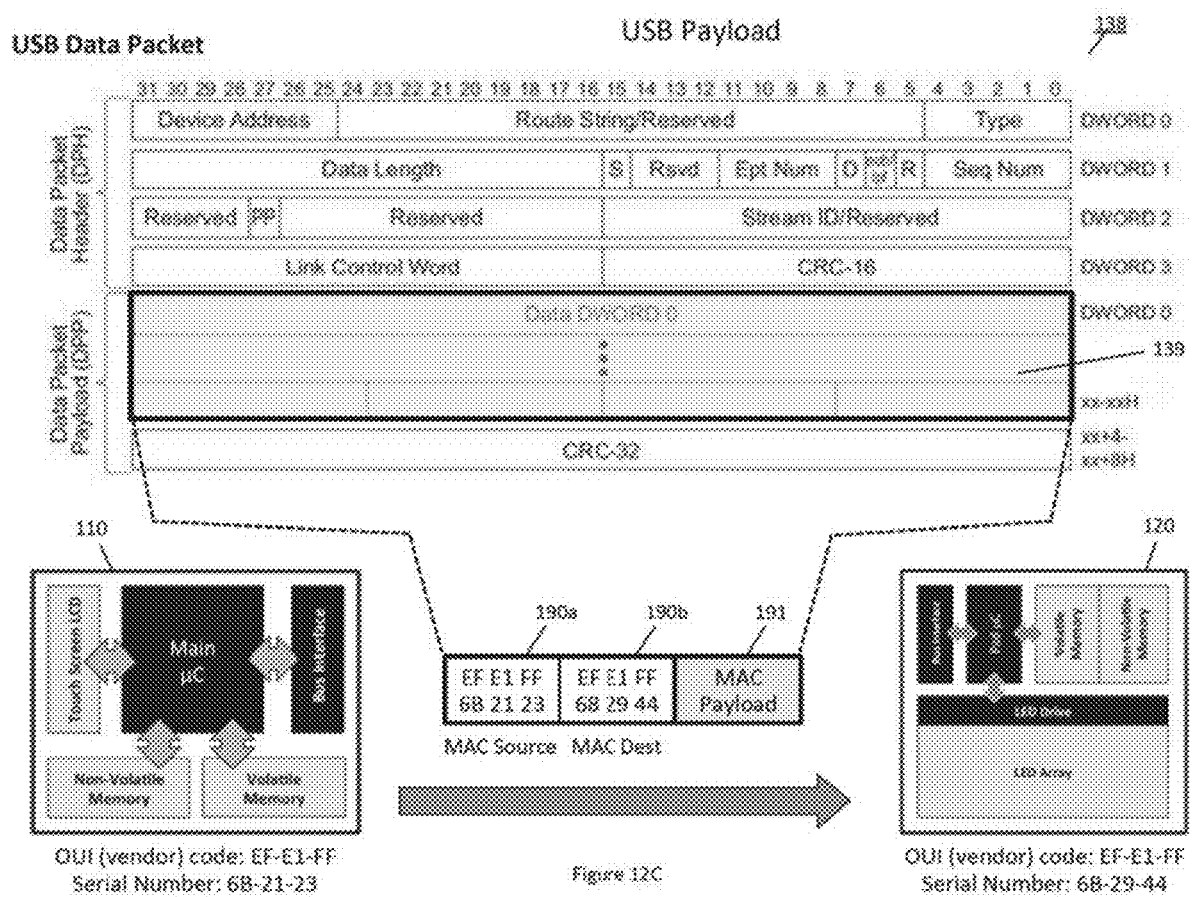

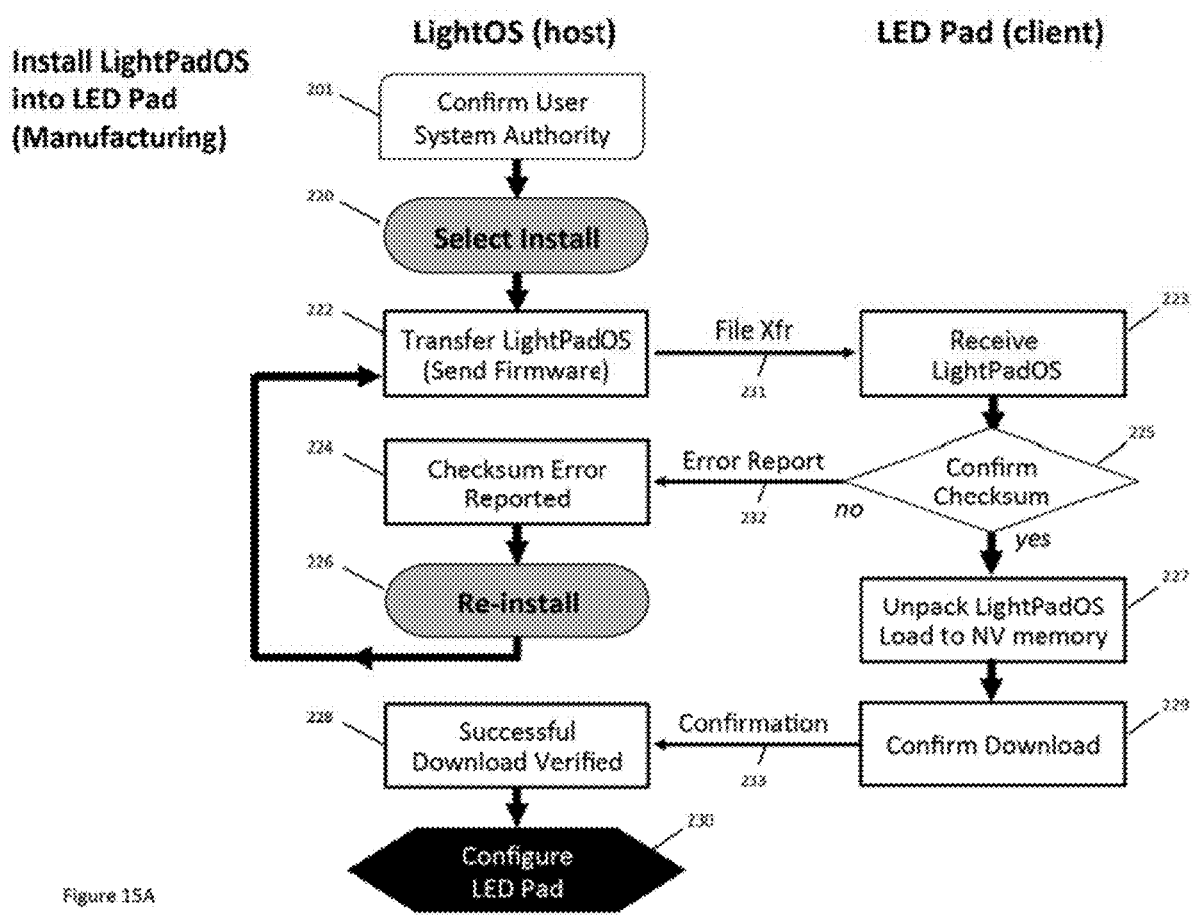

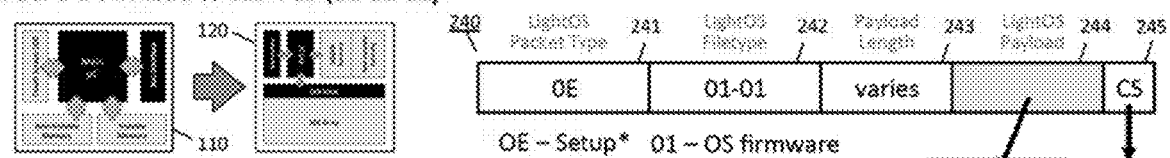
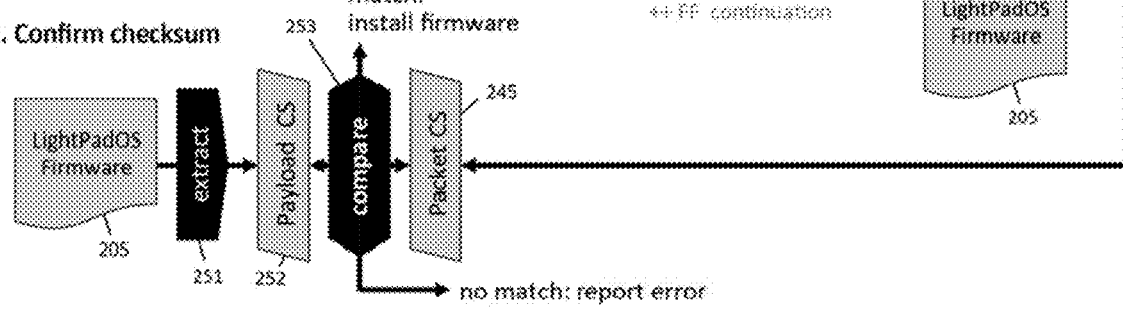
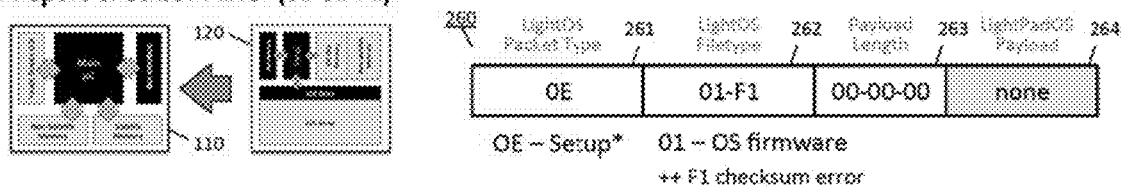
Figure 15B

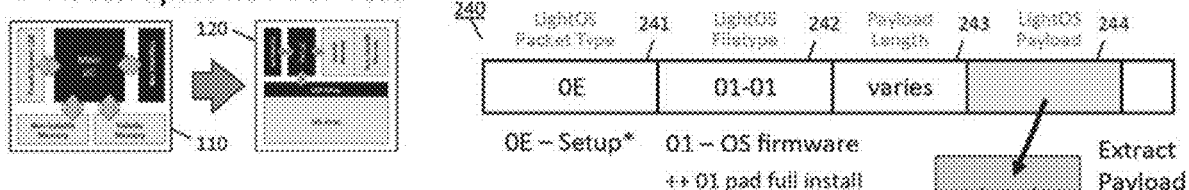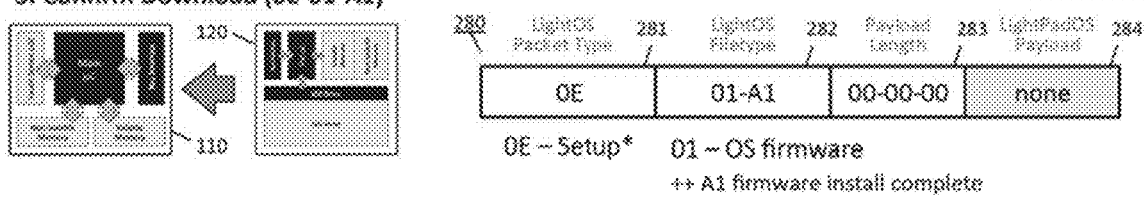
Figure 15C

Post Manufacturing Lock LED Pad Communication
1. Send Command to LED Pad (0E-02-FF)
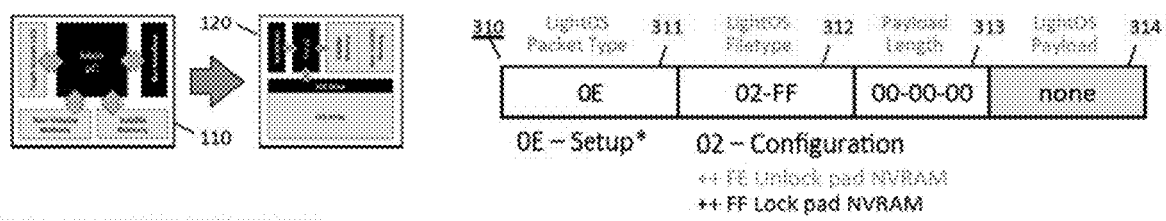
0E – Setup*  02 – Configuration
++ FF Unlock pad NVRAM
++ FF Lock pad NVRAM
2. Set Lock Bit in LightPadOS
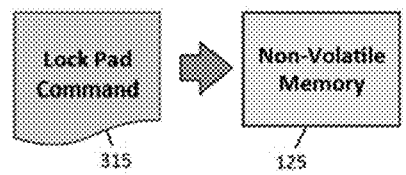
Figure 19
* Setup is limited to authorized users only (manufacturing)

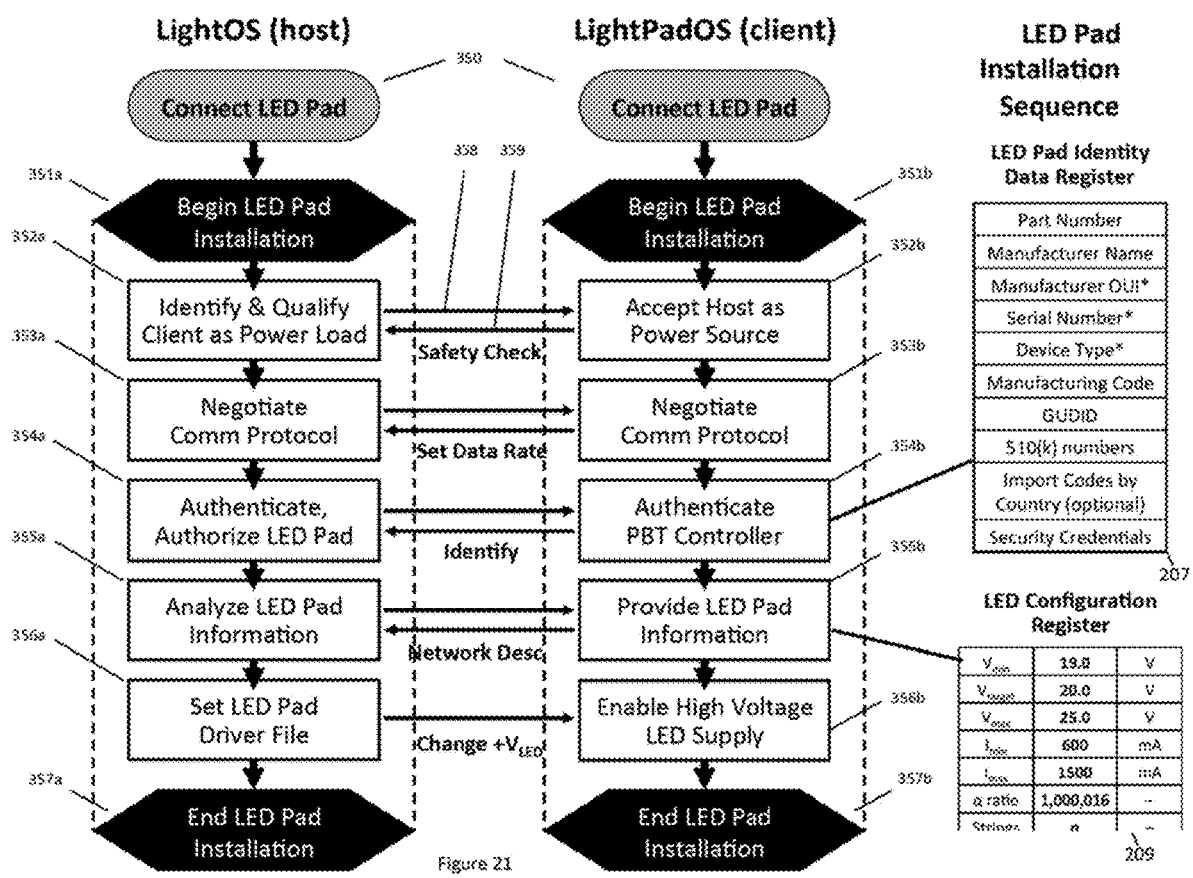

Connect Device (Without L7 Authentication) Communication

1. Request to Join Network (0F-03-01)

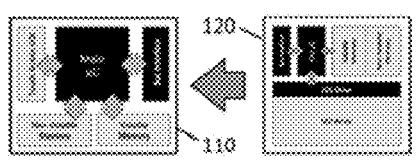

| 370 LightOS Packet Type | 371 LightOS Filetype | 372 Payload Length | 373 LightPadOS Payload 374 |
|---|---|---|---|
| 0F | 03-01 | 00-00-00 | none |

OF — Sys Message   03 — Connection
  ++ 01 Request to connect device
  ++ 02 Authentication rqst
  ++ 03 Authentication code
  ++ 04 Connection rejected
  ++ 05 Connection confirmed

2. Connection Confirmed (0F-03-05)

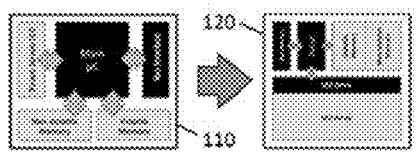

| 380 LightOS Packet Type | 381 LightOS Filetype | 382 Payload Length | 383 LightOS Payload 384 |
|---|---|---|---|
| 0F | 03-05 | 00-00-00 | none |

OF — Sys Message   03 — Connection
  ++ 05 Connection confirmed

Figure 22

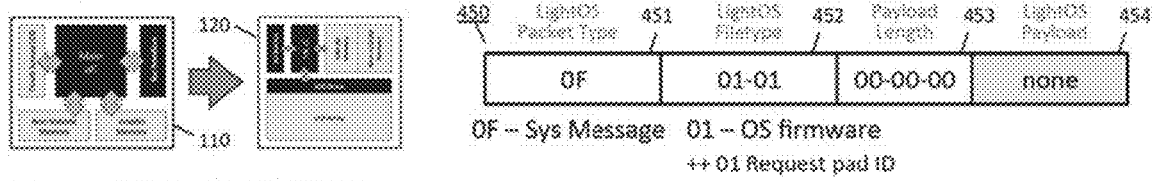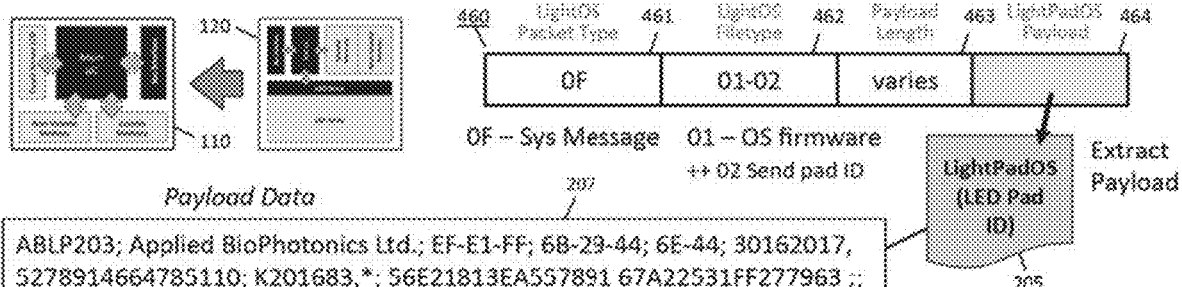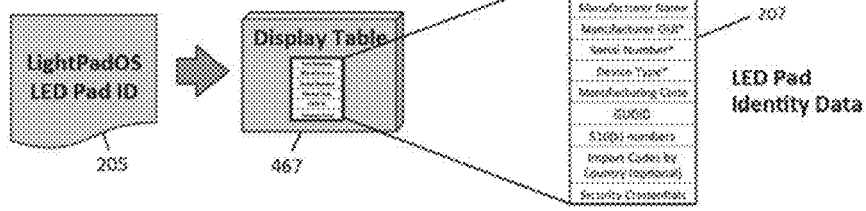
Figure 24

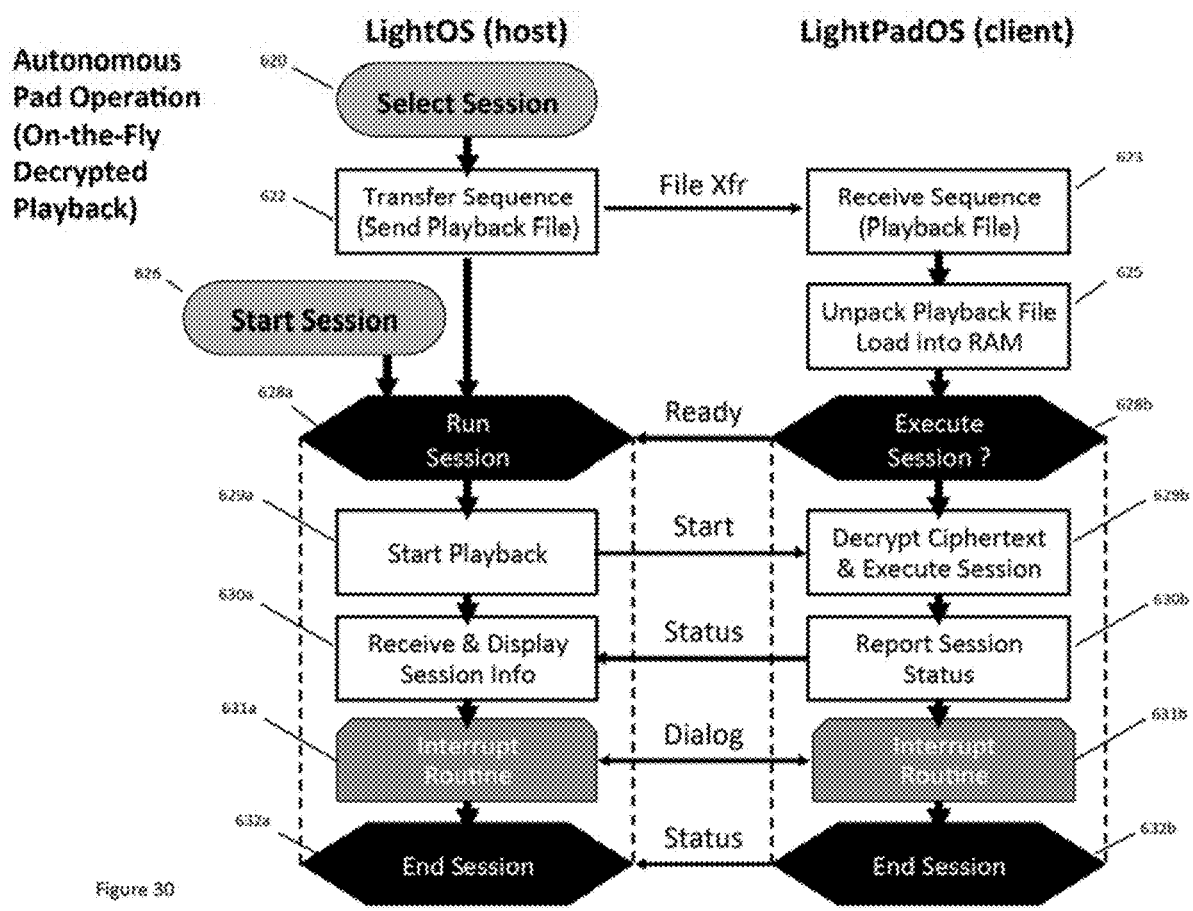

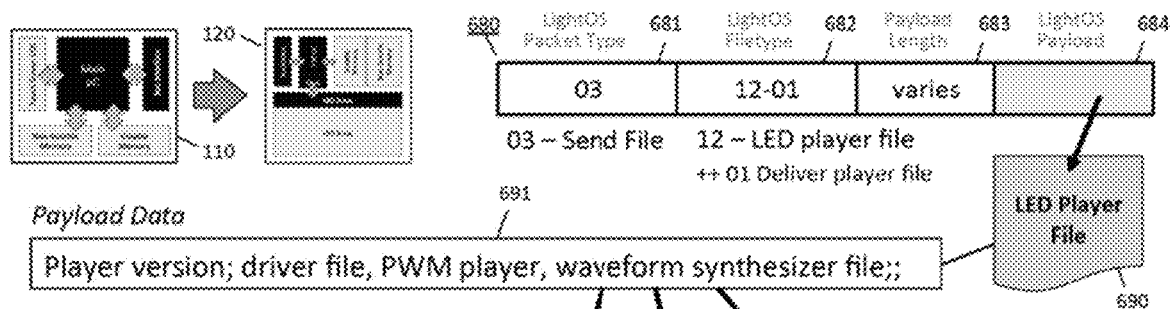
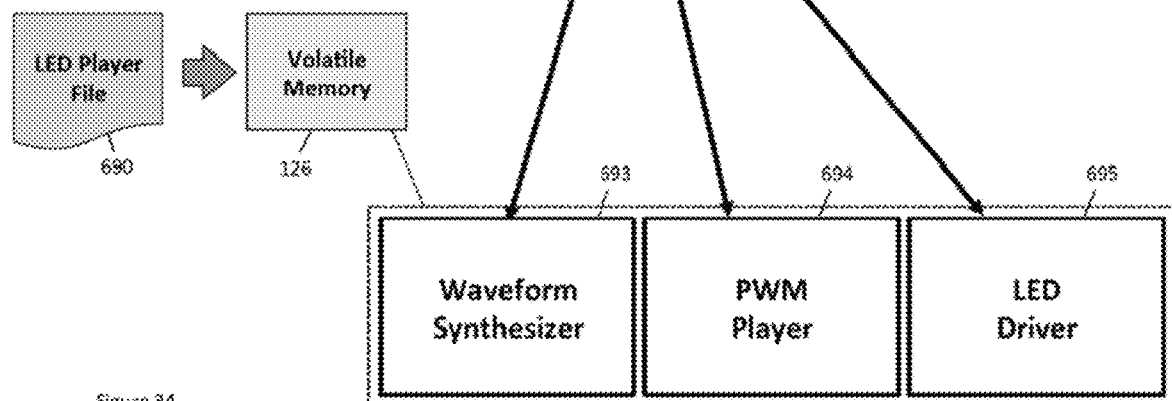
Figure 34

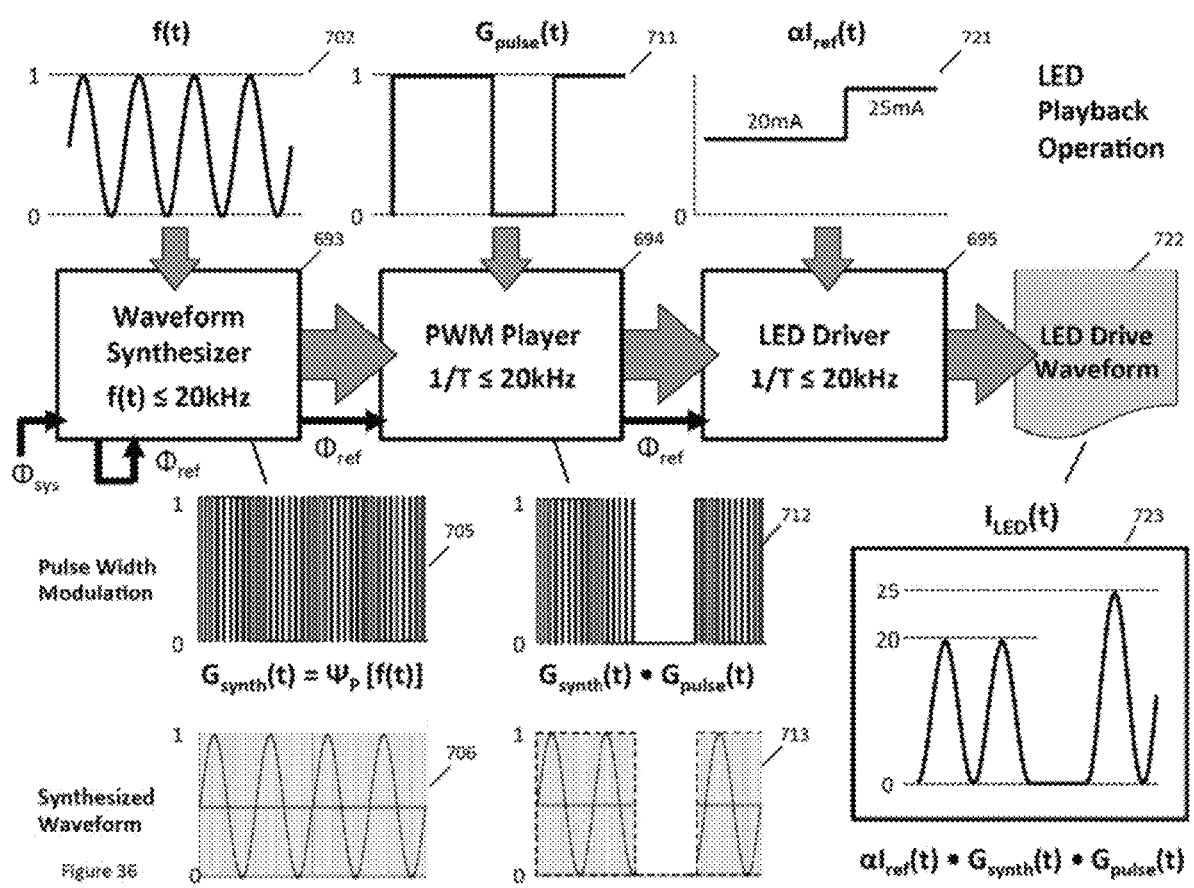

Synthesizer Block Diagram

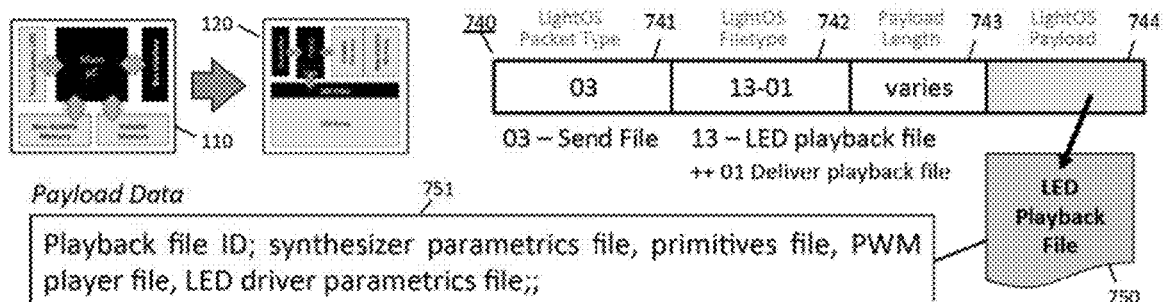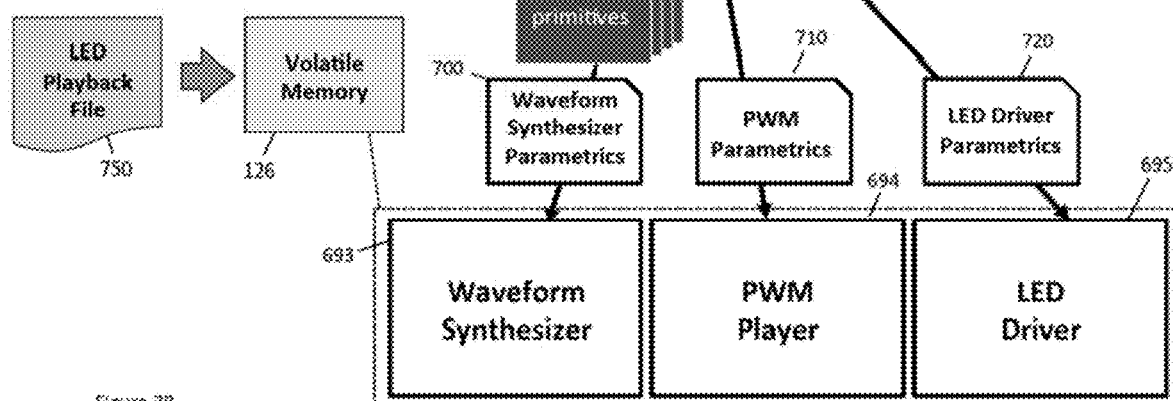
Figure 38

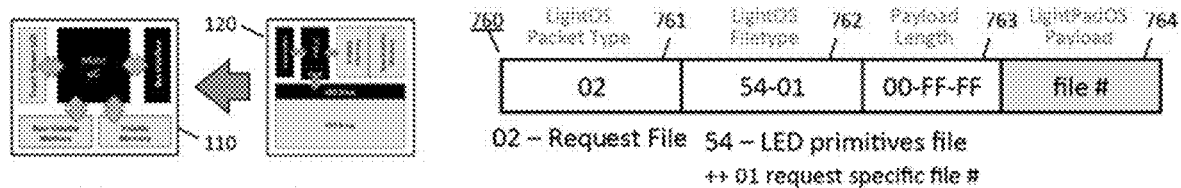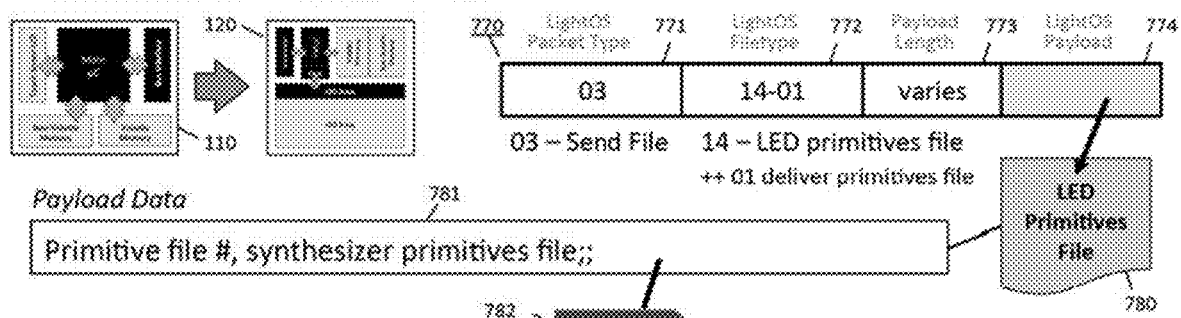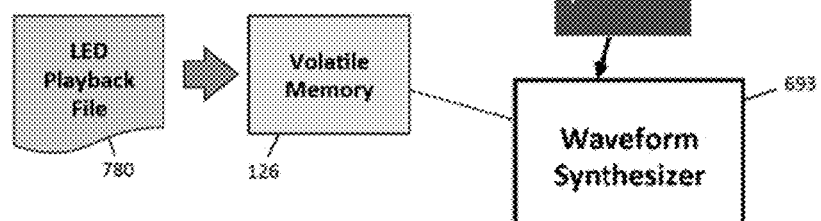
Figure 39

Start / Stop Playback of LED Pad Playback File Communication
1. Commence Playback of LED Pad (05-13-01)
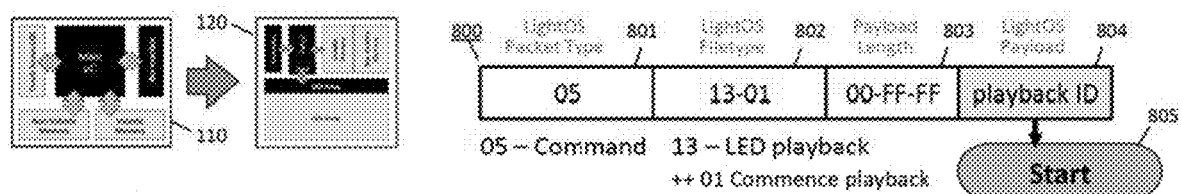
2. Clear LED Pad Counters & Enable Clock
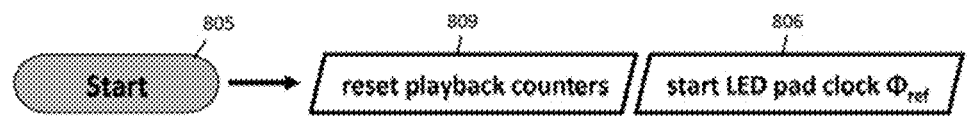
3. Pause Playback of LED Pad (05-13-02)
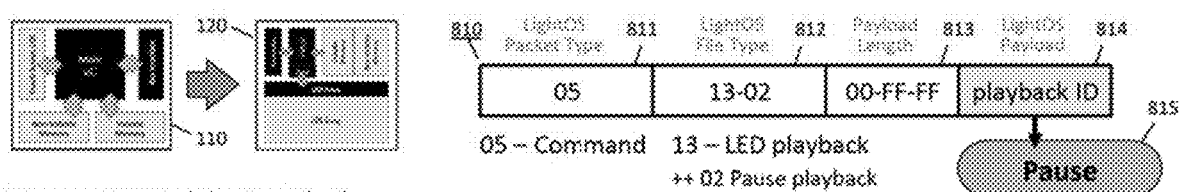
4. Pause LED Pad System Clock
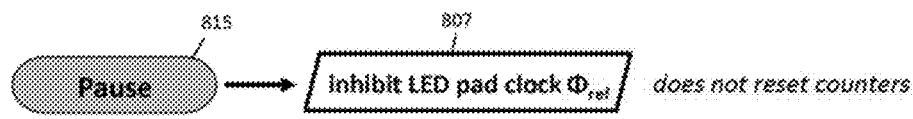
Figure 42A

Start / Stop Playback of LED Pad Playback File Communication
5. Restart Playback of LED Pad (05-13-01)
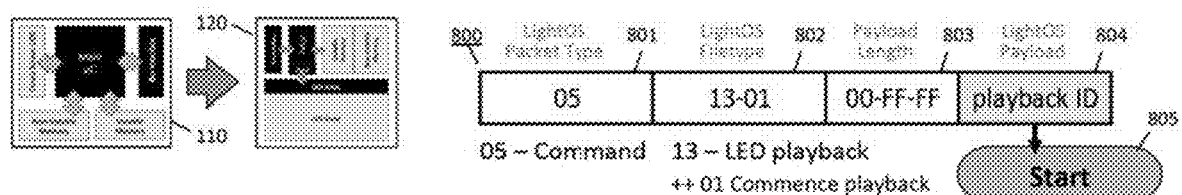
6. Enable Clock
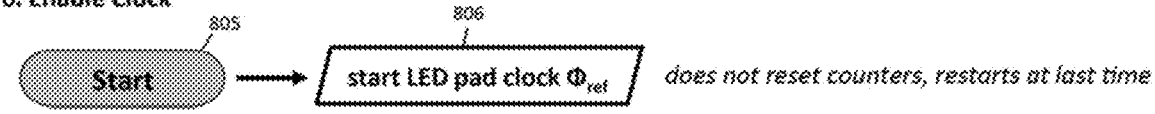
7. Cancel Playback of LED Pad (05-13-03)
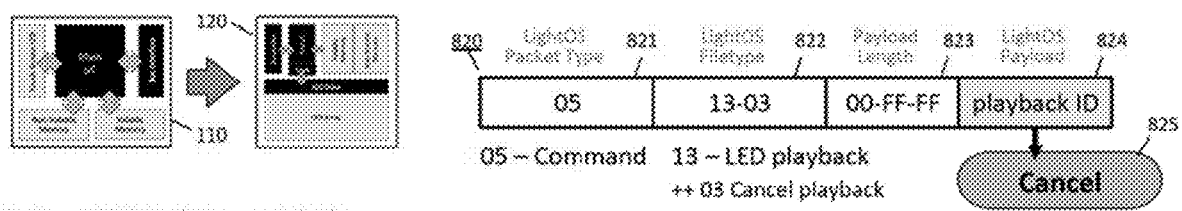
8. Reset LED Pad System Clock
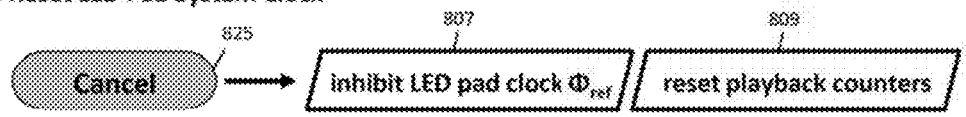
Figure 42B

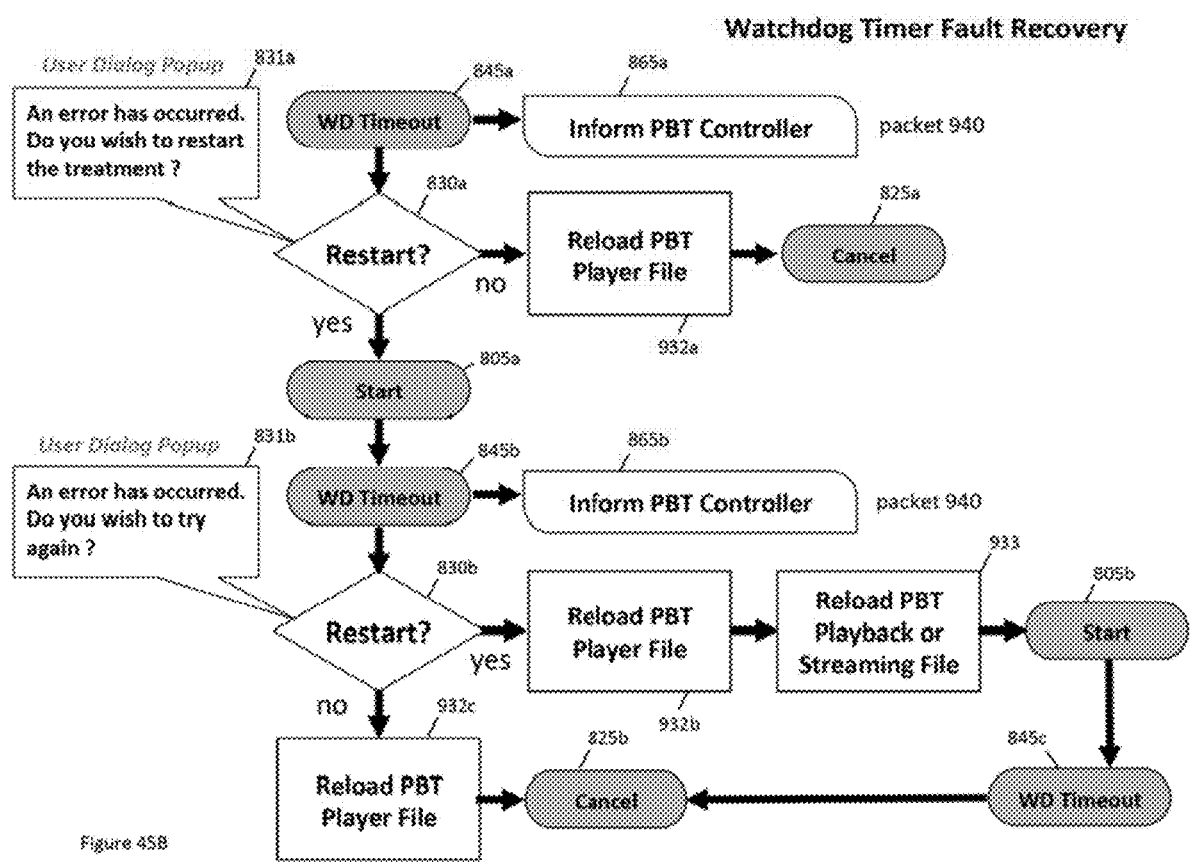

| Layer | TCP Field | Size | TCP Function |
|---|---|---|---|
| 4 | Source Port | 2B | Senders port, port for which reply should be sent |
| 4 | Destination Port | 2B | Receiver's port (required), well known port # if server |
| 4 | Sequence Number | 4B | Packet counter (SEQ #) incrementing each ACK reply by one |
| 4 | Acknowledgement # | 4B | Acknowledges receipt of each packet in a sequence by sequence # |
| 4 | Offset | 4b | Size of TCP header (offset from TCP header to data start), 20B to 60B |
| 4 | Reserved | 3b | Reserved for future, default to 000 binary |
| 4 | Flags | 9b | Control bits for congestion, urgency, acknowledgement, sync & reset |
| 4 | Window Size | 2B | Size of the receive window |
| 4 | Checksum | 2B | Error checking comprising 16b checksum of header and payload data |
| 4 | Urgent Pointer | 2B | Offset from SEQ # indicating last urgent data byte (if URG is set to 1) |
| 4 | Options | 1B to 40B | Option- Kind (1B required), Length (1B option), Data (var), as per Offset |
| 4-7 | TCP Payload | variable | TCP payload data |

Figure 53B

| Port Number | UDP | TCP | Port Description | Registered |
|---|---|---|---|---|
| 0 to 1,023 | UDP | TCP | System Ports | Generally |
| 1,024 to 49,151 | UDP | TCP | Registered Ports, Open (Dynamic) Ports | Mixed |
| 49,152 to 65,535 | UDP | TCP | Open (Dynamic), Private and Ephemeral Ports | No |

Figure 53D

| Port # | UDP | TCP | Port Description | Registered |
|---|---|---|---|---|
| 7 | UDP | TCP | Echo/Ping (generally superseded by ICMP) | Official |
| 20 | UDP | TCP | FTP Data Transfer | Official |
| 21 | -- | TCP | FTP Control (command) | Official |
| 22 | UDP | TCP | Secure shell (SSH) for secure login (SCP), SFTP, port forwarding | Official |
| 23 | UDP | TCP | Telnet | Official |
| 25 | -- | TCP | Simple Mail Transfer (SMTP) | Official |
| 26 | UDP | TCP | Encrypted SMTP | Official |
| 53 | UDP | TCP | Domain Name Server (DNS) | Official |
| 80 | -- | TCP | Hypertext Transfer Protocol (HTTP) | Official |
| 110 | -- | TCP | Post Office Protocol (POP3) | Official |
| 143 | -- | TCP | Internet Mail Access Protocol (IMAP) | Official |
| 220 | UDP | TCP | Internet Mail Access Protocol (IMAP v3) | Official |
| 443 | -- | TCP | Hypertext Transfer Protocol over TLS/SSL (HTTPS) | Official |
| 465 | -- | TCP | Simple Mail Transfer Protocol over TLS/SSL (SMTPS) | Official |
| 989 | UDP | TCP | FTPS Protocol (data): FTP over TLS/SSL | Official |
| 990 | UDP | TCP | FTPS Protocol (control): FTP over TLS/SSL | Official |
| 992 | UDP | TCP | TELNET protocol over TLS/SSL | Official |
| 993 | -- | TCP | Internet Message Access Protocol over TLS/SSL (IMAPS) | Official |
| 995 | -- | TCP | Post Office Protocol 3 over TLS/SSL (POP3S) | Official |

Figure 33E.

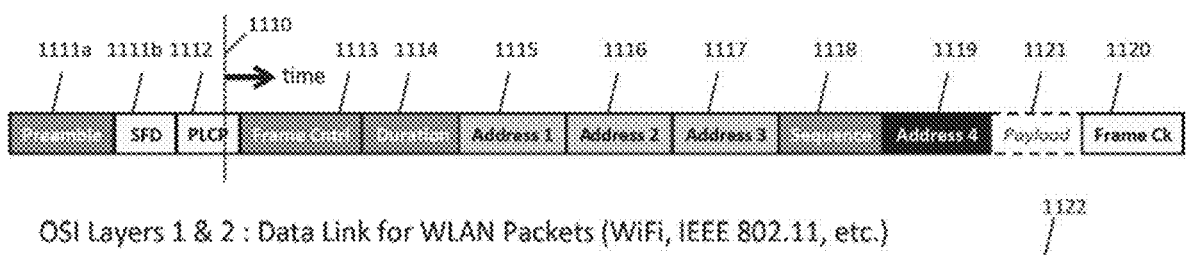

OSI Layers 1 & 2 : Data Link for WLAN Packets (WiFi, IEEE 802.11, etc.)

| Layer | Packet Field | Size | Function |
|---|---|---|---|
| 1 | Preamble | 10B | Data frame header |
| 1 | SFD | 2B | Synchronize hardware devices (start frame delimiter) |
| 1-2 | PLCP | 2B | Physical layer convergence procedure (length, rate, header error ck) |
| 2 | Frame Control | 2B | Version Type (Management, Control, Data, Reserved), To/From DS |
| 2 | Duration & ID | 2B | NAV duration (except in power save mode, then Station ID) |
| 2 | Address 1 | 6B | BSS receiving station address (depends on To DS / From DS setting) |
| 2 | Address 2 | 6B | BSS transmitting station address (depends on To DS / From DS) |
| 2 | Address 3 | 6B | Conditional address (depends on To DS / From DS setting) |
| 2 | Sequence Cntrl | 2B | Sequence & fragment number defining the packet frame |
| 2 | Address 4 | 6B | Source station address in WDS (wireless distribution system) mode |
| 2-7 | Payload | 0 - 2312B | Content of packet (including network, IP, app info & data) |
| 2 | Frame Check | 4B | Checksum of entire packet (32-bit CRC data link trailer) |

Figure 59B

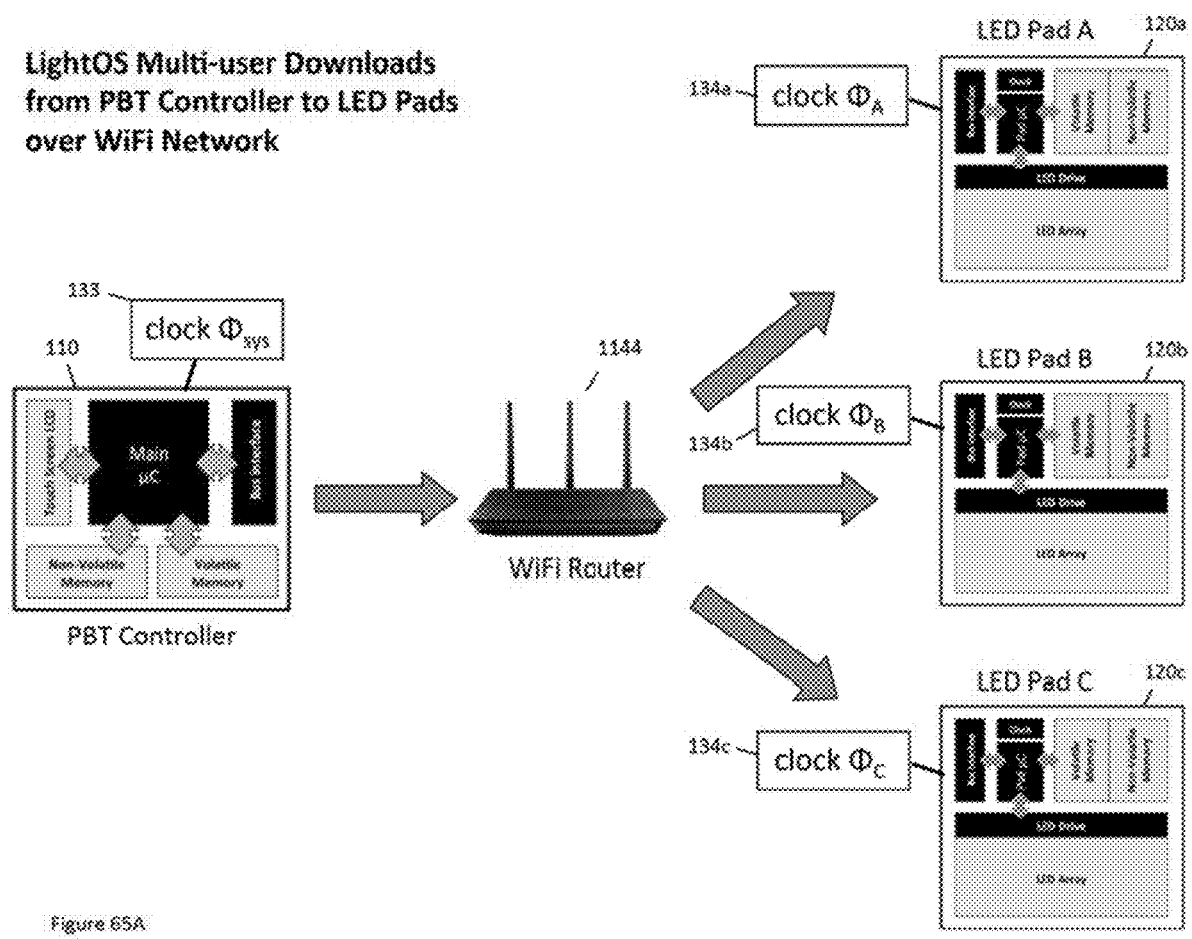

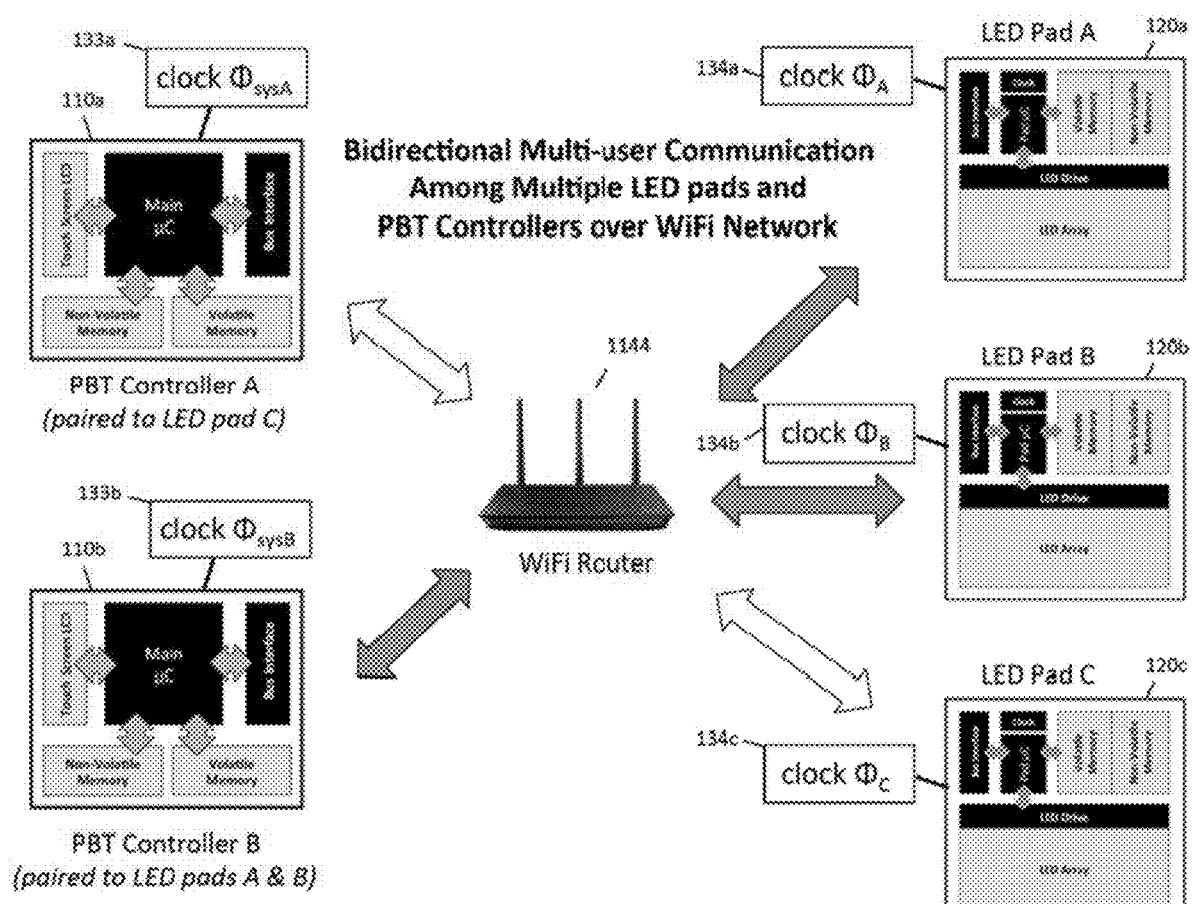

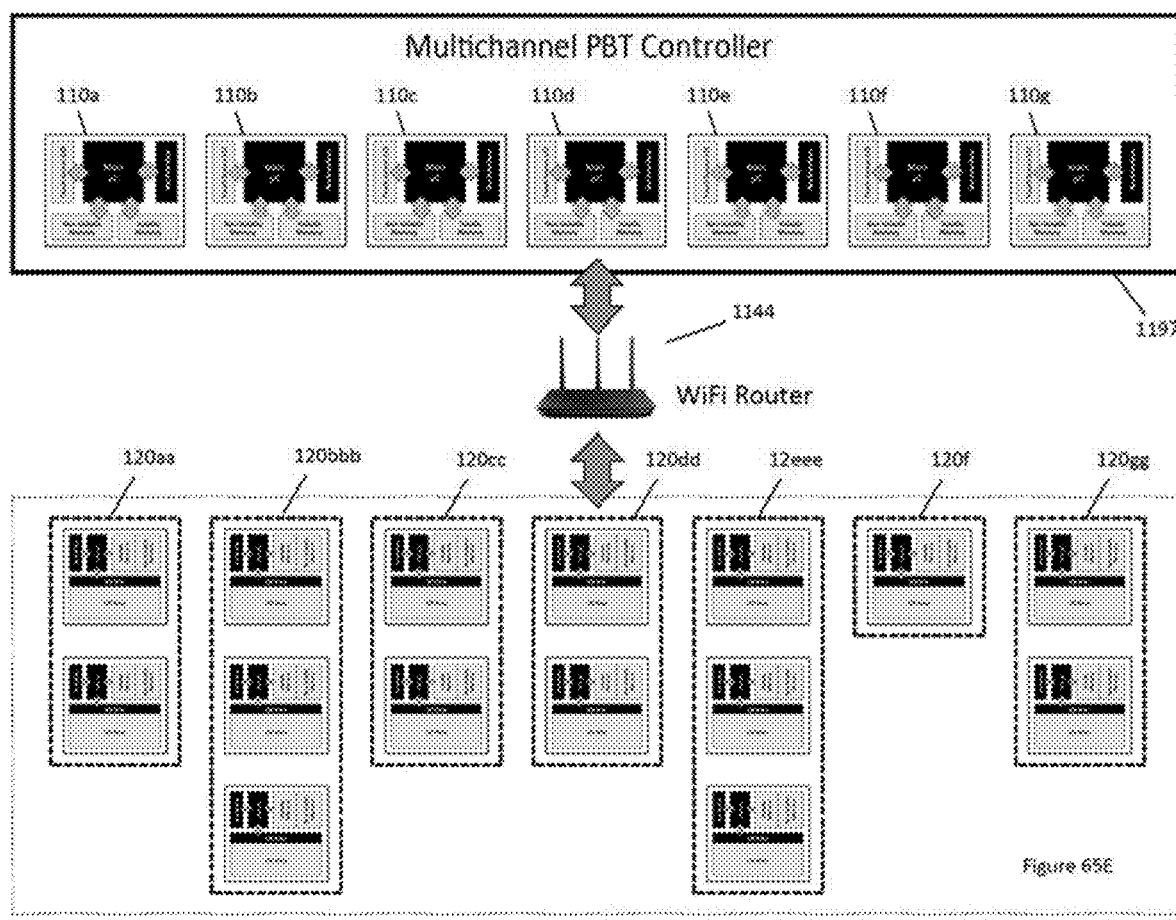

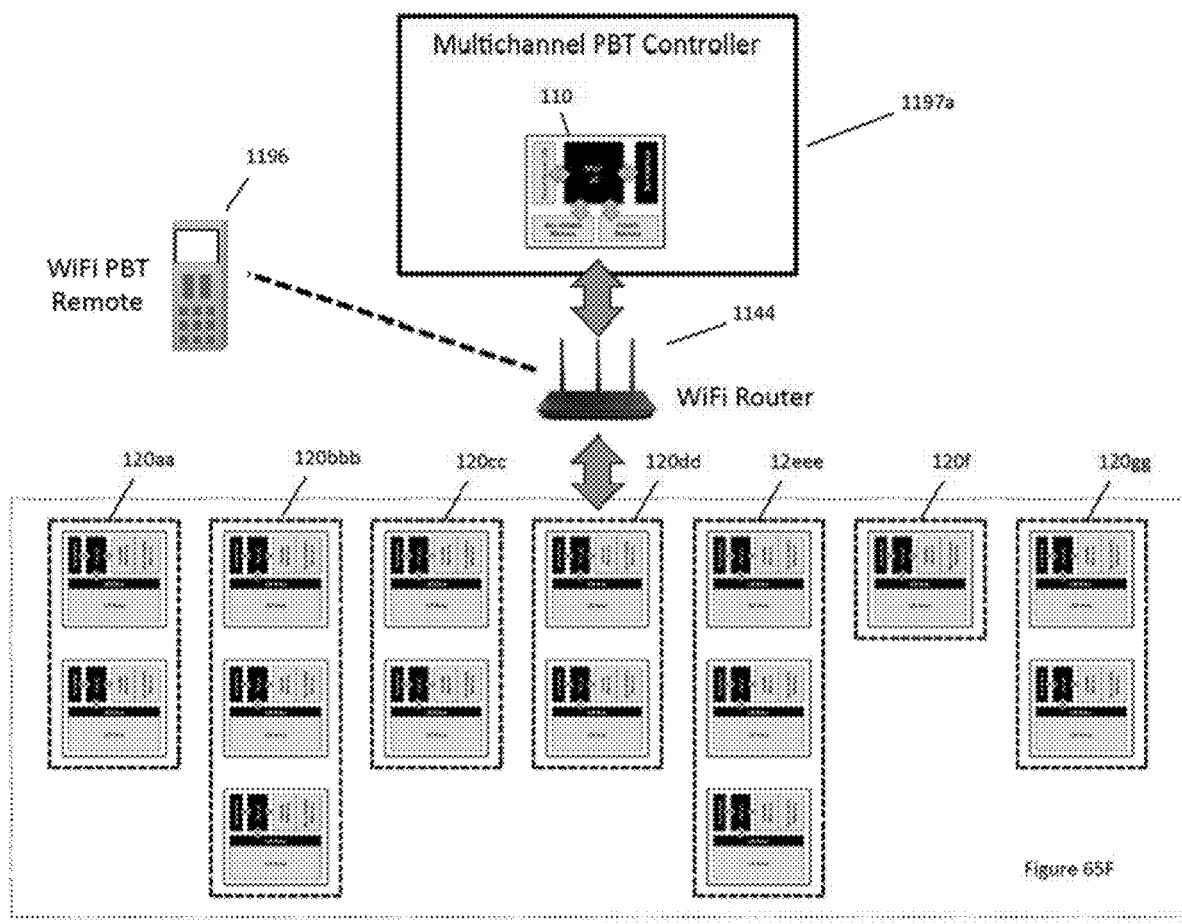

Connect to Server (with Authentication) Communication

1. Request to Connect (OF-02-01)

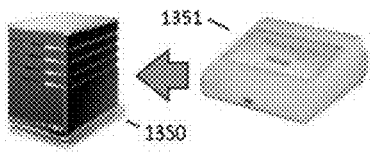

| 1370 LightOS Packet Type | 1371 LightOS Filetype | 1372 Payload Length | 1373 LightOS Payload 1374 |
|---|---|---|---|
| OF | 02-01 | 00-00-06 | 12E75F7F6436 |

OF – Sys Message  02 – Connection
↔ 01 Rqst server connection    1379 PBT Controller Device ID 2. Request Authentication (OF-02-02)

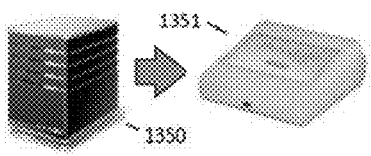

| 1380 LightOS Packet Type | 1381 LightOS Filetype | 1382 Payload Length | 1383 LightOS Payload 1384 |
|---|---|---|---|
| OF | 02-02 | 00-00-06 | 32F12EF7FE72 |

OF – Sys Message  02 – Connection
↔ 02 Authentication request    1389 PBT Database Device ID 3. Supply Authentication (OF-02-03)

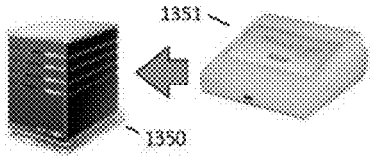

| 1390 LightOS Packet Type | 1391 LightOS Filetype | 1392 Payload Length | 1393 LightOS Payload 1394 |
|---|---|---|---|
| OF | 02-03 | 00-00-03 | 2F-10-B4 |

OF – Sys Message  02 – Connection
↔ 03 Supply authentication code

4. Connection Confirmed (OF-02-05)

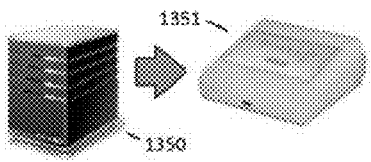

| 1400 LightOS Packet Type | 1401 LightOS Filetype | 1402 Payload Length | 1403 LightOS Payload 1404 |
|---|---|---|---|
| OF | 02-05 | 00-00-03 | 2F-10-B4 |

OF – Sys Message  02 – Connection
↔ 05 Connection confirmed

Figure 72

Identify PBT Controller Location, Confirm Account
5. Request Location File (02-B0-01)
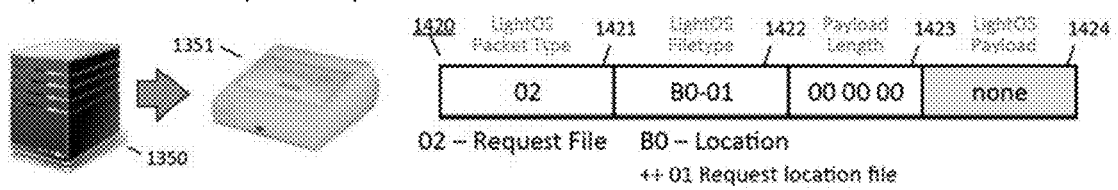
6. Supply Location File (03-A0-01)
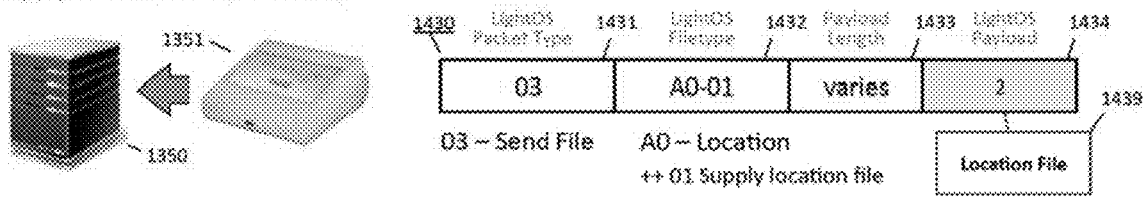
7. Confirm Account User
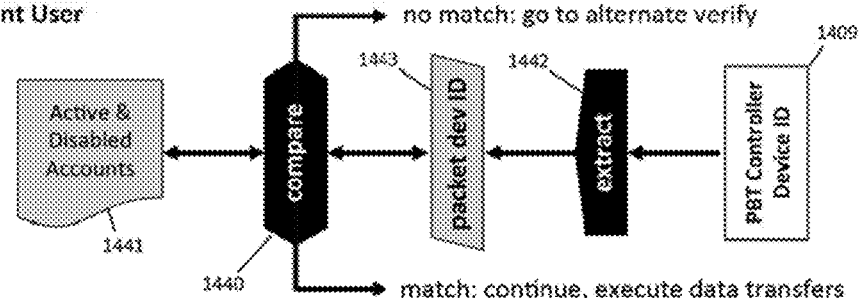
Figure 73

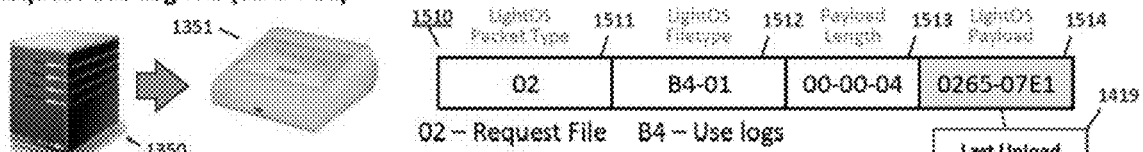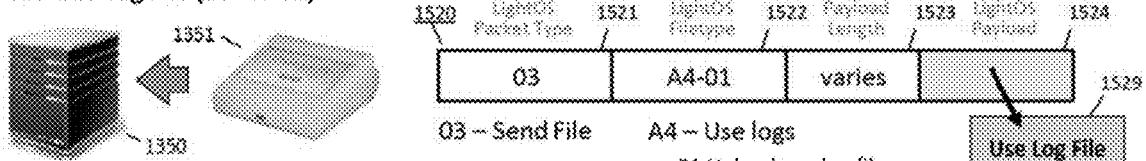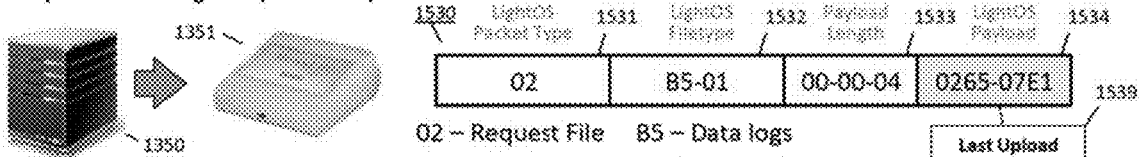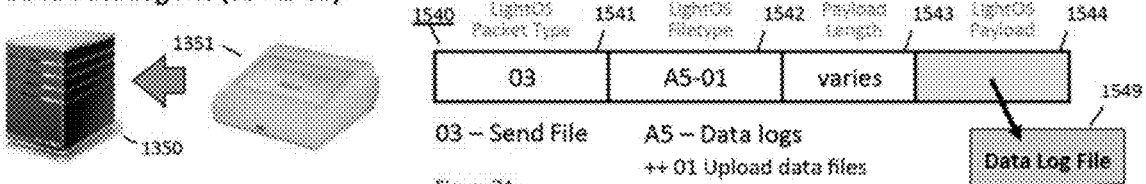
Figure 74

Server Rejects Connection to PBT Controller
4. Connection Rejected (0F-02-04)
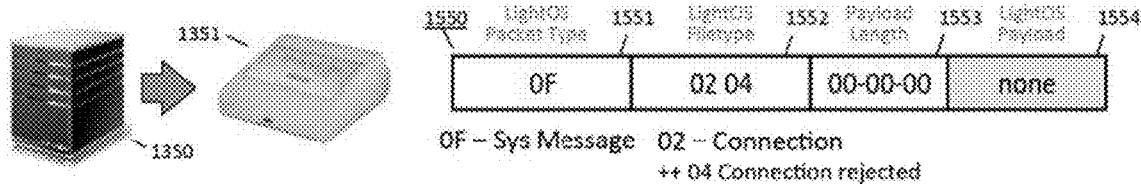
0F – Sys Message   02 – Connection
++ 04 Connection rejected
5. User Verification
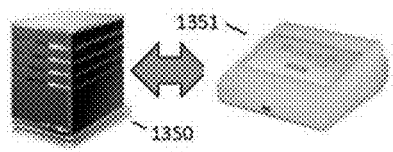
6. After 2nd Failure: Wipe LightPadOS from LED Pad (0F-FF-FF)
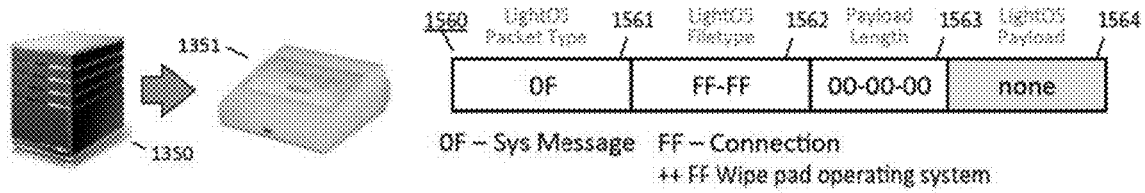
0F – Sys Message   FF – Connection
++ FF Wipe pad operating system
Figure 75

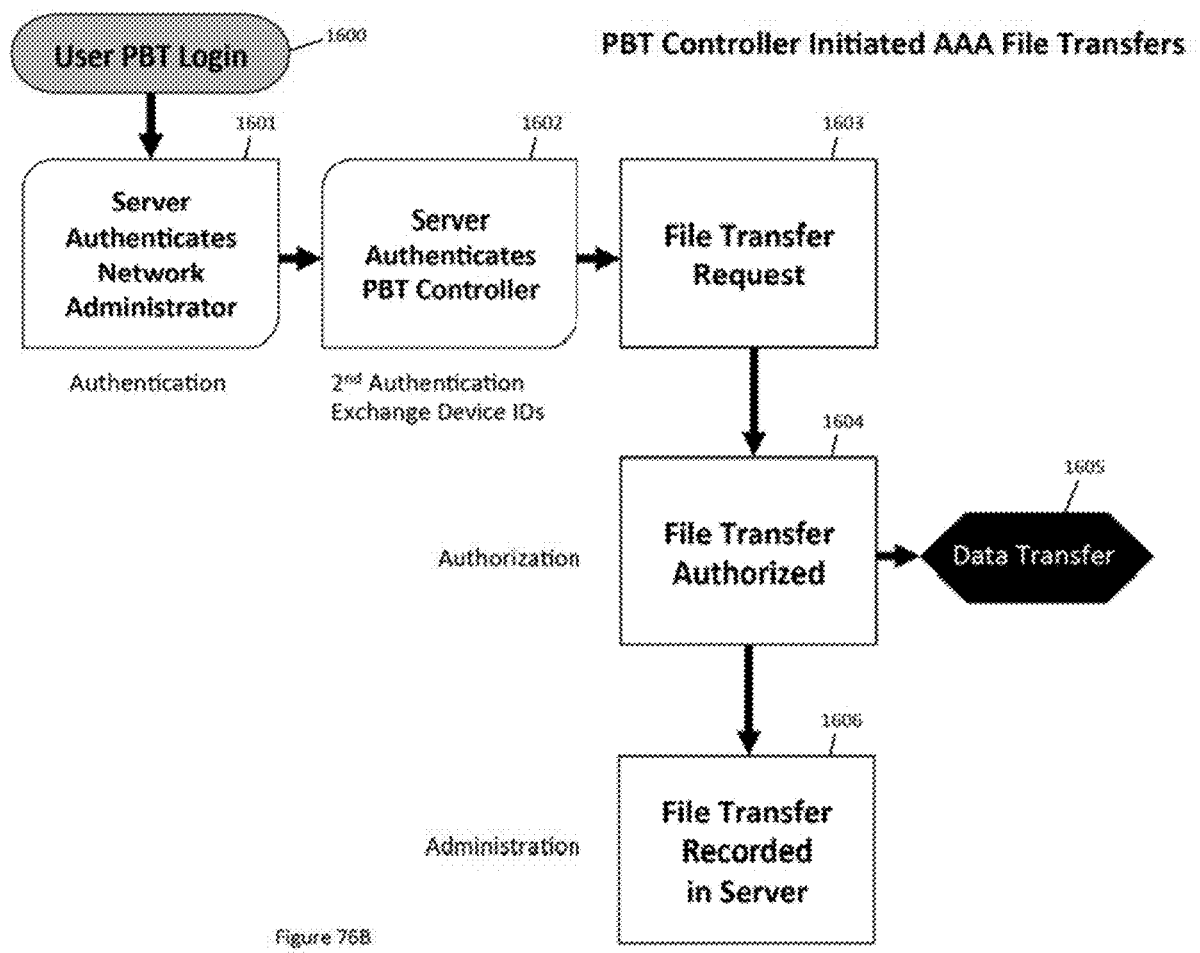

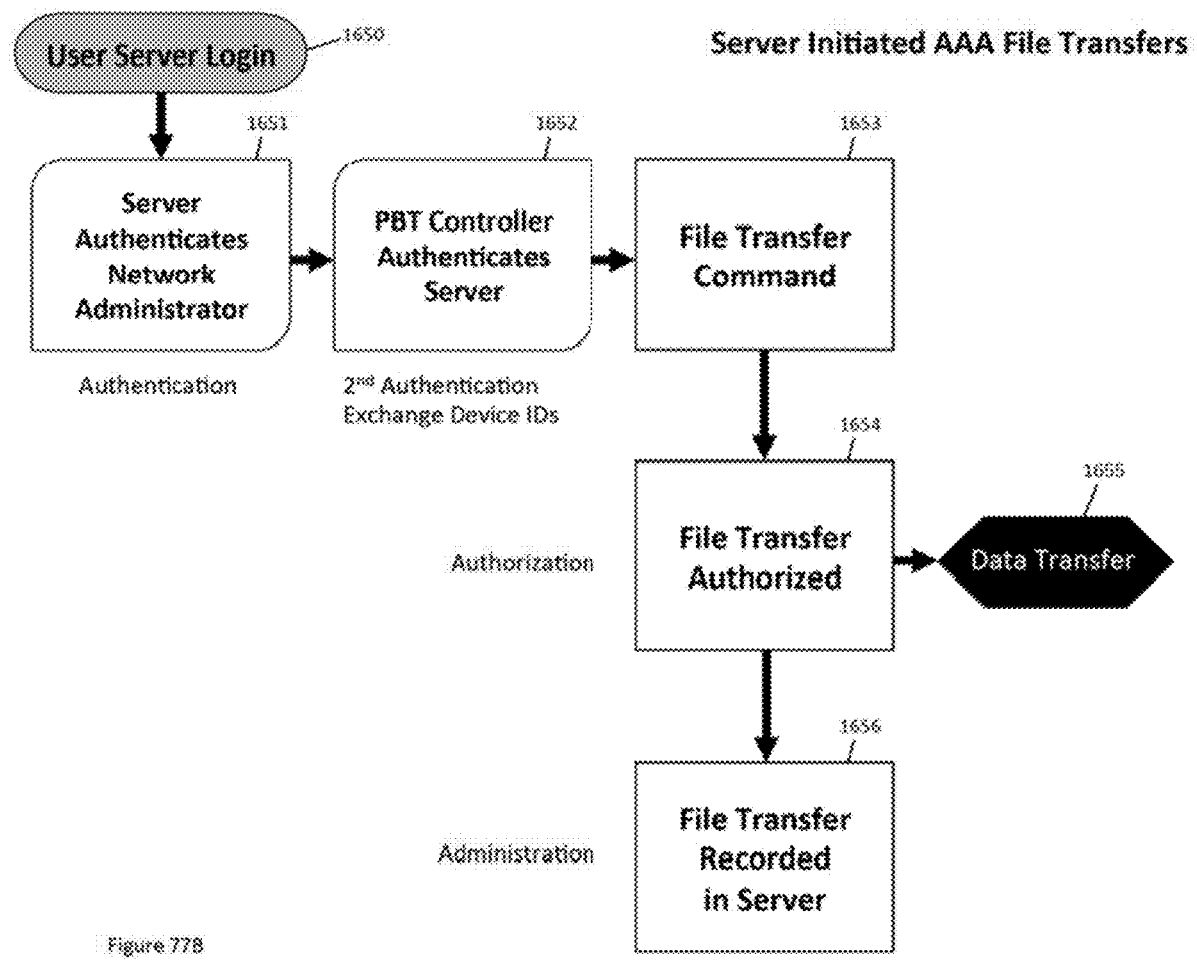

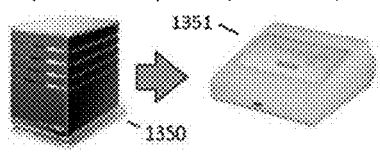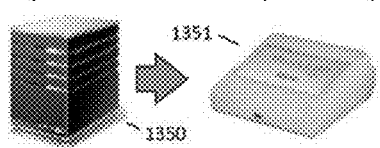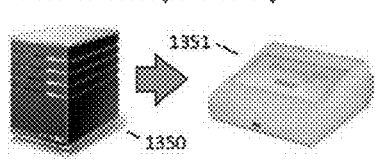
Figure 77C

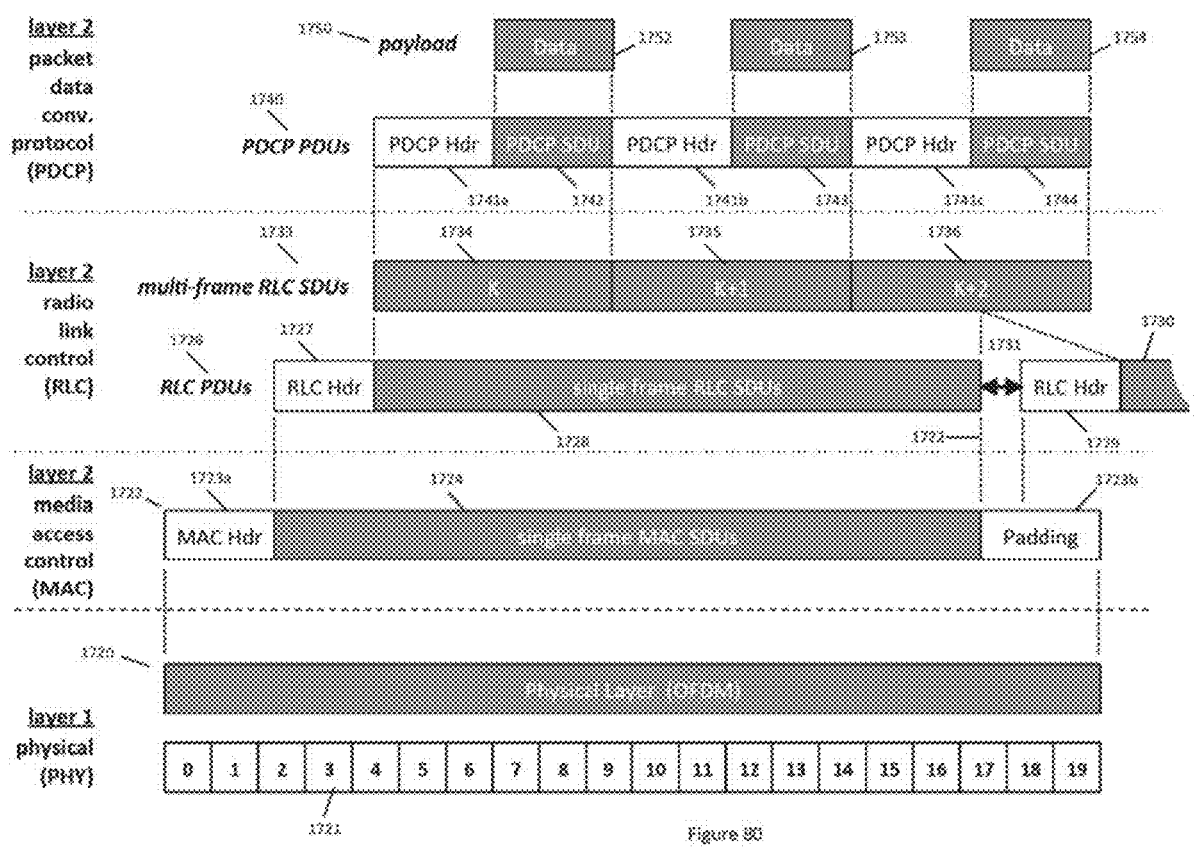

Integrated Sensor Array Static Images
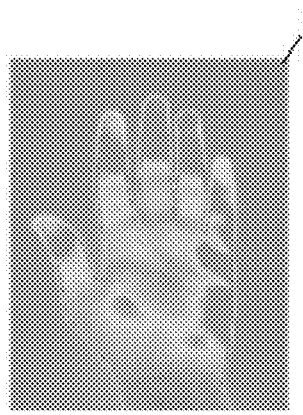  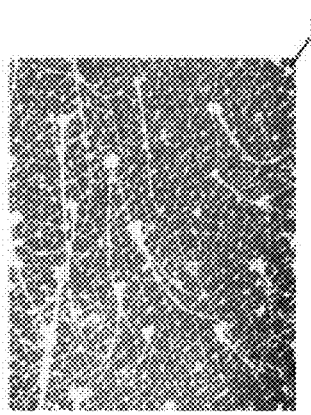
Thermograph · Ultrasound · Biosensor (Skin)
Figure 84A

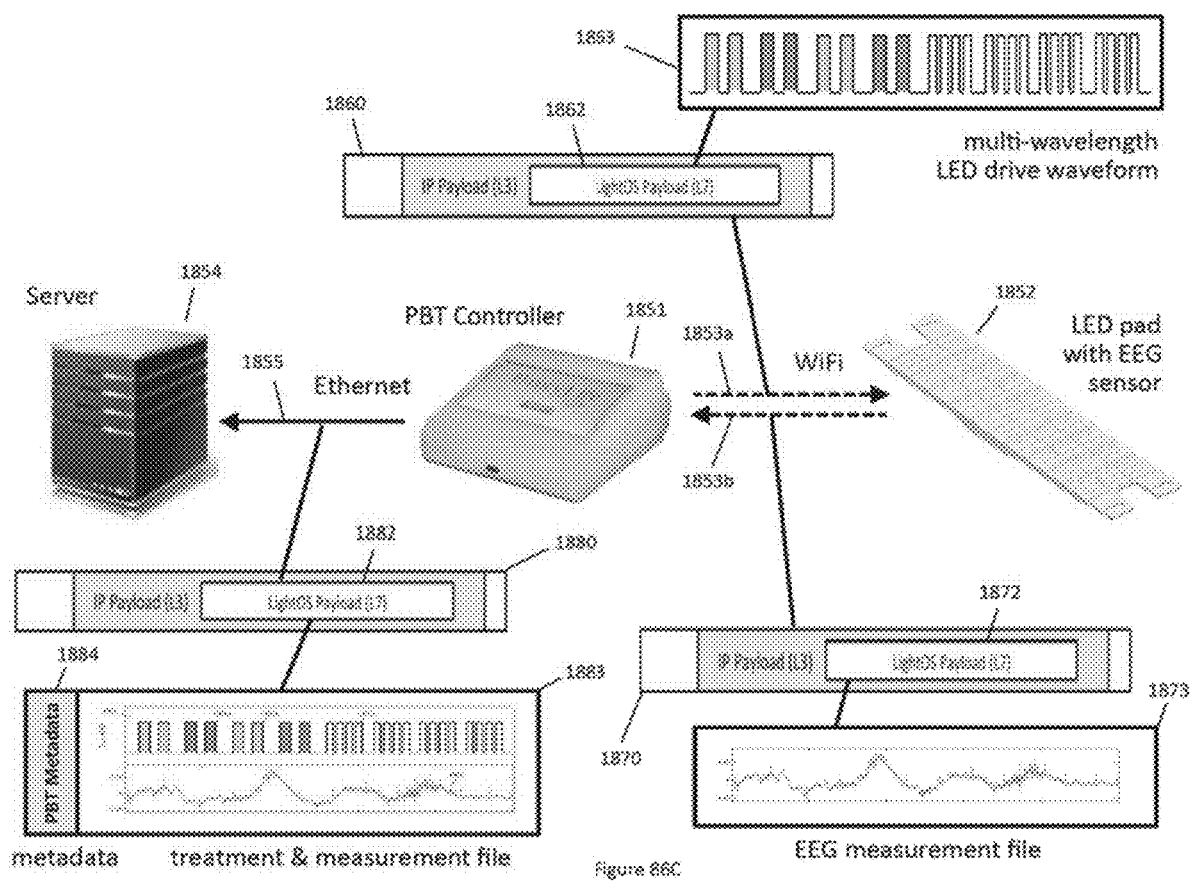

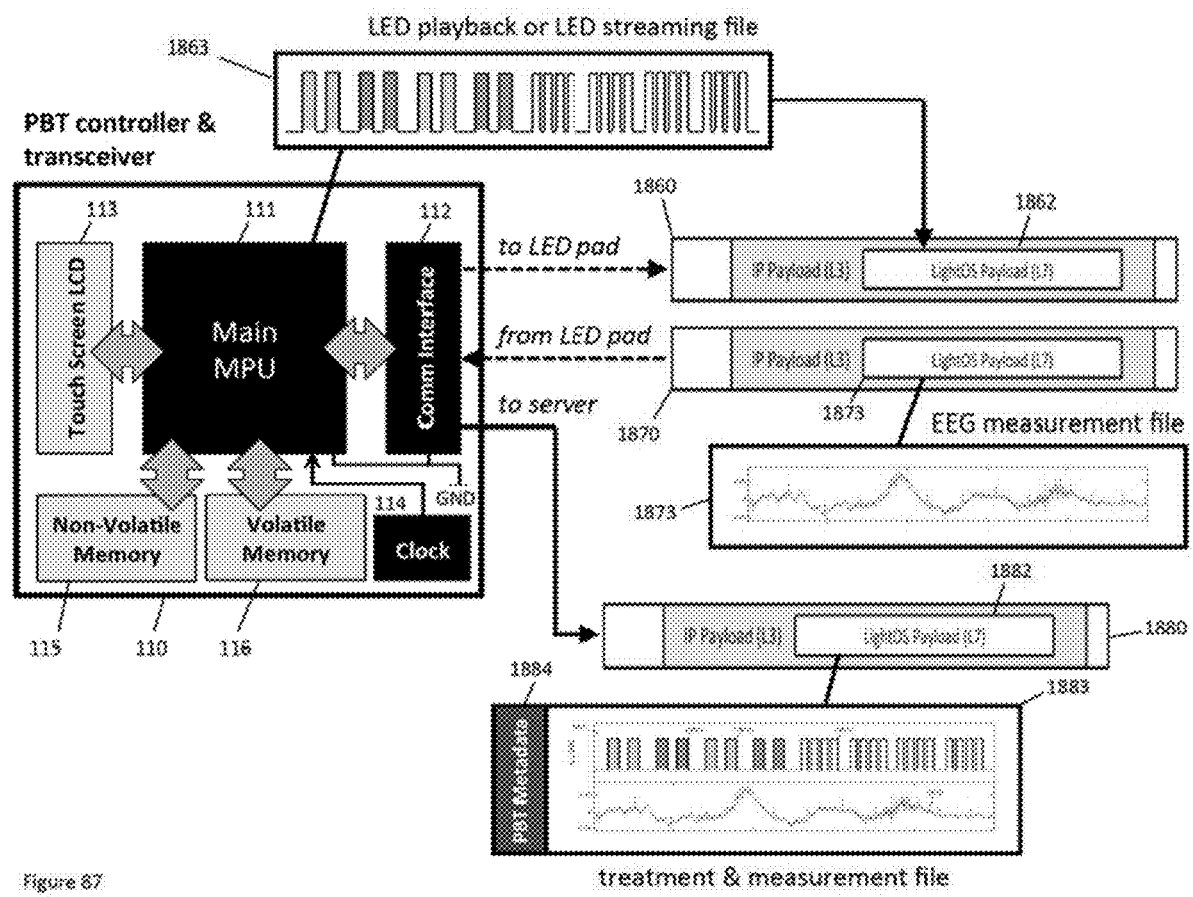

Figure 97

| Name | Length | Description | Layer | Value Range |
|---|---|---|---|---|
| MAC Source | 6B | MAC source address | 2 | 0 to FFFF FFFF FFFF |
| MAC Dest | 6B | MAC destination address | 2 | 0 to FFFF FFFF FFFF |
| MAC Type | 2B | MAC type | 2 | 0 to FFFF |
| LightOS Cipher Tag | 3B | Key, partial key, or packet tag ID | 6 | 0 to FFFFFF |
| LightOS Device ID | 18B | Unique device and network ID | 7 | $2^{144}$ combinations |
| LightOS Packet Type | 1B | Description of action (see table) | 7 | 0 to FF |
| LightOS Filetype | 2B | Description of filetype (see table) | 7 | 0 to FFFF |
| Sequence Number | 3B | Sequence no. of parsed payload | 7 | 0 to FFFFFF |
| Payload Length | 2B | Length of LightOS payload | 7 | 0 to FFFF |
| LightOS Payload * | 0 to 65,520B | LightOS payload | 7 | $2^{524,160}$ combination |
| LightOS Checksum | 4B | Hash, parity, or checksum | 7 | 0 to FFFF FFFF |

| Name | Length | Description | Layer | Value Range |
|---|---|---|---|---|
| Device Source Addr | 6B | 4-layer MAC static source addr | 7 | 0 to FFFF FFFF FFFF |
| Device Dest Addr | 6B | 4-layer MAC static dest addr | 7 | 0 to FFFF FFFF FFFF |
| VLAN | 4B | 16b type +4b cntrl+12b VLAN ID | 7 | 8100 xxxx |
| MAC Type | 2B | MAC type | 7 | 0 to FFFF |

Figure 98

DISTRIBUTED PHOTOBIOMODULATION THERAPY SYSTEM WITH INTELLIGENT LED PAD

CROSS-REFERENCE TO RELATED APPLICATIONS

This application claims the priority of Provisional Application No. 62/653,855, titled "Distributed Photobiomodulation Therapy Devices And Methods, Biofeedback, And Communication Protocols Therefor," filed Apr. 6, 2018.

This application is a continuation-in-part of application Ser. No. 15/857,002, titled "Phototherapy Process Including Dynamic LED Driver With Programmable Waveform," filed Dec. 28, 2017, which in turn is a divisional of application Ser. No. 14/073,371, filed Nov. 6, 2013, now U.S. Pat. No. 9,877,361, issued Jan. 23, 2018, which claimed the priority of Provisional Application No. 61/723,950, filed Nov. 8, 2012.

This application is related to the following applications: application Ser. No. 14/461,147, titled "Sinusoidal Drive System And Method For Phototherapy," filed Aug. 15, 2014; application Ser. No. 14/919,594, titled "3D Bendable Printed Circuit Board With Redundant Interconnections," filed Oct. 21, 2015, now U.S. Pat. No. 10,064,276, issued Aug. 28, 2018; and application Ser. No. 16/377,181, titled "Distributed Photobiomodulation Therapy System And Method," filed concurrently herewith.

Each of the foregoing applications and patents is incorporated herein by reference in its entirety.

BACKGROUND

Field of Invention

This invention relates to biotechnology for medical and health applications, including photobiomodulation, phototherapy, and photobiomodulation therapy (PBT).

Discussion of Related Art

As a brief introduction to semantics of the field, biophotonics is the biomedical field relating to the electronic control of photons, i.e. light, and its interaction with living cells and tissue. Biophotonics includes surgery, imaging, biometrics, disease detection, and phototherapy. Phototherapy, broadly meaning the therapeutic application of light, comprises a variety of therapies and treatment regimens including photo-optical therapy, photodynamic therapy (PDT), and photobiomodulation therapy (PBT). Photo-optical therapy involves visual stimulation of the eyes, optic nerve and visual cortex and is often used in behavioral training. Photo-optical therapy does not affect the morphology of the eye or cellular metabolism. Photodynamic therapy or PDT is the photochemical activation of topical ointments or photochemicals ingested or injected into a patient to invoke therapeutic effects—effects otherwise absent without stimulation of the proper wavelength of incident light. PDT does not directly affect cellular metabolism, but instead indirectly achieves therapeutic benefit by temporarily dissociating or activating a chemical or drug into a reactive form, a method particularly useful to restrict toxicity effects to a target area, organs, or tissue.

Photobiomodulation therapy or PBT, the main subject of this disclosure, is the controlled application of light photons, typically infrared, visible and ultraviolet light for medically therapeutic purposes including combating injury, disease, pain and immune system distress. More specifically, PBT involves subjecting cells and tissue undergoing treatment to a stream of photons of specific wavelengths of light either continuously or in repeated discontinuous pulses or periodic waveforms to control the energy transfer and absorption behavior of living cells and tissue. The photochemical response to PBT treatment is referred to as photobiomodulation or PBM. Mechanisms of PBT may include supportive or destructive effect on cells, e.g. killing bacteria or repairing damaged tissue. While blue and ultraviolet light are known to damage cellular reproduction of virulents and pathogens, red and near infrared light are absorbed by chromophores involved in regulation of NO (nitric oxide), generation of ATP, and control of cellular metabolic processes. Far infrared light used for heating and FIR spas comprises photons having energies less than 1% that of near infrared light and is therefore semantically referred to as 'thermotherapy' rather than phototherapy or photobiomodulation therapy.

FIG. 1 illustrates elements of a LED based PBT system capable of continuous or pulsed light operation including an LED driver 1 controlling and driving LEDs as a source of photons 3 emanating from LED pad 2 on tissue 5 for the patient. Although a human brain is shown as tissue 5, any organ, tissue or physiological system may be treated using PBT. Before and after, or during treatment, doctor or clinician 7 may adjust the treatment by controlling the settings of LED driver 1 in accordance with monitor observations.

While there are many potential mechanisms, as shown in FIG. 2, it is generally agreed that the dominant photobiological process 22 responsible for photobiomodulation during PBT treatment of human or animals using red and infrared light occurs within mitochondria 21, an organelle present in every eukaryotic cell 20 comprising both plants and animals including birds, mammals, horses, and humans. To the present understanding, photobiological process 22 involves a photon 23 impinging, among others, a molecule cytochrome-c oxidase (CCO) 24, which acts as a battery charger increasing the cellular energy content by transforming adenosine monophosphate (AMP) into a higher energy molecule adenosine diphosphate (ADP), and converting ADP into an even higher energy molecule adenosine triphosphate (ATP). In the process of increasing stored energy in the AMP to ADP to ATP, charging sequence 25, cytochrome-c oxidase 24 acts similar to that of a battery charger with ATP 26 acting as a cellular battery storing energy, a process which could be considered animal "photosynthesis". Cytochrome-c oxidase 24 is also capable of converting energy from glucose resulting from digestion of food to fuel in the ATP charging sequence 25, or through a combination of digestion and photosynthesis. To power cellular metabolism, ATP 26 is able to release energy 29 through an ATP-to-ADP-to-AMP discharging process 28. Energy 29 is then used to drive protein synthesis including the formation of catalysts, enzymes, DNA polymerase, and other biomolecules.

Another aspect of photobiological process 22 is that cytochrome-c oxidase 24 is a scavenger for nitric oxide (NO) 27, an important signaling molecule in neuron communication and angiogenesis, the growth of new arteries and capillaries. Illumination of cytochrome-c oxidase 24 in cells treated during PBT releases NO 27 in the vicinity of injured or infected tissue, increasing blood flow and oxygen delivery to the treated tissue, accelerating healing, tissue repair, and immune response.

To perform PBT and stimulate cytochrome-c oxidase 24 to absorb energy from a photon 23, the intervening tissue between the light source and the tissue absorbing light cannot block or absorb the light. As illustrated in FIG. 3, the electromagnetic radiation (EMR) molecular absorption spectrum of human tissue is illustrated in a graph 40 of absorption coefficient versus the wavelength of electromagnetic radiation λ (measured in nm). As shown, the relative absorption coefficient of oxygenated hemoglobin (curve 44a), deoxygenated hemoglobin (curve 44b), cytochrome c (curves 41a, 41b), water (curve 42) and fats and lipids (curve 43) as a function of the wavelength of the light. As illustrated, deoxygenated hemoglobin (curve 44b) and also oxygenated hemoglobin, i.e. blood, (curve 44a) strongly absorb light in the red portion of the visible spectrum, especially for wavelengths shorter than 650 nm. At longer wavelengths in the infrared portion of the spectrum, i.e. above 950 nm, EMR is absorbed by water ($H_2O$) (curve 42). At wavelengths between 650 nm to 950 nm, human tissue is essentially transparent as illustrated by transparent optical window 45.

Aside from absorption by fats and lipids (curve 43), EMR comprising photons 23 of wavelengths λ within in transparent optical window 45, is directly absorbed by cytochrome-c oxidase (curves 41aa, 41b). Specifically, cytochrome-c oxidase 24 absorbs the infrared portion of the spectrum represented by curve 41b unimpeded by water or blood. A secondary absorption tail for cytochrome-c oxidase (curve 41a) illuminated by light in the red portion of the visible spectrum is partially blocked by the absorption properties of deoxygenated hemoglobin (curve 44b), limiting any photobiological response for deep tissue but still activated in epithelial tissue and cells. FIG. 3 thus shows that PBT for skin and internal organs and tissue requires different treatments and light wavelengths, red for skin and infrared for internal tissue and organs.

Present Photonic Delivery Systems

In order to achieve maximum energy coupling into tissue during PBT, it is important to devise a consistent delivery system for illuminating tissue with photons consistently and uniformly. While early attempts used filtered lamps, lamps are extremely hot and uncomfortable for patients, potentially can burn patient and doctors, and are extremely difficult in maintaining uniform illumination during a treatment of extended durations. Lamps also suffer short lifetimes, and if constructed using rarified gasses, can also be expensive to replace regularly. Because of the filters, the lamps must be run very hot to achieve the required photon flux to achieve an efficient therapy in reasonable treatment durations. Unfiltered lamps, like the sun, actually deliver too broad of a spectrum and limit the efficacy of the photons by simultaneously stimulating both beneficial and unwanted chemical reactions, some involving harmful rays, especially in the ultraviolet portion of the electromagnetic spectrum.

As an alternative, lasers have been and continue to be employed to perform PBT. Like lamps, lasers risk burning a patient, not through heat, by exposing tissue to intense concentrated optical power. To prevent that problem, special care must be taken that laser light is limited in its power output and that unduly high current producing dangerous light levels cannot accidentally occur. A second, more practical problem arises from a laser's small "spot size", the illuminated area. Because a laser illuminates a small focused area, it is difficult to treat large organs, muscles, or tissue and it is much easier for an overpower condition to arise.

Another problem with laser light results from its "coherence," the property of light preventing it from spreading out, making it more difficult to cover large areas during treatment. Studies reveal there is no inherent extra benefit from PBT using coherent light. For one thing, bacterial, plant and animal life evolved on and naturally absorbs scattered, not coherent light because coherent light does not occur naturally from any known light sources. Secondly, the first two layers of epithelial tissue already destroy any optical coherence, so the presence of coherence is really relegated to light delivery but not to its absorption.

Moreover, the optical spectrum of a laser is too narrow to fully excite all the beneficial chemical and molecular transitions needed for to achieve high efficacy PBT. The limited spectrum of a laser, typically a range of ±1 nm around the laser's center wavelength value, makes it difficult to properly excite all the beneficial chemical reactions needed in PBT. It is difficult to cover a range of frequencies with a narrow bandwidth optical source. For example, referring again to FIG. 3, clearly the chemical reactions involved in making the CCO absorption spectra (curve 41b) is clearly different than the reactions giving rise to absorption tail (curve 41a). Assuming the absorption spectra of both regions are shown to be beneficial it is difficult to cover this wide range with an optical source having a wavelength spectrum only 2 nm wide.

So whiles sunlight exhibits an excessively broad spectrum, photobiologically exciting many competing chemical reactions with many EMR wavelengths, some even harmful, laser light is too narrow and does not stimulate enough chemical reactions to reach full efficacy in phototherapeutic treatment. This subject is discussed in greater detail in a related application entitled "Phototherapy System And Process Including Dynamic LED Driver With Programmable Waveform", by Williams et al. (U.S. application Ser. No. 14/073,371), incorporated herein by reference and for which this application represents a continuation in part. Another disadvantage of broad-spectrum PBT is that light wavelengths that do not invoke any beneficial photobiological effect are none-the-less absorbed and elevate the temperature of tissue under treatment. If PBT is performed at the maximum safe temperature, e.g. under 44° C. then heating resulting from absorption of light wavelengths not photobiologically beneficial means that a lower energy density and treatment dose can be administered at the frequencies that are beneficial. In essence the maximum energy budget is wasted by useless light wavelengths. As such, PBT mitochondrial activation is best administered using light wavelengths covering all (or a portion) of the absorption spectra of CCO not blocked by water and hemoglobin, i.e. transparent optical window 45, but not at other wavelengths outside of this optical window.

To deliver PBT by exciting the entire range of wavelengths in the transparent optical window 45, i.e. the full width from approximately 650 nm to 950 nm, even if four different wavelength light sources are employed to span the range, each light source would require a bandwidth almost 80 nm wide. This is more than one-and-a-half orders of magnitude wider than the bandwidth of a laser light source. This range is simply too wide for lasers to cover in a practical manner. Today, LEDs are commercially available for emitting a wide range of light spectra from the deep infrared through the ultraviolet portion of the electromagnetic spectrum. With bandwidths of ±30 nm to ±40 nm, it is much easier to cover the desired spectrum with center frequencies located in the red, the long red, the short near infrared (NIR) and the mid NIR portions of the spectrum, e.g. 670 nm, 750 nm, 810 nm, and 880 nm.

Photobiomodulation is not the same thing as photo-optical therapy. As shown in FIG. 4A, PBT involves direct stimulation of tissue 5 with photons 3 emitted from LED pad 2. Tissue 5 is unrelated to the eyes and may comprise organs associated with the endocrine and immune systems such as kidneys, liver, glands, lymph nodes, etc. or the musculoskeletal system such as muscles, tendons, ligaments, and even bone. PBT also directly treats and repairs neurons including peripheral nerves, the spinal cord, as well (as shown) brain 5 and the brain stem. PBT transcranial treatment penetrates the skull and exhibits significant and rapid therapeutic benefits in concussion recovery and repairing damage from mild traumatic brain injury (mTBI). In other words, PBT energy is absorbed by chromophores in cells not associated with the optic nerve. Photo-optical therapy in contrast is based on exciting the retina with colored light or images to invoke an emotional response or to help synchronize the body's circadian rhythms to its surroundings. In such cases, image 12 from light source 12 stimulates the optic nerve in eye 11 to send electrical signals, i.e. neural impulses, to the brain 5.

Several rudimentary tests highlight the many and vast differences between PBT and photo-optical therapy. For one, photo-optical therapy only works on the eyes, whereas PBT affects any cell including internal organs and brain cells. Photo-optical therapy converts light into electrical signals carried to the brain, where PBT stimulates chemical transformations, ionic, electron and thermal transport within treated cells and tissue with no need for signal transduction to the brain. The effect is local and systemic without the assistance of the brain. For example, blind patients respond to PBT but not to photo-optical therapy. One demonstration of this effect involved mice poisoned by methanol to induce blindness. While those treated by infrared PBT recovered 80% of their vision, the control group not receiving PBT remained permanently blind.

Another distinction between photo-optical therapy and PBT is illustrated in FIG. 4B. In the case of sight, i.e. photo-optical stimulation or vision, the combination of red light 15A and blue light 15B emanating from light source 14 once received by eye 11 send an electrical signal 9 to brain 5, which perceives the color of the impinging light as purple. In reality, violet/purple light has a much shorter wavelength than blue or red light, and as such comprises photons with higher energy than red light 15A and blue light 15B. In the case of PBT, cell 16 and the mitochondria 17 contained therein will respond photo-chemically to light source 14 as though it is emitting red light 15A and blue light 15B (which it truly is), and not respond as though purple light is present. Only true short wavelength purple light emitted from a violet or ultraviolet light source can produce a photobiomodulation response to purple light. In other words, mitochondria and cells are not fooled by the blending of different colored light the way the eye and the brain are. In conclusion photo-optical stimulation is not the same thing as photobiomodulation not should photo-optical therapy be misconstrued as prior art anticipatory of the mechanisms and benefits of photobiomodulation.

The foregoing discussion does not mean that PBT cannot benefit the health of the eye, its optic nerve, surrounding tissue, or vision quality—it simply means the medical benefits of red and NIR light PBT on the eye does not involve vision, optical stimulation, or optical pattern recognition in the brain. As a caveat, PBT treatments performed over the eyes, e.g. during facial treatments, should be limited to the long wavelength portion of the visible spectrum. Specifically bright blue, violet, and ultraviolet light can damage the retina and optic nerve. PBT of the face at these frequencies should include special attention to cover the eyes and block short wavelength light from reaching the eye. It should be noted photobiomodulation therapy is not limited to red and NIR treatments for mitochondrial activation. Other photobiomodulation mechanisms exist unrelated to CCO. For example, blue light is found to inhibit or kill microbes such as fungus and bacterial and well as to impede viral reproduction and gene expression. The exact photochemical and photobiological mechanisms are still under investigation. Similarly, purple, violet, and ultraviolet light are found to treat certain skin conditions such as psoriasis. Red, green, and yellow light are also observed to cause a release of triglycerides from adipose tissue, i.e. to shrink fat cells.

Present Day Photobiomodulation Therapy Systems

Today's state-of-the-art photobiomodulation therapy systems, shown by example system 50 in FIG. 5A, comprises controller 51, electrically connected to two sets of LED pads. Specifically, output A of controller 51 is connected by cable 53a to first LED pad set A comprising electrically interconnected LED pad 52b. LED pads 52a and 52c are optionally connected to LED pad 52b by electrical jumpers 54a and 54b to create first LED pad set A operating as a single LED pad comprising over 600 LEDs and covering a treatment area exceeding 600-cm$^2$. In a similar manner, output B of controller 51 is connected by cable 53b to first LED pad set B comprising electrically interconnected LED pad 52e. LED pads 52d and 52f are optionally connected to LED pad 52d by electrical jumpers 54c and 54d to create first LED pad set B operating as a single LED pad comprising over 600 LEDs and covering a treatment area exceeding 600-cm$^2$. In the system shown, controller 51 not only generates the signals to control the LEDs within the pads but also provides a source of power to drive the LEDs. The electrical power delivered from controller 51 to the LED pads is substantial, typically 12 W for two sets of six pads. An exemplary electrical schematic of the system is shown in FIG. 5B, where controller 61 includes an internal switch-mode power supply SMPS 65 used to convert power from the 120-V to 220-V AC mains 64 into at least two regulated DC voltage supplies, namely 5 V for control and logic, and a higher voltage supply +$V_{LED}$ used for powering the strings of LEDs in the LED pads. Typical voltages for +$V_{LED}$ range from 24-V to 40-V depending on the number of LEDs connected in series. To facilitate algorithmic control microcontroller µC 67 executes dedicated software in response to user commands input on touchscreen LCD panel 66. The result is a series of a pulses output in some alternating pattern on outputs A from logic buffers 68a and 68b used to independently control red and near infrared (NIR) LEDs in the LED pads connected to output A. A similar arrangement is included for output B using its own dedicated logic buffers but where µC 67 is able to manage and control both A and B outputs concurrently.

The signal on output A is then routed to one or more LED pads 62 through shielded-cable 63 comprising high current power lines ground GND 69a, 5-V supply line 69b, and +$V_{LED}$ supply line 69c, as well as LED control signal 70a for controlling conduction in NIR LEDs 71a through 71m, and LED control signal 70b for controlling conduction in red LEDs 72a through 72m. Control signals 70a and 70b in turn drive the base of either bipolar junction transistor 73a or 73b, the transistors operating as switches to pulse the corresponding strings of LEDs on and off. When the input to either bipolar is low, i.e. biased to ground, no base current and no collector current flow and the LED string remains dark. When the input to either bipolar is high, i.e. biased to 5-V, base current flows and in a corresponding manner collector current flows illuminating the LEDs in the corresponding LED string. The current flowing is set by the sum of the LED turn on voltages and the current limiting resistors 74a or 74b. Using resistors to set LED brightness is not preferred because any variation in the LED voltage either from manufacturing stochastic variability or from variations in temperature during operation will result in a change in LED brightness. The result is poor uniformity in LED brightness across a LED pad, from LED pad to LED pad, and from one manufacturing batch to the next. An improvement in maintaining LED brightness uniformity can be gained by replacing resistors 74A and 74b with fixed value constant current sources or sinks (not shown).

Limitations of such the PBT systems as described above are numerous, impacting the system's utility, functionality, safety, and expandability and include:

Electrical "signal" communication to LED pad—Signals from the PBT controller to LED pads are simple digital pulses, not differential communication between a bus transceiver pair. These signals are sensitive to common mode noise and ground loops affecting the magnitude and duration of the pulses controlling LED operation. As simple electrical pulses, the system also lacks any error checking capability so malfunctions cannot be corrected or even detected.

Unidirectional signal flow from PBT controller to LED pad—With unidirectional data flow, PBT controllers cannot authenticate any LED pad connected to its output, nor once connected can they monitor a pad's operating condition. Unidirectional data also prevents feedback of a LED pad's status or reporting of other pad information to the host PBT controller.

Inability to detect a multi-pad misconnection short—Through user error, the misconnection of two outputs of a PBT controller to the same LED pad or pads, i.e. inadvertently shorting two outputs together, means both outputs are driving the same LED strings. This misconnection error can damage the LED driver circuitry, cause LED overheating, patient burn risk, and potentially fire.

Inability to identify approved LED pads or certified manufacturers—Lacking any ability to identify a LED pad's pedigree a PBT system will unknowingly drive any LED connected to it including illegal, counterfeit, or knock-off LED pads. Driving pads not made or certified by the system specifier or manufacturer has unknown consequences ranging from loss of functionality and reduced efficacy to safety risks. Commercially, the merchandizing and sale of counterfeit and copycat LED pads also robs IP licensed PBT device merchants of legal income.

Inability to identify a connected device is a LED pad—Without the ability to confirm if a device connected to a PBT controller output is a LED pad (rather than a completely unrelated peripheral such as a speaker, battery, motor, etc.), connection of an unauthorized electrical load to a PBT system's output will invariably damage either the accessory, the PBT controller, or both. When driving an unknown electrical load, high voltage present on the controller's output pins during operation also presents a fire hazard.

Inability to identify power sources—The inability of a PBT controller to identify connection of its output to a power source (such as AC power adapters, batteries, car electrical power, or generators) represents a real safety risk, whereby the power supply contained within the PBT controller competes with the external power source. The interconnection of two dissimilar power supplies may result in excessive currents, voltages, power dissipation, or uncontrolled oscillations leading to damage of the external power source, the PBT controller, or both.

Inability to control or limit driver output current—Connection of a shorted load such as a damaged pad, a wire short, or any load that exhibits an high inrush current (such as a motor) represents a high current risk and possibly a fire hazard. Inductive loads such as solenoids also can momentarily create excessive voltages damaging low-voltage components.

Inability to detect batteries connected to a PBT system's output—Connecting a battery pack to a PBT system's output has the potential for damaging the battery pack, accidentally charging the battery with the wrong charging conditions and giving rise to over-voltage, over-current, or over-temperature conditions in the electrochemical cells. Improper charging of wet-chemistry or acid batteries has the potential for acid or electrolyte leaks. The improper charging of lithium ion batteries can cause overheating, fire, and even explosions.

Inability to detect over-temperature conditions in LED pads—Overheating of a LED pad risks patient discomfort and burns, pad damage, and in extreme cases the possibility of fire.

Inability to identify the LED configuration within a LED pad—Unable to identify the series-parallel array configuration of LEDs in a LED pad, the PBT controller is unable to determine if the pad is compatible with the PBT system or even if LED operation is possible. For example, too few series connected LEDs can damage the LEDs with too much voltage. Too many series connected LEDs will result in dim or no illumination. Too many parallel strings of LEDs can result in excessive total pad current and consequentially overheating, as well as large voltage drops across interconnections, poor light uniformity across a LED pad, and possible damage to PCB's conductive traces.

Inability to identify the types of LEDs contained within a LED pad—Unable to detect what wavelength LEDs are in a pad, a PBT system has no means by which to match its treatment programs to the LED array or to select the right wavelength LEDs for each specific waveform in the treatment protocol.

PBT controller outputs are each limited to a fixed number of control signals—With only one or two control signals per output, today's PBT controllers are incapable of driving three, four, or more different wavelengths of LEDs within the same pad with different excitation patterns.

Limited mobility—In present day medical grade PBT systems, the connection of a central PBT controller to LED pads requires cable connections. While such tethered PBT systems are generally acceptable in hospital applications (and possibly in clinical settings), in consumer, paramedic, and military applications limiting mobility with cables or wires is not useful.

Incapable of waveform synthesis—PBT systems lack the technology to drive LEDs with any waveforms other than square wave pulses. Square wave pulsed operation limits LED illumination patterns to one-frequency-at-a-time operation. Since pulse frequency affects the energy coupling to specific tissue types, a single frequency PBT system can only optimally treat once tissue type at a time, extending the required therapy time and patient/insurance cost. Analysis also reveals square wave pulses waste energy producing off harmonics not necessarily beneficial to a therapy. LED drive using sinusoids, chords, triangle waves, sawtooth waveforms, noise bursts, or audio samples requires complex waveform synthesis within the LED pad. Although host PBT controllers should have sufficient compute capability to synthesize such waveforms, the capability is not beneficial because the signal cannot be delivered over long cables without suffering significant waveform distortion. Unfortunately, LED pads cannot perform the task. Using cheap discrete components, present day LED pads are incapable of performing any waveform synthesis whatsoever, not to mention the communication protocols needed to remotely select or change the synthesized waveform do not exist.

Distribution of new LED driver algorithms—Present PBT systems lack the ability to download software updates from a database or server to correct software bugs or to install new treatment algorithms.

Inability to capture and record real time patient biometric data—Present PBT systems lack the ability to collect biometric data such as brain waves, blood pressure, blood sugar, blood oxygen, and other biometrics during a treatment or the ability to embed this collected data into the treatment file record or to append biometric data into a treatment file using a common time base as a reference.

Inability to gather real time images of treatment area—Present PBT systems lack any means by which to measure or create images of tissue during treatment. The systems also lack the ability to store still and video images or to match the images to a PBT session's treatment time.

Inability for users (doctors) to create new treatment algorithms—Present PBT systems lack any capability for users such as physicians or researchers to create new algorithms or to string existing treatments together to form complex therapy specific treatments, e.g. optimizing an excitation sequence for activating injected stem cells (useful in accelerating stem cell differentiation while reducing rejection risks.)

Electronic distribution of documentation—Present PBT systems are unable to distribute and update any documentation electronically. It would be beneficial if the distribution of FDA advisories or rulings, as well as errata and updates to PBT operating and therapy manuals, treatment guides, and other documentation can be provided electronically to all PBT system users. Such capability is not available in any medical devices today.

Treatment tracking—Present PBT systems are unable to track the treatment use history, capture the system's use in a treatment log, and upload the treatment log to a server. Lacking real time treatment logs via network connectivity, the widespread commercial adoption of PBT systems by physicians, hospitals, clinics, and spas is problematic. Without uploaded use logs, present day PBT systems cannot support revenue-sharing lease business models because the leaser is unable to verify the leasee's system use. Similarly hospitals and clinics cannot confirm PBT systems use for insurance audits and for fraud prevention. In pay-to-use SaaS (software as a service) payment models, the PBT service agent is unable to confirm a client's use history.

Electronic prescriptions—No physical medicine devices today including PBT systems are capable of securely transferring and distributing doctor prescriptions into a medical device.

Remote disable—No PBT system today is capable of disabling device operation in the case of non-payment or in the case of theft to stop black market trade.

Location tracking—No PBT system today is capable of tracing the location of a stolen PBT system to track the thieves.

Secure communication—Since PBT systems today use electrical signals rather than packet based communication to control LED pads, then hacking and direct measurement of communication between a host PBT system and a LED pad is trivial, lacking any security whatsoever. Moreover, PBT systems today lack any provision for Internet communication and the security methods needed to prevent content hacking and to thwart identity theft in compliance with HEPA regulations. In the future, encryption alone is expected to be inadequate in securing data communication across the Internet. In such cases connectivity to private hypersecure networks will also be required.

Medical Device Interconnectivity

One of the biggest limitations of PBT systems is their network connectivity or more specifically their lack thereof. Unlike a thermostat, light bulb, or refrigerator which can be connected to the Internet indiscriminately, class 2 medical devices are regulated and must insure a number of unique guarantees not offered in conventional Internet connected devices commonly referred to as Internet of Things or IoT. In essence, Internet of Medical Things (IoMT), like connected autonomous vehicles, have special requirements to avoid a malfunction from injuring someone. For example, if a device is being controlled over the Internet and the network becomes slow or drops altogether, how can the system insure the patient doesn't receive too much exposure? Because PBT is biphasic, meaning too little or too much photonic radiation can reduce treatment efficacy, accidental over-dose can result in dehydration and reduction in a treatment's therapeutic value, discouraging a patient from continuing treatment.

Without proper safeguards, a network failure could also allow a large or rapid rise in pad temperature with the potential for burn risk. Moreover, lacking proper network security safeguards, a network connected PBT device can be hacked and hijacked, allowing a cybercriminal to take control of a person's therapy for mischievous or even nefarious purposes. Information extracted from a system could reveal a person's identity (identity theft risk), their medical treatments (insurance fraud risk), and even their medical conditions (blackmail risks). Even if by poor design and inadequate awareness of network risks, these attack vulnerabilities are clear violations of HIPAA regulations, the "Health Insurance Portability and Accountability Act" enacted as law 104-191 by the United States Congress on 21 Aug. 1996. Lacking the provisions to overcome these safety and security vulnerabilities, today's medical devices are totally incapable of insuring a level of quality, reliability, and security needed to guarantee IoMT operation.

Synopsis of Background

In summary, present-day PBT systems comprising a controller unit driving passive LED pads are limited both in their therapeutic and diagnostic capability. Such limitations include an inability to deliver distortion-free waveform synthesis in LED drive, an inability of extracting real time biometric data and images, and lacking the capability for the system or device to communicate over a wired or wireless network with computer servers, data storage devices and clouds, or with doctors and caregivers. As such the architecture of present day PBT systems is completely outmoded, and requires an entirely new system architecture, new control methods, and new communication protocols to facilitate an efficacious, flexible, versatile, and secure solution to providing photobiomodulation therapy. These methods must be HIPAA compliant, able to insure a Class-2 device can deliver efficacious therapy while guaranteeing safety, security, and privacy as a network connected IoMT device.

SUMMARY OF THE INVENTION

In the photobiomodulation therapy (PBT) process of this invention, defined patterns (e.g., sequences of square-wave pulses, sine waves, or combinations thereof) of electromagnetic radiation (EMR) having one or more wavelengths, or spectral bands of wavelengths, are introduced into a living organism (e.g. a human being or animal) using a distributed system comprising two or more distributed components or "nodes" communicating using a bus or transceiver to send instructions or files between or among the constituent components. The radiation is normally within the infrared or visible parts of the EMR spectrum, although ultraviolet light may sometimes be included.

EMR of a single wavelength may be used, or the pattern may include EMR having two, three or more wavelengths. Rather than consisting of radiation of a single wavelength, the EMR may include spectral bands of radiation, often represented as a range of wavelengths centered on a central wavelength, e.g., $\lambda \pm \Delta\lambda$. The pulses or waveforms may be separated by gaps, during which no radiation is generated, the trailing edge of one pulse or waveform may coincide temporally with the leading edge of the following pulse, or the pulses may overlap such that radiation of two or more wavelengths (or spectral bands of wavelengths) may be generated simultaneously.

In one embodiment, the distributed PBT system's components comprise a PBT controller and one or more intelligent LED pads communicating using a unidirectional serial data bus sending data, files, instructions, or executable code from the PBT controller to the intelligent LED pads. In a second embodiment, the distributed PBT system's components comprise a PBT controller and one or more intelligent LED pads communicating using a bidirectional data bus or transceiver whereby the PBT controller is able to send data, files, instructions, or executable code to the intelligent LED pad and conversely the intelligent LED pad is able to return data to the PBT controller involving the pad's operating status or patient condition including LED pad configuration data, program status, fault conditions, skin temperature, biometric data, or other sensor data. Other sensor may include two-dimensional temperature maps, two- or three-dimensional ultrasound images, or may comprise biometric data such as pH, humidity, blood oxygen, blood sugar, or skin impedance etc., which in turn may optionally be used to change the treatment conditions, i.e. operating in a closed biofeedback loop.

In one embodiment, the EMR is generated by light-emitting diodes (LEDs) arranged in serial "strings" connected to a common power supply. Each LED string may comprise LEDs designed to generate radiation of a single wavelength or band of wavelengths in response to a defined constant or time varying current. The LEDs may be embedded in a flexible pad designed to fit snuggly against a skin surface of a human body, allowing the target tissue or organ to be exposed to a uniform pattern of radiation. Power may be delivered to each intelligent pad from a cable connecting the LED pad to the PBT controller or alternatively may be provided to the LED from a separate power source. In an alternative embodiment, semiconductor laser diodes may be used in place of LEDs configured in an array to create a uniform pattern of radiation or alternatively mounted in a large area panel or in a handheld wand to create a spot or small area of concentrated radiation.

In the distributed PBT system disclosed herein, each of the LED strings is controlled by an LED driver, which in turn is controlled by a microcontroller contained within the intelligent LED pad. The LED pad's microcontroller communicates with another microcontroller or computer comprising the PBT controller via a communication bus, which may include wired connectivity such as USB, RS232, HDMI, I²C, SMB, Ethernet, or proprietary formats and communication protocols, or which may alternatively comprise wireless media and protocols including Bluetooth, WiFi, WiMax, cellular radio using 2G, 3G, 4G/LTE, or 5G protocols, or other proprietary communication methods. For interoperability, the distributed PBT system may employ TCP/IP compatible communication compatible with the 7-layer Open Systems Interconnection (OSI) model for packet switched networks. Alternatively other packet switched communication protocols such as the Secure Dynamic Network and Protocol (SDNP) may be used so long that they are compatible with the hardware hosts and follow the OSI model for seven layers of abstraction.

Using a display, keyboard or other input device connected to the PBT controller, a doctor or clinician can select the particular algorithm (process sequence) that is suited to the condition or disease being treated. The instructions are then communicated from the PBT controller over the wired or wireless data bus or network to one or more intelligent LED pads instructing the pad's microcontroller when to commence or suspend a PBT treatment and to specify what treatment is to be performed. Pad status and pad sensor measurements are optionally communicated back to the PBT controller over the same communication network. Additional sensor and biometric data may be sent to the PBT controller via the same communication network or over a different bus. Regardless of the network carrying biometric measurements the biofeedback is collected and stored in a treatment or session history file. In such files, time-based data is synchronized to PBT treatment conditions by employing a common time clock reference, which may comprise network time or employ custom time references. In asynchronous systems having different clock rates, the distributed components may exchange time correction codes to reference a component's local time to the reference time clock. Such corrections are valuable when merging files into a common time base so that measurement and treatment condition files are accurately aligned in depicting contemporaneous events.

To effectuate multi-layer secure communication in the disclosed distributed PBT system, the operating system of the PBT controller (LightOS) and the operating system of the intelligent LED pads (LightPadOS) comprise parallel communication stacks using consistent protocols and shared secrets not discernable to a device operator, hackers, or unauthorized developers. As such the distributed PBT system operates as a protected communication network with the ability to execute security on any number of communication layers including data link Layer-2, network Layer-3, transport Layer-4, session Layer-5, presentation Layer-6, or application Layer-7.

The need for security in inter-component communication of a distributed PBT system is to prevent intentional usurpation of system control (hacking), thwart unauthorized monitoring of data (surveillance), and to reduce the likelihood and severity of accidental system malfunction arising from corrupted command and control packets or ambient EMI. The need for securing databases and executable code is to prevent corporate espionage and to confound knock-off suppliers attempts to clone a system or component. In some cases such as clinical trial studies, secure communications and blockchain applications are needed to chronicle and securely store measurement and treatment data in an incorruptible (indelible) time-stamped database comprising a unitary blockchain, multi-tree directed acyclic graphs (DAG), or across multiple interacting dynamic directed acyclic graphs (DyDAGs).

For example, a numeric code installed and cryptographically hidden in both a PBT controller and an intelligent LED pad, i.e. a shared secret, can be used to confirm the authenticity of a network connected intelligent LED pad without ever divulging the key itself. In one method of LED pad validation executed on data link Layer-2, the PBT controller passes a random number to the intelligent LED pad over the network or communication bus. In response, the microcontroller in the LED pad decrypts its copy of the shared secret (numeric code), merges it with the received random number then performs a cryptographic hash operation on the concatenated number. The intelligent LED pad then openly returns the cryptographic hash value across the same transceiver link.

Concurrently the PBT controller performs an identical operation decrypting its own copy of the shared secret (numeric code), merging it with the generated random number it sent to the LED pad then performing a cryptographic hash operation on the concatenated number. The PBT controller next compares the received and locally generated hash values. If the two numbers match the pad is authentic, i.e. it is 'authorized' to connect to the network. The aforementioned authentication algorithm may be executed on any PHY Layer-1 and/or data-link Layer-2 connection over any data bus or packet switched network including USB, Ethernet, WiFi or cellular radio connections. In the event of a WiFi connection, the data link may also be established using WiFi protected access protocol WPA2.

For 'administrative' purposes and security tracking, the authorization time and date (and as available the GPS location) of the authenticated component is stored in non-volatile memory and optionally uploaded to a server. The benefit of employing secure communication and AAA (authentication, authorization, administration) validation of all connected components in the distributed PBT system is crucial to ensure safety and protection from the intentional connection of uncertified and potentially unsafe imposter devices. In this way, imposter devices cannot be driven by the distributed PBT system. AAA validation also protects against the accidental connection of devices not intended for operation as part of the PBT system such as lithium ion battery packs, unapproved power supplies, speakers, disk drives, motor drivers, high power Class III and Class IV lasers, and other potential hazards unrelated to the PBT system.

The security of a distributed PBT system using a packet switched network (such as Ethernet or WiFi) may also be enhanced using dynamic addressing on network Layer-3 and dynamic port assignment on data transport Layer-4. In operation of a PBT controller not connected to the Internet or any other local area network, the PBT controller generates a dynamic IP address and a dynamic port address, then broadcasts the address to the other network connected devices to which the intelligent LED pads respond with their own dynamic IP addresses and their own dynamic port addresses. In the event that the distributed PBT system is in contact with a router or the Internet, a dynamic host configuration processor (DHCP) is used to assign dynamic IP addresses. Similarly, a remote procedure call (RPC) is used to perform a dynamic port number assignment. Since dynamic IP addresses and dynamic ports change whenever a device is connected to a network, the cyber attack surface is reduced. Additional Layer-4 security can be added using TLS 'transport layer security', IPSec security protocol, or other protocols.

Once the components of a distributed PBT system are established through Layer-2 authentication, and Layer-3 and Layer-4 network and port address assignments, the distributed PBT system is ready to execute treatments. Upon the PBT controller receiving a user 'start' command, PBT treatment commences with an exchange of encryption keys or digital certificates between the PBT controller and the network-connected intelligent LED pads to establish a Layer-5 session. Once the session is opened, the PBT controller and intelligent LED pad maintain their secure link during the exchange of files and commands until the treatment is completed or is terminated. Additional network security can be performed using encryption on presentation Layer-6 or at the application Layer-7. As such, the distributed PBT system functions as a single virtual machine even though is components are spread across a network and not necessarily located in proximity of one another.

In one embodiment serial based communication among intelligent LED pads and a controller occurs across a local area network, i.e. within a subnet, using PHY Layer-1, MAC addressing on Data Link Layer-2, encrypted Presentation Layer-6 datagrams containing Application Layer-7 content including LightOS header data (such as device ID, packet type, file type, sequence number, payload length, checksum, and the LightOS payload itself. By maintaining Application Layer-7 as a cryptographic cipher during transport, surveillance and hacking of system operation is concealed. Within the LightOS header, the device ID fields include source and destination device or IP addresses, VLAN options, and device type information.

LightOS packet types include addresses for a variety of tasks including test mode, requesting a file, sending a file, interrupt related data, common and control packets, setup mode packets, system messages, and backup instructions. These instructions apply to a variety of LightOS filetypes including OS firmware, component configuration data, network connection data, device status info, execution instructions and files, user log files, alert flags, and reset commends. In controlling PBT treatments and sessions, LightOS filetypes include LED streaming files, LED player files, LED playback files and LED primitives files. For sensor data and biofeedback, LightOS filetypes include location data, temperature data, image files, and sensor data file type. In one embodiment the LightOS payload has a variable length specified by a 'payload length" field ranging from 0B to 65,526B, a length consistent with Ethernet packets. The benefit of a variable length LightOS payload length is that communication packets are compact, being no longer than needed to execute a specific command without overhead. Compact files are particularly valuable in real time applications like therapy and biometric monitoring when safety, accuracy, and timeliness are paramount.

Device validation in the disclosed distributed PBT system includes MAC addresses used to confirm an OUI vendor code and a serial number. Absent the proper codes a fraudulent device will be unable to communicate with the local subnet. The method is applicable to USB communication as well as to Ethernet, WiFi, fiber, and cellular hosted packet switched networks.

In one embodiment, the communication network used in device operation is initially employed to set up and program the intelligent LED pad including loading LightPadOS firmware into the LED pad, configuring the LED driver circuitry, and locking out future changes in the pad. Data is stored in encrypted form whenever possible. LightPadOS firmware include part number, manufacture, serial number, manufacturing code, GUDID (i.e. the FDA good ID number), 510-k numbers as applicable—import codes by country, and static security credentials. The LED configuration file describes the number of LEDs, their wavelengths and how they are connected, i.e. the number is series and parallel in each type of LED string. Examples of various wavelength LEDs include near UVA, purple, blue, green, yellow, orange, red, deep red, and at least three different wavelength near infrared (NIR) LEDs. Mid and far infrared LEDs are also possible.

The LED configuration information is important later during PBT treatment because it is used to match the driving waveforms to the LED string. For example a blue LED protocol will not run on an intelligent LED pad that has no blue LEDs in it. In another embodiment a login screen is required to access executive operations of a PBT controller, e.g. in executing the setup and pad programming functions. Subsequent menu based operations facilitate execution of installation operations. Although programming is generally executed at the manufacturing factory, such a feature may be required to deploy a firmware update without the need for a recall, or to potentially repair a malfunctioning LED pad without the need to return the component to the manufacturer. Installation includes a variety of checks to confirm a clean installation.

In operation the distributed PBT system involves validating a pad's connection to the controller or to its network. In the connection process, the pad is first authenticated, then the LED pad info and the LED configuration data is uploaded to the PBT. In the connection process, safety checks and communication data rates are decided before the high voltage LED supply is ever enabled. The validation process can occur at Application Layer-7 or at Layer-5 as desired.

After connection of one to six or more intelligent LED pad to the network, the PBT treatment or PBT session is then selected by the user using the UI/UX on the PBT controller graphical interface. Treatments may be executed using streaming or using file playback.

In data streaming the PBT controller sends a stream of data packets specifying the LED driving waveforms including the timing of when an LED is instructed to conduct current and the magnitude of the current to be conducted. The streaming instructions sent by the controller are selected from a "pattern library" of algorithms each of which defines a particular process sequence of pulses or waveforms of the EMR generated by the LED strings. Upon receiving the data packets over the data bus, the intelligent LED pad stores the instruction in memory, then commences "playback" of the streaming data file, i.e. driving the LEDs in accordance with the instructions received. In some cases the files are encrypted and must be decrypted either in bulk on "on the fly", i.e. packet by packet as they arrive. During streaming playback, bus communication from the PBT controller to the intelligent LED pad may be interrupted to accommodate system safety checks or to allow the intelligent LED pad to report its status or to upload sensor data to the PBT controller.

Unlike prior art PBT systems, in the disclosed distributed PBT system the PBT controller is not constantly sending electrical signals to the intelligent LED pads. During intervals when the PBT controller is silent, either listening to the bus, or receiving data from the intelligent LED pads, each intelligent LED pad must operate autonomously and independently from the PBT controller and the other LED pads connected on the same data bus or communication network. This means the PBT controller must send sufficient data to the intelligent LED pad to be stored in the pad's memory buffer to support uninterrupted LED playback operation until the next data file can be delivered. This means data playback instructions are stored in streaming buffers in sufficient amounts that an interruption in network communication will not interrupt the PBT treatment.

In another embodiment, referred to herein as "file playback" the PBT controller delivers a complete playback file to the intelligent LED pad defining the entire execution sequence of a PBT treatment or session. In this method the file is delivered prior to commencing playback, i.e. before executing treatment. Files are transferred as ciphertext LightOS payloads and may involve multiple levels of security provisions as described previously. As soon as the decrypted file is loaded into the memory of the intelligent LED pad, the in-pad local microcontroller can execute playback made in accordance with the file's instructions. The transferred playback file may comprise either (i) an executable code file including the totality of all LED driving waveform instructions, (ii) a passive playback file defining the treatment durations and settings that is interpreted by executable code comprising a LED player software, or (iii) data files comprising waveform primitives that are subsequently combined in a prescribed manner by the LED pad's microcontroller to control the LED illumination pattern and execute a PBT treatment or session.

In the latter two examples, the executable code needed to interpret the playback file, i.e. the LED player, must be loaded into the intelligent LED prior to commencing playback. This LED player can be loaded into the intelligent LED pad at the time a user instructs the PBT controller to commence therapy, or can be loaded into the intelligent pad at a previous date, e.g. when the LED pad is programmed during manufacturing or at the time the PBT controller is turned on and establishes the intelligent LED pad is connected to the controller's local area network. In such cases where the LED player file is previously loaded into an intelligent LED pad and stored in non-volatile memory for extended durations, the distributed PBT system must include provisions to check if the loaded software is still current or has become obsolete. If the system detects the LED player is up-to-date LED playback can commence immediately. Alternatively if PBT controller detects the LED player is obsolete, expired, or just not up-to-date, the PBT controller can download the new LED player executable code either immediately or by first obtaining user approval. In some instances performing treatments using obsolete LED player executable code may result in improper playback or a system malfunction. In such cases, the intelligent pad's LED player may have its operation mandatorily suspended by the PBT controller until the software download and update is executed.

In the event that a multiple treatment "session" is to be performed, the individual treatments are loaded into the intelligent as subroutines or playback files and the session file instructs the assemblage of the treatments in tandem into a single session protocol.

The ability for an LED pad to function independently and autonomously for a defined duration distinguishes the LED pad as "intelligent" compared to passive LED pads. Passive LED pads in contrast are limited to only responding to real time signals sent from the PBT controller where any interruption in communication will immediately result in disruption in the LED pad's operation, affecting the LED pulse train or waveform. In other words, bus communication between the PBT controller and one or more intelligent LED pads can be considered as a packet-switched local area network (LAN).

Another key feature of the disclosed distributed PBT system is its autonomous safety systems—protection and safety functions operating in each intelligent LED pad independent of the PBT controller. Specifically in network connected professional medical devices, safety systems must continue to operate without fail even when network connectivity is lost. As a key feature of this invention, during operation each intelligent LED pad regularly executes a safety related subroutine to ensure the software is operating normally and that no dangerous conditions exist. These intelligent LED pad embedded protective features include a software related "blink timer" subroutine, a watchdog timer, overvoltage protection, LED current balancing, and over-temperature protection. The autonomous safety functions involve firmware comprising the intelligent LED pad's local operating system (referred to herein as LightPadOS) stored in non-volatile memory and executed by the embedded microcontroller present within each intelligent LED pad. Upon receiving an instruction to commence therapy, a specific pad's LightPadOS starts a software timer and concurrently resets and starts a hardware counter in the microcontroller. The LightPadOS then launches the executable code to perform a PBT treatment executed as a streaming data file or as a LED player (playing a specific playback file) in synchronous with an advancing program counter. The program counter advances at a defined frequency as defined by either a shared system clock or a precision time reference specific to one or several intelligent LED pads. Such time references can be established using a RC relaxation oscillator, a RLC resonant tank oscillator, a crystal oscillator, or a micromechanical machine based oscillator. In this manner pulses with nanosecond precision can be used to synthesize square wave pulses, sine waves, and other waveforms varying in frequency and in duration. The synthesized waveforms are then used to drive strings of varying waveform LEDs in the selected patterns according to defined algorithms.

During program execution, both the software blink timer and the hardware based watchdog timer continue to count in synchronous with the program counter time base. When the blink timer reaches a certain predefined time (referred to herein as the blink interval), e.g. 30 seconds, the software timer generates an interrupt signal sent to the pad's local control LightPadOS which suspends the treatment's program counter and commences an 'interrupt service routine" or ISR. The ISR then performs housekeeping functions, which may include reading the temperature of one or more sensors in the intelligent LED pad, sending the temperature data across the transceiver to the PBT controller, and concurrently comparing the highest measured temperature to a defined range. If the temperature exceeds a warning level a warning flag is also generated and communicated to the PBT controller as a request for the system to take some action, e.g. to reduce the LED duty factor (on time per cycle) to lower the pad's temperature or to suspend treatment.

If however, the highest measured temperature exceeds a predetermined safety threshold, the intelligent LED pad immediately suspends execution of the treatment program and simultaneously sends a message via transceiver to the PBT controller. Unless the PBT restarts the program the overheating intelligent LED pad will remain off indefinitely. In this manner, if an over-temperature condition occurs while the PBT controller is unavailable or malfunctioning, or if the network or communication bus is busy or unavailable, the default condition is to stop the treatment.

During the ISR the intelligent LED pad can perform other safety tests, for example checking for excessive input voltages resulting from a power supply failure, excessive currents resulting from an internal pad short circuit, or detecting excessive moisture resulting from sweat or water contacting the intelligent LED pad, possibly resulting a missing or improperly applied sanitary barrier between the patient and the LED pad. In any case the malfunctioning intelligent LED pad firsts suspends operation then sends a message to the PBT controller informing the distributed system of the fault. In such a case the other LED pads may continue to operate independently (even though one pad has discontinued operation) or alternatively all the intelligent LED pads may be shut down concurrently (either by the PBT controller or via direct pad-to-pad communications). After the ISR is complete, control is returned to the performing the PBT treatment by restarting the program counter, restarting the software blink timer, and restarting the watchdog timer.

In the event that a software execution failure occurs either in the LED playback executable code or in the ISR subroutine, the program counter will not resume operation and the blink timer will not be reset and restarted. If the watchdog timer reaches its full count without being reset (e.g. at 31 seconds) without being reset, it means software execution has failed. A watchdog timer time-out instantly generates an interrupt flag suspending program execution in the offending LED pad and sending a fault message to the PBT controller and optionally to the other LED pads. As such, a software failure always defaults to a non-operational state for the malfunctioning LED pad to ensure patient safety even in the absence of network connectivity.

Aside from autonomous safety features, in another embodiment the disclosed distributed PBT system includes centralized protection of the networked components administered by the PBT controller. Specifically, the PBT operating system operating with the PBT controller, referred to herein as LightOS, includes a number of protective provisions including the ability to detect if a component attached to the network or communication bus is an authorized component or a fraud. If a user attempts to connect a light pad or other component to the PBT controller's network that cannot pass a prescribed authentication process, then the component will be denied access to the network. The PBT controller's LightOS operating system can prohibit unauthorized access in any number of ways including shutting down the entire distributed system until the offending device is removed, not sending any data packets to the fraudulent device's IP address, or encrypting the commands to be unrecognizable by the unauthorized component.

As disclosed, the network-connected distributed PBT system functions as a single unified virtual machine (VM) able to reliably and safely perform photobiomodulation therapy using multiple intelligent LED pads offering No waveform distortion resulting from cable parasitics Bidirectional communication between PBT controller and intelligent LED pad Ability to detect a multi-pad misconnection short Ability to identify approved LED pads or certified manufacturers Ability to identify a connected device as an intelligent LED pad Ability to identify power sources and to control their operating voltage Ability to control and limit driver LED current Ability to detect batteries and prevent their connection to a PBT system's output Ability to detect over-temperature conditions in LED pads Ability to identify the LED configuration within a LED pad Ability to identify the types and configuration of LEDs contained within an intelligent LED pad Ability to independently control multiple outputs Ability to perform distortion free waveform synthesis within an intelligent LED pad Ability to distribute new LED driver algorithms to intelligent LED pads Ability to capture and record real time patient biometric data Ability to gather real time images of treatment area Support the ability for users (doctors) to create new treatment algorithms Ability to support the electronic distribution of documentation Ability to perform treatment tracking Ability to manage the distribution of electronic prescriptions Ability to support a network connected remote control Ability to perform location tracking of PBT systems Ability to perform secure communication among components In another embodiment, the disclosed distributed PBT system comprises three stage waveform generation involving digital waveform synthesis, PWM pulse generation, and a dynamic multiplexed multichannel LED driver able to produce square wave, triangle wave, sawtooth, and sine wave waveforms. Waveforms may comprise a single periodic function or a chord of multiple frequency components. Aside from the analog circuitry performing LED current drive, the PBT player is entirely executed in software.

Playback first requires an updated PBT player is loaded into the intelligent LED pad comprising an LED driver, a PWM player, and a waveform synthesizer. Downloaded LED player file payload data includes player version and the executable code for the synthesizer file, PWM player file, and the LED driver file. The waveform synthesizer generates a high-frequency pulse chain of varying width pulses based on a clock frequency well beyond the highest frequency to be synthesized. Synthesis comprises either a unit function generator or a primitive processor (with a waveform primitives library) controlled by waveform parametrics file specifying component frequencies, durations, etc. In operation, the synthesizer can generate chords based on a prescribed key and frequency scale, e.g. a chord comprising two, three, or four different frequencies including noise filtering. Waveforms can also be produced from audio samples or by combining chords of scalable audio primitive waveforms of varying resolution and frequency. Waveforms may be stored in libraries based on waveform synthesizer parametrics and waveform primitives to generate sine waves and sinusoidal chords including major, minor, diminished, augmented chords, octaves, and inversions. The output of the waveform synthesizer is the input to the PWM player.

In the PWM player stage, digital pulsing is used to generate simple square-wave pulsed PBT or to chop a synthesized waveform including the PWM frequency for controlling tissue specificity and the duty factor to control brightness, treatment temperature, and total dose (fluence). Together the series combination of the waveform synthesizer and the PWM player produce a diverse range of modulation waveforms. In one embodiment the PWM player is set to 100% duty factor (always on) so that the generated waveform is determined by the output of the waveform synthesizer, which may comprise single frequency sine waves, chords of multiple frequency sine waves, triangle waves, sawtooth waves, or digital audio samples. In another embodiment, the waveform synthesizer is set to a digital high state so that the PWM player exclusively determines the generated waveform. In yet another embodiment the PWM player is pulsed whereby when it is on, the output is the output of the waveform synthesizer and when it is off the output is zero. This operation represents 'strobed' analog waveform synthesis. The software-controlled LED driver includes I/O mapping comprising multiplexing via a cross point matrix), dynamic current control for analog waveform modulation using a A/D converter, and various dynamic programmable current references.

System control involves start, pause, and cancel commands and system generated interrupts for blink time timeouts, watchdog timer timeouts, and over temp flags to enable or interrupt a system clock used to control the waveform synthesizer, PWM player, and LED driver modules. A two-tiered temperature sensing circuit includes two thresholds—one to set a warning flag and to warn the PBT controller, and a higher temperature threshold to trigger a shutdown of the overheating pad's operation. In an alternative embodiment the temperature data is measured by a calibrated sensor and converted into a digital representation by an A/D converter. In yet another embodiment sensor data includes both temperature and humidity/moisture detection and fault condition communication to the PBT controller.

In the distributed PBT system, network components may include a PBT controller communicating with one or more intelligent LED pads over Ethernet with optional POE (power over Ethernet) to power the LEDs. The OSI communication protocol may include Transport Layer-4 certificate exchange, Session Layer-5 based authentication, Presentation Layer-6 based encryption, and a Application Layer-7 payload based on a LightOS header data including a LightOS device ID source address, destination address, VLAN code, and device type data separate from the Network Layer-3 IP addresses and routing data. As described the distributed PBT system is compatible with both IPv4 and IPv6 routing on Network Layer-3, supports both TCP and UDP transport and dynamic port assignment on Transport Layer-4.

Using all seven OSI layers, the components comprising the disclosed distributed PBT system do not need to reside in the same subnet, but can communicate across routers, a feature very important to implement the system in a hospital where different wards are likely to use their own dedicated routers and local subnets. Such routers may comprise Ethernet switches and routers or may utilize WiFi communication and routing between the PBT controller and the router and between the router and the intelligent LED pads. Commands from one or several PBT controllers can be sent to multiple intelligent LED pads as broadcasts or as a sequence of separate communiqués carried by a shared router. The same router can route separate messages from the individual pads back to their respective controllers. In another embodiment, a distributed PBT system comprises multiple sets of intelligent LED pads controlled from a centralized multi-channel PBT control station. An optional WiFi PBT remote is included to facilitate local start-start and pause control.

In yet another embodiment, the PBT controller comprises an application running on a mobile device or smartphone controlling intelligent LED pads. The mobile application includes intuitive UI/UX control and biofeedback display. The app may also connect to the Internet or to a PBT server as a therapy database. Server communication may include authentication of the PBT controller with the server including location and account confirmations. Optional administrator may be required including AAA validated file transfers and uplinks.

In another embodiment of this invention, sensors located in an intelligent LED pad or operating separately up load biometric data to the PBT controller and optionally to the server such as blood oxygen, EEG and concussion brain data, ECG and HRV heart data, blood pressure data, blood sugar data, skin hydration and muscle tension EMG, or other reflective or transmission based biosensor data. Sensors may be integrated into PBT pads to provide measurement data or to upload images or movies comprising thermograph, ultrasound, and biosensor data. Sensor arrays may be multiplexed to reduce the number of connections across an intelligent LED pad.

BRIEF DESCRIPTION OF THE DRAWINGS

FIG. 4B illustrates the photochemical stimulation of intracellular organelle mitochondria by blended wavelength light dramatically differs from vision and brain color perception.

FIG. 6 represents a distributed PBT system with an intelligent LED pad.

FIG. 8 is a network description of a PBT system with intelligent LED pads using a 3-layer OSI communication stack.

FIG. 12B illustrates exemplary data packets and corresponding MAC addresses for directing data flow between a PBT controller and two intelligent LED pads.

FIG. 12C illustrates exemplary data packets and corresponding embedded MAC addresses between a PBT controller and an intelligent LED pad over a USB serial connection.

FIG. 15A is a flow chart of LightPadOS pad operating system installation in intelligent LED pad.

FIG. 15B illustrates data packet communication for downloading and confirming LightPadOS firmware transfers into an intelligent LED pad.

FIG. 15C illustrates data packet communication for storing LightPadOS firmware into an intelligent LED pad's NVRAM.

FIG. 19 illustrates data packet communication for locking (disabling) LED pad write access to in-pad NVRAM.

FIG. 21 is a flow chart of an intelligent LED pad authentication sequence.

FIG. 22 illustrates data packet communication for connecting a device to the PBT controller's communication network (without authentication) and subsequently confirming the connection.

FIG. 24 illustrates data packet communication for requesting and receiving an intelligent LED pad manufacturing ID data from a network-connected LED pad.

FIG. 30 is a flow chart of LED pad autonomous pad playback using on-the-fly decryption during playback.

FIG. 34 illustrates data packet communication for downloading and installing a LED player file into a LED pad's volatile memory including executable code for waveform synthesizer, PWM player, and LED driver modules.

FIG. 35B is a flow chart describing the operation of "PWM player" module.

FIG. 36 is a block diagram showing waveform generation using waveform synthesizer, PWM player, and LED driver modules.

FIG. 38 illustrates data packet communication for downloading a LED playback file into a LED pad's volatile memory.

FIG. 39 illustrates data packet communication to a PBT controller for a LED pad missing file request and a responsive download of a missing primitive file

FIG. 42A illustrates data packet communication for commencing, pausing playback of a LED playback file.

FIG. 42B illustrates data packet communication for restarting or cancelling playback of a LED playback file.

FIG. 45B is a flow chart for watchdog timer recovery.

FIG. 53B includes additional Layer-4 descriptions of TCP based Internet protocol datagrams.

FIG. 53D is a Layer-4 description of TCP and UDP port numbers.

FIG. 53E is a Layer-4 description of official registered TCP and UDP port numbers.

FIG. 59B illustrates a Layer-2 data packet for WiFi communication.

FIG. 60B illustrates block diagram of a WiFi radio enabled PBT controller.

FIG. 63 illustrates extraction of LightOS device ID information from LightOS datagram WiFi-based communication between PBT controller and LED pads traversing multiple subnets.

FIG. 65A illustrates an exemplar distributed PBT system performing multi-packet communication downloads from a central PBT controller to multiple LED pads over a WiFi network.

FIG. 65B illustrates an exemplar distributed PBT system performing multi-packet communication uploads from multiple LED pads to a central PBT controller over a WiFi network.

FIG. 65C illustrates a distributed PBT system comprising a performing multi-packet communication among multiple PBT controllers controller over a WiFi network.

FIG. 65E is an exemplar distributed PBT system comprising a multichannel PBT controller comprising multiple microprocessors to independently drive an array of LED pads over a WiFi network.

FIG. 65F is an exemplar distributed PBT system comprising a multichannel PBT controller comprising a single microprocessor to independently drive an array of LED pads over a WiFi network.

FIG. 72 illustrates communication in an autonomous PBT system during authentication.

FIG. 73 illustrates communication in an autonomous PBT system during location reporting.

FIG. 74 illustrates communication comprising autonomous server requests to a PBT controller.

FIG. 75 illustrates communication server rejection of a PBT system request to connect.

FIG. 76B is a flow chart of a PBT system with AAA PBT controller-requested IoT transactions.

FIG. 77B is a flow chart of a PBT system with AAA server-requested IoT transactions.

FIG. 77C illustrates communication in a PBT system during server-requested file transfers.

FIG. 80 illustrates exemplar PHY Layer-1 and Data Link Layer-2 communication frame construction of OFDM 4G telephonic communication used in the PBT app's Internet connection.

FIG. 81B illustrates exemplar mobile phone sub-menus for selecting and running a PBT session.

FIG. 81C illustrates exemplar mobile phone sub-menus for linking mobile PBT app program to LED pads.

FIG. 82A illustrates discrete biosensors.

FIG. 82B illustrates additional discrete biosensors.

FIG. 82C illustrates operation of a discrete optical biosensor.

FIG. 82D illustrates operation of a eye tracking biosensor.

FIG. 83A illustrates intelligent LED pads with integrated sensor arrays.

FIG. 83B illustrates intelligent LED pads with integrated sensor and emitter arrays.

FIG. 83C illustrates types of intelligent LED pad integrated sensor arrays.

FIG. 84A illustrates static images from intelligent LED pad integrated sensor array.

FIG. 84B illustrates thermographic video images from intelligent LED pad integrated sensor array.

FIG. 85 illustrates operation of an intelligent LED pad integrated sensor array.

Figure 86A:
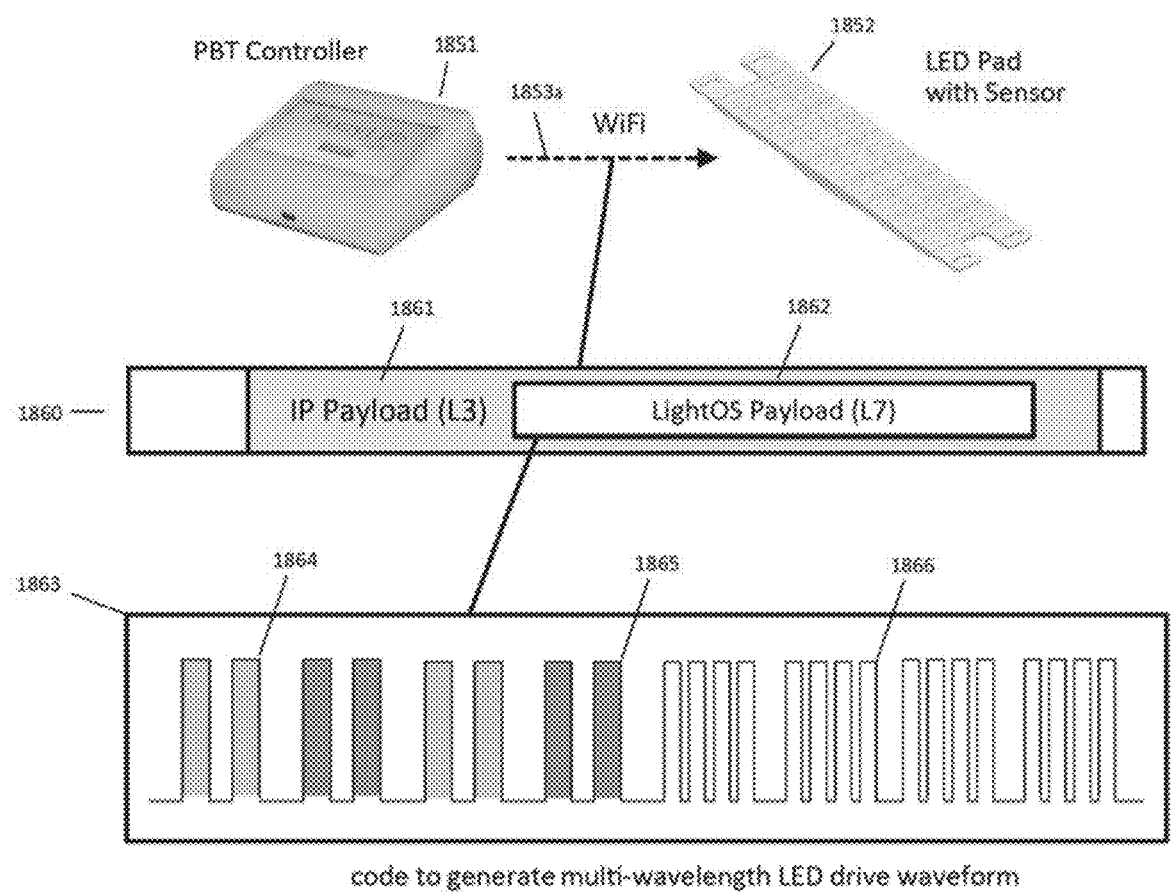
Figure 868:
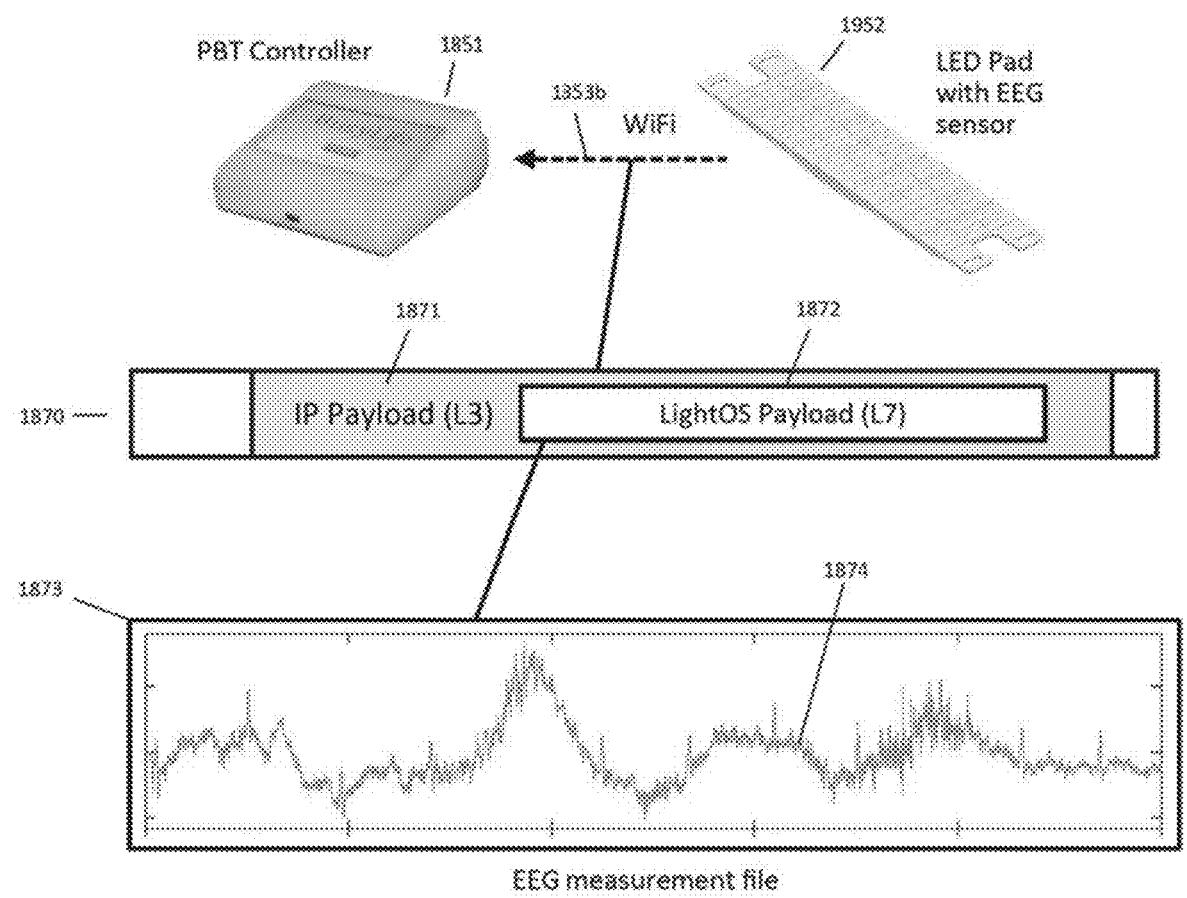

FIG. 86A illustrates PBT controller communication packet containing LED playback data file.

FIG. 86B illustrates an intelligent LED pad communication packet containing pad integrated sensor EEG measurement data.

FIG. 86C illustrates server upload of communication packet with concatenated treatment and measurement file.

FIG. 87 illustrates PBT controller preparation of concatenated treatment and integrated measurement file.

Figure 88A:
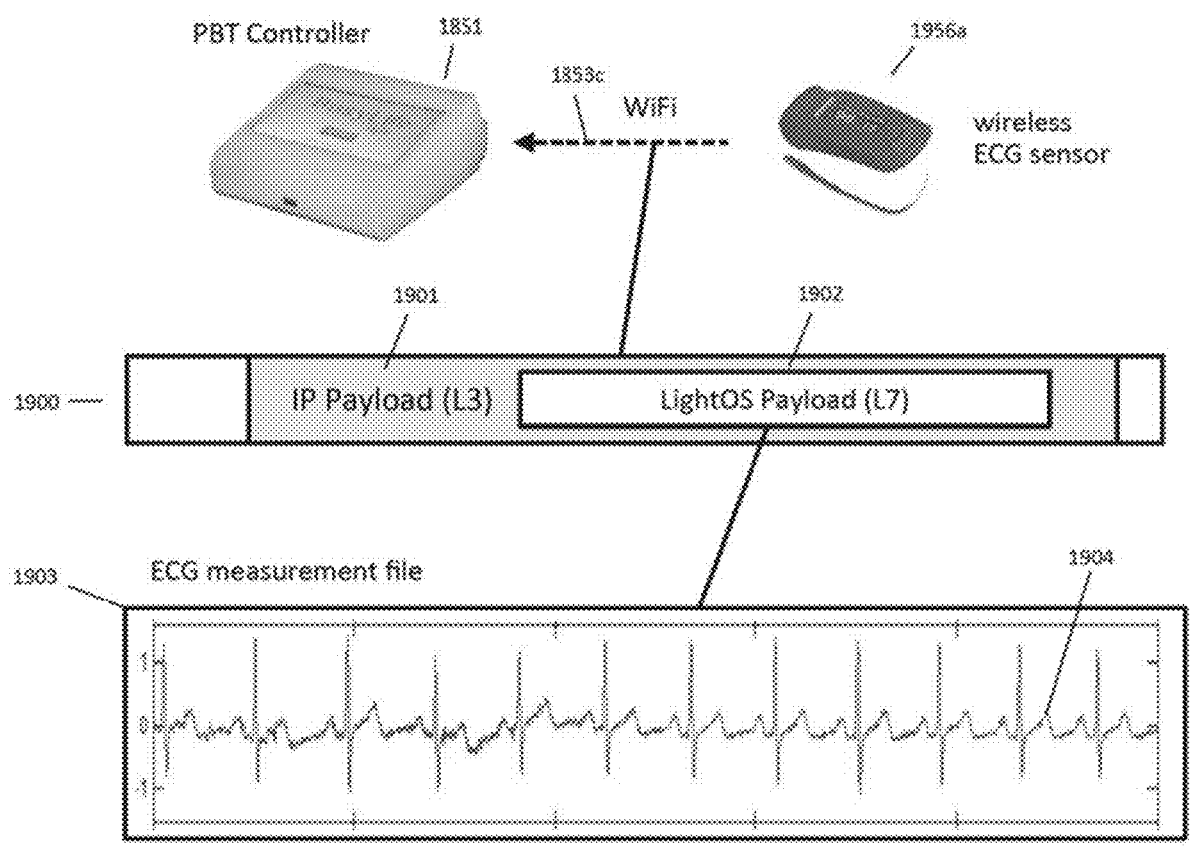
Figure 888:
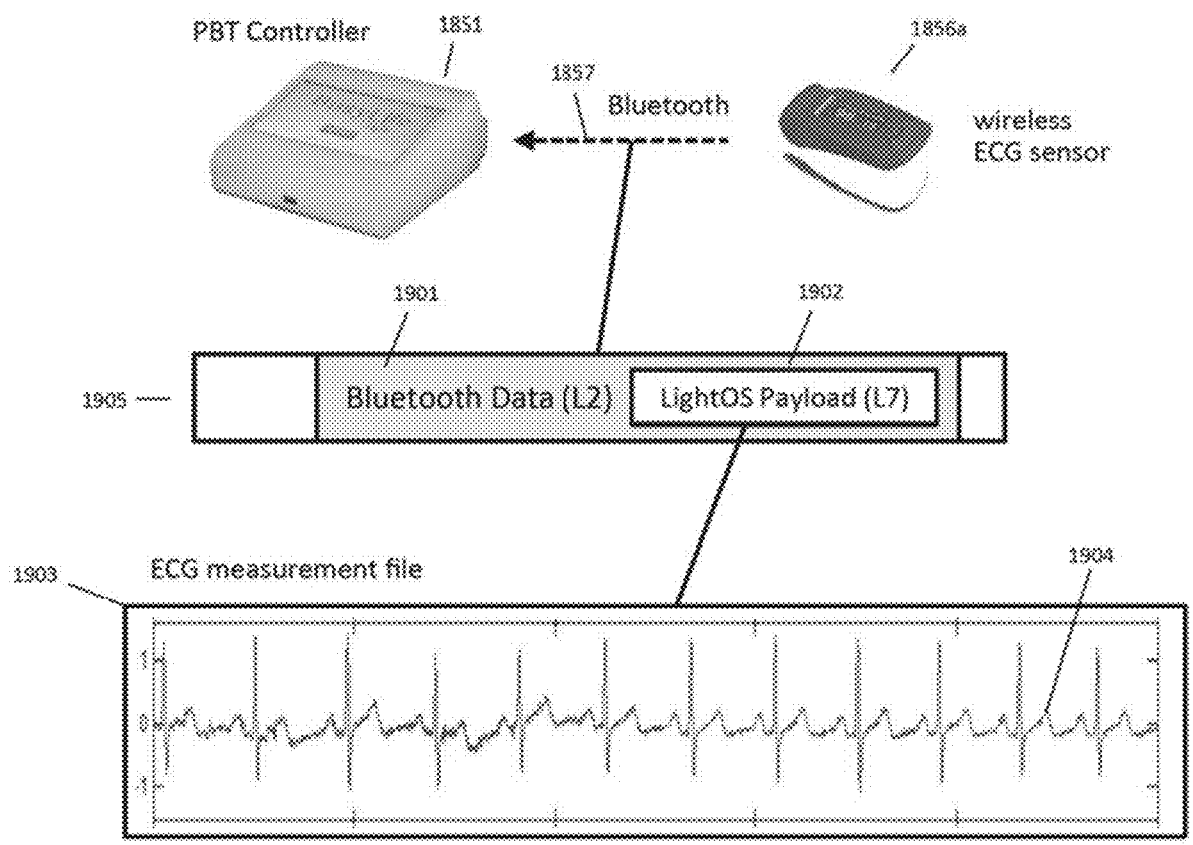

FIG. 88A illustrates PBT controller WiFi upload of communication packet containing discrete sensor measurement data.

FIG. 88B illustrates PBT controller Bluetooth upload of communication packet containing discrete sensor measurement data.

Figure 89:
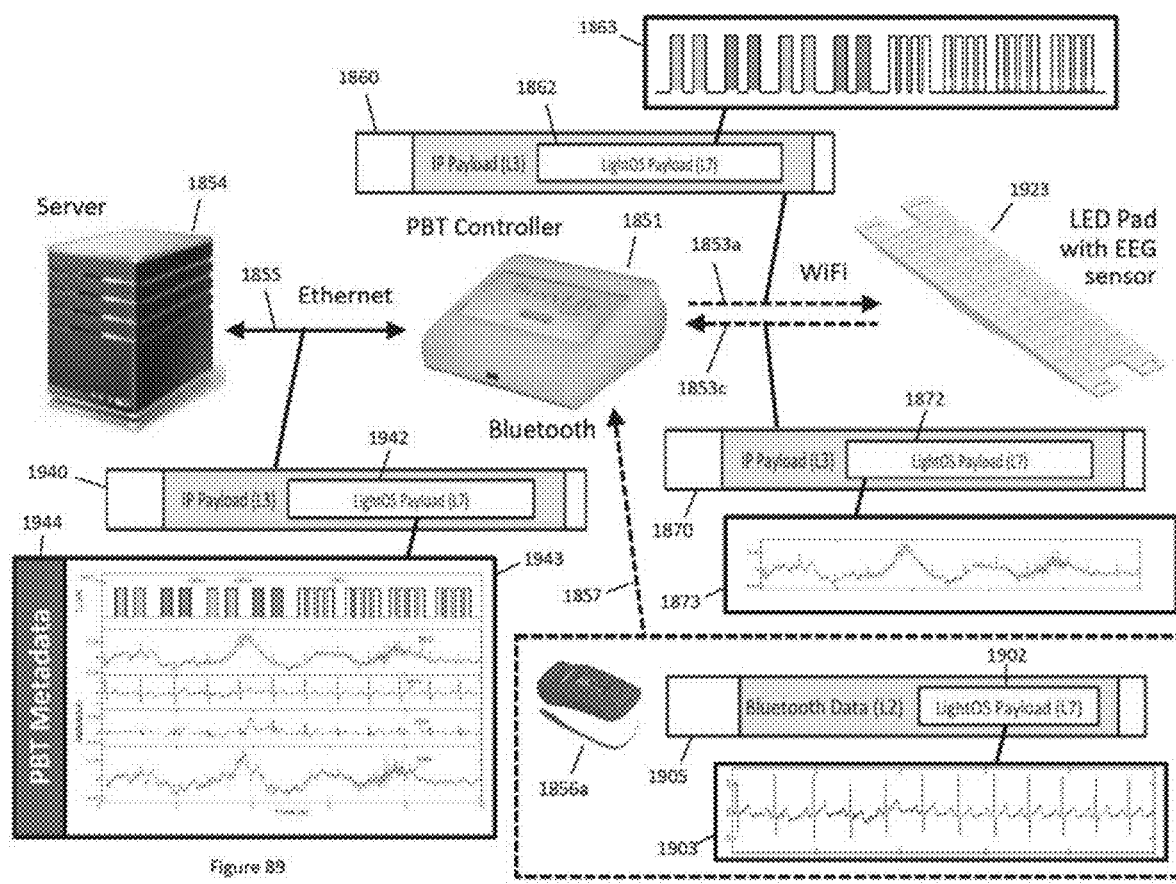

FIG. 89 illustrates PBT controller preparation of concatenated treatment and integrated measurement file.

Figure 90:
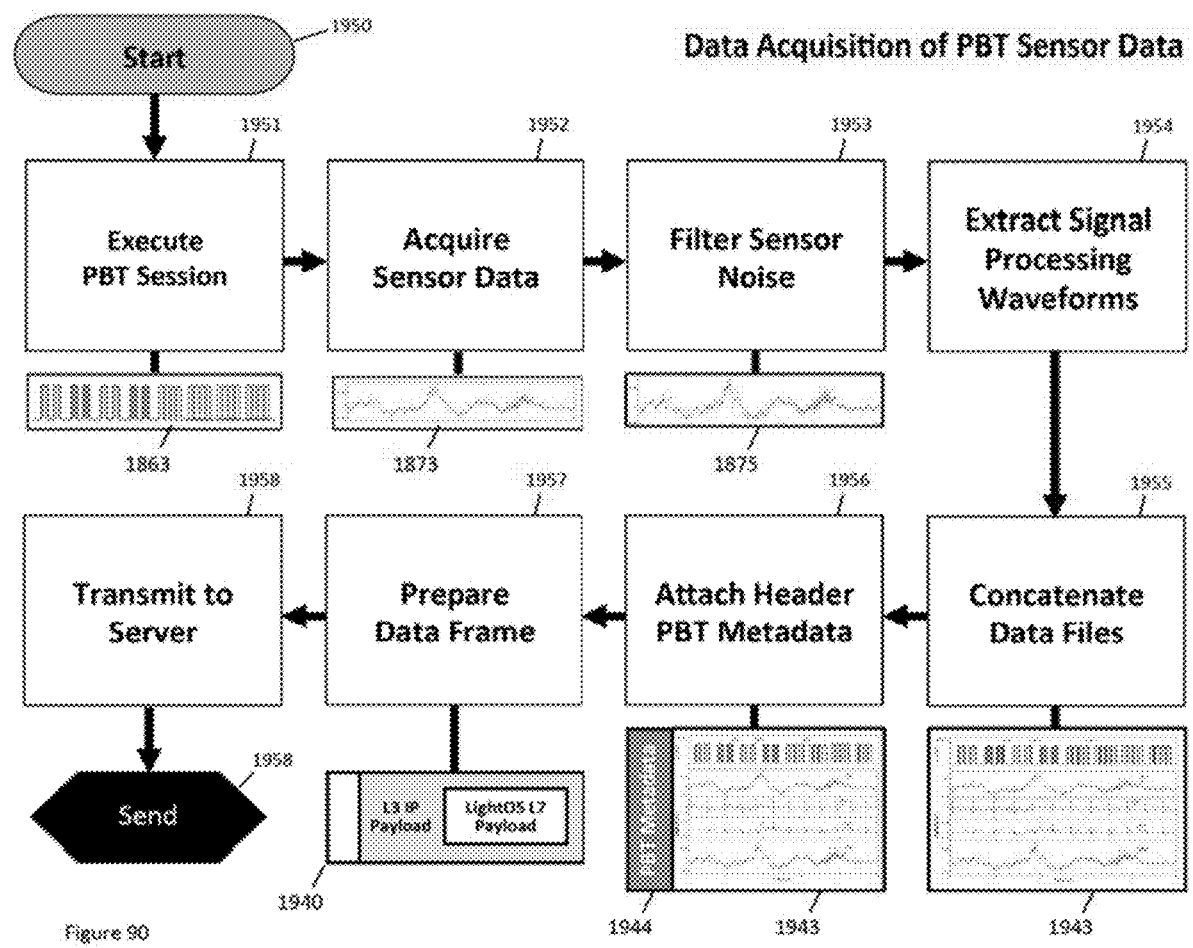

FIG. 90 is a flow chart of PBT sensor data acquisition.

Figure 91:
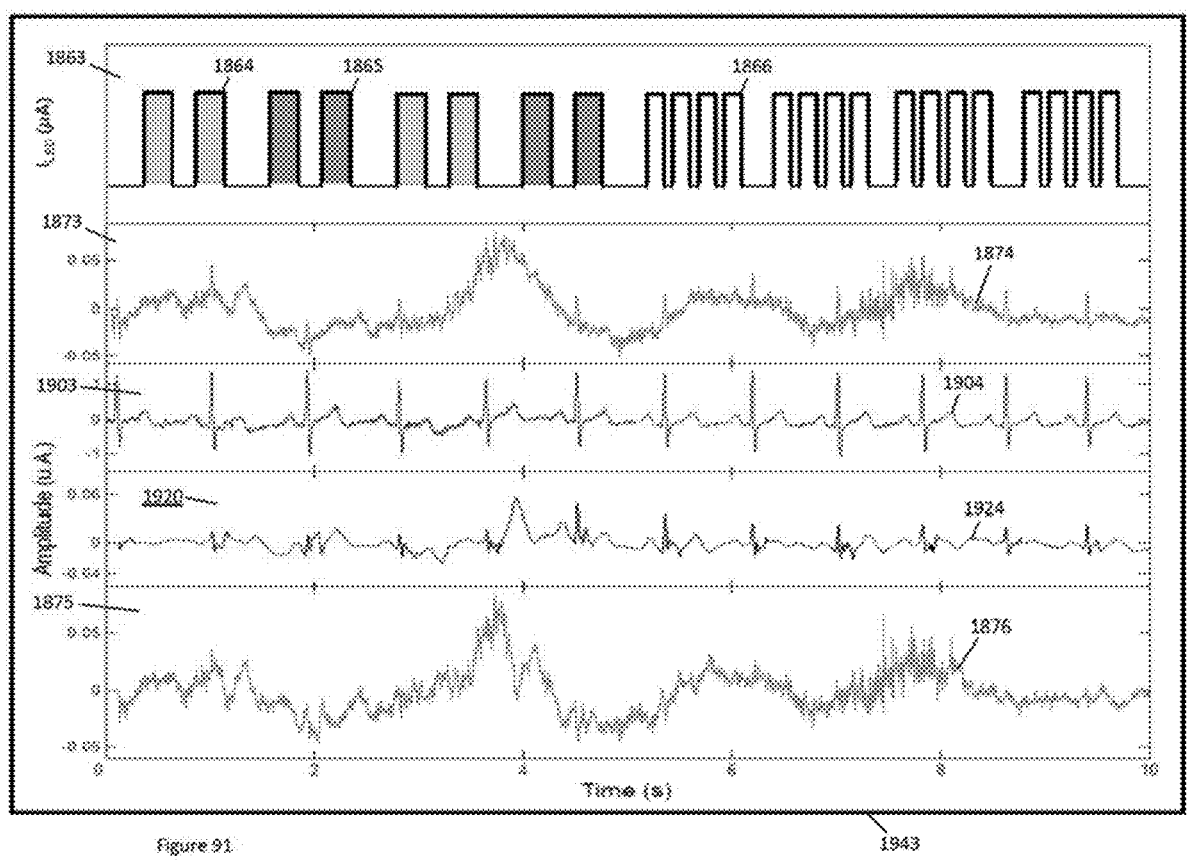

FIG. 91 is an exemplary concatenated treatment and integrated measurement file.

Figure 92:
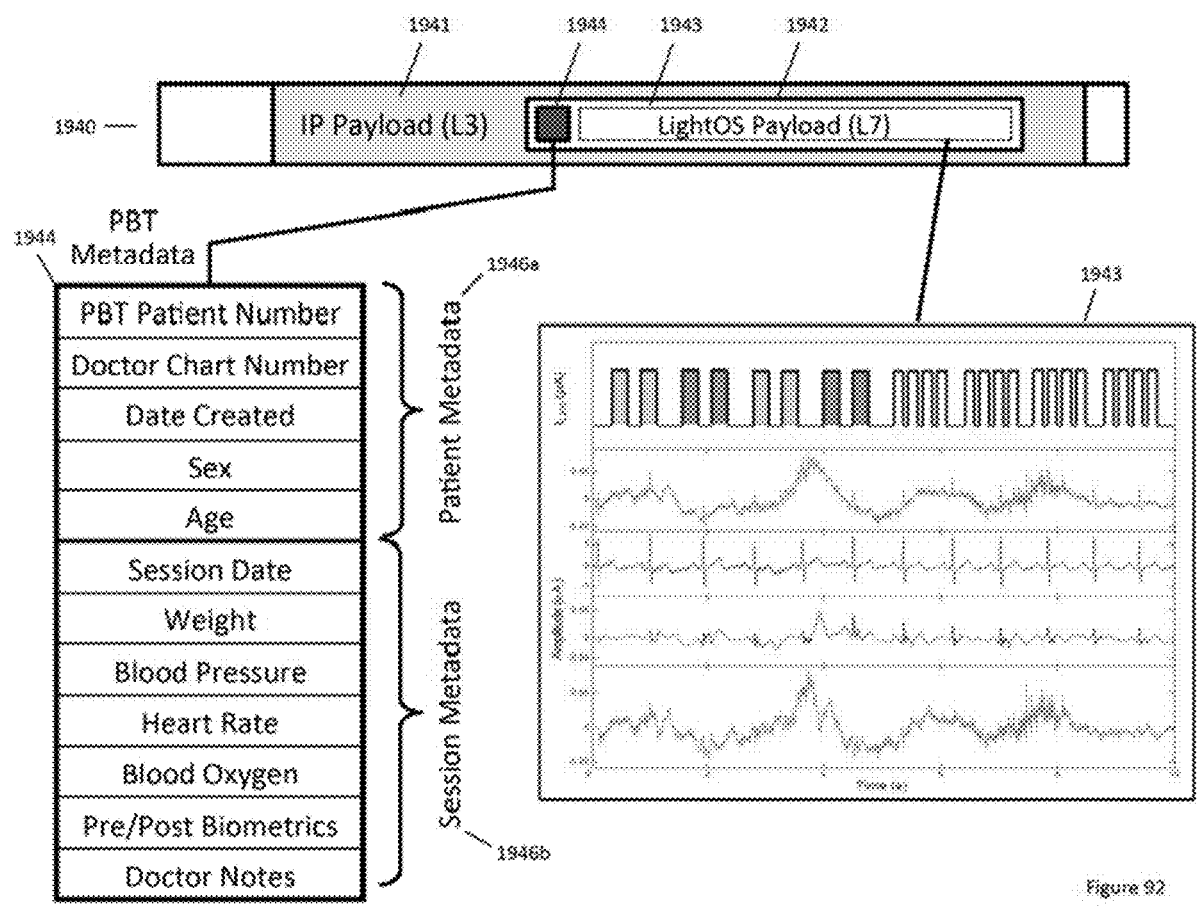

FIG. 92 illustrates server upload of communication packet containing PBT metadata and concatenated treatment and integrated measurement file.

Figure 93:
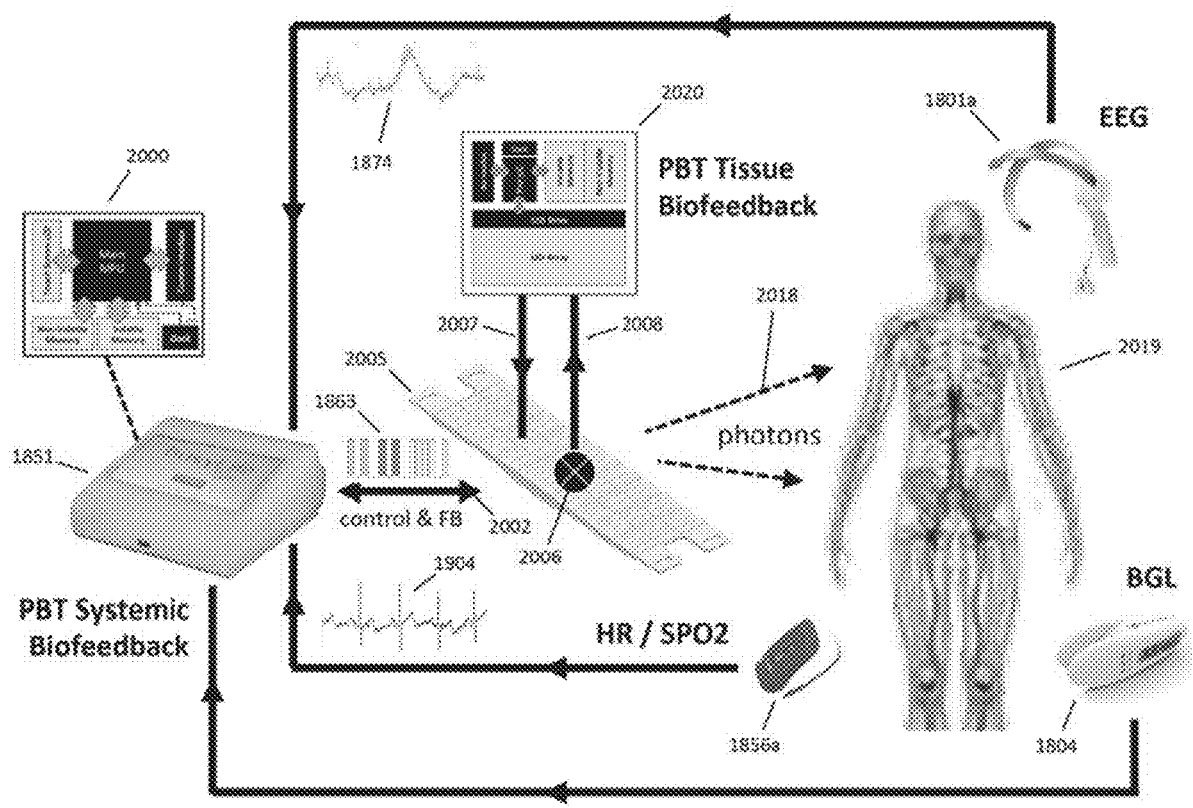

FIG. 93 illustrates tissue and systemic biofeedback to PBT controller.

Figure 94:
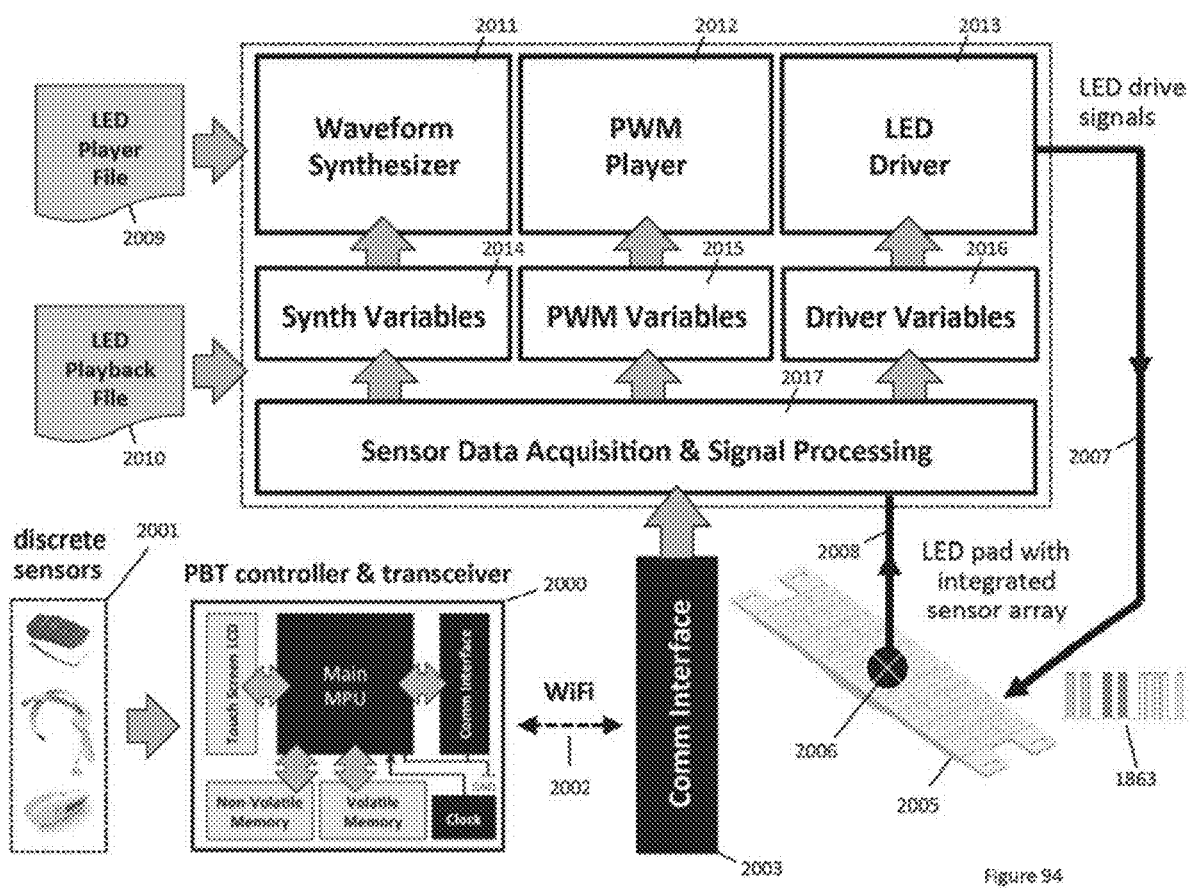

FIG. 94 illustrates biofeedback control of PBT LED player operation.

Figure 95A:
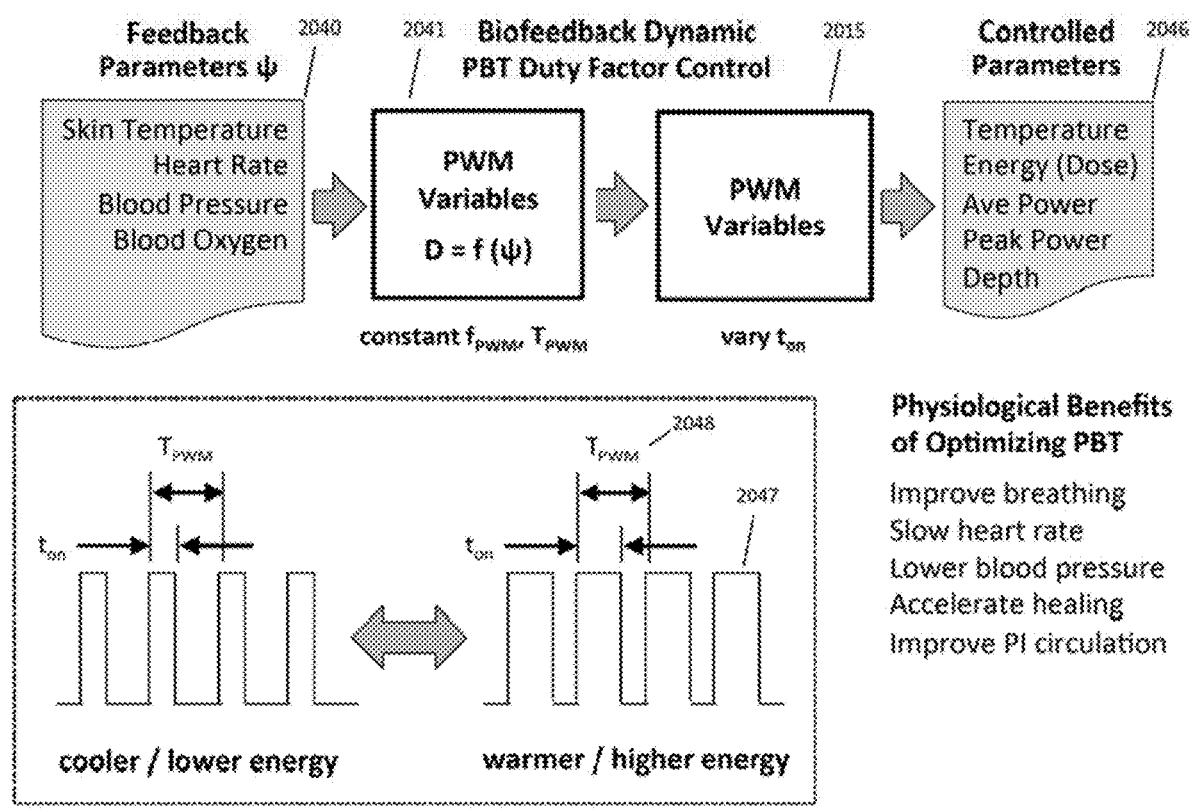
Figure 958:
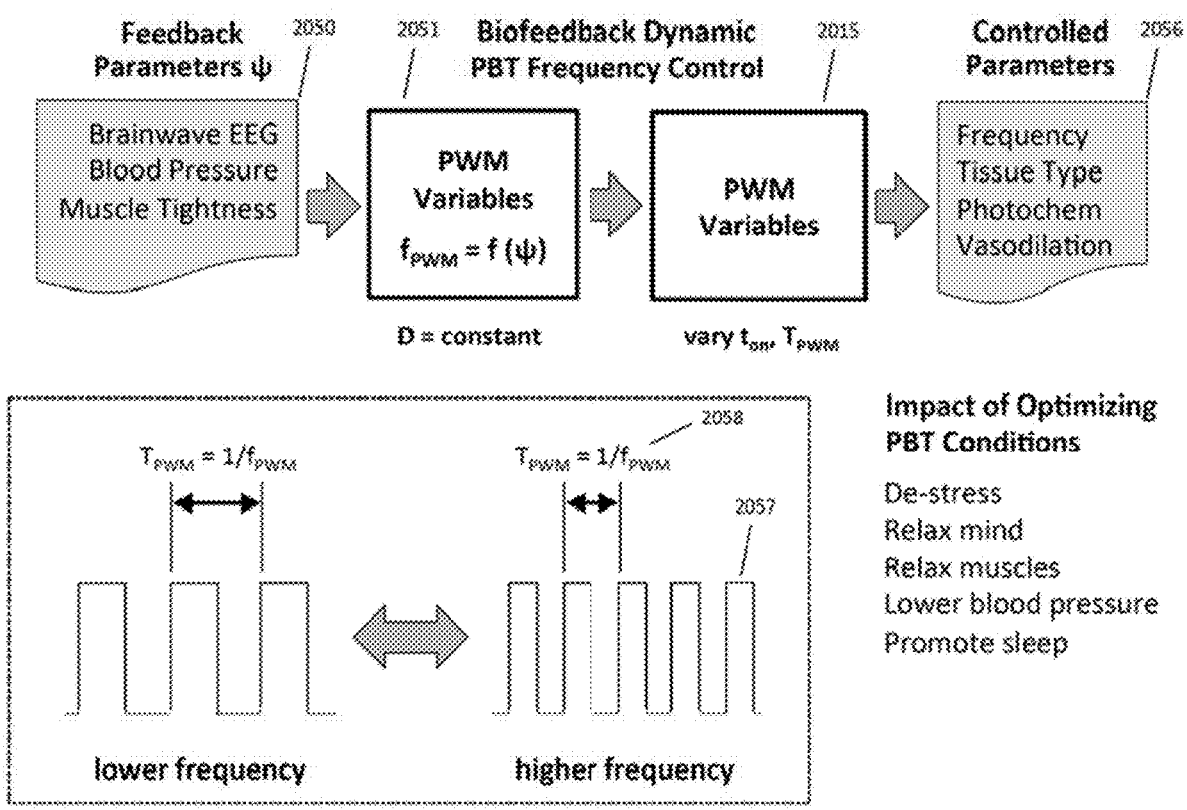

FIG. 95A illustrates exemplary biofeedback dynamic PBT duty factor control.

FIG. 95B illustrates exemplary biofeedback dynamic PBT frequency control.

Figure 96:
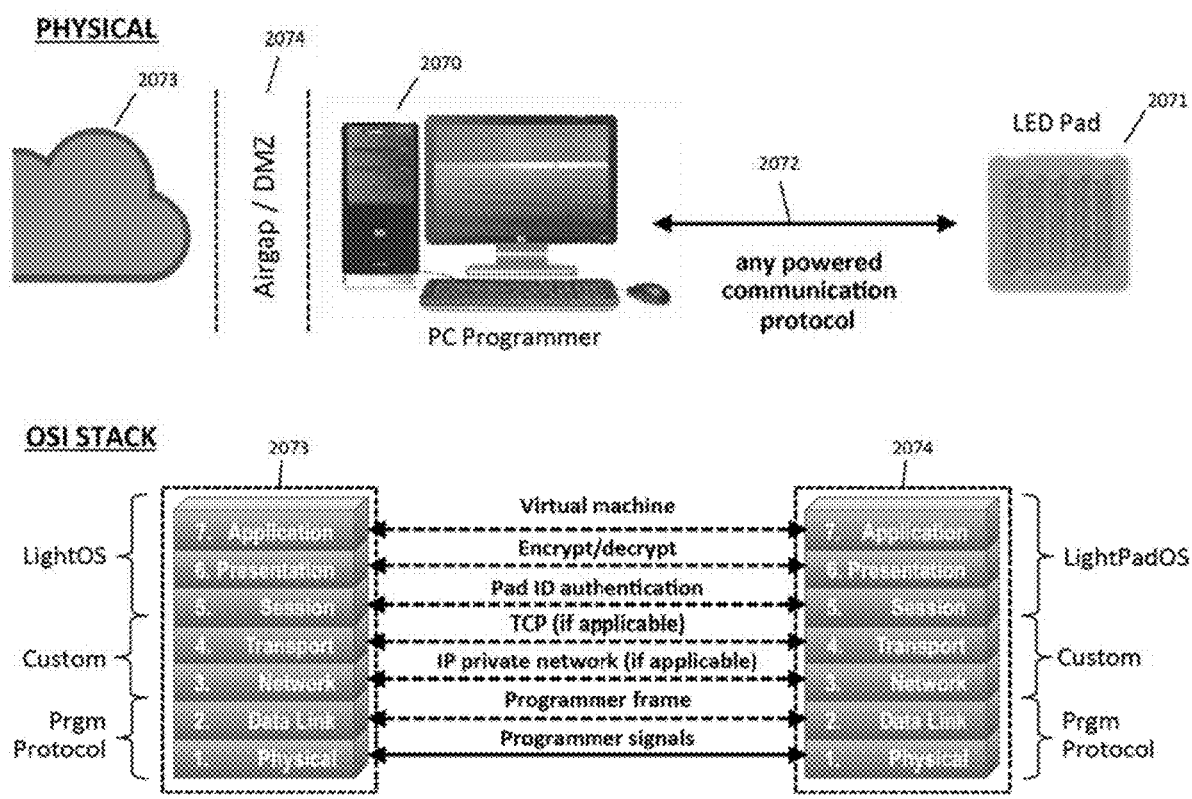

FIG. 96 is a network description of an air-gapped PBT programming system for intelligent LED pads using a 7-layer OSI stack.

FIG. 97 is a table showing examples of various types of data fields in a four-layer LightOS communication packet.

FIG. 98 is a table summarizing the static data contained in a LightOS device ID field.

DESCRIPTION OF THE INVENTION

As previously described photobiomodulation therapy (PBT) or phototherapy, is the controlled application of light photons, typically infrared, visible and ultraviolet light for medically therapeutic purposes including combating injury, disease, pain and immune system distress. As a matter of semantics, use of the term LLLT is discouraged as it ambiguously confers two different meanings, either as "low level laser therapy" also known as "cold laser" technology uniquely defined for the use of laser apparatus, or a "low level light therapy" meaning phototherapeutic treatments performed using any source of light including lamps, lasers or LEDs generally synonymous with the common broadly defined term "phototherapy". For the purpose of this disclosure, the terms for PBT and phototherapy will be used in the broad context even if the example shown is specific to LEDs.

In order to overcome the aforementioned limitations facing existing generation PBT systems, a completely new system architecture in required. Specifically, the generation of sinusoidal waveforms and chords combining sine waves must occur within close proximity of the LEDs being driven to avoid significant waveform distortion from cabling. Such a design criteria mandates relocating waveform synthesis, moving it out of the PBT controller and into the LED pad. To accomplish this seemingly minor re-partitioning of functions is in fact a significant design change, and requires converting the LED pad from a passive component into an active system or "intelligent" LED pad. While a passive LED pad contains only an array of LEDs, current sources, and switches, an intelligent LED pad must integrate a microcontroller, volatile and non-volatile memory, a communication transceiver or bus interface, LED drive electronics, and the LED array. Because of the need for long cabling or wireless operation the time reference for the microcontroller must also be relocated into the LED pad. Essentially each intelligent LED pad becomes a small computer, which once instructed, is able to independently produce LED excitation patterns. Although the terms active LED pad and intelligent LED pad can be used interchangeably, i.e. with the identical denotation, by connotation the term intelligent LED pad implies a LED pad offering greater functionality than active pads. In other words all intelligent pads use active circuitry and a bus or communication interface, but not all active pads can be considered intelligent.

So rather than using a centralized PBT controller producing and distributing electrical signals to passive LED pads, the new architecture is "distributed", comprising a network of autonomously operating electronic components lacking centralized real time control. This distributed PBT system, the first of its kind, requires the invention of intelligent LED pads—a therapeutic light delivery system whereby the LED pads perform all calculations needed to generate dynamic LED excitation patterns and safely execute LED drive accordingly. In distributed PBT operation, the role of the PBT controller is dramatically diminished to that of a UI/UX interface, allowing a user to select therapy treatments or sessions from available protocol libraries, and to start, pause, or terminate treatments. This lack of central hardware control is virtually unheard of in medical devices because ISO13485, IEC, and FDA regulations demand, for reasons of safety, hardware controllability at all times. As such, the implementation of effective safety systems in distributed hardware medical devices requires a new and innovative approach where safety functions must be performed locally and communicated system wide. Such a safety protocol must be specified, designed, verified, validated and documented in accordance with FDA design regulations and international safety standards.

Another implication of a distributed PBT system with intelligent LED pads is the replacement of electrical signal communication with command-based instructions. Such command-based communication involves the design and development of a private communication network among the distributed system's components, adapting digital communication to meet the unique and stringent requirements of medical device control. Packet routing, security, and data payloads must be designed to prevent hacking or system malfunction, and must carry all requisite information to perform all necessary PBT operations.

The inventive matter associated with implementing a distributed PBT system with intelligent LED pads involves two sets of interrelated innovations. In this disclosure, the data communication hierarchical stack and control protocol of a distributed PBT system are disclosed, along with communication security and device authentication, auto-detect functions, biofeedback and sensor arrays, bidirectional data flow, and network interoperability. In the above-referenced application titled "Distributed Photobiomodulation Therapy Devices and Methods," [U.S. patent application Ser. No. 16/377,181] filed concurrently with this application, the intelligent LED pad's operation is disclosed including time based LED excitation patterns delivered by streaming or by file transfer including waveform synthesis, PWM player operation, dynamic LED drive as well as requisite safety functions.

In the distributed PBT systems as disclosed herein, LED playback can be controlled using either a time-based instruction sequence or through command-based waveform generation and synthesis. In either event, data packets carry the LED excitation pattern digitally in their payload. In operation, through a graphical interface a user or therapist selects a PBT treatment or therapy session, and agrees to commence treatment. The command is then packetized, i.e. prepared, formatted, compressed, and stuffed into a communication packet, and delivered over a serial peripheral communication bus, LAN, broadband connection, WiFi fiber or other media to one or more intelligent LED pads. Although the payload data being carried in each data packet is digital comprising bits organized as octets or hexadecimal words, the actual communication medium is analog comprising differential analog signals, radio waves, or modulated light.

In wired communication, the communication bus typically uses electrical signals comprising analog differential waveforms modulated at a specified rate known as the symbol rate or baud rate (https://en.wikipedia.org/wiki/Symbol_rate). Each symbol may comprise a frequency or code for a define duration. The detection of each sequential symbol is immune to distortions caused by reactive parasitics in a cable or by noise sources and therefore overcomes all the issues associated with digital pulse signal transmission in prior art PBT implementations. In WiFi communication, incoming serial data is split and transmitted in small packets across multiple frequency sub-bands, known as OFDM, i.e. orthogonal frequency division multiplexing to achieve a high-symbol rate and low bit-error rate. Similar frequency splitting methods are used in fiber channel and DOCSIS communication to achieve high symbol rates. Since each transmitted symbol is capable of representing multiple digital states, the serial bus bit data rate is therefore higher than the media's symbol rate. The effective bit data rate (https://en.wikipedia.org/wiki/List_of_device_bi-t_rates) of several of the most common serial and wireless communication protocols above 50 MB/s are summarized here below for reference:

| Standard | Year | Media (PHY) | Bit Data Rate |
|---|---|---|---|
| Bluetooth 5.0 personal area network (PAN) | 2016 | Wireless PAN | 50 Mb/s |
| IEEE 802.11a | 1999 | WiFi | 54 Mb/s |
| IEEE 802.11g | 2003 | WiFi | 54 Mb/s |
| Fast Ethernet (100 BASE-X) | 1995 | LAN | 100 Mb/s |
| Firewire 400 (IEEE 1394) | 1995 | Peripheral | 393 Mb/s |
| USB 2.0 | 2000 | Peripheral | 480 Mb/s |
| IEEE 802.11n | 2009 | WiFi | 600 Mb/s |
| Gigabit Ethernet (1000 BASE-X) | 1998 | LAN | 1 Gb/s |
| Firewire 3200 (IEEE 1394b) | 2007 | Peripheral | 3.1457 Gb/s |
| USB 3.0 Superspeed | 2010 | Peripheral | 5 Gb/s |
| IEEE 802.11ac (max theoretical) | 2012 | WiFi | 6.8-6.93 Gb/s |
| IEEE 802.11ad (max theoretical) | 2011 | WiFi | 7.14-7.2 Gb/s |
| 10 Gigabit Ethernet (10 GBASE-X) | 2002-2006 | LAN | 10 Gb/s |
| DOCSIS v3.1 | 2015 | Broadband | 10 Gb/s |
| USB 3.1 Superspeed | 2013 | Peripheral | 10 Gb/s |
| Thunderbolt 2 | 2013 | Peripheral | 20 Gb/s |
| USB 3.2 Superspeed | 2017 | Peripheral | 20 Gb/s |
| Thunderbolt 3 | 2015 | Peripheral | 40 Gb/s |
| 100 Gigabit Ethernet (100 GBASE-X) | 2010-2018 | LAN | 100 Gb/s |

In response to a user's commands, the PBT controller converts instructions into communication data packets, which are subsequently sent to all connected and qualified intelligent LED pads. The intelligent LED pads receive the instructions and respond accordingly commencing a therapy session or performing other tasks. Because of high-bandwidth communication, the PBT system's user experience is that the treatment was instantaneous, i.e. users perceive a real time UI/UX response even though the system's operation was in fact performed as a sequence of inter-device communication and autonomous tasks.

The disclosed distributed PBT system involves multiple interacting components each of which performs a dedicated function or functions within the de-centralized system. The number of unique components integrated into the system affects the system's overall complexity and impacts the sophistication of the communication protocol, i.e. the "language" used in inter-device communication. Various components of the disclosed distributed PBT system may include:

A user interface comprising a central PBT controller or mobile application used for performing UI/UX based commands and dispatching instructions over the communication network.

Intelligent LED pads performing dynamic photobiomodulation therapy treatments with local in-pad excitation pattern generation and waveform synthesis, and optionally with integrated sensors or imaging capability.

Computer servers accessible over the Internet or private communication networks used for retaining and distributing PBT treatments, sessions, and protocols, or for uploading patient response, case study, or clinical trial data and associated files (e.g. Mills, X-rays, blood tests)

Optional therapeutic accessories such as laser wands or ultrasound therapy pads.

Optional biometric sensors (e.g. EEG sensors, ECG monitors, blood oxygen, blood pressure, blood sugar, etc.) used for capturing and uploading patient sample or real-time data Computer peripherals including high-definition displays and touchscreens, keyboards, mice, speakers, headphones, etc.

By combining or excluding various components in the PBT system, a variety of performance and system costs can be tailored for a wide range of users covering hospitals and clinics, and extending to individual users and consumers, spas, estheticians, sports trainers and athletes, as well as professional mobile applications for paramedics, police, or for military field doctors.

LED Control in Distributed PBT Systems

A distributed PBT system made in accordance with this invention shown in FIG. 6 comprises three components—a PBT controller 100, a power supply 101, and a single intelligent LED pad 103 with an intervening USB cable 102. In this implementation, intelligent LED pad 103 is active, i.e. not passive, meaning it generates LED driving waveforms locally within each intelligent LED pad rather than responding to real-time electrical signals continuously sent over USB cable 102. True to its namesake, another inventive feature of intelligent LED pad 103 is that the pad is intelligent, meaning each intelligent LED pad receives its instructions using a communication language, not simply real time electrical signals. The pad in turn must interpret what the instructions mean and how to execute them.

Figure 1:
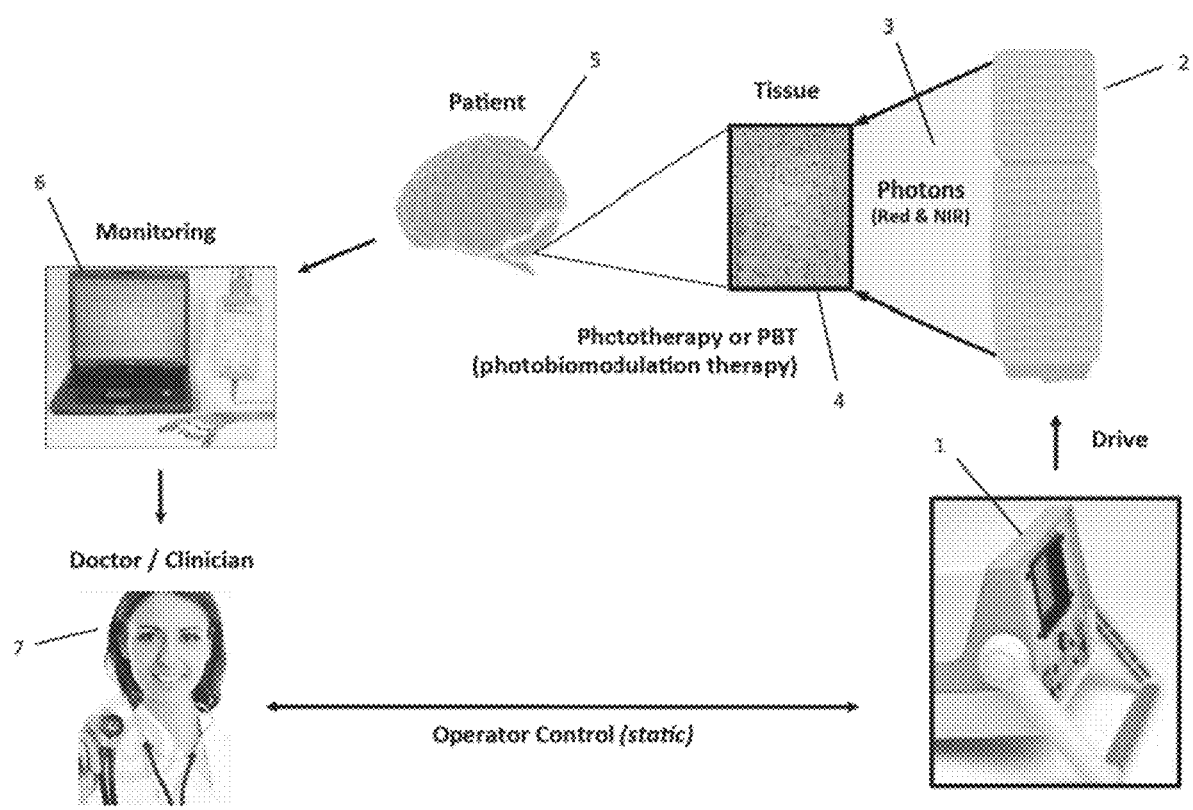
FIG. 1 illustrates a photobiomodulation system operating under therapist control.
Figure 2:
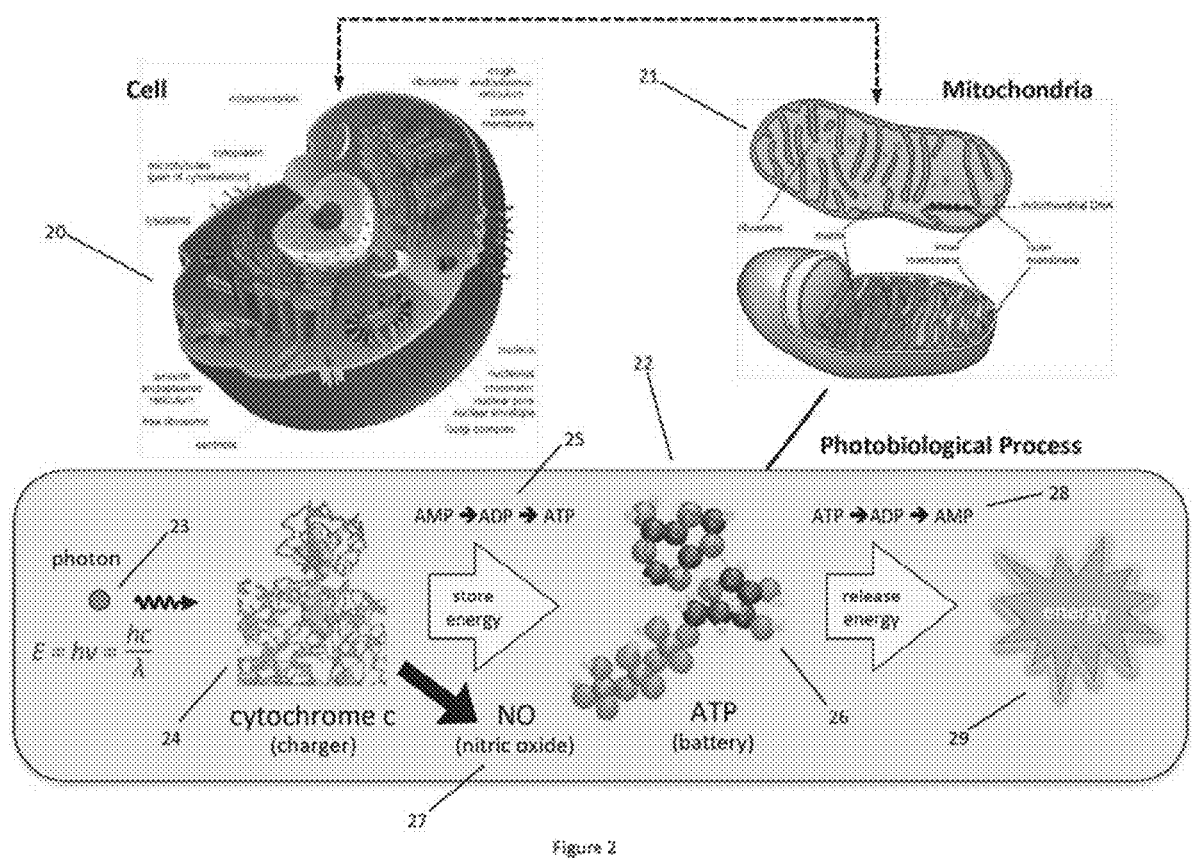
FIG. 2 illustrates photobiomodulation of mitochondria.
Figure 3:
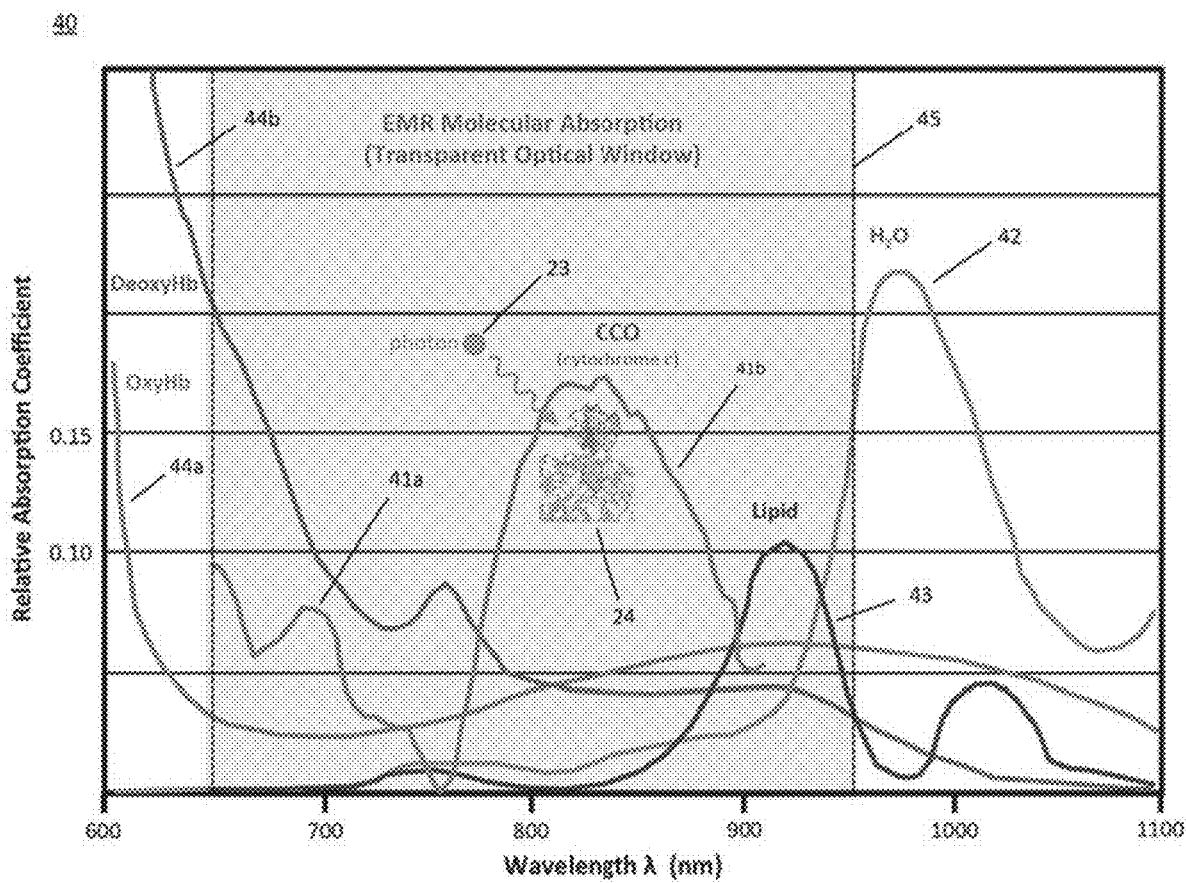
FIG. 3 illustrates the optical absorption spectra of various biomaterials.
Figure 4A:
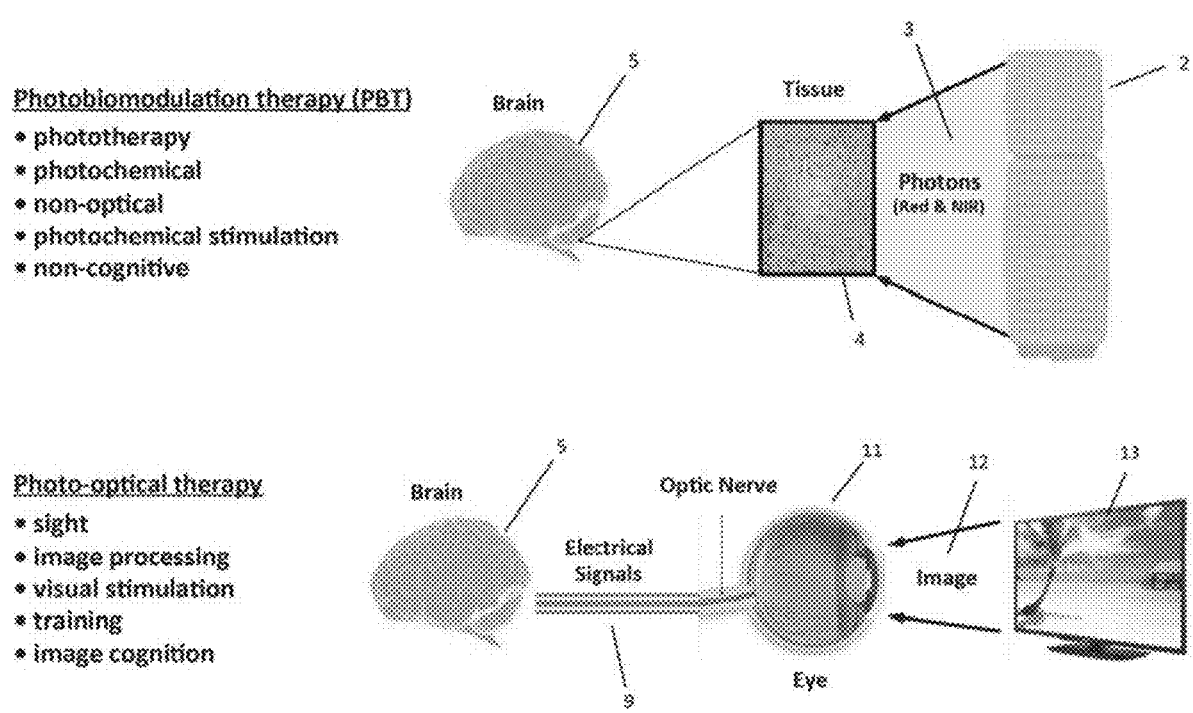
FIG. 4A contrasts differences between photo-optical therapy and photobiomodulation therapy.
Figure 5A:
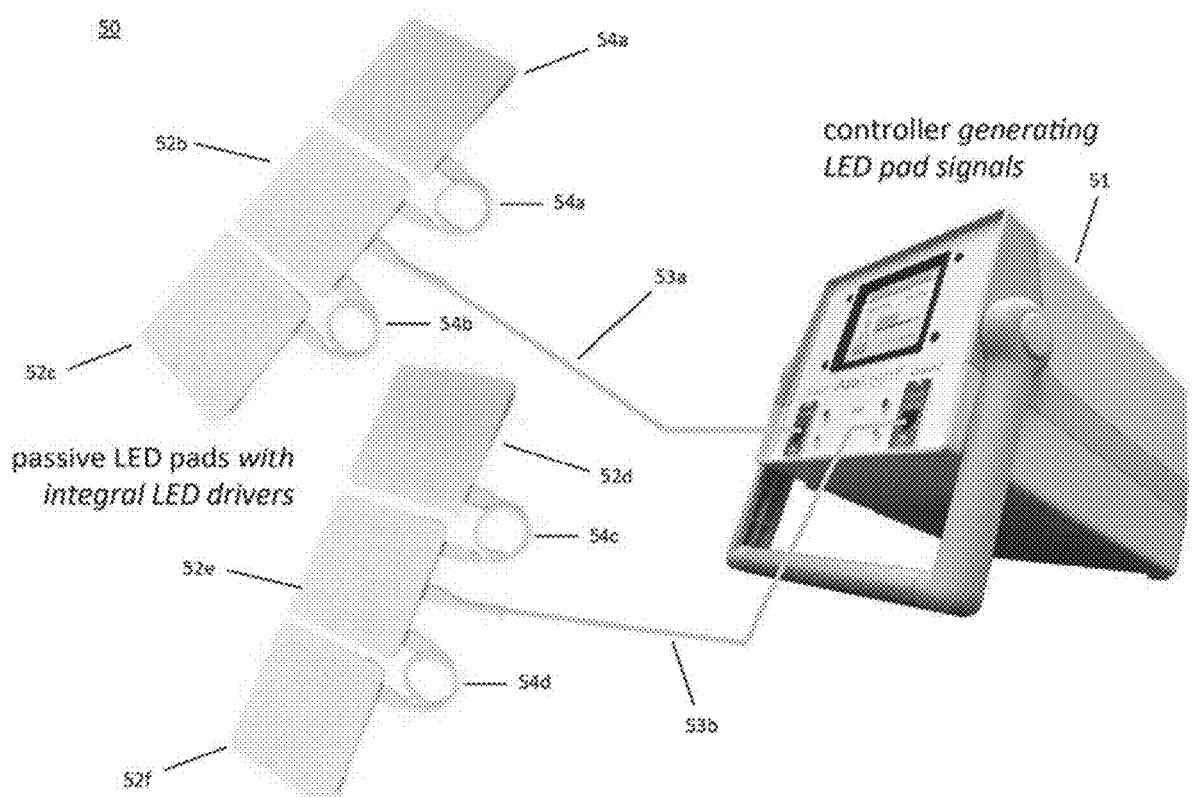
FIG. 5A depicts a 2-channel PBT system with passive LED pads.
Figure 5B:
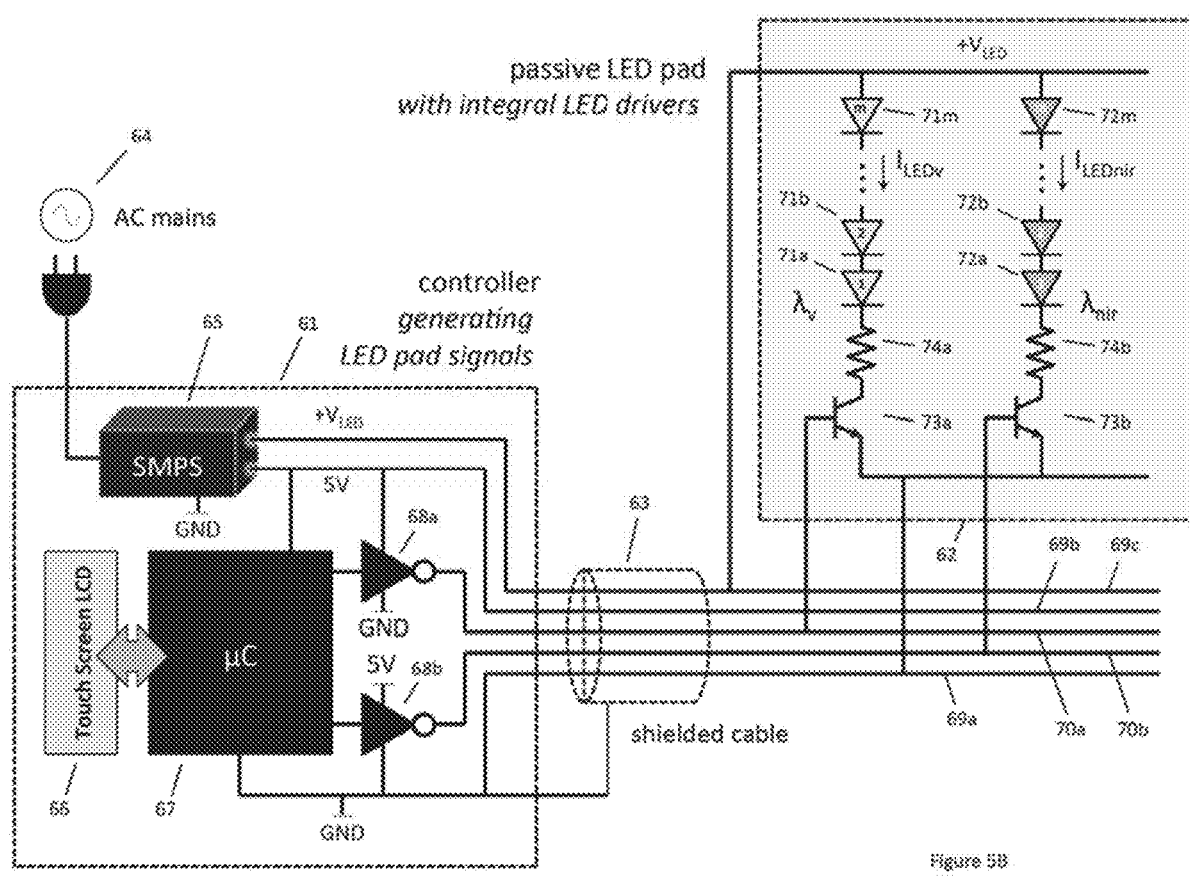
FIG. 5B is a schematic representation of a present day PBT system with passive LED pads using current limiting resistors.

In prior-art passive LED pad based PBT systems, communication occurs electrically over a sustained electrical connection or "circuit" during the entire duration of treatment, in a manner analogous to circuit switched telephony such as the plain old telephone system (POTS) and public branch exchanges (PBX). For example in the prior art PBT system of FIG. 5A, once a circuit connection is "made," between controller 51 and passive LED pads 52d, 52e, and 52f, the connected devices lock the communication circuit for their dedicated use during the entire duration of a treatment protocol. Any interruption or alternation of this circuit will halt the LED drive operation, meaning the pads will no longer illuminate or pulse even though PBT controller 51 is still generating the driving waveforms. Because each circuit is dedicated, in circuit switched networks multiple pad sets cannot be simultaneously driven from a single output or communication channel. For example, LED pads 52a, 52b, and 52c must be connected to a different channel than LED pads 52d, 52e, and 52f, i.e. each pad set must exclusively connect to their own respective wired dedicated network.

In the distributed PBT system of FIG. 6, instructions are supplied to intelligent LED pad 103 as a group of data packets sent in bursts across USB cable 102. The duration required for communication is a small fraction of the treatment time, which means that one communication bus can control multiple LED pads independently without bus contention issues interfering with their concurrent, i.e. parallel, function and program execution. In operation of the disclosed PBT system, files are delivered rapidly across the network followed by extended durations of inactivity where no data is transferred. In this regard, communication among the distributed components is digital comprising data "packets" carried over a digital serial bus or over a "packet switched" network. Once the file is delivered to the pad and a "start treatment" instruction is received, the intelligent LED pad executes the instruction autonomously, employing its own intelligence to interpret the instructions and its own clock to calculate pulse durations and to advance the program execution counter.

Since serial bus and packet-switched networks do not require a continuous connection, the disclosed distributed PBT system necessarily operate asynchronously where PBT controller 100, intelligent LED pad 103, and USB communication 102 all occur using their own clock. Essentially data packet communication is prepared using a system, i.e. PBT controller 100 synchronized to one clock, sent across the digital bus 102 or network at a different data rate, and executed with each intelligent LED pad 102 using a different clock, one local to each individual LED pad. Theoretically the PBT system could "synchronize" each of these functions to a common master clock using master-slave architecture, but many problems arise in maintaining clock integrity and signal reconstruction over long wires and variable distances. The likelihood of momentary desynchronization is great if not inevitable potentially halting a treatment while the system attempts to reacquire clock synchronization. Unreliable and jittery LED pad operation will result in inconsistent treatment waveforms.

And since each pad and the controller operate autonomously, there is no real benefit or need to maintain a common clock or phase-lock among the various components. In fact, while the LED pulse width (on-time) and pulse frequency of a PBT treatment has been demonstrated to be an important control parameter affecting treatment efficacy, no evidence whatsoever suggests maintaining precise synchronization among intelligent LED pads or to the PBT controller has any effect on treatment efficacy whatsoever. In essence, pulse frequency determines tissue specificity in photobiomodulation but the phase delay between a PBT treatment performed on one body part and another has no meaning. For example, if the same light pulse pattern commences on the liver 5-µs after the same treatment has begun on the hypothalamus, the body's physiology doesn't care. In fact electronic delays in the microsecond range are undetectable by the human body, where nerve transduction (the fastest signals in the body) operates only in kilohertz range, three to six orders of magnitude slower than electronic digital clocks. In summary, asynchronous communication in a multi-clock implementation is a key feature of a reliable distributed PBT system.

Figure 7A:
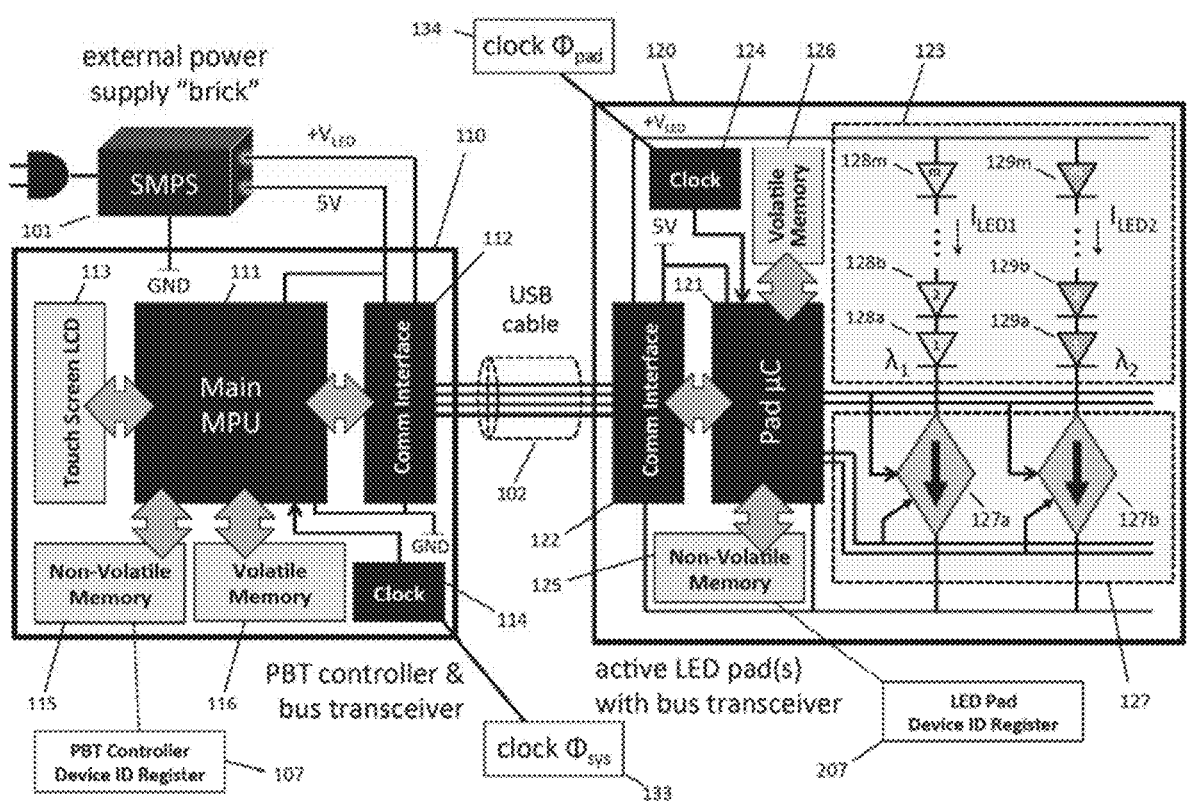
FIG. 7A is a schematic description of a distributed PBT system with an intelligent LED pad.

FIG. 7A is a block diagram representation of an exemplar distributed PBT system's implementation illustrating a PBT controller 110, one or more intelligent LED pads 120, USB cable 102, and external power supply "brick" 101. As shown, PBT controller 110 with bus transceiver includes a main MPU 111, touchscreen LCD 113, non-volatile memory 115, volatile memory 116, and bus interface 112. Construction of main MPU 111 may comprise a fully integrated single-chip microcontroller or a microprocessor based module, optionally containing main system clock 114, bus interface 112, and portions of non-volatile memory 115 and volatile memory 116.

The clock and memory elements are shown separately from main MPU 111, to represent their function and are not intended to describe a specific realization or component partitioning. Any number of partitions is possible including using multiple silicon integrated circuits, system on chip (SOC) integration, system in package (SIP), or as modules. For example, non-volatile memory 115 may comprise electrically erasable programmable random access memory (EPROM) or "flash" memory, which may be integrated all, or in part, within MPU 111. Similarly, volatile memory 116 may comprise dynamic random access memory (DRAM), or static random access memory (SRAM). This memory may be integrated all, or in part, within main MPU 111 or may be realized by separate integrated circuits. Within PBT controller 110, high capacity non-volatile data storage may also be realized using moving media storage such as optical disks (CDs/DVDs), by magnetic hard disk drives (HDDs), and even through network connections to cloud storage.

Figure 7B:
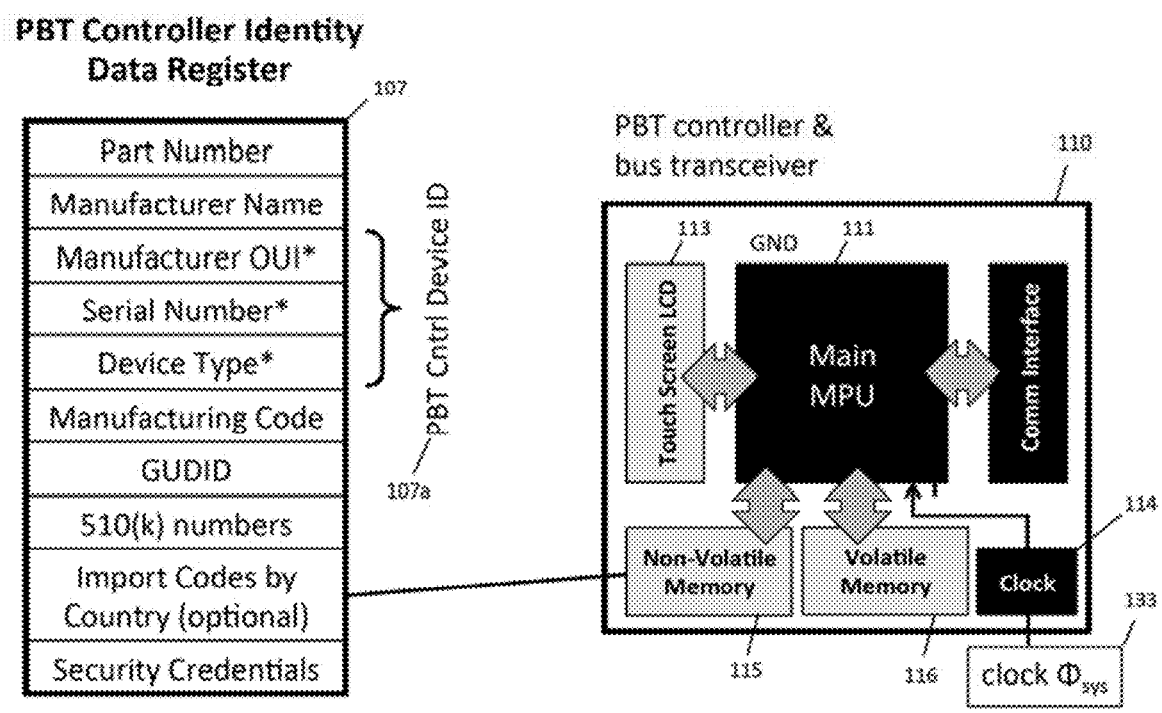
FIG. 7B is the PBT controller identity data register stored in the NVRAM of PBT controller.

The role of non-volatile data storage 115 within PBT controller 110 is multipurpose, including storage of the main operating system, referred to here as LightOS, as well as to retain program libraries of PBT treatments and sessions, generally stored in encrypted form for security reasons. Non-volatile memory 115 may also be used capture treatment logs, upload sensor data, and possibly retain patient data. It may also be used for the PBT controller device ID register 107 as depicted in FIG. 7B. The role of volatile memory 116 in PBT controller 110 is primarily that of scratchpad memory, holding data temporarily while calculations are performed. For example, in preparing a PBT session comprising a sequence of separate PBT treatments, the encrypted treatment algorithms must first be decrypted, assembled into a PBT session, re-encrypted, then assembled into a communication packet ready for network transport. Volatile memory holds the data content during the process of preparing communication packets.

Another consideration in a distributed PBT system is power distribution needed to power the PBT controller and the intelligent LED pads. Options include the following:

Power the PBT controller using an internal power supply, then deliver power to the intelligent LED pads over the communication bus, Power the PBT controller using an external power supply (brick), then deliver power to the intelligent LED pads over the communication bus, Power the PBT controller using either an internal power supply, and powering the intelligent LED pads using their own dedicated external power supply or supplies (bricks), and Power the PBT controller using either an external power supply (brick), and powering the intelligent LED pads using their own dedicated external power supply or supplies (bricks).

External power-supply brick 101 powers the entire PBT system providing 5 V to integrated circuits and $+V_{LED}$ to the strings of LEDs. USB cable 102 carries transceiver symbol data from PBT controller's bus interface 112 to intelligent LED pad's bus interface 122. USB cable 102 also supplies power; specifically ground (GND), 5V, and $+V_{LED}$ to intelligent LED pad 120, generally carried on thicker lower-resistance copper conductors than the cable's signal lines. Once delivered to the intelligent LED pad, the 5V supply be further reduced using a linear voltage regulator or a switching voltage regulator such as a Buck converter (not shown). Aside from bus interface 122, each intelligent LED pad comprises pad µC 121, volatile memory 126, non-volatile memory 126, time reference clock 124, LED driver 127, and LED array 123. LED drivers 127 include switched current sinks 127a, 127b, and others (not shown), one current sink for each string of LEDs. LED array 123 includes a string of series connected LEDs of wavelength $\lambda_1$ comprising LEDs 128a through 128m, a string of series connected LEDs of wavelength $\lambda_2$ comprising LEDs 129a through 129m, and other strings of LEDs (not shown).

Memory within intelligent LED pad 120 including both volatile memory 126 and non-volatile memory 125 is similar to that of the semiconductor memory employed in PBT controller 110 except that the total capacity can be smaller, and preferably consumes lower power. Memory in intelligent LED pad 120 must comprise semiconductor solutions because the risk of mechanical shock and breakage of moving media storage to integrate fragile data storage into LED pad 120. Specifically, volatile memory 126 (labeled RAM) in intelligent LED pad 120 may comprise dynamic random access memory (DRAM), or static random access memory (SRAM) that may be integrated all, or in part, within pad µC 121. In the intelligent LED pad, volatile memory is useful to hold data that need not be retained except during use such as LED streaming files, LED player files and LED playback files. The advantage of only temporarily retaining executable code needed to perform the current PBT treatment (and not the entire library of treatments), is that the capacity and cost of memory within intelligent LED pad 120 can be greatly reduced compared to that of the PBT controller 110. It also has the advantage that it renders reverse engineering and copying of the treatment programs more difficult because anytime power is removed from intelligent LED pad 120, all the data is lost.

Non-volatile memory 125 may comprise electrically erasable programmable random access memory (EPROM) or "flash" memory, which may be integrated all, or in part, within pad µC 121. Non-volatile memory 125 (labeled NV-RAM) is preferably employed to hold firmware that doesn't change often, such as the operating system for the intelligent LED pad, herein referred to as LightPadOS, along with manufacturing data including pad identification data, i.e. the LED pad device ID register 207, and manufacturing related LED configuration data. Non-volatile memory 125 may also be used to retain user logs of what treatments have been performed. Low-cost design for intelligent LED pads is another important economic consideration because one PBT controller is often sold with multiple intelligent LED pads, up to 6 or 8 per system. To lower the overall memory cost it is beneficial to concentrate memory, especially non-volatile memory, into the PBT controller where there is only a single device, and to minimize the memory contained within each intelligent LED pad, which occurs in multiple instances per system.

In operation user commands input via a UI/UX interface on touchscreen LCD 133 are interpreted by main µC/MPU 134, which in response retrieves treatment files stored in non-volatile memory 128 and transfers these files through USB bus interface 112, over USB cable 102 to bus interface 122 within intelligent LED pad 120. The treatment files once transferred are temporarily stored in volatile memory 126. Pad µC 121, operating in accordance with the LightPadOS operating systems stored in non-volatile memory 125, then interprets the treatments stored in volatile memory 126 controlling the LED drivers 127 in accordance with the LED excitation patterns of the selected treatment, where LED array 123 illuminates the strings of various wavelength LEDs in a desired manner. As described, key features differentiating the disclosed distributed PBT system to prior art PBT implementations include:

A distributed PBT system comprising two or more microcontrollers or computers 111, 121 and others (not shown), where one microcontroller main MPU 111 or computer applications running on a computer (not shown) comprises or performs the functions of PBT controller 110; and where microcontroller 121 integrated with one or more intelligent LED pad 120 and others (not shown), performs algorithmic execution in accordance with commands it receives. Prior art PBT systems employ only a single microcontroller to execute PBT treatments and sessions.

A distributed PBT system comprising two or more digital clocks 114, 124, and others (not shown) or time references, where clock 133 having a frequency $\Phi_{pad}$ is used as a time source in PBT controller 110; the other clock 124 where clock 134 having a frequency $\Phi_{sys}$ are used as a time reference for timing control of the intelligent LED pad 120, and others time references are used for timing control in other intelligent LED pads (not shown). Prior art PBT systems employ only a single clock or time references to execute PBT treatments and sessions.

A distributed PBT system including an asynchronous communication link comprising a bus such as exemplar USB bus 101 or packet switched network (not shown) connecting the PBT controller 110 to one or more intelligent LED pads 120. Prior art PBT systems do not employ communication buses or active LED pads. Passive LED pads are unable to interpret complex instructions.

A distributed PBT system comprising two or more independent non-volatile memories 115, 125 and others (not shown), where one non-volatile memory 115 is contained within PBT controller 110 and used for preserving various algorithms for PBT treatments and sessions and for hosting a PBT operating system; and where non-volatile memory 125 and others (not shown) and contained within LED pad 120 and others (not shown) and used for storing LED pad specific information such as pad identification and LED configuration data. Prior art PBT systems employ only a single non-volatile memory to execute PBT treatments and sessions.

A distributed PBT system comprising two or more independent volatile memories 116, 126 and others (not shown), where one volatile memory 116 is contained within PBT controller 110 and used in part as scratch pad memory for preparation of communication packets; and where volatile memory 126 and others (not shown) and contained within intelligent LED pad 120 and others (not shown) and used among other purposes for temporarily storing PBT treatment algorithms, waveform synthesis, PWM frequency control, and LED drive and their execution. Prior art PBT systems employ only a single volatile memory to execute PBT treatments and sessions.

A distributed PBT system comprising two or more independent bus interface 112, 122 and others (not shown), where interface 112 sends control and treatment instructions to intelligent LED pads and receives information back from these intelligent LED pads, and where interface memory 122 and others (not shown) and contained within intelligent LED pad 120 receive commands and PBT treatment files from PBT controller 122 and to which intelligent LED pad 120 relays treatment progress, measurements and sensor data. Prior-art PBT systems do not utilize bus communication and cannot communicate bi-directionally between each connected intelligent LED pads and the host PBT controller.

A distributed PBT system comprising two or more microcontrollers or computers 111, 121 and others (not shown) executing PBT-specific operating systems, where one microcontroller main MPU 111 executes an operating system (herein as "LightOS") performing the required interface and operational functions of PBT controller 110; and where microcontroller 121 integrated within one or more intelligent LED pad 120 and others (not shown), performs algorithmic execution in accordance with commands interpreted by a intelligent LED pad resident operating system (herein as "LightPadOS"); and where LightOS in PBT controller 110 and where LightPadOS within intelligent LED pad 120 and others (not shown) operate conjunctively as a virtual machine to execute PBT treatments and sessions. Prior art PBT systems employ only a single microcontroller and software to execute PBT treatments and sessions and do not operate as a distributed virtual system.

In the foregoing, without limitation the term microcontroller shall broadly be construed to mean any programmable digital logic or mixed-signal device including microprocessors, MPUs, microcontrollers, microcomputer based system-on-chip (SoC), microprocessor modules, microcontroller system in package (SiP), programmable logic arrays (PLAs), or other firmware controlled logic devices capable of numeric calculation algorithmic execution. Similarly the term computer application shall mean any electronic computing device including the aforementioned description of microcontrollers, along with computer servers, personal computers, notebook computers, tablet computers, and smartphones running software or firmware programs to perform the tasks and functions of a PBT controller.

As shown in FIG. 8, PBT operation can also be interpreted as a sequence of communications used to control hardware operations. Using an OSI representation, PBT controller 100 contains communication stack 130 comprising application Layer-7, data link Layer-2 and physical Layer-1. Within PBT controller 100, application Layer-7 is implemented using a customized operating system for photobiomodulation referred to herein as LightOS. Instructions received by LightOS user commands are passed down to the Layer-2 data link layer and together with the PHY Layer 1 communicate using the USB protocol using USB differential signals 132 to the corresponding PHY Layer 1 of communication stack 131 resident within intelligent LED pad 103. So although electrical signals comprise Layer-1 communications, the data constructs of USB behave as though the PBT controller and intelligent LED pad are communicating on Layer-2 with the packets arranged in time as USB data "frames".

Once communication stack 131 receives a USB packet, the information is transferred up to the application Layer-7 executed by the intelligent LED pad's resident operating system referred to herein as LightPadOS. Provided that the PBT controller's LightOS and the intelligent LED pad's operating system LightPadOS are designed to communicate and execute instructions in a self-consistent manner, the bidirectional link between communication stacks 130 and 131 functions as a virtual machine at the application layer, meaning the distributed device behaves the same as if it were a single piece of hardware. PBT system communication, shown here as exemplar USB differential signals 132, occurs asynchronously at a communication clock rate independent from PBT controller clock $\Phi_{sys}$ 133 and from intelligent LED pad clock $\Phi_{pad}$ 131, all operating unsynchronized and at their own frequencies.

PBT treatments, sessions, and protocols define intellectual property comprising sequences of photoexcitation patterns and operating parameters including LED wavelength, modulation pattern and frequency, treatment durations, and the LED intensity (brightness), together determining the instantaneous power, average power, therapeutic dose (total energy), and ultimately therapeutic efficacy. In order to discourage copying or duplication, these sequences should be stored and communicated securely, using encryption and other methods. Although some data security methods and related security credentials can be executed as part of the application, i.e. in LightOS and LightPadOS, a added level of security can be achieved by inclusion of a "presentation" Layer-6 in the communication stack of the PBT controller host and any network connected intelligent LED pad clients.

Figure 9:
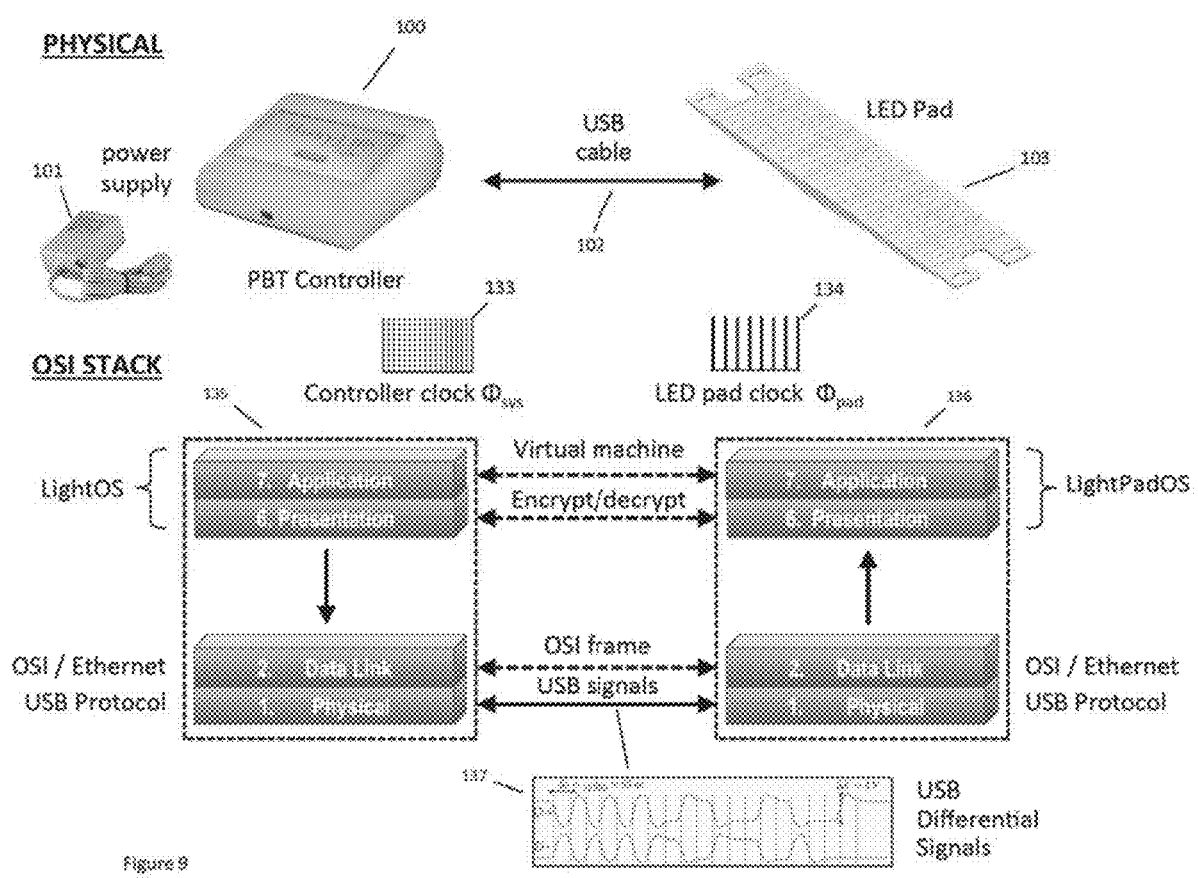
FIG. 9 is a network description of a PBT system with intelligent LED pads using a 4-layer OSI stack and encrypted communication.

The presentation layer is schematically represented in FIG. 9, where PBT controller 100 includes OSI communication stack 135 comprising application Layer-7, presentation Layer-6, data link Layer-2 and physical Layer-1. As previously stated, within PBT controller 100, application Layer-7 is implemented using the PBT specific operating system called LightOS. In operation, Layer 7 LightOS program execution results in actions requiring communication to the intelligent LED pad. These actions are encrypted in the presentation Layer 6 then passed to the lower level communication layers in encrypted form, i.e. as ciphertext. Specifically, the ciphertext passed down to the Layer-2 data link layer is then packetized, i.e. converted into a series of communication packets comprising a non-encrypted header and a ciphertext payload in accordance with a particular communication protocol such as USB, I²C, FireWire, then communicated over the physical PHY Layer-1 to the intelligent LED pad. For example PHY Layer-1 may communicate using the USB protocol using USB differential signals 137 to the corresponding PHY Layer-1 of communication stack 136 resident within intelligent LED pad 103. So although electrical signals comprise Layer-1 communications, the data constructs of USB behave as though the PBT controller and intelligent LED pad are communicating on Layer-2 with the packets arranged in time as USB data "frames". Once communication stack 136 receives a USB packet, the ciphertext payload is extracted is transferred up to the presentation Layer-6 where it is decrypted and converted into plaintext. The plaintext file is then passed to the application Layer-7 where it is executed by the intelligent LED pad's operating system LightPadOS. Provided that the PBT controller's LightOS and the intelligent LED pad's operating system LightPadOS are designed to communicate and execute instructions in a self-consistent manner, the bidirectional link between communication stacks 135 and 136 functions as a virtual machine at the application layer, meaning the distributed device behaves the same as if it were a single piece of hardware, and at the presentation layer to bidirectionally execute encryption and decryption. In this manner data can be transferred between the PBT controller and the intelligent LED pad. To prevent copying of the source code, however, the library of treatments is stored in encrypted form. For added security, the encryption key used for storing the algorithms in different than the key used for communication. So before a treatment file can be securely communicated it must first be decrypted.

Figure 10:
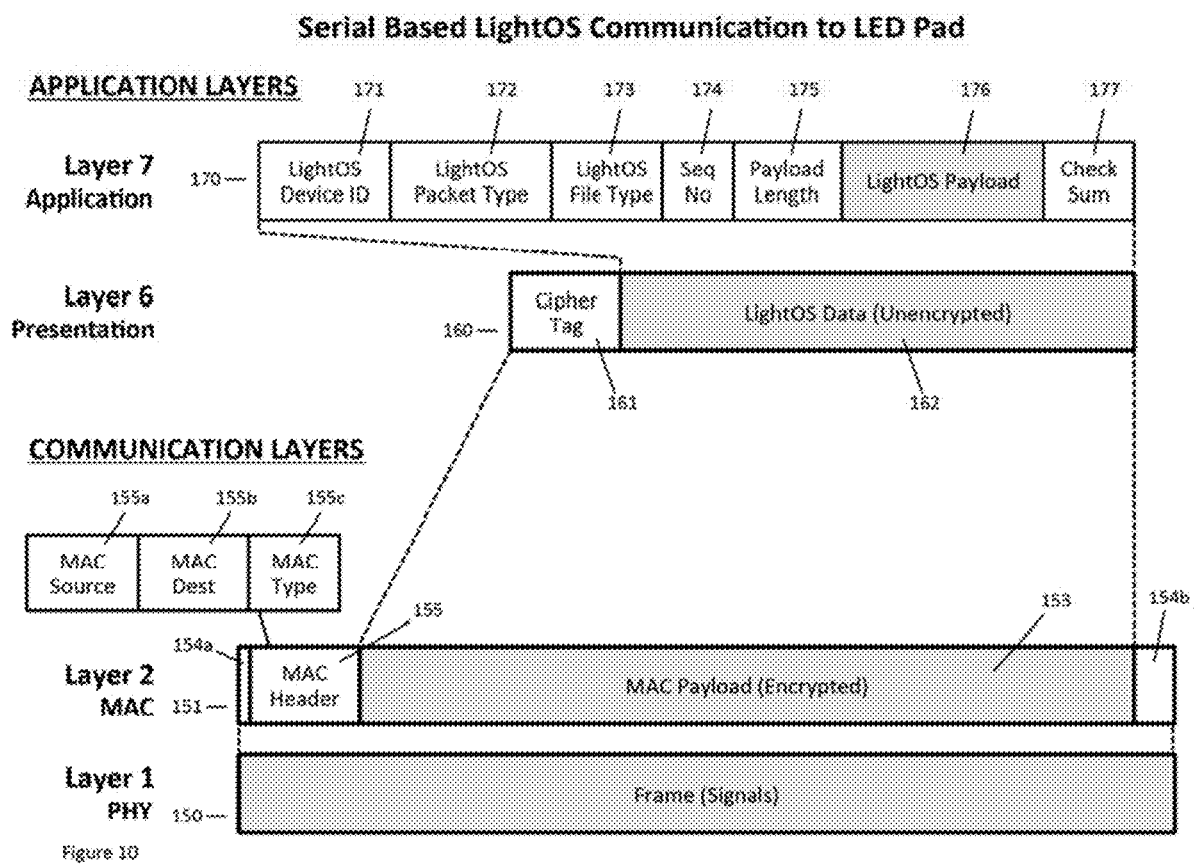
FIG. 10 illustrates data packet construction for intelligent LED pads using a 4-layer OSI communication stack and encrypted communication.

As shown in FIG. 10, serial bus communication in a PBT system employs embedded packets nested one inside another. The outer packet representing the physical or PHY Layer-1 comprises a data frame 151 of electrical, electromagnetic, or optical signals. Data frame 151 in turn contains Layer 2 MAC data 402 comprising MAC header 155 and the encrypted MAC payload 153 along with padding, i.e. header 154a and trailer 154b. The data frame, i.e. the repeating portion, varies in duration, not only with the size of the payload but also with overhead required to establish an electrical connection, and to check the contents of each frame was received with integrity (error checking). For this reason the PHY data frame 150 is slightly longer than the combined length of MAC header 155 and MAC data field 153. This difference is graphically represented by header 154a and trailer 154b. Note that some graphical depictions of an OSI stack illustrate the header 154a as a leading segment in PHY Layer-1 data frame rather than as a Layer-2 header. For all practical purposes, there is no insight gained by this alternative representation. For simplicities sake we adopt the Layer-2 representation for header 154a. To reiterate, MAC Layer-2 data comprises packet 151 containing MAC header 155 and the encrypted MAC payload 153 along with header 154a and trailer 154b. The term MAC is an acronym for media access control, and a media access control address is commonly referred to as a MAC address. The MAC address of a device is a unique identifier assigned to network interface controllers for communications at the data link Layer-2 of a network segment. MAC addresses are used as a network address for most IEEE 802 network technologies, including Ethernet and Wi-Fi. MAC header 155 contains MAC source address 155a, i.e. the device identification number of the PBT controller 100, and MAC destination 155b, the device identification number of one specific LED pad 103 and others (not shown), as well as a field for MAC type 185c. It should also be mentioned that in the literature, the term "frame" is used interchangeably for Layer-1 and Layer-2 because the durational length of PHY Layer 1 data signals 150 and MAC packet 151 are the same. For clarity's sake we herein refer to the PHY Layer-1 frame as "data frame 150" and MAC Layer-2 frame 151 as either a MAC Layer-2 packet 151 or as a "MAC frame", the distinction being only as to how the same information is represented, i.e. either as data/signals or as "media". While the MAC source address 155a and MAC destination address 155b are device specific identifiers, the term MAC type is also known as Ethertype. The use of this field varies depending on the code, defining either an Ethernet II data link or used to define a packet length in accordance with IEEE 82.3 specification. Optionally a 4-B long VLAN field may be inserted into the data packet in accordance with specification IEEE 802.1Q.

Note that in its four-layer communication implementation lacking any Layer-3 network and Layer-4 transport layer data, only the hardware MAC addresses 155a, 155b and MAC type 155c are available to identify communication routing. This means the bidirectional connection must occur exclusively between PBT controller 100 and LED pad 103 (or other pads not shown) with no intervening devices, i.e. the connection is peer to peer between only two devices. Without Layer-3 network and Layer-4 transport layer data, the communication packets cannot be routed through another device or network, or it will get lost. In essence four-layer communication provides a secure bidirectional communication for exclusively for direct connections between the PBT controller and one or more LED pads.

The usable portion of MAC Layer-2 packet 151, MAC payload 153 contains Presentation Layer-6 data 160 comprising cipher-tag 161 and LightOS data 162. MAC payload 153 may be encrypted in total or in part. For example, cipher-tag 161 may be unencrypted and aid in decryption of portions MAC payload 153 comprising LightOS data 162, e.g. as a complete or partial crypto-key. Alternatively an alternative decryption method may be employed that does not require the use of cipher tag 161, e.g. a symmetric key exchange can occur independently to enable decryption of MAC payload 153. In such, cases cipher tag 161 may be utilized as a post-decryption ID field to aid in the reassembly or use of the decrypted payload, i.e. LightOS unencrypted data 162. The contents of this LightOS data contains Application Layer-7 data 170 contains several data fields including without limitation LightOS device ID 171, LightOS packet type 172, LightOS field type 173, sequence number 174, payload length 175, LightOS payload 176 and checksum 177.

Figure 11:
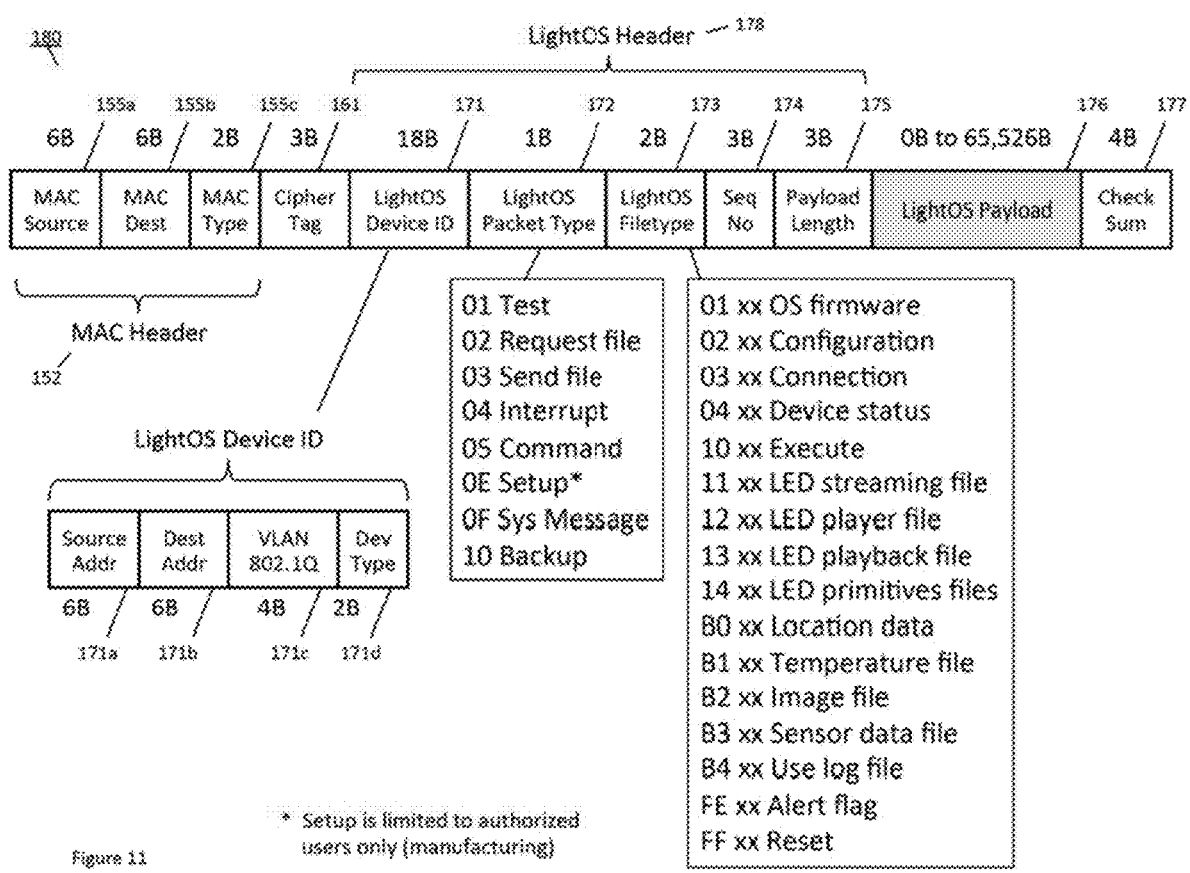
FIG. 11 illustrates an exemplary data packet containing various fields for serial bus communication between a PBT controller and intelligent LED pads.

As illustrated, serial communication of received data occurs using an outside-to-inside progression as data moves up an OSI stack. Conversely in preparation for transmission data traverses the OSI layers in an inside-to-outside progression as the packets ripples down the communication stack. Sometimes it is beneficial to represent the nested data structure in a "flattened" format. As such nested data fields embedded with LightOS PHY Layer-1 communication packet comprising frame 150 can be represented in an un-nested format by explicitly illustrating each header field as shown in the exemplar LightOS communication packet 180 of FIG. 11. This representation includes Layer-2 MAC header data 152 comprising MAC source address 155a, MAC destination address 155b, and MAC type 155c; Layer-6 data comprising cipher tag 161 and LightOS data 162; followed by Layer-7 application layer data comprising LightOS specific data comprising LightOS device type 171, LightOS packet type 172, LightOS filetype 173, payload sequence number 174, payload length 175. LightOS payload 176 and payload checksum field 177. It should be noted that flattened formats such as packet 180 may be inaccurate in timing estimations as the representation intentionally excludes headers, trailers, checksums, and other data other than routing and the payload.

The 4-layer LightOS communication packet 180 shown is a succinct and convenient for rapid transport between two devices. To avoid unnecessary transport overhead, the exemplar LightOS communication packet 180 utilizes a variable length structure where payload length 176 specifies the length of the LightOS payload 177. In the exemplar flattened LightOS communication packet 180 as shown, the bit length of various fields are defined in accordance with a standard designed in accordance with the LightOS for interoperability across devices and platforms and for compatibility with Ethernet. The defined fields and their corresponding bit lengths (having field lengths specified in bytes), are shown for illustrative purposes and are not intended to be limiting in the construction or use of the data packets. Examples of various types data fields in four-layer LightOS communication packet 180 are shown in FIG. 97.

The LightOS device ID 171 provides a field for communicating devices to confirm their identities at the Application Layer-7. Although this field can comprise any manufacturing information to identify a device, for convenience the data field can be set to be a OUI (Organizationally Unique Identifier) and serial number—the same addresses as those used as MAC addresses in point-to-point device communication. As such, in 4-layer communication packets 180 LightOS device source address 171a is the same as MAC source address 155a, LightOS destination address 171b is the same as MAC destination address 171b, and MAC type 171d is the same as MAC type 155c. VLAN field 171c is added to facilitate additional control. Note that while in 4-layer communication the LightOS device ID 171 contains the same data as MAC header 152, in 7-layer (full OSI stack) communication, the MAC header 152 is set dynamically hop-by-hop as a data packet traverses the network, and therefor is not the same as the static data contained in LightOS device ID 171 field, as summarized in FIG. 98.

The LightOS specific packet type 172 and filetype 171b are employed by the LightOS operating system (and its subset LightPadOS) in order to determine what command or data is being sent or requested. This field is used to inform selected intelligent LED pad what kind of operation is required. While most of these processes are available during operation, Setup instructions require manufacturing authentication in order to access. The LightOS packet type includes the following exemplar codes:

| Hex | LightOS Packet Type |
|---|---|
| 01 | Test |
| 02 | Request file |
| 03 | Send file |
| 04 | Interrupt |
| 05 | Command |
| 0E | Setup (requires authentication) |
| 0F | System message |
| 10 | Backup |

Exemplary LightOS filetypes 173 include, without limitation, the following codes comprising a 2-B long hex word:

| Hex | LightOS Filetype |
|---|---|
| 01 xx | OS firmware |
| 02 xx | Configuration |
| 03 xx | Connection |
| 04 xx | Device status |
| 10 xx | Execute |
| 11 xx | LED streaming file |
| 12 xx | LED player file |
| 13 xx | LED playback file |
| 14 xx | LED primitives files |
| B0 xx | Location data |
| B1 xx | Temperature file |
| B2 xx | Image file |
| B3 xx | Sensor data file |
| B4 xx | Use log file |
| B5 xx | Calibration file |
| FE xx | Alert flag |
| FF xx | Reset |

By interpreting the LightOS packet type 172 and filetype 173, the resulting 3-B long hexadecimal word accommodates up to $16^3=4,096$ combinations (not counting cipher tag 183). The advantage of including payload length 175 is that the number of bytes sent in the payload field 176 can vary to accommodate only the length required, avoiding the need to send large "empty" packets. The shortest payload is zero bytes, typically used in the LightOS communication protocol for alerts, system messages, and commands. In such cases the only required overhead in the packet is the 3-B used for the payload length field 175. While in the vast majority of cases the LightOS payload is relatively compact, the variable length field provides flexibility to accommodate large files like sensor images without adding packet overhead. This feature enables the disclosed LightOS and PBT platform to expand into new applications and markets beyond that of photobiomodulation, e.g. magnetotherapy, ultrasound imaging, biosensors, etc.

MAC routing over a packet switched network is based on the MAC address of a device. MAC addresses are numbers comprising a unique vendor code called an OUI followed by a manufacturer's serial number. An OUI or Organizationally Unique Identifier is a 3-B long number that uniquely identifies a vendor/manufacture (https://en.wikipedia.org/wiki/Organizationally_unique_identifier). The OUI, first three Bytes of a MAC address are purchased and assigned by the Institute of Electrical and Electronic Engineers (IEEE). The last three Bytes comprise the manufacturer's serial code. Every packet-switched network connected device requires an OUI and MAC address.

Figure 12A:
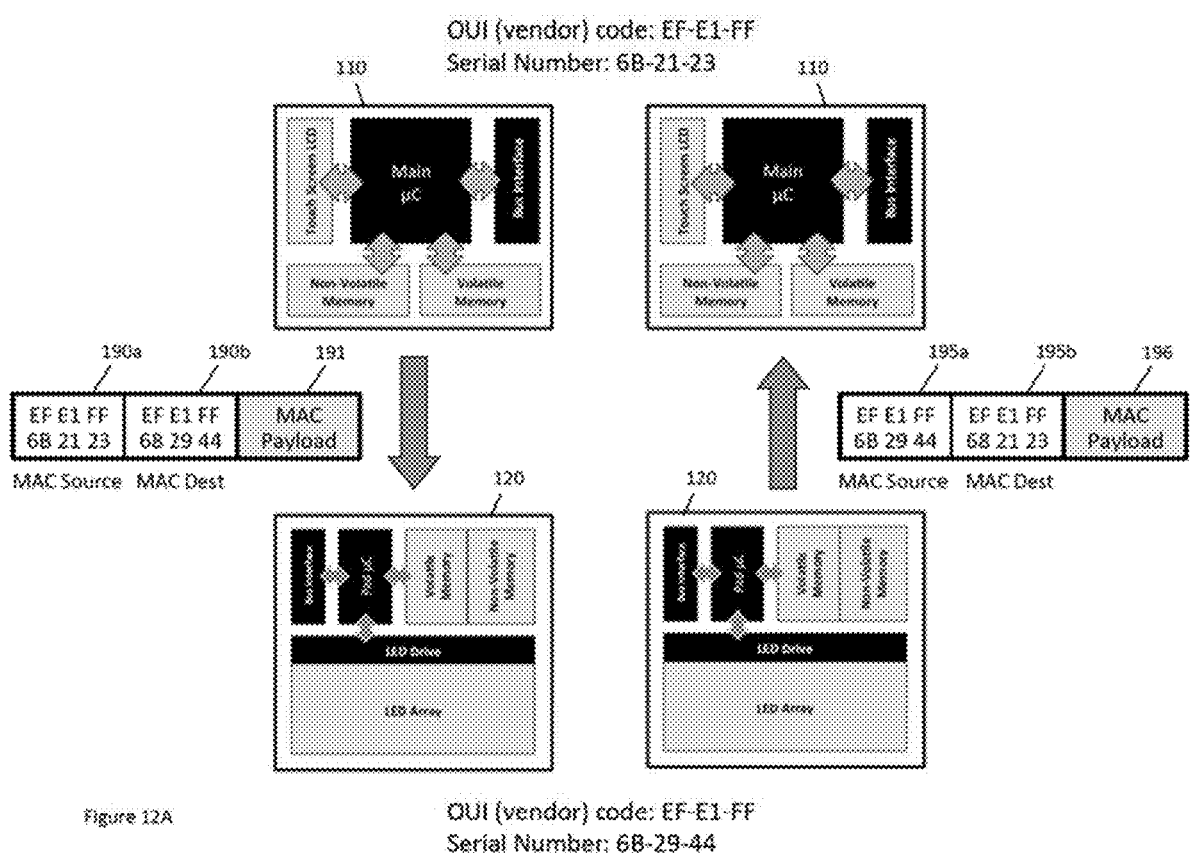
FIG. 12A illustrates exemplary data packets and corresponding MAC addresses for directing bidirectional data flow between a PBT controller and an intelligent LED pad.

An example of routing using MAC addresses is shown in FIG. 12A where PBT controller 110 and intelligent LED pad 120 communicate bidirectionally. In this exemplar, both the PBT controller and intelligent LED pad have a fictitious vendor code EF-E1-FF where PBT controller 110 has a unique serial number 6B-21-23 and where intelligent LED pad 120 has a unique serial number 6B-29-44. As illustrated in communication of MAC payload 191 from PBT controller 110 to intelligent LED pad 120, the source MAC address 190a is EFE1FF-6B2123 and the destination MAC address 190b is EFE1FF-6B2944. Conversely, as illustrated in communication of MAC payload 196 from intelligent LED pad 120 to PBT controller 110, the source MAC address 195a is EFE1FF-6B2944 and the destination MAC address 195b is EFE1FF-6B2123. The MAC routing method, applicable to any TCP/IP compliant communication medium including Ethernet, WiFi, 4G, 5G, and DOCSIS3, is also capable of concurrently driving more than intelligent LED pads.

For example in FIG. 12B, PBT controller 110 concurrently drives both intelligent LED pads 120 and 120b. In particular, MAC payload 194 is delivered to LED 120a at destination 190b with MAC address EFE1FF-6B2945 while concurrently MAC payload 191 is delivered to LED 120 at destination 190b with MAC address EFE1FF-6B2944. Concurrent delivery means PBT controller 110 is able to direct both intelligent LED pads 120 and 120b through one serial interface. Although serial control is by definition sequential and therefore not simultaneous, the delay occurs the microsecond range, which compared to biological time clocks is virtually instantaneous.

In the disclosed invention, the OSI format communication stacks are maintained within the LightOS operating system compatible with 4-layer and 7-layer OSI implementations, even when more primitive forms of communication such as a USB or I$^2$C are used for the physical communication layer. For example, although a USB connection employs ad-hoc addresses assigned at the time of a connection and therefore does not actually require a registered MAC address, the MAC address can still be used by to identify connected devices in the application Layer-7, i.e. by the LightOS operating system. For example, even if PHY Layer-1 communication utilizes a USB communication protocol the LightOS compatible data packets maintain the OSI structure from Layer-2 and up anyway even though USB doesn't require it. The advantage of this self-imposed discipline is that products developed for USB communication can be adjusted for Ethernet, WiFi, DOCSIS3, 4G or 5G telephony, without rewriting all the computer code. Only the Layer-1 and possibly Layer-2 communication subroutine call must change to create a new PBT system.

For example in PHY Layer-1 communication over USB shown in FIG. 12C, the USB packet 138 contains data field 139. After delivery, the payload is extracted containing the MAC source address 190a of PBT controller 110, the MAC destination 190b of intelligent LED pad 120, and MAC payload 191. This packet data is eventually passed up to the application Layer-7 where the pad's operating system Light-PadOS is interpreted and executed. One disadvantage of using any of the standard serial communication busses (such as USB, I$^2$C, token ring, etc.) is that without MAC addressing and routing, all the data packets are distributed to every connected device, even if they are not the intended recipients. By in essence broadcasting the same packets to every device, each receiving device, i.e. intelligent LED pad, must on its own accord determine if the data packet in intended for it or not. If it is the intended recipient it must process MAC payload 191 accordingly. If it is not the intended recipient, the intelligent LED pad's processor must discard the packet. MAC layer information is therefore beneficial in distributed PBT systems involving device-to-device communication.

As a caveat, routing communication through a $3^{rd}$ party router such as an Ethernet router/switch, a WiFi router, or a router/server will not work because the MAC address of a packet's destination is replaced each time the packet passes through a device. For example an intelligent LED pad sending a WiFi packet through a WiFi router to an up-stream PBT controller cannot because the MAC data fields are overwritten as the packet passes through the WiFi router. For example, the data packet sent from the intelligent LED pad to the PBT controller uses the router's MAC address as the destination and the intelligent LED pad's MAC address as its source address, but after the packet passes through the router the MAC addresses are changed, whereby the router's MAC address becomes the MAC source and the destination changes to the MAC address of the PBT controller. In the process the MAC address of the intelligent LED pad disappears altogether. As such routing through a $3^{rd}$ party router requires the use of the network Layer-3 and transport Layer-4 in full OSI communication stack (described later in this disclosure) and cannot be performed using the simpler 4-layer packet construction described here.

In conclusion, a distributed PBT system as disclosed comprising a PBT controller with LCD touchscreen and one or more connected intelligent LED pads with numerous advantages over existing and prior art systems, namely:

- The ability to perform PBT treatments where the intelligent LED pads and patient being treated are not required to be in close physical proximity to the PBT controller.
- The ability for a user-interface controlled PBT controller to reliably communicate commands and to control operation of the active/intelligent LED pads wirelessly or over long cables without distorting LED-drive waveforms including the user of high speed bus communication methods such as USB, high bandwidth packet switched network communication such as Ethernet, and high speed wireless communication using WiFi or 4G/LTE/5G telephony.
- The ability for a PBT controller to communicate to active/intelligent LED pads at a high-level using files and packetized bursts of data where the communication bus or channel is not constantly occupied by clock or real time control signals.
- The ability for a PBT controller to communicate to active/intelligent LED pads bidirectionally facilitating the communication of status and fault conditions or sensor measurements from a intelligent LED pad to the PBT controller.
- The ability for a PBT controller to uniquely identify and to authorize intelligent LED pads connected to it or to identify and reject imposter LED pads or unrelated peripherals. Identification of the PBT system components may utilize a manufacturer specific OUI and MAC address to identify the manufacturer.
- The ability for an intelligent LED pad to autonomously execute programs and generate LED waveforms for PBT treatments and sessions in response to commands received from a PBT controller including treatments involving a mix of different patterns, excitation frequencies, and LED wavelengths.
- The ability for the PBT system to operate asynchronously where the time base (clock) for a PBT controller, the intelligent LED pads, and their communication can operate at dissimilar frequencies and do not require maintaining synchronization.
- The ability for the PBT system to store, to communicate, and to utilize encrypted data during operation to prevent hacking and thwart copycats and fraudulent manufacturers.
- The ability for the intelligent LED pads to retain executable code in volatile memory so that attempts to read, copy, or download the pad's executable code are lost with an interruption of power or a disconnection of the intelligent LED pad from the PBT controller.
- Communication between a PBT controller and a pad comprising a standardized compact data packet compatible with packet switched networks, TCP/IP protocols, and the 7-layer OSI model.

Figure 13:
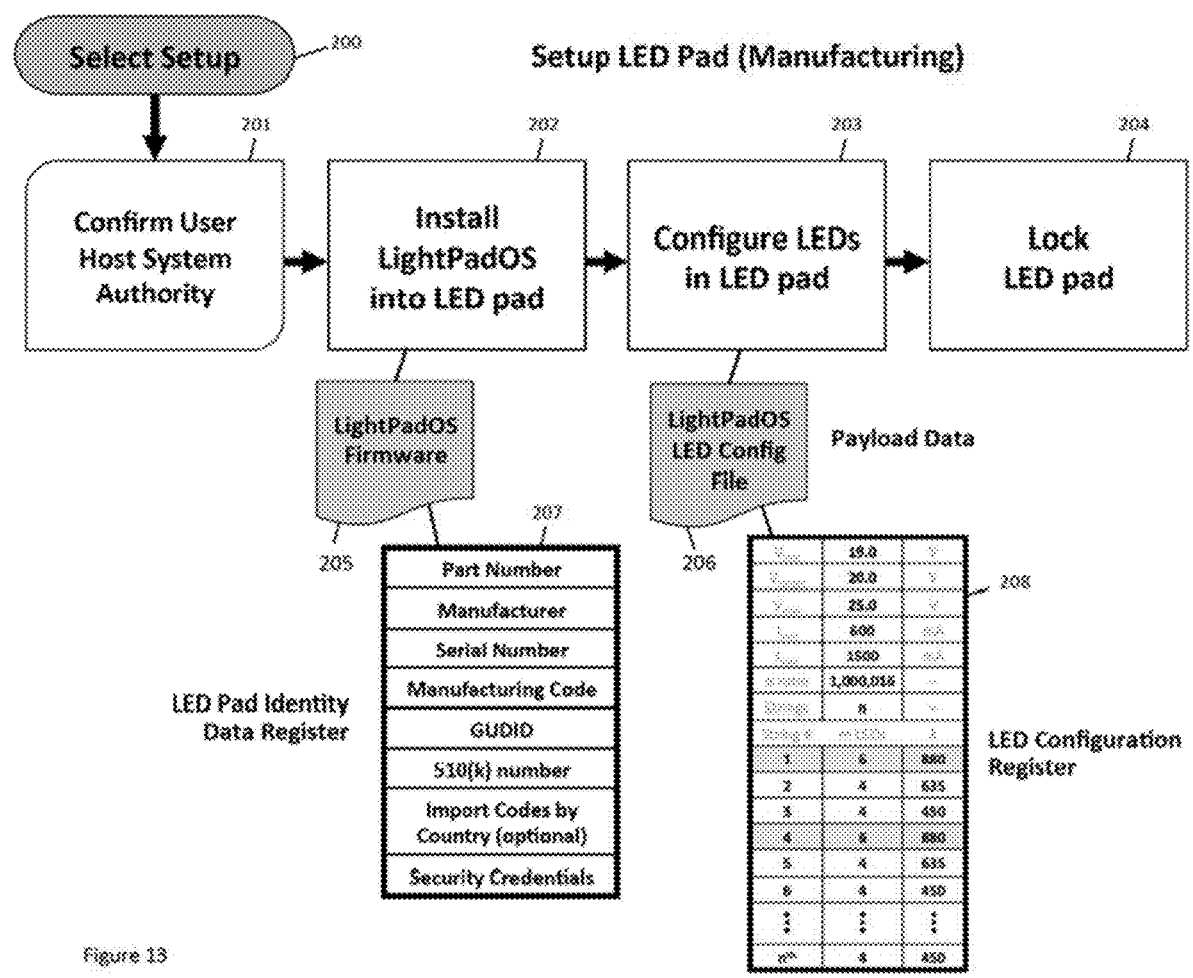
FIG. 13 illustrates the manufacturing flow for setup (firmware installation) of an intelligent LED pad.

Intelligent LED Pad Manufacturing Manufacturing of intelligent LED pads utilizes the same communication bus methods used for control and playback. The general process for the setup of an intelligent LED pad is illustrated in FIG. 13 where upon Select Setup 200 on a PBT controller, the identity and authority of the user must be confirmed in step 201. Once user authentication is completed, the pad to be programmed is connected to the PBT controller and selected, after which the intelligent LED pad is programmed with a PBT specialized operating system in step 202 entitled "Install LightPadOS Into LED Pad." This operation involves the transfer of file 205, LightPadOS firmware, from the PBT controller to the intelligent LED pad. The LightPadOS operating system is installed into non-volatile memory using the pad's microcontroller operating kernel to facilitate download, decryption, error checking, and file storage.

In operation the installed LightPadOS runs atop the pads native processor's operating system analogous to the way Apple's MacOS runs atop a UNIX operating system and kernel. The download also includes storage of the LED pad identity register 207 into non-volatile memory, uniquely identifying the identity of the intelligent LED pad using a format that PBT controller can recognize and interpret. After the LightPadOS is installed and operational, the PBT controller and intelligent LED pad form a virtual machine communicating at the application Layer-7. As a virtual machine, the intelligent LED pad's operating system LightPadOS is able to communicate through the OSI stack to the PBT controller's operating system LightOS. Since LightPadOS is a compatible subset of LightOS, it facilitates LightOS control of the PBT as though it were integrated into the host controller.

In step 203 "Configure LEDs in LED Pad," the LightPadOS LED configuration file 206 is downloaded and stored in the pad's non-volatile memory indelibly identifying what LEDs are in the pad and how they are configured, as specified in the embedded table 208, the "LED Configuration Register." Finally upon verification, in the Lock LED Pad operation 204, the non-volatile memory addresses for LightPadOS, as well as for "LED Pad Identity Data Register" 207 and "LED Configuration Register" 208. Locking the pad means these files cannot be overwritten.

Figure 14A:
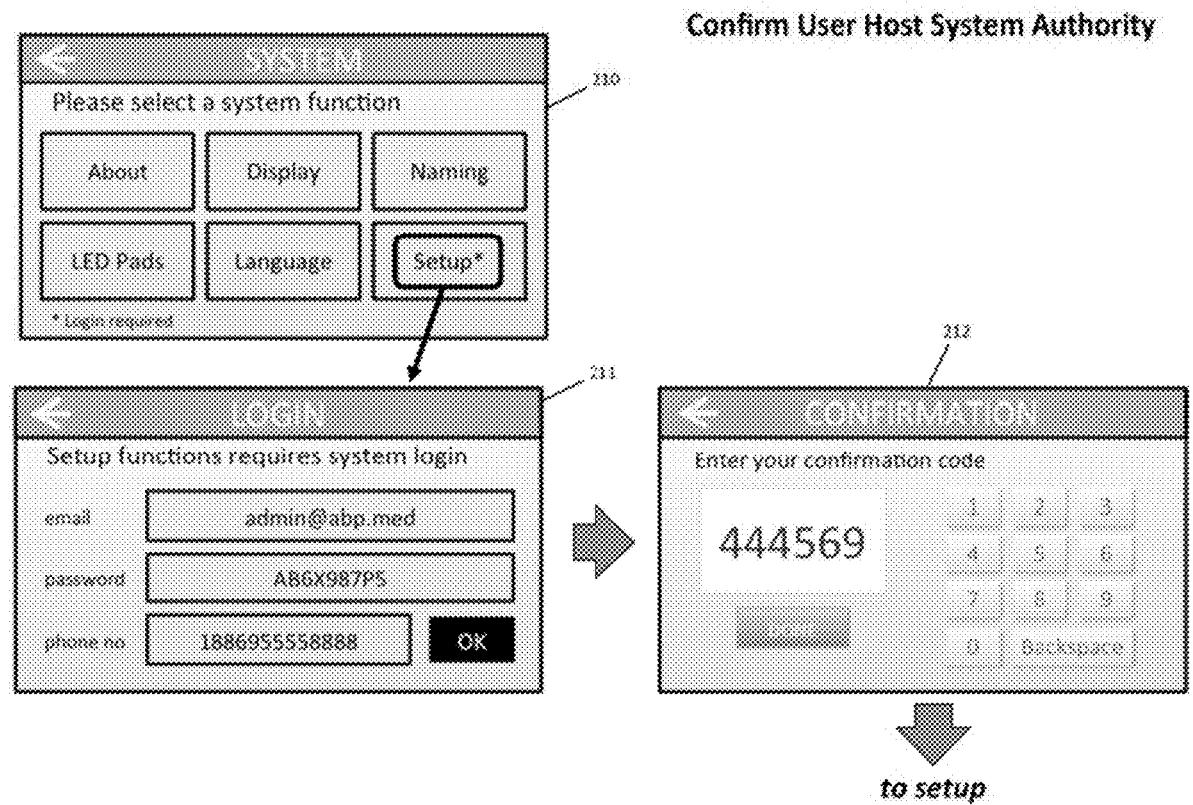
FIG. 14A is the UI/UX flow for confirming LightOS user host authority.
Figure 14B:
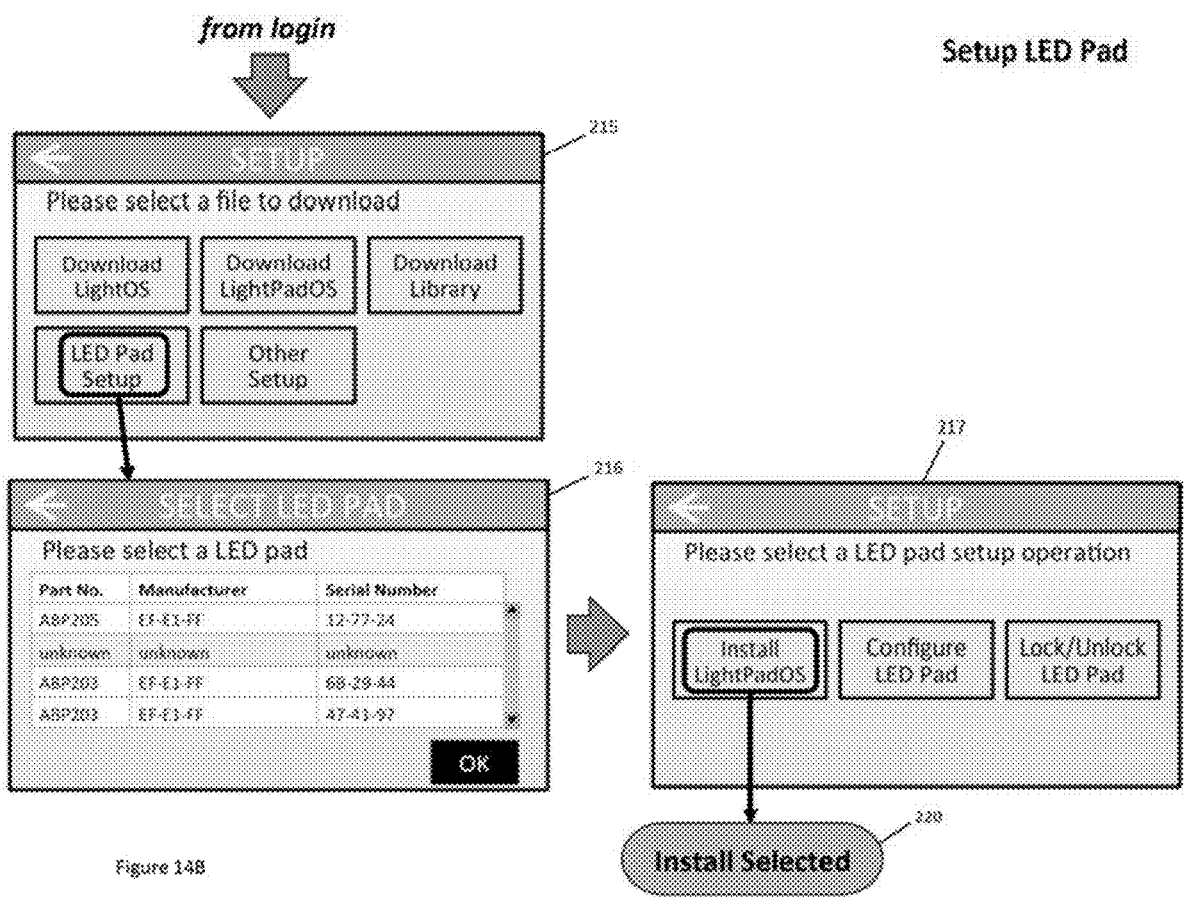
FIG. 14B is the UI/UX flow for installing LightPadOS firmware into an intelligent LED pad.

As detailed execution of the described setup process, first involves host system user authority authentication sequence as shown in the UI/UX process illustrated in FIG. 14A. In this process the programmer first selects the system menu screen 210 on the PBT controller's touchscreen, then selects the "Setup" button. This action automatically opens Login screen 211 for user authentication prompting some combination of user ID or email address, password, and phone number. Provided that the user enters the proper user password, the secondary authentication screen 212 entitled "Confirmation" opens. Meanwhile the secondary authentication process sends a unique authorization code to the user's phone, which must be entered on the keypad. After entering the data by selecting "Done", a valid response allows the user to proceed to the setup menu. The advantage of this procedure is that a user in a remote location may be able to update firmware provided they are properly authorized. Without this feature a intelligent LED pad must be returned to the factory to have its firmware updated, an expensive and inconvenient process. Once authorized, the user proceeds to the UI/UX sequence shown in FIG. 14B starting with selecting the "LED Pad Setup" button on screen 215. The user is then prompted in screen 216 to "Select LED Pad". To avoid confusion or the risk of programming the wrong LED pad it is preferable that only one LED be attached to the PBT controller at a time, in which case the Select LED Pad screen 216 will display only one choice. After the desired intelligent LED pad is selected and confirmed by depressing the OK button, the "Setup" screen 217 opens, allowing the user to decide what task they wish to perform including "Install LightPadOS", Configure LED Pad", or "Lock/Unlock LED Pad". Selecting Install LightPadOS begins the installation process "Install Selected" 220.

The LightPadOS operating system installation process proceeds in accordance with the flowchart shown in FIG. 15A where following the aforementioned steps of "Confirming User System Authority" 201 and "Select Install" 220, the installation can commence. As the installer LightOS will default to the most current version of the intelligent LED pad software. Additional menus can be added if it is desirable to select an older version of the code, but this option is generally not recommended as it may create compatibility conflicts by mixing unrelated versions of code. In the flowchart, two columns are depicted one describing actions of the host PBT controller running LightOS and the other describing the intelligent LED Pad prior to installing the LightPadOS. In step 222 "Transfer LightPadOS" the intelligent LED pad's firmware is transferred 221 from the PBT controller to the intelligent LED pad, where it is received 223. In step 225 the intelligent LED pads own microcontroller operating system performs a checksum error test 225. If the test fails the installation file was corrupted during transfer in which case a checksum Error Report 232 is sent to the host and once received 224 initiates a reinstall process 226 where by step 22 is repeated. Once the intelligent LED pad confirms a valid transfer and checksum 223, the operating system is unpacked from the communication packet 227 and loaded into non-volatile memory. Once loaded 229, a confirmation 233 is sent to the PBT controller. Once received 228 the install process continues to configure the intelligent LED pad 230 either automatically or by manual selection.

The data packets used in the install process are shown in FIG. 15B. In step 1, a setup instruction is sent from PBT controller 110 to the LED pad 120 as data packet 180 having a packet type 241 of |OE|. As described previously in the above tables, a packet type 241 comprising OE corresponds to a Setup instruction. The Filetype 242 having a value |01-01| corresponds to an instruction OS Firmware and sub-instruction "pad, full install". The payload length 243 varies with the size of the LightOS payload 244 containing the LightPadOS firmware 205 but would typically range from 0.5 MB to 2 MB in size. If the size of the file is too large for a single packet, the file can be broken into pieces and sent in several successive packets. In its 4-Layer implementation, this process must be performed manually. If however, the 7-layer full OISI stack is employed (described later in this disclosure), then breaking up the packets and reassembling them is performed by Session Layer-5 utilities such as "sockets" and the no coding for separating and recombining payloads is required. The exemplar sub-instruction |FF| is used to describe as an indication of the continuation of the prior packet's files, i.e. where |0E-01-FF| is a continuation of the file sent of the installation instruction |0E-01-01|.

For each packet sent checksum field 245 is used to confirm no data corruption. The confirm checksum process is illustrated in step 2 of FIG. 15B where the payload LightPadOS firmware 205 is extracted 251 and the checksum calculated 252 then compared 253 to the packet's stored checksum 245. If the numbers don't match, an error has occurred and the process must be repeated. In such an event shown in step 3, intelligent LED pad 120 transfers data packet 260 where the packet type 261 is |0E| with a filetype 262 of |01-F1| meaning the instruction Setup/OS Firmware/Checksum Error. Since this packet contains only a message, the payload length 263 is |00-00-00| and therefore the payload field 264 is a null field.

Once a valid installation packet is received, the software can be installed as shown in FIG. 15C where LightPadOS 205 containing LED pad identity register 207 is extracted from payload field 244 of data packet 240 and in step 2 installed into non-volatile memory 125. The download is confirmed in step 3 where data packet 280 is sent from intelligent LED pad 120 to PBT controller 110 containing the message |0E-01-A1| meaning Setup/OS Firmware/Install Complete in a packet with a zero length payload 284.

Figure 16:
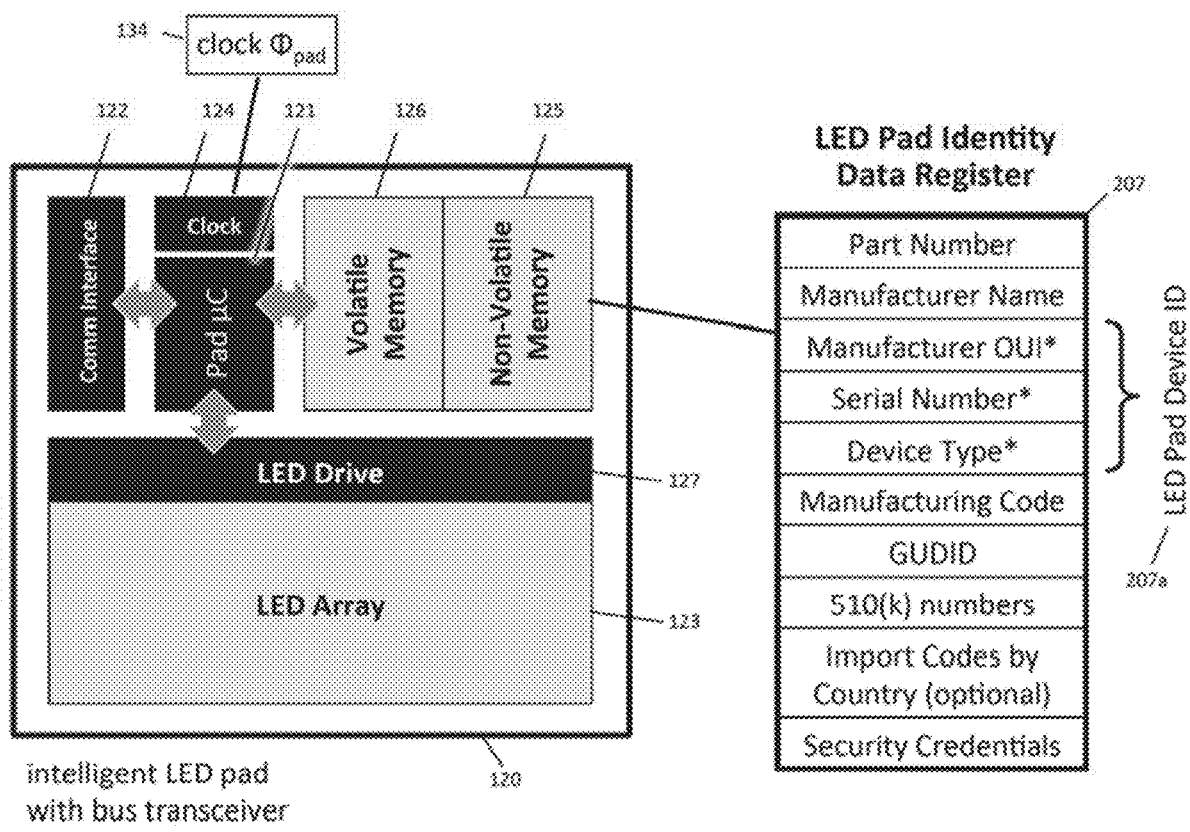
FIG. 16 illustrates a block diagram of an intelligent LED pad with identity data register.

FIG. 16 illustrates an example of the type of product manufacturing information included in "LED pad identity data register" 207 stored in the intelligent LED pad's non-volatile memory 125. This data may include the manufacturer's part number, the name of the manufacturer, the unit's serial number, a manufacturing code linked to a description of the specific unit's manufacturing history or pedigree, the USFDA specified global unique device identification database (GUDID) number [https://accessgudid.nlm.nih.gov/about-gudid], and as applicable a related 510(k) number. The register may also optionally include country specific codes for importing the device and other customs related information e.g. export license numbers or free-trade certificates. This register is stored in non-volatile memory 125 during manufacturing. The LED pad identity data register 207 also includes security credentials (such as encryption keys) used in the authentication process. The security credentials may be static as installed during manufacturing, or dynamically rewritten each time the intelligent LED pad is authenticated, or alternatively rewritten after a prescribed number of valid authentications.

Figure 17A:
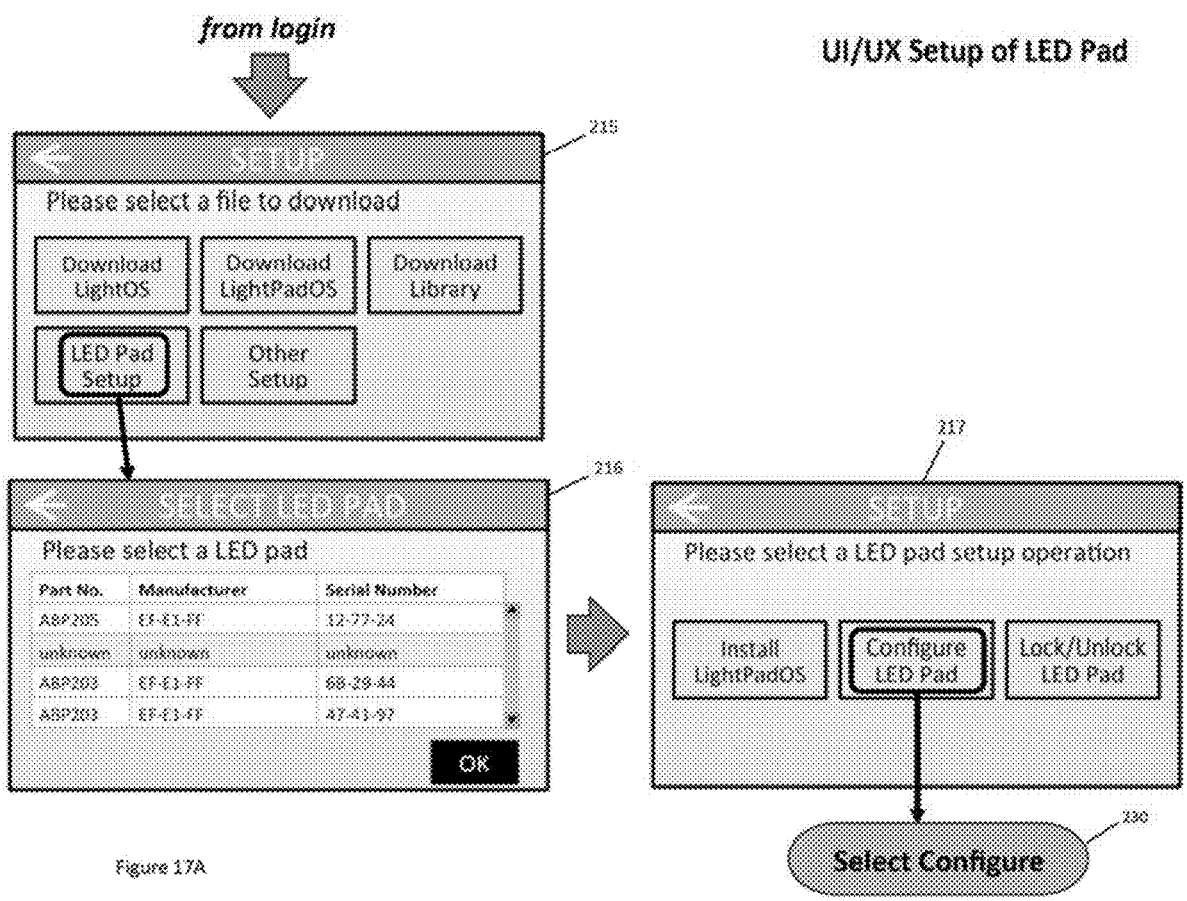
FIG. 17A is the UI/UX flow for set up of an intelligent LED pad.
Figure 17B:
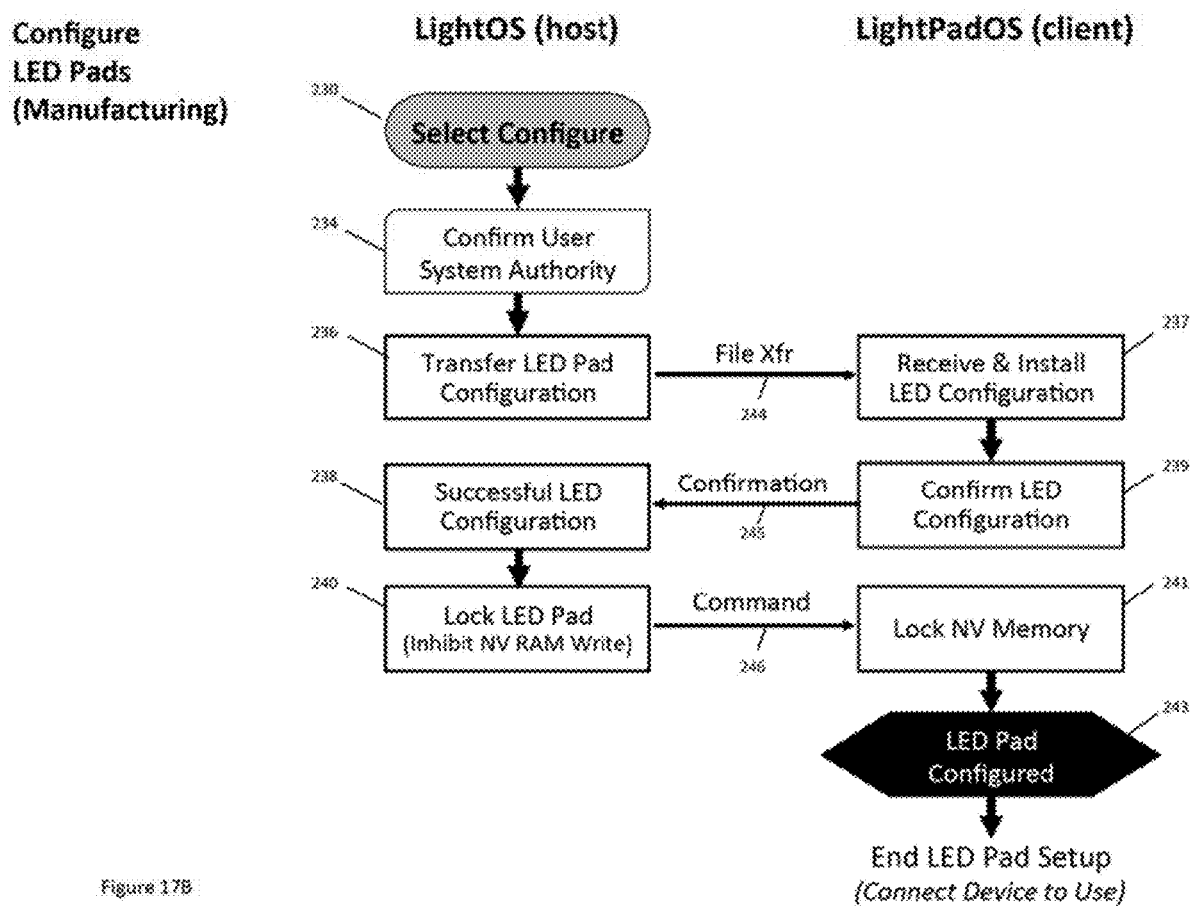
FIG. 17B illustrates data packet communication to write and store LED configuration data into an intelligent LED pad during manufacturing.

After loading the LightPadOS, LED pad setup is less complex than during the OS installation because the pad can communicate at a higher level, i.e. communicating with a common language as a virtual machine operating LightOS. FIG. 17A illustrates the LED pad setup process following login and LightPadOS installation. On Setup screen 215 the user then selects LED Pad Setup and on Select LED Pad screen 216, selects the pad to be setup, opening the Setup screen 217. If this process immediately follows the LightPadOS installation these selection steps can be skipped going directly to Setup screen 217. The user then selects Configure LED Pad commencing the Select Configure routine 230. This routine is detailed in the flowchart of FIG. 17B. Following confirmation of the user's system authority 234, PBT controller 110 proceeds to prepare the LED pad configuration 236 for transfer. Following transfer 244, the LED pad 120 receives and then installs the LED configuration file 237, then confirms the configuration by reading back the stored data 239 and sending confirmation 245. In recognizing a successful LED configuration 238, PBT controller stores the LED pad configuration in its non-volatile memory for backup purposes. The PBT controller then prepares 240 and sends a command 246 to lock the non-volatile memory 241 to prevent overwriting of the NV RAM memory addresses. This step completes the procedure, signifying the LED pad is configured 243 and ready for use.

Figure 17C:
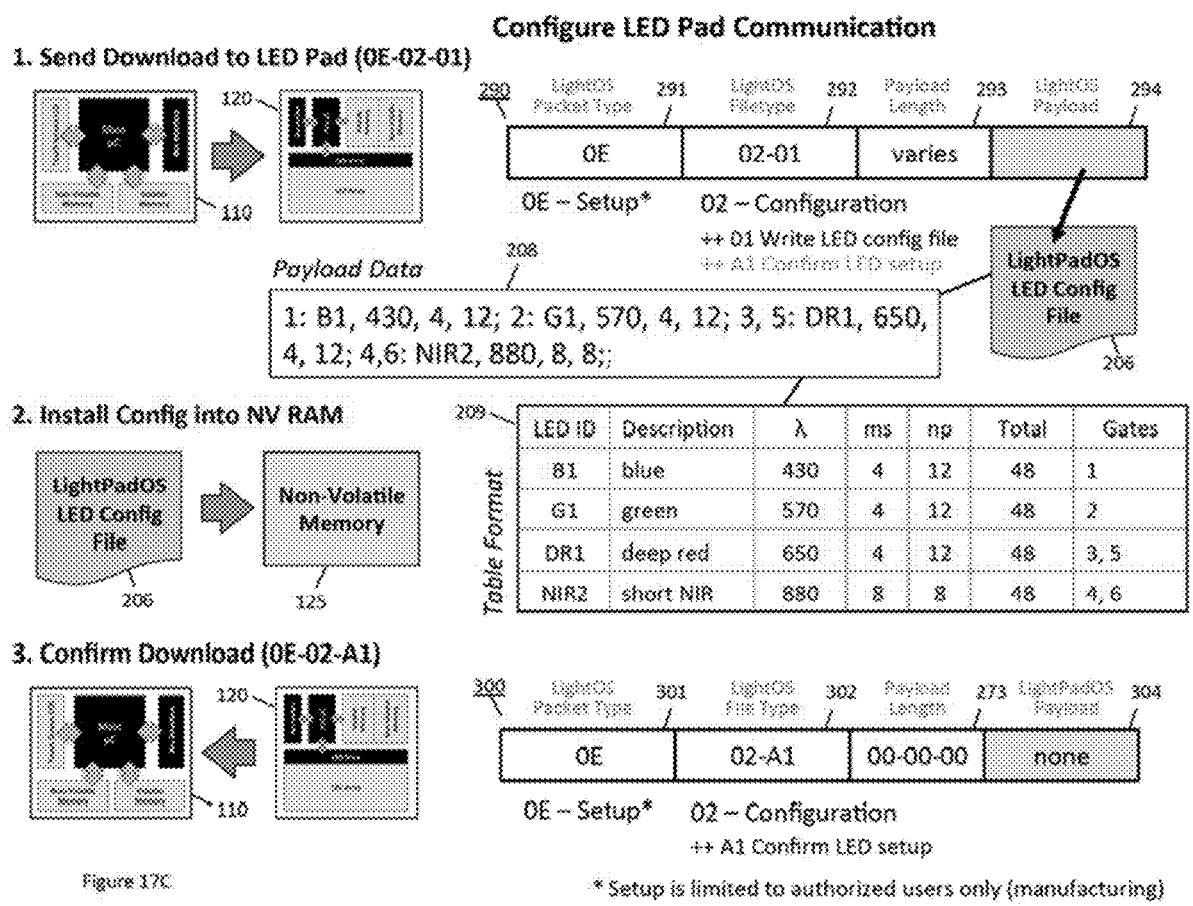
FIG. 17C illustrates data packet communication for downloading LED configuration data into an intelligent LED pad during manufacturing, storing into NVRAM, and confirming the stored LED configuration data.

The data packets used in the intelligent LED pad configuration process are shown in FIG. 17C. In step 1, a LightPadOS LED pad configuration file 206 is sent from PBT controller 110 to the LED pad 120 as payload 294. The packet is identified in packet type 291 as a Setup with hex code |OE| with a filetype 292 of |02-01| together having an instructional meaning "Setup/Configuration/Write LED Configuration File." The payload length 293 varies with LightPadOS LED pad configuration file 206 containing a alphanumeric string comprising payload data 208. In step 2 the configuration file 206 is written and stored in non-volatile memory 125 within intelligent LED pad 120. The stored data when represented in table format contain the information of table 209, shown in abbreviated form describing each wavelength LED string (LED ID), its color, its corresponding wavelength, the number m of series connected LEDs "s" in each string, the number "n" of parallel strings "p" of LEDs for that specific wavelength (color), the total number of LEDs=m·n, and the LED driver gates driving the strings. After successful storage if LED configuration file 206, a reply message data packet 300 is sent from intelligent LED pad 120 to PBT controller 120 comprising packet type 301 of |OE| and filetype 302 of |02-A1| meaning "Setup/Configuration/Confirm LED Setup" has been completed. The payload length 273 is zero and the payload 304 is a zero length null file.

Figure 18A:
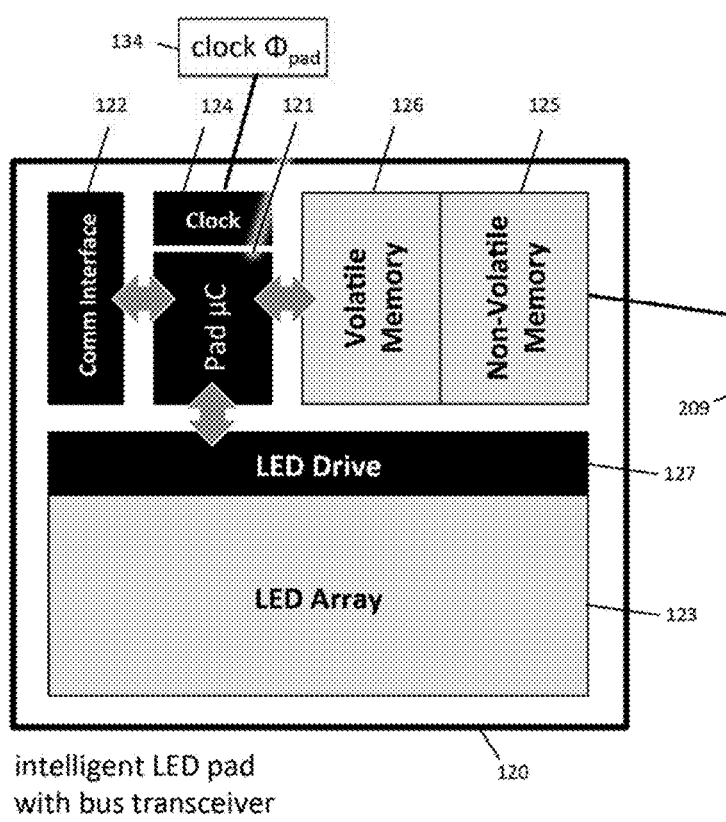
FIG. 18A illustrates a block diagram of an intelligent LED pad with LED configuration register.

As shown in FIG. 18A, the pad's LED configuration information is stored in the intelligent LED pad's non-volatile memory 125 in "LED configuration register" 209, written during the pad's manufacturing process. The register stores the number of LED strings "n" and the specific information description of the LEDs in the string including the LED's wavelength λ and the number "m" of LEDs connected in series in each string. In operation, this LED string information is used for matching a LED treatment to a specific type of intelligent LED pad. For example, treatments designed exclusively for driving red LEDs will not function if an intelligent LED pad containing blue or green LEDs is attached. A user's IU/UX, i.e. menu choices on the PBT controller's touchscreen are adjusted in accordance with the intelligent LED pads connected to the system. If the corresponding intelligent LED pads are not attached, the menu selections requiring that type of pad are hidden or grayed out.

Figure 18B:
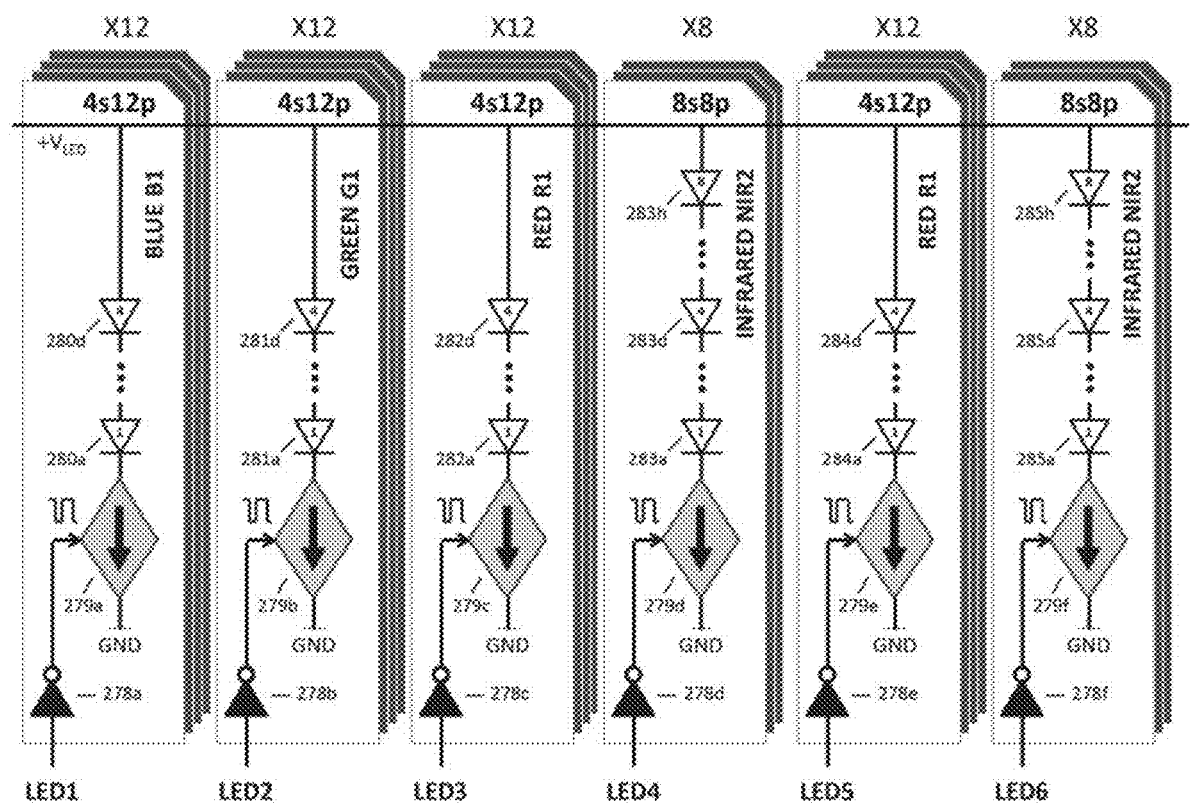
FIG. 18B is an exemplar schematic representation of a four-wavelength an active/intelligent LED pad.

The LED configuration register 209 is essentially a tabular description of an intelligent LED pad's circuit schematic. Referring to an example schematic of FIG. 18B depicting a portion of a intelligent LED pad comprising LED-drivers 278a through 278f; and corresponding current sinks 279a through 279c, driving an array of LEDs having varying numbers of series connected LEDs in each string, whereby String #1 with input signal LED1 represents 1-of-12 parallel strings of blue B1 LEDs comprising four series-connected LEDs 280a through 280d driven by current sink 279a and inverter 278a. With n=12 and m=4, LED1 signal controls a 4s12p array of 48 blue B1 LEDs.

String #2 with input signal LED2 describes 1-of-12 parallel strings of green G1 LEDs comprising four series-connected LEDs 281a through 281d driven by current sink 279b and inverter 278b. With n=12 and m=4, LED2 signal controls a 4s12p array of 48 green G1 LEDs.

String #3 with input signal LED3 describes 1-of-12 parallel strings of red R1 LEDs comprising four series-connected LEDs 282a through 282d driven by current sink 279c and inverter 278c. With n=12 and m=4, LED3 signal controls a 4s12p array of 48 red R1 LEDs.

String #4 with input signal LED4 describes 1-of-8 parallel strings of NIR2 infrared LEDs comprising eight series-connected LEDs 283a thru 283h driven by current sink 279d and inverter 278d. With n=8, m=8, LED4 signal controls an 8s8p array of 64 infrared NIR2 LEDs.

String #5 with input signal LED5 describes 1-of-12 parallel strings of red R1 LEDs comprising four series-connected LEDs 284a through 284d driven by current sink 279e and inverter 278e. With n=12 and m=4, LED5 signal controls a 4s12p array of 48 red R1 LEDs.

String #6 with input signal LED6 describes 1-of-8 parallel strings of NIR2 infrared LEDs comprising eight series-connected LEDs 285a thru 285h driven by current sink 279f and inverter 278f With n=8, m=8, LED6 signal controls an 8s8p array of 64 infrared NIR2 LEDs.

Figure 18C:
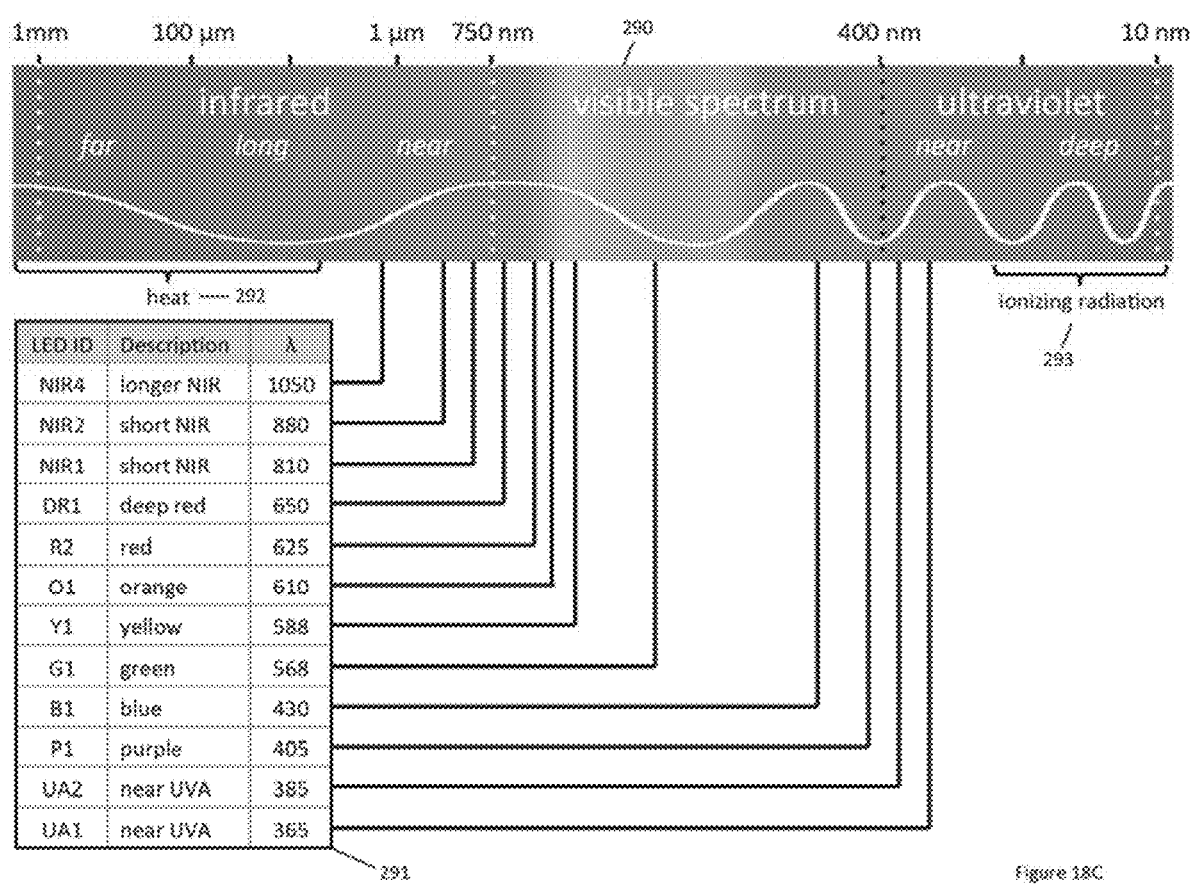
FIG. 18C is a graphical representation of the electromagnetic spectrum illustrating various wavelength LEDs and their communication packet nomenclature.

The foregoing is intended to exemplify without limitation, data formatting of LED configuration register 209 and its corresponding schematic equivalent, not to represent a specific design. In particular the number of LED strings "n" and the number of LEDs connected in series in a given string "m" contained within the intelligent LED pad are likely to exceed the numbers shown in this example. The maximum number of series connected LEDs m depends on the forward voltage of the LEDs. The forward voltage increases with the semiconductor bandgap, and inversely with the wavelength of emitted light. As such, purple light and blue light has the shortest wavelength and the largest forward voltages while infrared light has the longest wavelengths and the lowest forward voltages. The portion of the electromagnetic spectrum 290 ranging from 1 mm infrared to 10 nm ultraviolet light is shown in FIG. 18C. PBT treatment spans the range from wavelengths covering the visible spectrum and extending into the near infrared shorter than heat 292 and extending into UVA with wavelengths longer than ionizing radiation 293. Various wavelengths applicable for PBT are detailed in table 291 ranging from NIR4 at 1050 nm to UA1 at 365 nm.

In practice, the number of LEDs in the various strings may be identical or may differ from string to string. For example, an intelligent LED pad may include 15 strings comprising fourteen LEDs in series, or 210 LEDs. These LEDs are arranged into three groups of five LED-strings each: one-third NIR, one-third red, and one-third blue. Each LED type is configured with 5 parallel strings and 14 series connected LEDs, i.e. three 14s5p arrays.

LED configuration register 209 in FIG. 18A also includes the minimum and maximum operating voltages for the intelligent LED pad. For proper LED operation, the power supply voltage $+V_{LED}$ must exceed the minimum voltage specification $V_{min}$ of the intelligent LED pad to insure uniform illumination, but to avoid damage from excessive voltage or heat the power supply voltage should not exceed the specified maximum voltage $V_{max}$. In other words the value of the supply voltage acceptable for powering the intelligent LED pad must meet the criteria $V_{min} \le +V_{LED} \le V_{max}$. The manufacturer's specified value of $V_{min}$ stored in LED configuration register 209 must on a statistical basis exceed the highest voltage string of LEDs in the intelligent LED pad to insure that so long that the criteria $V_{min} < +V_{LED}$ is maintained, the pad's highest voltage strings will still be fully illuminated in operation. If the $V_{min}$ voltage is specified too low, in some LED pads individual LED strings may be dimmer than others during treatment. Poor brightness uniformity adversely impacts treatment efficacy by limiting a PBT treatment's peak and average power and reducing a treatment's total energy (dose).

The highest voltage string in a LED pad is determined by both design and stochastic voltage variability in LED manufacturing. Each LED string of comprising m series connected LEDs where each LED has its own unique forward conducting voltage $V_{fx}$ where x varies from 1 to m and where the total string voltage is the summation of these individual LED voltages $\Sigma V_{fx}$. The highest voltage could occur in a string comprising a fewer series connected LEDs with higher-voltage or occur in a string comprising a larger number of lower forward voltage LEDs. A LED pad manufacturer must employ statistical sampling data of LED forward voltages on a lot-to-lot basis to insure no LED pad is manufactured with an LED string voltage exceeding the specified value of $V_{min}$.

Albeit less precise, the power supply must be capable of supplying a minimum required average current Irvin to illuminate all the LEDs of a particular color (wavelength) at once. Generally in a two wavelength LED pad, 50% of the n strings of LEDs may be conducting at the same time. While in a three color LED pad, it is likely that only one of the three LED wavelengths will be illuminated at a time to avoid overheating, a worst case assumption of $\frac{2}{3}^{rd}$ or 67% of the n-strings can be used to calculate the maximum current. The peak current in LED conducting in continuous operation will in the worse case not exceed 30 mA per string, i.e. $I_{LED} \leq 30$ mA. Using this worst case assumption, a pad with n=30, $\frac{2}{3}^{rd}$ of the strings illuminated at one time, and with $I_{LED} \leq 30$ mA will require a value of $I_{min} = 30(\frac{2}{3})(30 \text{ mA}) = 600$ mA.

The value of $I_{max}$ specified in LED configuration register 209 is not a description of the maximum current flowing in the LEDs, but a description of maximum safe current at 50% duty factor in the pad's conductive traces. This current includes the current flowing in the LED pad's own LED strings plus any current bussed through the intelligent LED pad to another intelligent LED pad. The specification is included to prevent operating the pad where significant voltage drops occur in the LED pad's power lines resulting in heating, malfunction, electromigration, or metal fusing. One possible design guideline for a LED pad's printed circuit board (PCB) is to utilize copper conductors capable of carrying more than twice its rated current, meaning the pad can safely carry its own current and the current of another LED concurrent. Added design guard band of $\delta$=25% is included as a safety margin. For example, if $I_{min}$=600 mA then using a 25% guard band, $I_{max}=2I_{min}=1(1+\delta)=1500$ mA.

The table also includes the mirror ratio $\alpha$ used to convert the reference current $I_{ref}$ into the LED string current $I_{LED}$ (or vice versa) in accordance with the relation $I_{LED} = \alpha \ I_{ref}$. If different ratios are used for each channel, the table can be modified accordingly to include $\alpha_1, \alpha_2, \alpha_3 \ldots$ whereby $I_{LED1} = \alpha_1 \ I_{ref1}$, $I_{LED2} = \alpha_2 \ I_{ref2}$, and so on. The specific circuitry for realizing current sinks 279a through 279f (or alternatively current sources), is described in a related application "Distributed Photobiomodulation Therapy System And Method," application Ser. No. 16/377,181, filed concurrently with this application. After completing the LED pad setup, the final step in manufacturing is to lock the intelligent LED pad's memory from accidental overwriting or corruption. The data packet used to lock the LED pad is shown in FIG. 19 comprising communication packet 310 set from PBT controller 110 to the intelligent LED pad 120 where packet type 311 has a value |OE| and where filetype 312 has a value |02-FF| executing the instruction "Setup/Configuration/Lock Pad NVRAM." In step 2, the lock pad command 315 is written into non-volatile memory 125. This step concludes the intelligent manufacturing.

In conclusion, manufacturing of intelligent LED pads made in accordance with this invention with numerous features not available in prior art systems, namely:

The ability to employ a communication bus to remotely download a dedicated PBT operating system for LED drive into an intelligent LED pad.

The ability to indelibly store manufacturing identification and LED configurations in non-volatile memory of the intelligent LED pad delivered remotely over a communication bus.

The ability to restrict access of manufacturing operations to authorized users.

The ability for a PBT controller to retrieve manufacturing and LED configuration data from an intelligent LED pad remotely over a communication bus.

A remotely programmed intelligent LED pad capable of performing PBT treatments in response to commands sent over a communication bus.

Connecting Intelligent LED Pads

Figure 20:
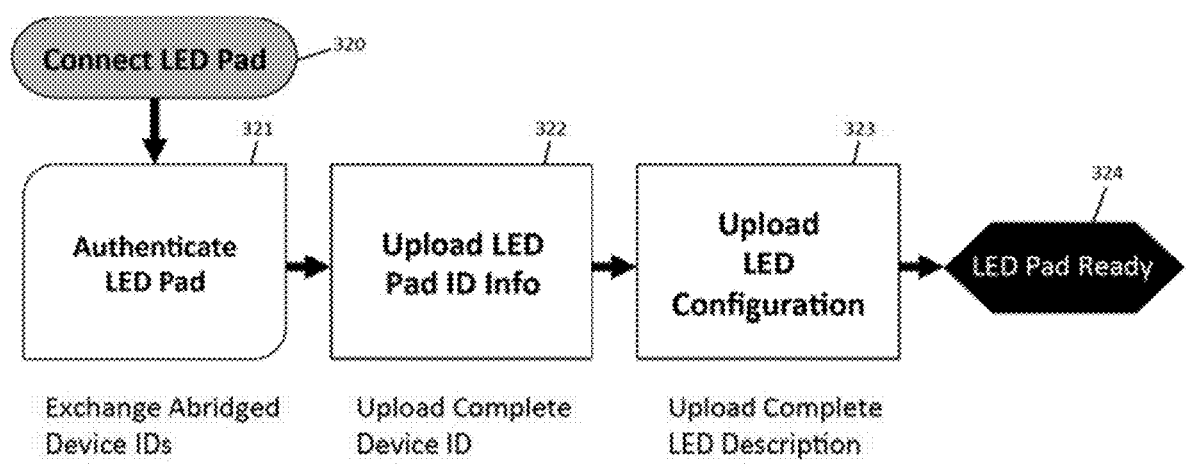
FIG. 20 is a flow chart representation of an intelligent LED pad to PBT controller connection procedure.

Before a PBT treatment can be performed, an intelligent LED pad must first be connected to the PBT controller, i.e. the intelligent LED pad must join the network. The intelligent LED pad connection process 320 is graphically illustrated in FIG. 20 where in step 321 the PBT controller 110 authenticates the intelligent LED pad 120 and the devices exchange device ID data. The authentication can be executed as a Layer-5 process, or using the device ID data as a Layer-7 authentication, or both. Although less convenient, additional authentications may also be executed using Layer-4 or Layer-6 verification mechanisms. After authentication, in step 322 the complete LED pad manufacturing ID data file is uploaded to PBT controller 110, followed by uploading the pad's LED configuration in step 333. Thereafter the intelligent LED is ready for operation 324.

The connection process is shown in greater detail in FIG. 21 where the role of the LightOS operating system PBT controller 110 and the concurrent role of the LightPadOS operating system in intelligent LED pad 120 during the LED pad installation process are both detailed. The process is initiated when the two devices connect. In the case of USB, Ethernet, or DOCSIS-3 (cable), the detection of the LED pad connect 350 occurs when the plug and socket are electrically connected. In addition to data rate and communication protocols, such wireline connections involve a device-to-device handshaking dialog regarding power delivery. In the case of WiFi (802.11) or telephony (3G-LTE/4G/5G) the handshaking involves only radio connectivity and security protocols. Except for very short distances, power supplied wirelessly using radios (as originally proposed by Tesla) violates FCC regulations and is forbidden in most nations.

In the sequence from step 351a to begin LED pad installations through 357a ending the process, the LightOS operating system in PBT controller 110 acts as a host to a newly connected intelligent LED pad. This process parallels the handshaking steps 351b through 357b occurring within the LightPadOS operating system running within intelligent LED pad 120. In step 352*a*, the PBT controller 110 identifies and qualifies the connected LED pad 120 as a valid client suitable to receive power from the PBT host. This process involves bidirectional communication 358 and 359 between the devices. For wireline communication, this operation involves a safety check step 352*b* where the intelligent LED pad accepts the PBT controller as a source of logic power at 5-V and where in step 352*a* the PBT controller accepts the intelligent LED pad as an electrical load able to draw power from its 5-V host. If the LED pad is already powered, i.e. if it already has power being delivered to it from another power supply, then the PBT controller will send only data to the pad but disable its power delivery. After the power connection is resolved, in step 353*a* and 353*b* entitled "negotiate comm. protocol" the devices negotiate the data rate and establish a connection and set the maximum valid data rate. This data rate depends entirely on the PHY Layer-1 and Data Link Layer-2 hardware and protocol.

In steps 354*a* and 354*b*, the PBT controller and intelligent LED pad go through a handshaking process where each device authenticates the other. This authentication process can occur in several ways. In one method the authentication occurs as part of a Session Layer-5 transaction wherein PBT controller 110 and intelligent LED pad 120 exchange security credentials to establish a semi-permanent link prior to initiating communication. Thereafter, establishing an application level connection involving a simple dialog shown in FIG. 22, where in step-1, LightOS communication packet 370 sent from intelligent LED pad 120 having packet type 371 and filetype 372 comprises the hex message |0E-03-01| meaning "system message/connection/request to connect device." Based on the Session Layer-5 authentication, PBT controller 110 responds with communication packet 380 sent to intelligent LED pad 120 having packet type 381 and filetype 382 comprises the hex message |0E-03-05| meaning "system message/connection/connection confirmed."

Figure 23:
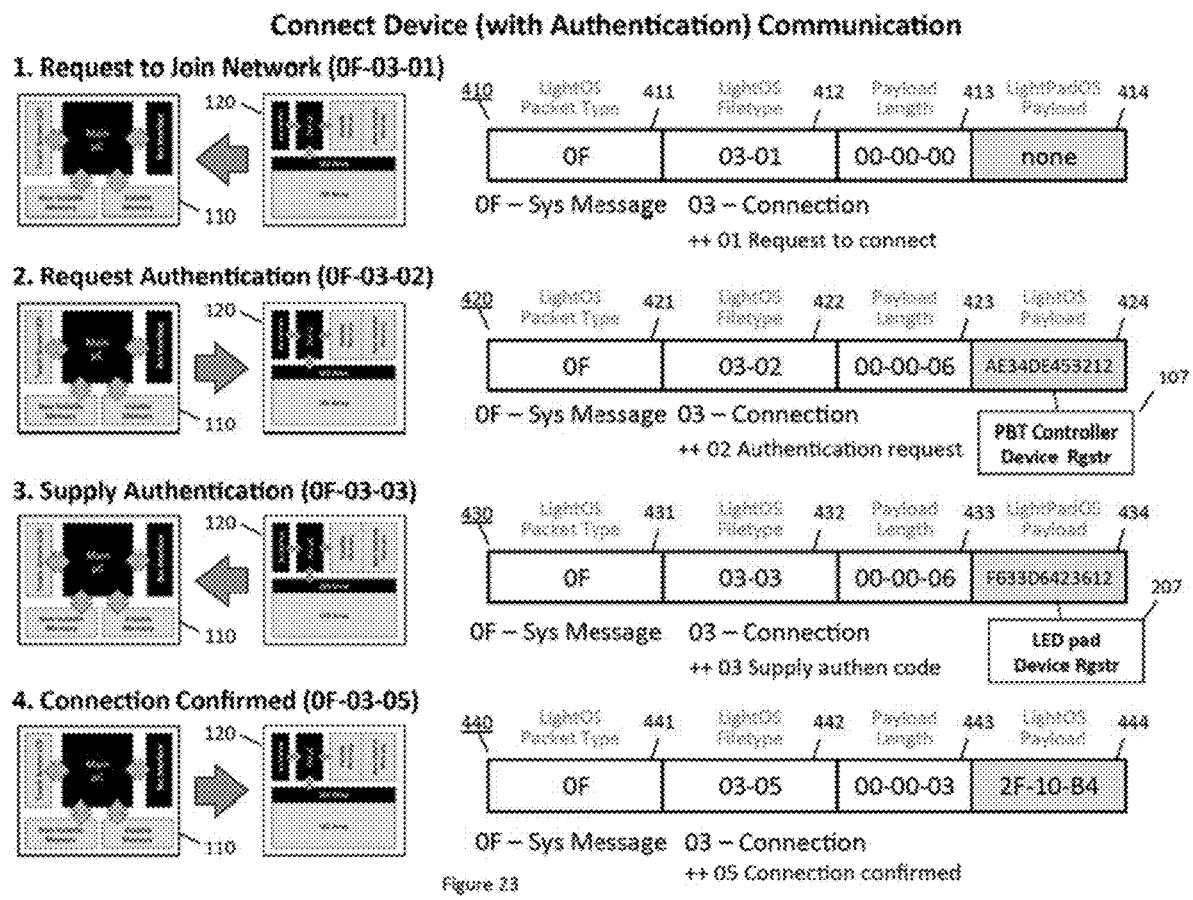
FIG. 23 illustrates data packet communication for connecting a device to the PBT controller's communication network (including authentication) and subsequently confirming the authentication and connection.

Should, Layer-7 authentication be required, the procedure shown in FIG. 23 is executed. In step-1, intelligent LED pad 120 requests to join the PBT controller 110 network with LightOS communication packet 410 having packet type 411 and filetype 412 comprises the hex message |0E-03-01| meaning "system message/connection/request to connect device." To request a Layer-7 authentication code, in step-2 PBT controller 110 responds with LightOS communication packet 420 having packet type 421 and filetype 422 comprises the hex message |0E-03-02| meaning "system message/connection/authentication request." The message includes payload 424 having a payload length 423 of |00-00-06| and content comprising PBT controller ID 107*a*, a subset of PCB identity data register 107.

In step 3, LED pad 120 then complies with the authentication request with LightOS communication packet 430 having packet type 431 and filetype 432 comprises the hex message |0E-03-03| meaning "system message/connection/supply authentication code." The message includes payload 434 having a payload length 433 of |00-00-06| and content comprising LED pad ID 207*a*, a subset of PCB identity data register 207 used to authenticate communication. In step-4 PBT controller 110 responds with communication packet 440 having packet type 441 and filetype 442 comprises the hex message |0E-03-05| meaning "system message/connection/connection confirmed." The message includes payload 444 having a payload length 423 of |00-00-03| and content comprising an authentication code, e.g. |2F-10-84|. This code can be used in subsequent communications to insure that the communicating devices are authorized to exchange commands and data.

Referring to FIG. 21 in 356*b* LED pad 120 sends LED pad manufacturing data and LED configuration data information to PBT controller 110. In turn PBT controller 110 analyzes LED pad configuration data 209. This process is shown in FIG. 24, where in step 1, PBT controller requests LED pad ID with LightOS communication packet 450 having packet type 451 and filetype 452 comprising the hex message |0E-01-01| meaning "system message/OS firmware/request pad ID." The message includes a null payload 454 having a payload length 453 of |00-00-00|. In step 2, LED pad 120 then complies with the ID information request with LightOS communication packet 430 having packet type 431 and filetype 432 comprises the hex message |0E-01-02| meaning "system message/OS firmware/send pad ID." The message includes a payload 464 having a variable payload length 463 containing LightPadOS payload 205 containing manufacturing data 207. Once uploaded, this data can be loaded into a table for display 467.

Figure 25:
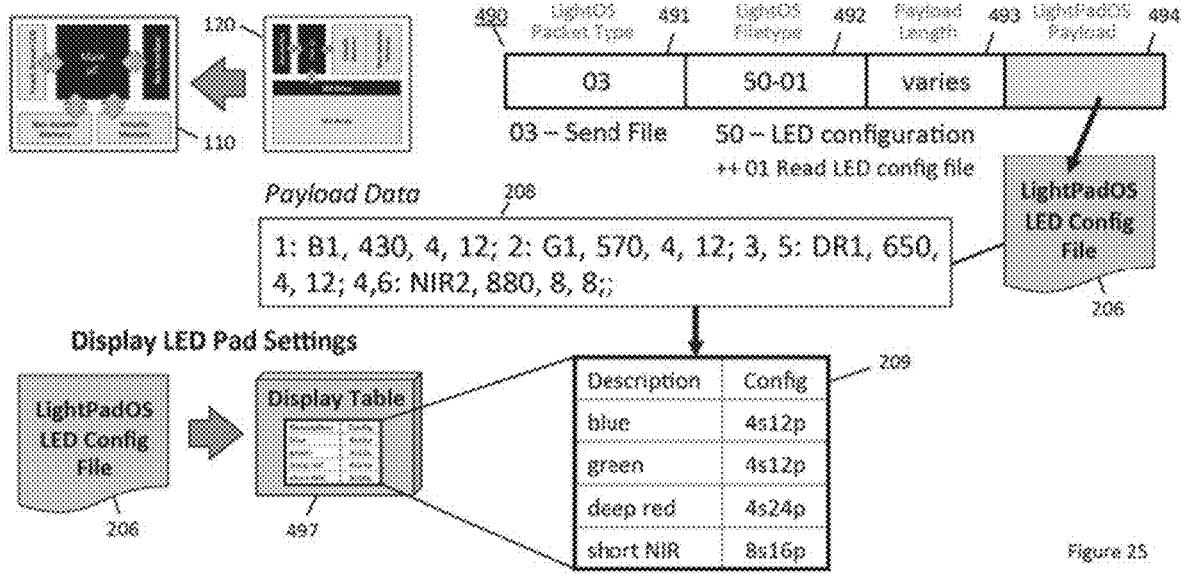
FIG. 25 illustrates data packet communication for requesting, receiving, and displaying an intelligent LED pad's LED configuration data.

This process is shown in FIG. 25, where in step 1, PBT controller requests LED configuration with LightOS communication packet 480 having packet type 481 and filetype 482 comprising the hex message |03-50-01| meaning, "request file/LED configuration/request LED config file." The message includes a null payload 484 having a payload length 483 of |00-00-00|. In step 2, LED pad 120 then complies with the ID information request with LightOS communication packet 490 having packet type 491 and filetype 492 comprises the hex message |03-50-01| meaning "send file/LED configuration/read LED config file." The message includes a payload 464 having a variable payload length 493 containing LightPadOS payload 206 containing LED configuration data 208. Once uploaded, this data can be loaded into a table for display 497.

Referring again to FIG. 21, in the final step 356*a*, PBT controller 110 send a message to LED pad 120 that the voltage of the LED supply is ready to be biased at a high voltage $+V_{LED}$, and in step 356*b* the LED pad accept the high voltage, by enabling a connection to the high voltage supply line. At this stage, the processes to end LED pad installation 367*a* and 367*b* are complete and the LED pads are ready to perform treatments.

Performing PBT Treatments

Performing a PBT treatment using the distributed PBT system made in accordance with this invention can be executed in two ways, either using LED streaming playback of data or using a LED playback file to execute a treatment. For the purpose of PBT treatments, streaming playback is a method where content is supplied before it is needed for execution (meaning playback commences before the full execution file is transferred). Streaming playback is not, however, real time LED drive waveforms like that of passive LED pad based, but simply portions of a file that are transferred piecemeal as the program executes. Moreover, in streaming playback, the file is executable, meaning program execution creates the driving waveforms for the LEDs without additional software. In contrast, file based playback means the entire file is loaded before playback of a treatment or session commences. Moreover, PBT playback files comprise non-executable files that can only be executed in conjunction with a LED player, which must be installed into an intelligent LED pad prior to program execution.

Figure 26:
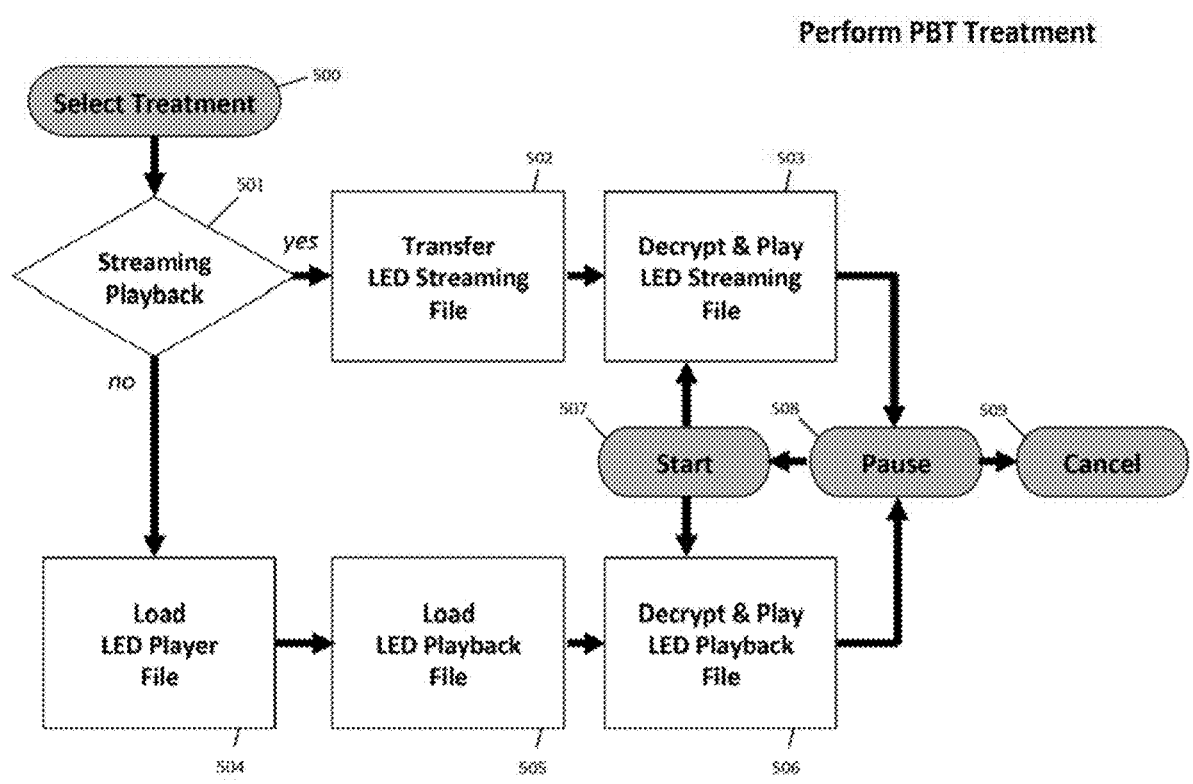
FIG. 26 is a flow chart depicting LED pad playback of streaming and playback files.

The flowchart of FIG. 26 commences with the step Select Treatment 500 after which test 501 determines whether the treatment is to be executed as a streaming file or using a playback file. If the program comprises a streaming file the streaming file is transferred in step 502 then upon a start command 507 the file is decrypted and executed 503 performing a PBT treatment. If the treatment is suspended by the Pause 508 command, program execution is stopped until the user selects either Start 507 resuming playback from where the treatment was last paused, or terminated by the Cancel 509 command. If test 501 is negative, i.e. is the PBT treatment is not a streaming file, then LED player 504 is first loaded into RAM followed by loading the LED playback file 505. Upon a start command 507 the file is decrypted and executed 506 performing a PBT treatment by executing the LED player file in accordance with LED playback file 505. If the treatment is suspended by the Pause 508 command, program execution is stopped until the user selects either Start 507 resuming playback from where the treatment was last paused, or terminated by the Cancel 509 command.

Figure 27A:
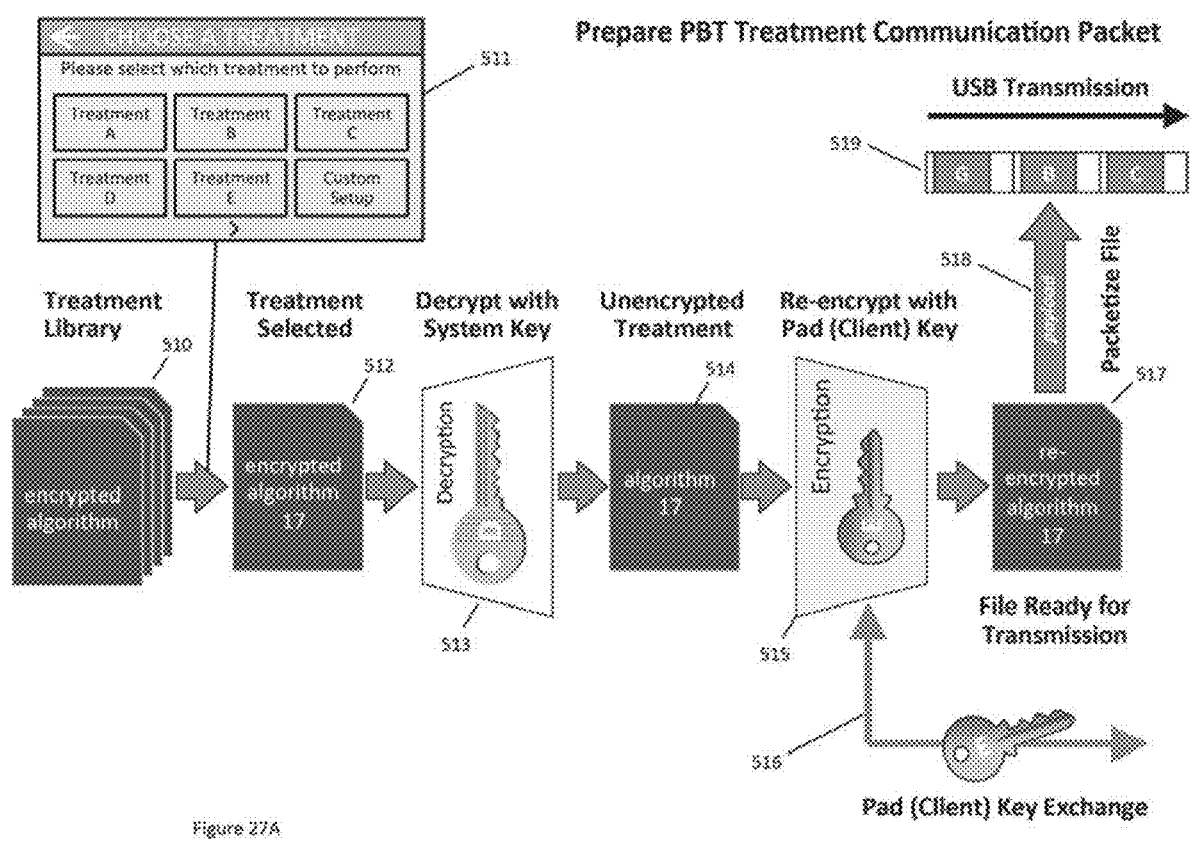
FIG. 27A illustrates encrypted packet preparation of PBT treatment file.

The role of encryption and decryption in either streaming or file-based treatments is an important security feature of the disclosed PBT system. The process for preparing, communicating, and executing an encrypted treatment is represented schematically in FIG. 27A, where through a graphical UI 511, a user chooses a treatment 512 from a library encrypted algorithms 510. Encrypted algorithm 17 is then decrypted 513 using the system key converting ciphertext into plaintext and restoring unencrypted treatment 514. In encryption process 515 the plaintext file of algorithm 17 is re-encrypted using encryption key 516 exchanged with the intelligent LED pad client. The resulting ciphertext 517 comprising re-encrypted algorithm 17 is then packetized 518 and transmitted 519 using USB or another appropriate communication medium.

Figure 27B:
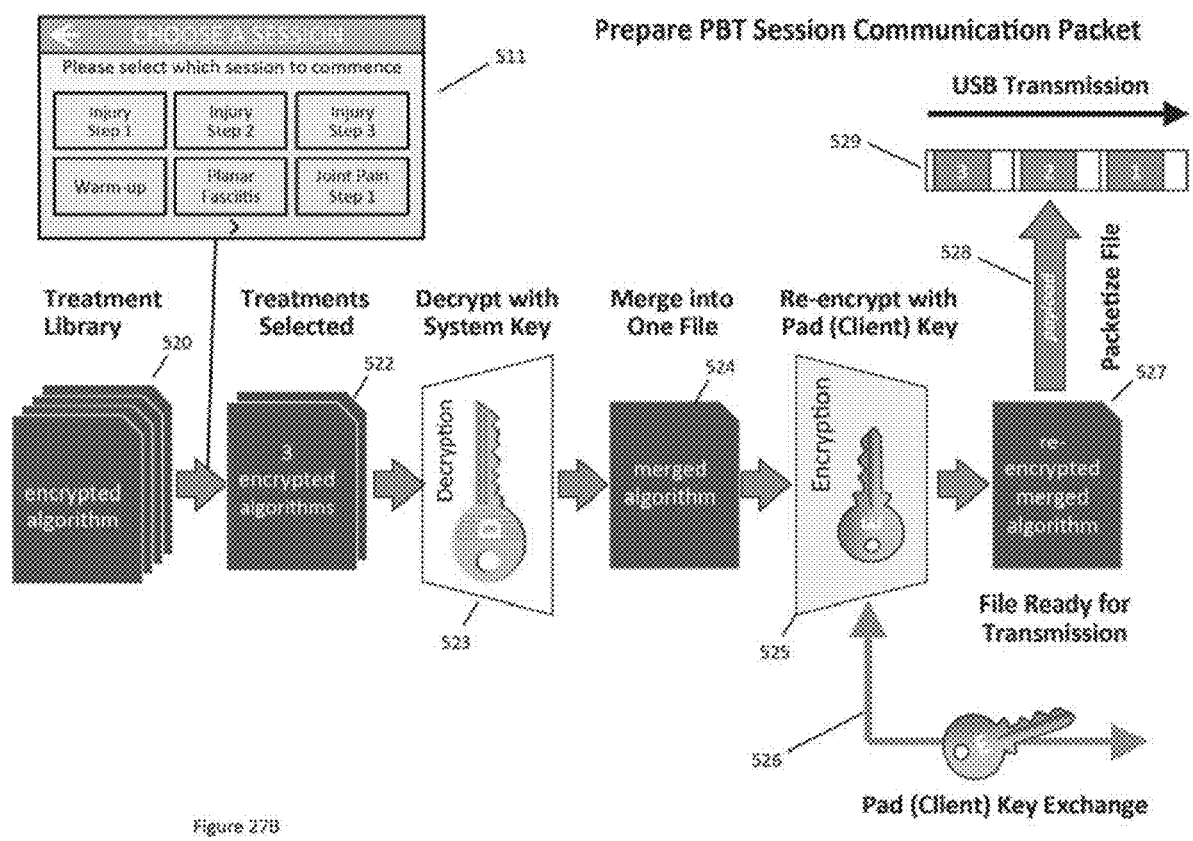
FIG. 27B illustrates encrypted packet preparation of PBT session file.

In addition to treatment data, the same method can be used to prepare and transfer PBT session data from the PBT controller to the intelligent LED pad. This process is shown in the schematic of FIG. 27B where through a graphical UI 511, a user chooses a set of treatments 522 selected from a library of encrypted algorithms 520 (in the example shown comprising three encrypted algorithms) in order to construct a multi-treatment session. Using the system encryption key, the ciphertext of each selected treatment is then decrypted 523 converting ciphertext into plaintext. The three plaintext files are then combined into one merged algorithm, comprising session file 524. Plaintext session file 524 is then encrypted 525 using encryption key 526 exchanged with the intelligent LED pad client. The resulting ciphertext 527 comprising the encrypted merged algorithm is then packetized 528 and transmitted 529 using USB, Ethernet, WiFi or another appropriate communication medium.

Figure 28:
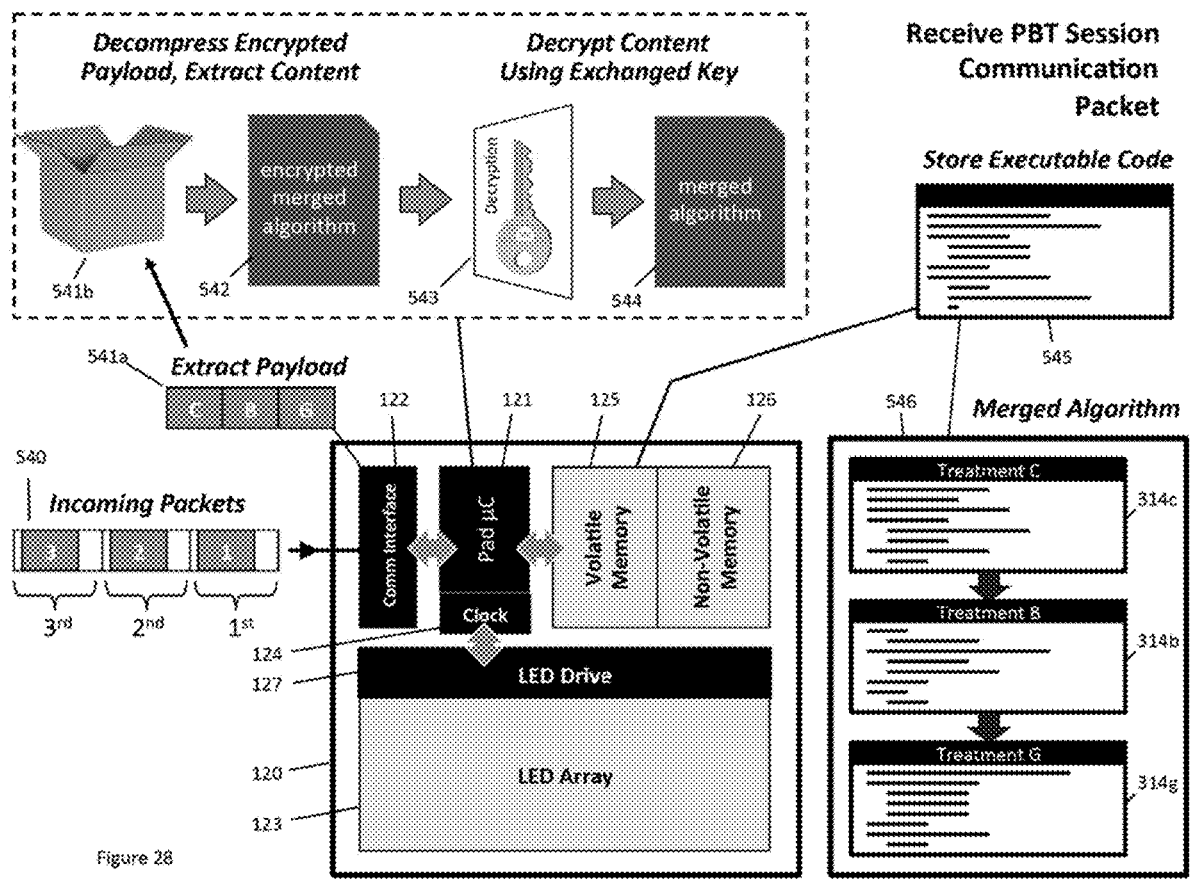
FIG. 28 illustrates active LED pad decryption and storage of incoming encrypted packet.

As shown in FIG. 28, incoming data packets 540 received by bus interface 122 in intelligent LED pad 120 are first processed to remove packet headers extracting payload 541a which is passed into Pad µC 121 as payload 541b. Pad µC 121 then decompresses payload 541b to extract encrypted merged algorithm 362. The ciphertext is then decrypted 543 using the key exchange to extract plaintext file 544 comprising the treatment algorithm or in the cases of a session file, the merged algorithm. The algorithm or merged algorithm 546 contained within executable code 545 is then stored by writing it into volatile memory 125. Since the treatment is saved in RAM, any interruption in power will erase the file, making copying of the unencrypted executable code difficult. Because the complete file is not encrypted, it is vulnerable to attack and should not be saved in non-volatile memory.

Figure 29A:
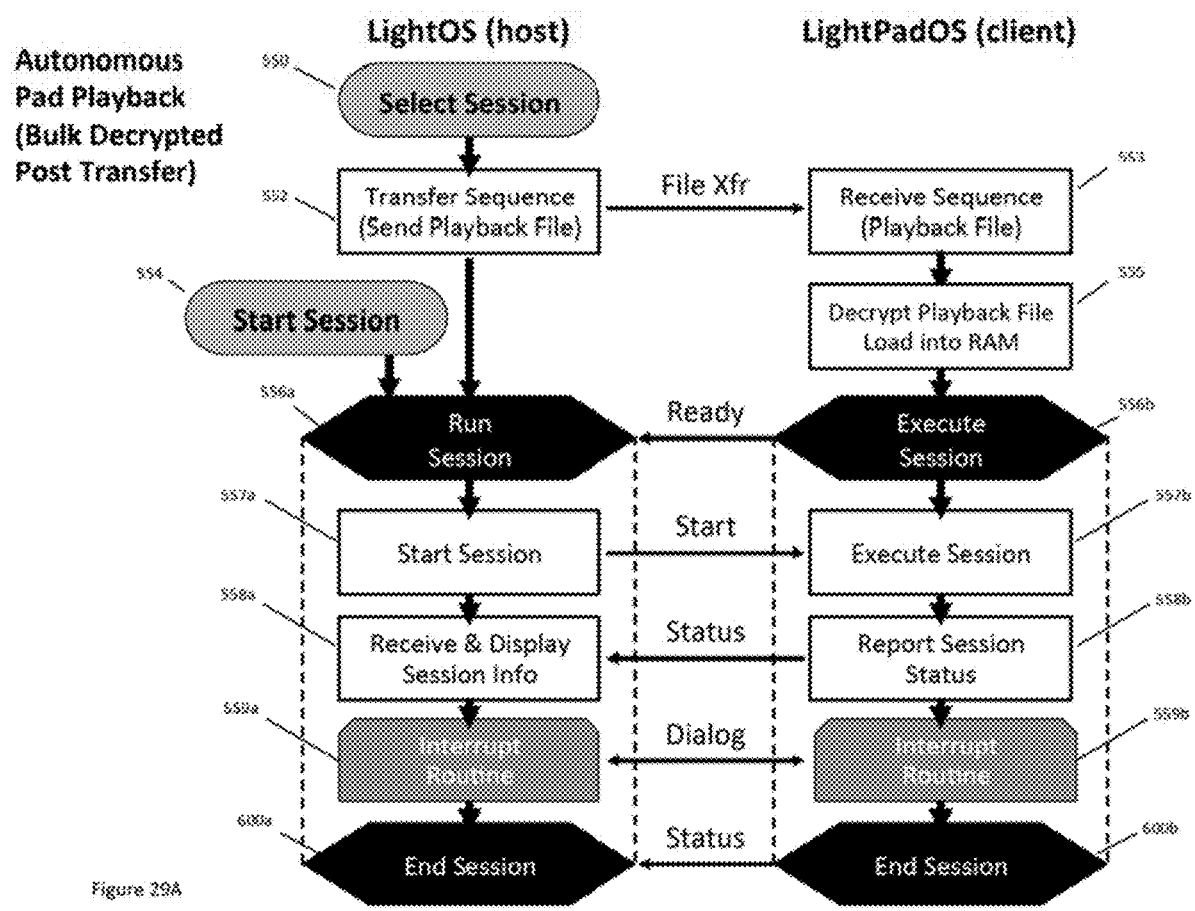
FIG. 29A is a flow chart of LED pad autonomous pad playback using post transfer file decryption.

As shown in FIG. 29A, autonomous pad playback of the PBT sequence with post transfer (pre-playback) bulk decryption involves user selection of the session 550 transferring 552 the encrypted file which once received 553 by the intelligent LED pad is decrypted 555 and loaded into RAM. In step 556b the LightPadOS informs the host PBT controller it is ready to commence the session. Once the user confirms they are ready by selecting the start treatment button 554 then in steps 556a the run session instruction is enabled starting in step 557a where the start session command is sent to the intelligent LED pad. LightPadOS responds in step 557b by commencing treatment by executing exemplar treatment algorithm 314. As the treatment progresses, the intelligent LED pad occasionally reports its status 558b to the host PBT controller including time, temperature, or other relevant programs status information, and which PBT controller may used to display in step 558a. Should a fault condition occur in the intelligent LED pad, then interrupt service routine 559b in LightPadOS and 559a in LightOS communicate and possibly negotiate what is to be done about the condition causing the interrupt. Once the fault is corrected the interrupt routine is closed and treatment resumes until in step 600b the intelligent LED pad informs the host PBT controller that the treatment program has been completed. In response, in end session step 600a, the PBT controller informs the user the session or treatment has been completed.

Figure 29B:
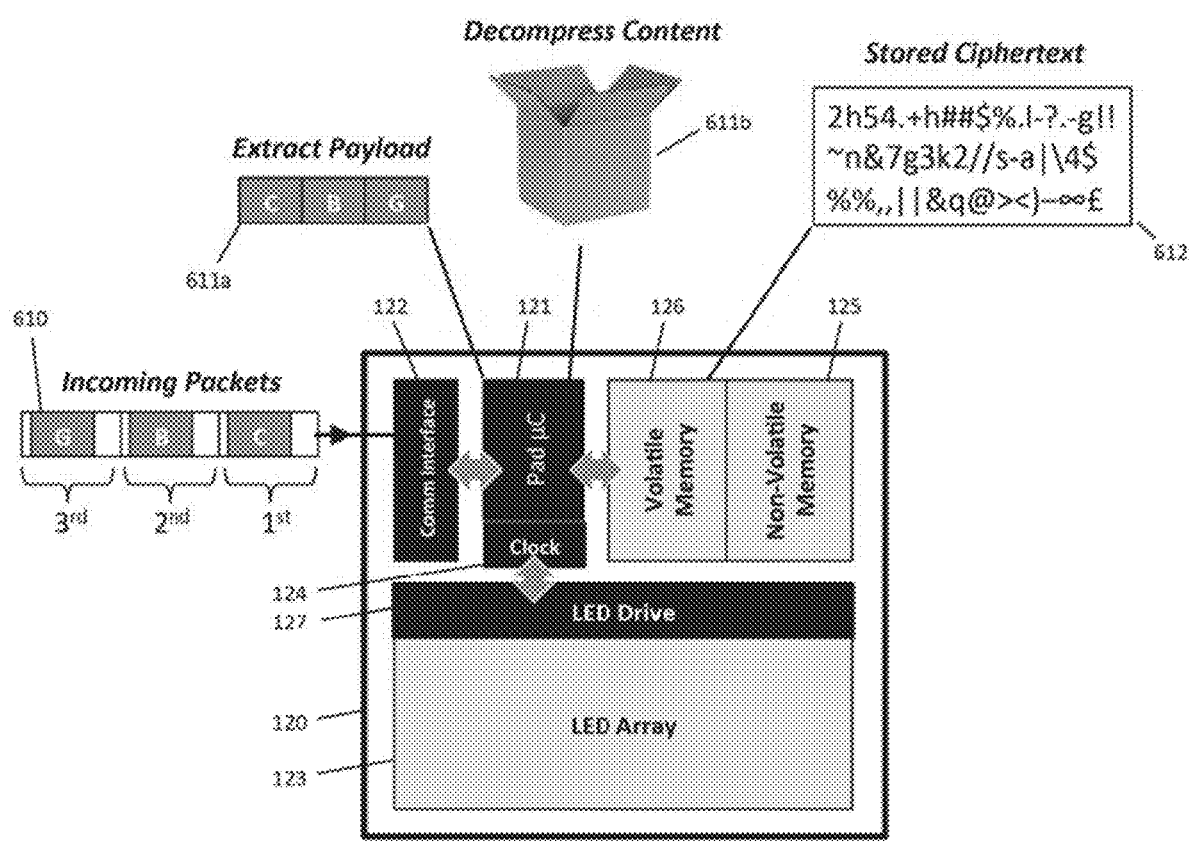
FIG. 29B illustrates ciphertext file storage in active LED pad.

Even greater security can be achieved by storing the algorithm in the intelligent LED pad in its encrypted form. As shown in FIG. 29B, incoming packets 610 received by bus interface 122 in intelligent LED pad 120 are processed to extract payload 611a, subsequently decompressed 611b, and then stored as ciphertext 612 in volatile memory 126. The file is played at the time the user starts the session by decrypting the file during playback as the file is executed, i.e. during autonomous playback. This process, known as "on the fly" decrypted playback, is illustrated in the flow chart of FIG. 30. The process is identical to that of bulk decrypted process flow shown in FIG. 29A except that after intelligent LED pad receives the sequence file 623 the next step is simply to unpack and as needed decompress the file 625 but not to decrypt it. During playback in step 629b, the ciphertext is read from volatile memory, e.g. SRAM, and decrypted on the fly, i.e. as playback proceeds.

Figure 31A:
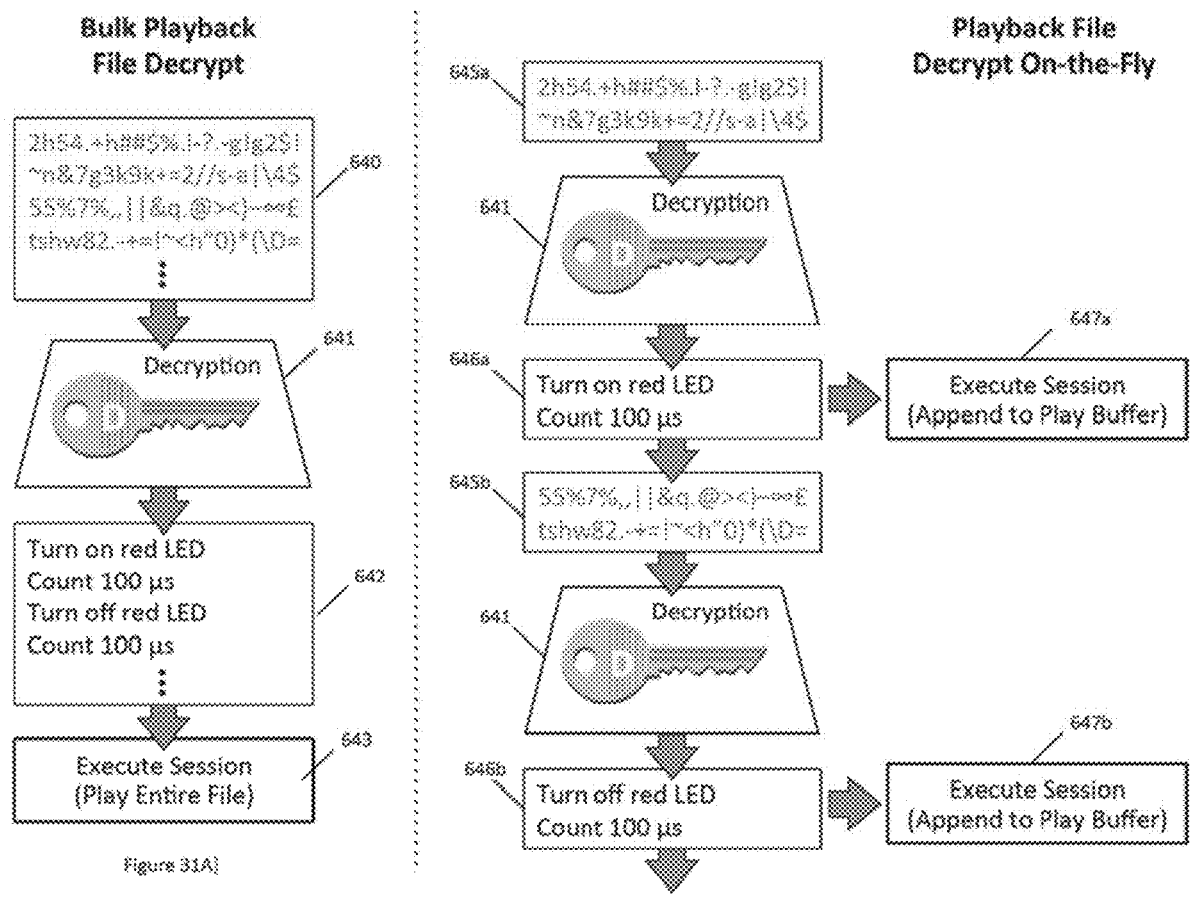
FIG. 31A is a file comparison of pre-playback bulk file decryption and on-the fly decryption during playback
Figure 31B:
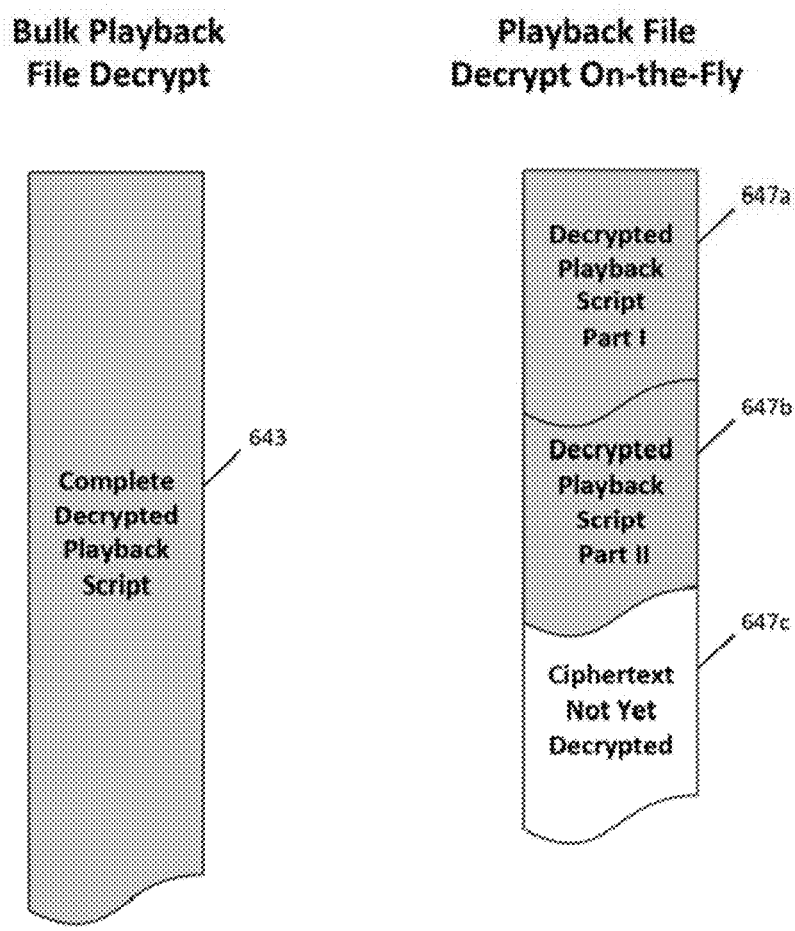
FIG. 31B is a comparison of bulk playback and decrypt on-the-fly playback streaming files.

FIG. 31A contrasts bulk discount and on the fly playback methods. In a bulk decryption, the entire playback file 640 stored in ciphertext is read from volatile memory, decrypted 641 to extract the plaintext instruction set 642 then executed to playback 643 the entire file. By contrast in decrypt on the fly playback, a portion 645a of the stored playback file is read and decrypted 641 then executed 646a by appending the new plaintext instructions to the play buffer 647a. In the meantime another section of the ciphertext 645b is read from the volatile memory, decrypted 641 to recover the plaintext executable files 646b, then executed 647b by appending this file onto the end of the playlist. The resulting streaming file comparing bulk decryption and on-the-fly encryption is graphically illustrated on FIG. 31B where in bulk decryption the complete file is decrypted before playback 643, in on-the-fly decryption, the file is decrypted in pieces as playback occurs with each new piece of content appended onto the ended of the playback file. For example, Part I of the playback content is decrypted 647a, followed by Part II content 647b, which is appended onto the end of the file 647a. Playback content 647c, not yet decrypted, will eventually be appended onto the end of 647b. In this disclosure, bulk decryption and on-the-fly decryption are independent from the concepts of streaming and file based playback. In fact all four combinations can be implemented. For streaming, executable files are sent from the PBT controller to the LED "just-in-time" (JIT) and appended onto the playback file as they arrive. In streaming PBT treatments, if the files are decrypted and appended onto the playback script as they arrive, that method is equivalent to bulk decryption, meaning that all the script content that has already arrived resides in the intelligent LED pad in decrypted form. Script 643 may not have been fully received yet but everything that has been received has been decrypted. If, however, during streaming, the files are stored in encrypted form and decrypted just prior to execution, the streaming content represents on-the-fly decryption. In a similar manner, if a playback file is received by a intelligent LED pad in encrypted form, then decrypted and stored in its entirety the process represents bulk decryption. Conversely, if the received playback file is stored in its encrypted form then decrypted just as it is required, playback employs on-the-fly decryption. Differences among the disclosed methods are summarized in the following table:

| Content Delivery | Bulk Decryption | On-the-Fly Decryption |
| --- | --- | --- |
| JIT Streaming Content (Executable Code) | Executable code decrypted upon arrival and appended onto script | Executable code stored upon arrival and decrypted just before use |
| Playback File (Requires Player) | File received, decrypted, and stored in decrypted form | File received and stored in encrypted form then decrypted just before use |

One important distinction in the disclosed methods of secure playback is that streaming content represents executable code while the playback file does not. So the advantage of JIT streaming files is they are self sufficient, able to be executed in a LightPadOS enabled intelligent LED pad with no additional code installations. Their disadvantage is that they must carry all the extra code for executing playback within every streaming file. In contrast, playback files cannot be executed on their own but require installation of a LED prior to PBT treatment execution. The LED player file is delivered in encrypted form, bulk decrypted and stored in volatile memory. The encrypted playback is delivered thereafter and may be executed using either bulk or on-the-fly decryption during playback.

The disadvantage of the LED playback file is it requires a two-step process, i.e. to install the LED player and then load the LED playback file, before the first PBT treatment can commence. Its advantage is that once the LED player is loaded, new playback files can be downloaded and executed quickly with reloading the player file and without the executable code overhead of a streaming file. The distributed PBT system disclosed herein is able to remotely operate using all the foregoing playback options for driving one or more intelligent LED pads over a communication bus (such as USB, Lightening, I²C, DDMI) or via a packet switched network (such as Ethernet, WiFi, 3G/LTE, 4G/5G, and DOCSIS3).

Figure 32:
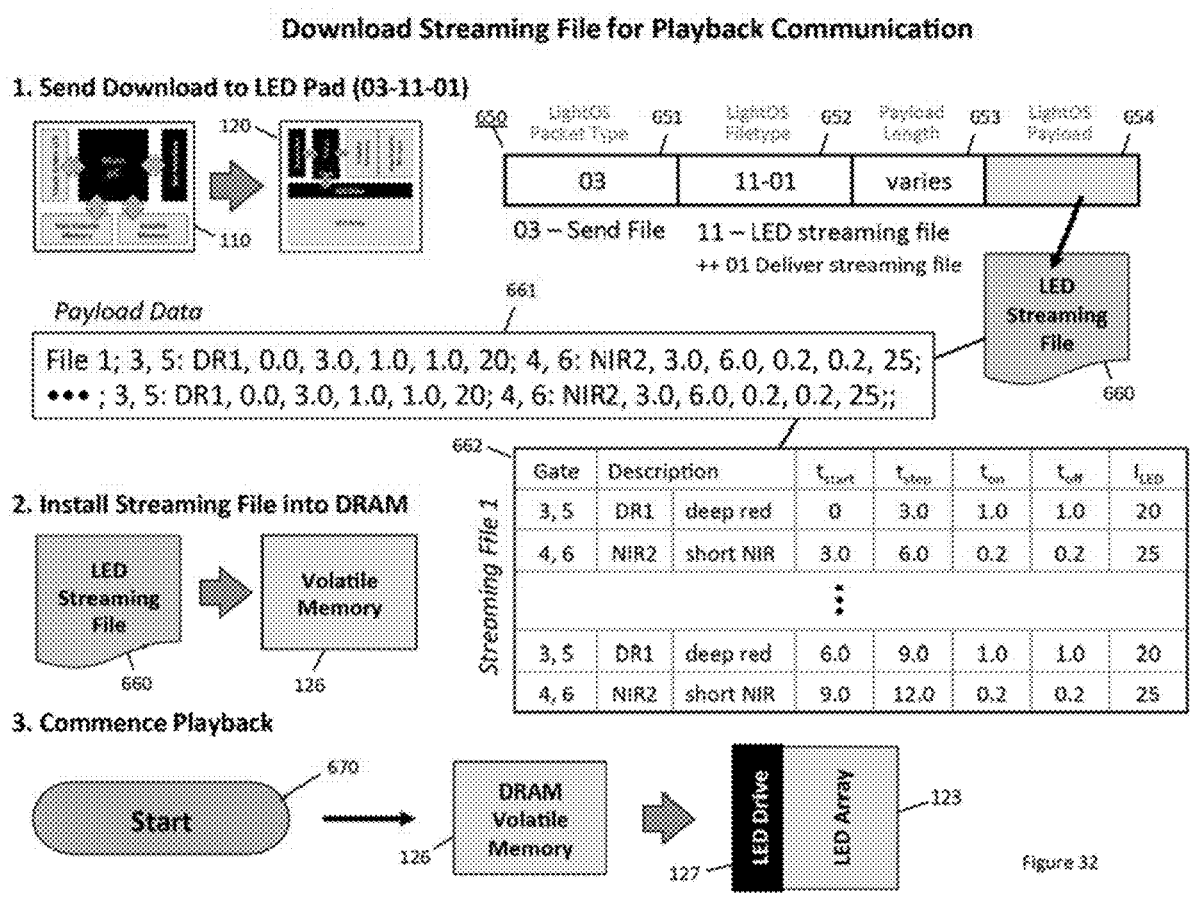
FIG. 32 illustrates data packet communication for downloading and installing a playback streaming file into a LED pad's volatile memory.

An exemplar communication data packet used in the downloading a streaming file for playback is shown in FIG. 32. In step 1, LED-streaming file 650 is sent from PBT controller 110 to the intelligent LED pad 120 containing payload 660 with embedded payload data 661. The packet is identified in packet type 651 as "send file" with hex code |03| with a filetype 652 of |11-01| together having an instructional meaning "Send File/LED Streaming File/Deliver Streaming File." Because treatments vary in length and complexity, payload length 653 varies in accordance with size of LED streaming files 660. In step 2, LED streaming files received 660 are stored into volatile memory 126. As shown in step 3, playback commences upon the start command 670 when the streaming file stored in volatile memory 126 is executed by pad µC 121 and used to instruct LED 127 to produce PBT illumination waveforms in LED array 32. Operation of the start command 670 is described later in this application and will not be repeated here.

Figure 33:
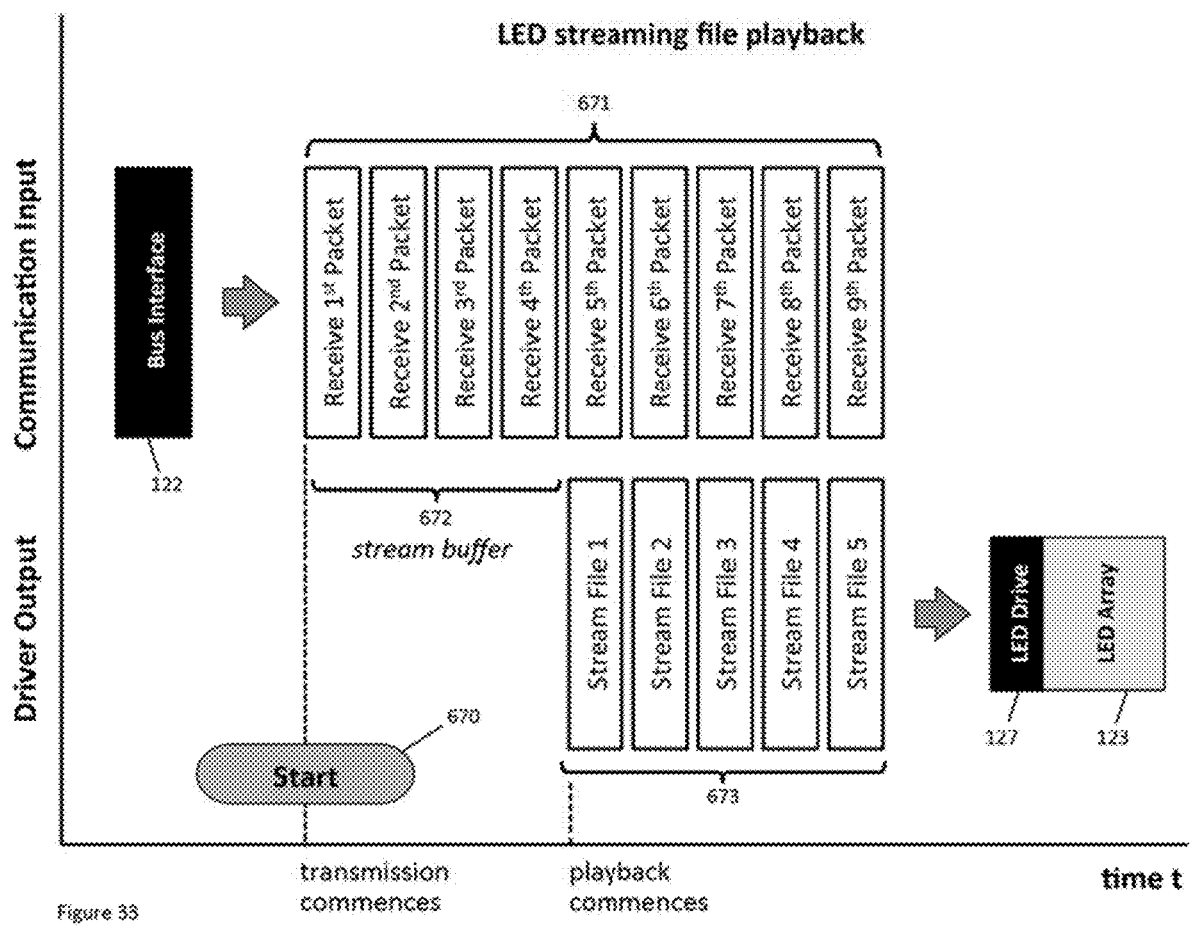
FIG. 33 illustrates LED streaming file playback with stream buffer.

Ignoring the implementation of bulk versus on-the-fly decryption, as described streaming involves two processes—one for receiving data over a communication bus, the other for playing, i.e. executing, the received executable file's program. This process is depicted graphically in a time-based flow chart in FIG. 33 separately identifying operation of the communication and the LED driver output. As shown, bus interface receives sequential data packets 671, the transmission and data transfer process generally starting upon Start instruction 670. Playback of stream files 673, the stored (and possibly converted) version of the incoming sequential data packets 671 driving LED driver 127 and LED array 123, occurs at a later time than the communication. The delay between communication and LED drive, the delay for stream buffer 672, is required to provide time for unpacking the communication packets and for decrypting the packet content to create the stream files 673. Without sufficient stream buffer 672, program execution could halt and the efficacy of the PBT treatment could be adversely impacted.

Considering the overhead of using streaming files with hard coded executable code, the use of playback files is a far more efficient method of intelligent LED pad control, possibly requiring as little as 5% to 10% of the streaming file to execute. The caveat of using LED playback files is that prior to executing the first playback file, executable code for the LED player must first be downloaded into the intelligent LED pad. Although the LED player can be downloaded and permanently stored in the intelligent LED pad, storing the player's executable code in non-volatile memory within the intelligent LED pad raises the cost of the intelligent LED pad and increases the risk of hackers breaking the encryption and cracking the LightPadOS code. So for economic and security reasons it is beneficial to download the LED player into a pad's volatile memory because DRAM or SRAM is much cheaper than E²PROM or flash NVRAM and because any interruption in power will result in loss of the stored player file rendering hacking difficult.

An exemplar communication data packet used in the downloading the LED player file from PBT controller 110 to the intelligent LED pad 120 is shown in FIG. 34. In step 1, LED player file 680 is sent containing payload 684 with embedded LED player file 690 comprising payload data 691 containing the LED player version number and executable code for LED driver, PWM player, and waveform synthesizer functions. The packet is identified in packet type 681 as Send File with hex code |03| with a filetype 682 of |12-02| together having an instructional meaning "Send File/LED Player File/Deliver Player File." Treatments vary in length and complexity, and as such payload length 683 varies in accordance with size of LED streaming files 690. In step 2, LED player 690 is installed in unencrypted form into volatile memory 126. Because the installed LED player 690 includes many branches and conditionals the executable code is non-planar and non-linear and therefore cannot be executed sequentially or decrypted "on-the-fly" as a playback or streaming file can. As such the entire LED player file 690 is bulk decrypted and stored in volatile memory 126 in unencrypted form. The installed executable code includes three separate software modules, namely waveform synthesizer 693, PWM player 694, and LED player 695.

LED Player Operation

Figure 35A:
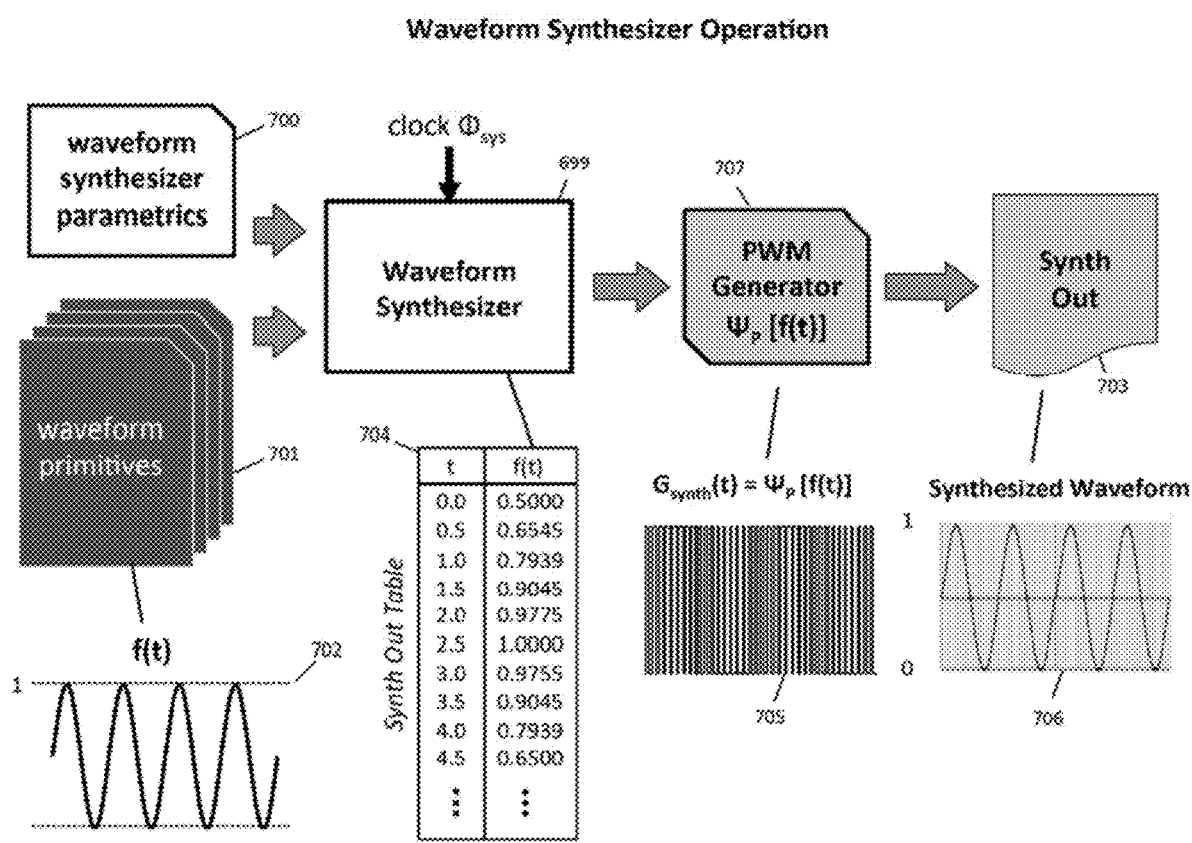
FIG. 35A is a flow chart describing the operation of "waveform synthesizer" module.
Figure 358:
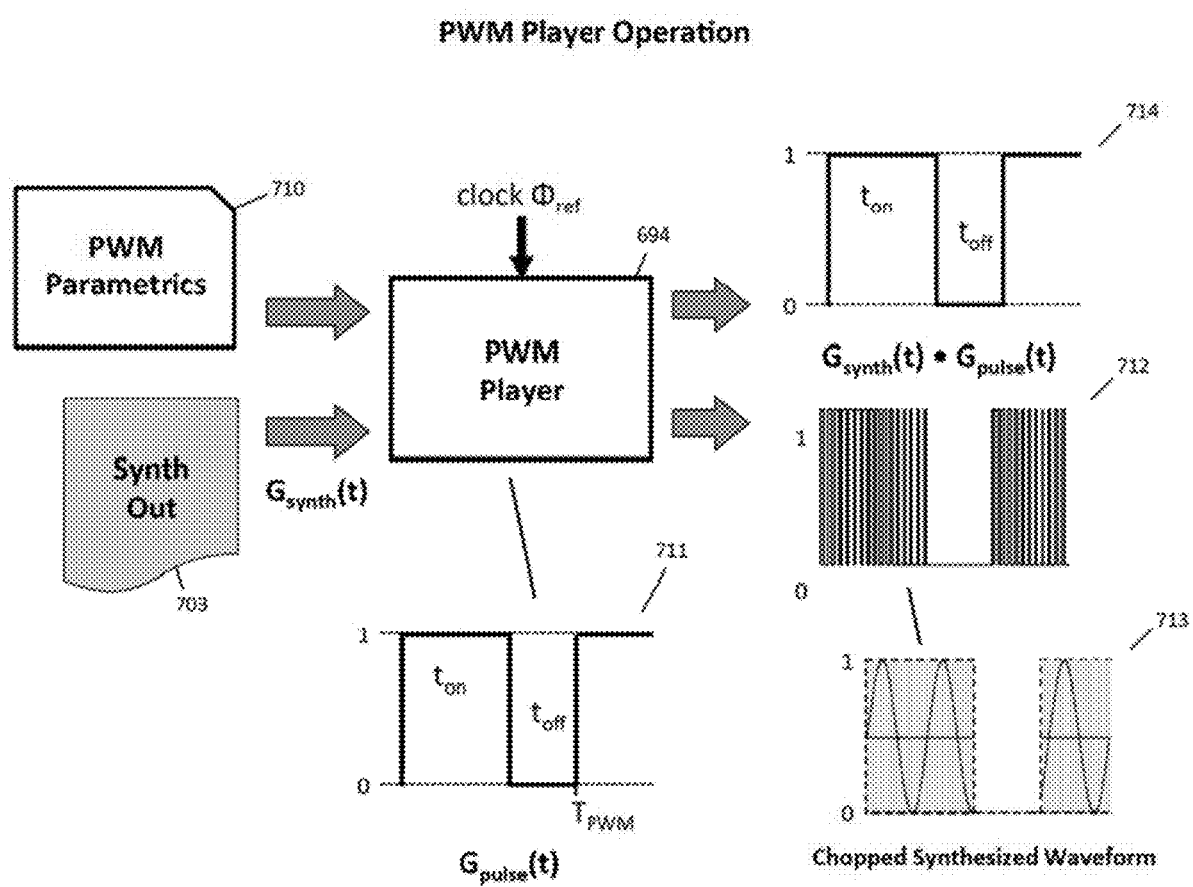

Waveform synthesis is an algorithmic generation of excitation patterns such as sine waves and chords of sine waves but is also able to generate triangle waves, sawtooth waves, and to even possibly to reproduce audio samples. Waveform synthesizer 693 operation shown in FIG. 35A involves waveform synthesizer 699 converting its input, waveform parametric file 700 with intelligent LED pad system clock $\Phi_{sys}$ to produce synth waveform f(t) represented as synth out data table 704, i.e. comprising the function table f(t) paired against elapsed time t. PWM generator 707 then converts the function table into a high frequency PWM pulse train 705 to produce synth out file 703 including synthesized waveform 706 embedded within the PWM output 705. Depending on the algorithm, waveform synthesizer 699 may also utilize waveform primitives 701. These waveform primitives 701 provide tabular descriptions of a variety of periodic functions including sinusoids, triangle waves, sawtooth waveforms, as wells as digital samples of audio components.

While the synthesizer can be realized in hardware, for waveforms up to 20 kHz, i.e. within the audio range, it can easy be implemented using software. For example, from 0.5 to 1.0 ms, the value of f(t)=0.6545. The process $\Psi_P[f(t)]$ converts the function f(t) into a PWM pulse train of on time and off time, where the output has a high (on) state 65.45% of the specified interval, i.e. from 0.500 to 0.827 ms, and has a low (off) state from 0.827 to 1.000 ms. So the time duration $t_{on}$=0.827−0.500 ms=0.327 ms, and the off time duration $t_{off}$=0.500−0.327=0.173. In other words, the value f(t) is the duty factor D during the period, where D=$t_{on}$/$T_{PWM}$ and where $T_{PWM}$=$t_{on}$+$t_{off}$.

Since the duty factor D is an analog value limited between 0% and 100% then for convenience f(t) is limited to any value between 0.0000 and 1.0000. If f(t) is allowed to exceed 1.000 then the value must be scaled by the function's maximum value i.e. f(t)=[f(t)unscaled)/f(t)$_{max}$] or the waveform will be clipped to the value 1.000 by the process $\Psi_P$[f(t)]. The PWM clock frequency called the symbol rate clock $\Phi_{sym}$ is given by $\Phi_{sym}$=1/$T_{PWM}$. The symbol rate is derived from the system clock $\Phi_{sys}$ and must exceed the highest frequency waveform f(t) being synthesized, or described mathematically as $\Phi_{sys}$>$\Phi_{sym}$>f(t). The table below describes the time intervals where $t_x$=(x−1)$T_{PWM}$ breaking each 500 ms interval into its start time $t_x$(on) and $t_x$(off).

| $t_x$ | $t_x$ + $T_{PWM}$ | f(t) = D | $t_{on}$ | $t_{off}$ | $t_x$(on) | $t_x$(off) |
|---|---|---|---|---|---|---|
| 0.0000 | 0.5000 | 0.6545 | 0.3225 | 0.1775 | 0.0000 | 0.3225 |
| 0.5000 | 1.0000 | 0.7939 | 0.3970 | 0.1030 | 0.5000 | 0.8970 |
| 1.0000 | 1.5000 | 0.9045 | 0.4523 | 0.0477 | 1.0000 | 1.4523 |
| 1.5000 | 2.0000 | 0.9775 | 0.4888 | 0.0112 | 1.5000 | 1.9888 |
| 2.0000 | 2.5000 | 1.0000 | 0.5000 | 0.000 | 2.0000 | 2.5000 |
| 2.5000 | 3.0000 | 0.9775 | 0.4888 | 0.0112 | 2.5000 | 2.9888 |
| . | | | | | | |
| . | | | | | | |
| . | | | | | | |

The second process in the LED player is the PWM Player function 694 shown in FIG. 35B, which in response to its input PWM parametrics 710 and reference clock $\Phi_{ref}$ processes synth out data file 703 to produce PWM player output 712 and optionally a second output 714. In operation PWM player 694 generates a pulse width modulated (PWM) pulse train 712 comprising the algebraic product $G_{synth}$(t)·$G_{pulse}$(t) where the waveform 711 of $G_{pulse}$(t) comprises a repeating pulse consisting of a duration $t_{on}$=D$T_{PWM}$ and off for a duration $t_{off}$=(1−D) $T_{PWM}$.

Although the PWM player function can be performed in hardware, it is easily performed in software. Described in logical pseudo-code in terms of a fast counter and x (incremented on each loop), then:

If (t≥x$T_{PWM}$) AND (t<((x+D)$T_{PWM}$))
Then OUT=$G_{synth}$(t)
Else OUT=0 which means that in each cycle of duration $T_{PWM}$ from time x$T_{PWM}$≤t≤(x$T_{PWM}$+D$T_{PWM}$) the PWM player's output is equal in magnitude to the input (on state), and for an interval (x$T_{PWM}$+D$T_{PWM}$)≤t<(x+1) $T_{PWM}$ the PWM player's output is grounded, a digital "0". By chopping the input $G_{synth}$(t) with the PWM pulse $G_{pulse}$(t), the output 712 waveform is digital with an equivalent value of $G_{synth}$(t)·$G_{pulse}$(t). The underlying waveform 713 is shown superimposed atop the PWM signal 705. Although typically PWM player 694 outputs only a single digital waveform, it can produce more than one output as needed. For example in the example shown although output 712 includes the multiplicative combination of two PWM pulses, output 714 is identical to $G_{pulse}$ (0, meaning $G_{synth}$(t)=1. PWM Player 694 can also output a constant time-invariant value $G_{synth}$(t)·$G_{pulse}$(t)=1.

Figure 35C:
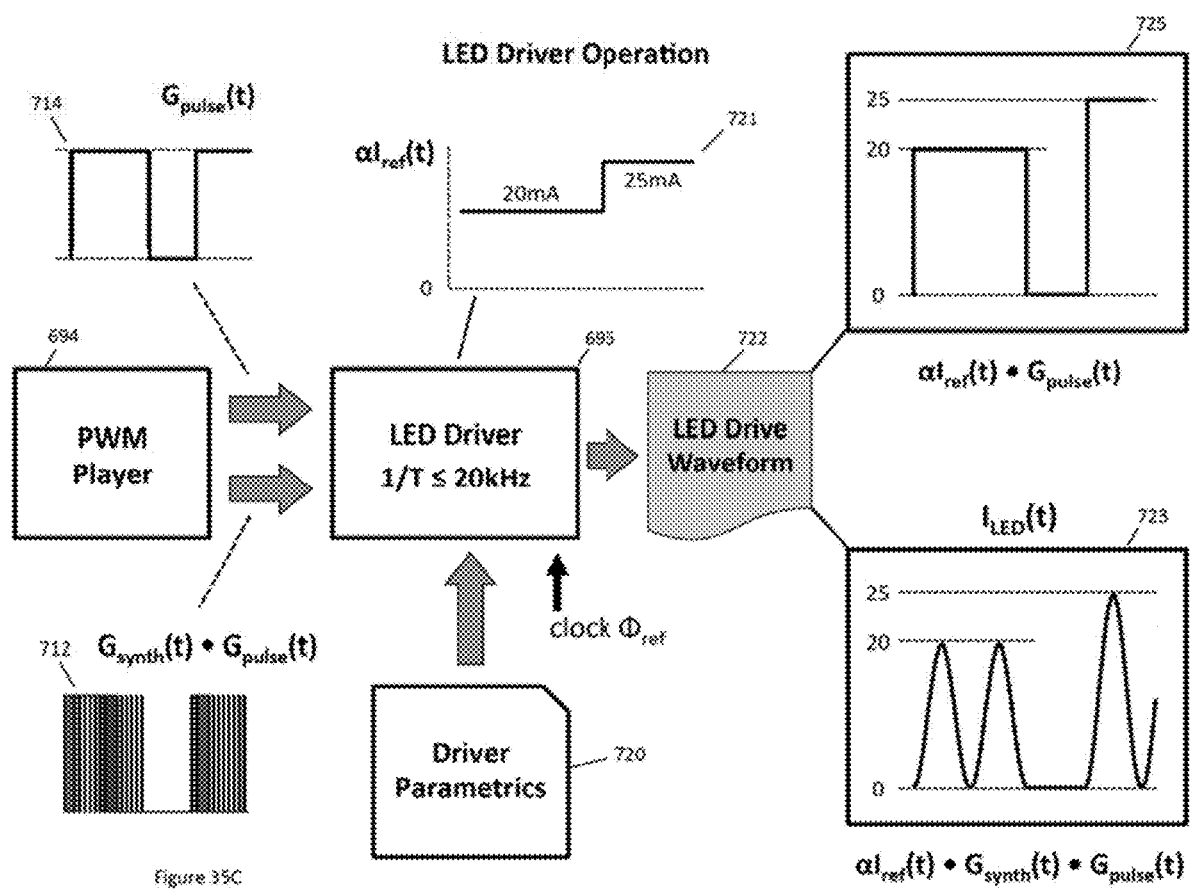
FIG. 35C is a flow chart describing the operation of "LED driver" module.

The third step in LED player operation is LED driver 695. As shown in FIG. 35C, LED driver 695 synchronized to reference clock $\Phi_{ref}$ combines driver parametrics 720 with the output or outputs of PWM player 694 to produce LED drive streams 723 and 725. Unlike waveform synthesizer 699 and PWM player 694, which outputs digital signals, the output of LED driver 695 is analog. Using driver parametrics 720 a programmable reference current 721 is generated with magnitude $\alpha I_{ref}$(t) and multiplied by the outputs of PWM player 694, specifically $G_{synth}$(t)·$G_{pulse}$(t) to produce output 723 comprising $\alpha I_{ref}$(t)·$G_{synth}$(t)·$G_{pulse}$(t), and $G_{pulse}$(t) with output 725 comprising $\alpha I_{ref}$(t)·$G_{pulse}$.

The output waveform LED shown in graph 723 reveals a time varying waveform, specifically sinusoid, digitally pulsed, and varied in current over time. Although PWM player 484 may output a single output as an input to LED driver 695, it is also possible to provide two (or more) different outputs if necessary, resulting in a second square wave output 725. Such cases could for example be useful in large PBT systems where many zones are required to treat each part of the body uniquely, i.e. with good tissue specificity.

The entire process of LED playback is summarized for a single output exemplar in FIG. 36 sequentially utilizing waveform synthesizer 693, PWM player 694, and LED driver 695 to generate LED drive stream 723. Unlike in prior-art methods, LED drive in the disclosed distributed PBT system is generated entirely within an intelligent LED pad while advantageously maintaining all treatment libraries and PBT system control in a common PBT controller, separate and distinct from the intelligent LED pad or pads. The waveform generation process utilizes a system clock of frequency $\Phi_{sys}$ produced within the LED to perform its tasks, thereby eliminating the need for distributing high-speed clocks over long lines. To insure synchronization of the PWM player 694 and the LED driver 695 with the waveform synthesizer 693, system clock $\Phi_{sys}$ is divided using software or hardware counters to produce reference clock $\Phi_{ref}$.

As such LED playback within a given intelligent LED pad is fully synchronous. While both waveform synthesizer 693 and PWM player 694 output digital PWM signals comprising repeating transitions between digital 0 and 1 states of varying duration, the output of LED driver is analog capable of driving LED brightness with any waveform include without limitation, square waves, sine waves, chords of sine waves, triangle waves, sawtooth waves, audio samples of acoustic or electronic music, audio samples of cymbal crashes and other noise sources and at any frequency within the audio spectrum from 20 Hz to 20 kHz, i.e. from the $0^{th}$ to the $9^{th}$ musical octave. It is also producing modulating LED conduction in the infrasound range, i.e. in the $-1^{st}$ and $-2^{nd}$ octaves, e.g. down to 0.1 Hz, or to drive LEDs with direct current (0 Hz), i.e. providing continuous wave (CW) operation.

It should be noted that since each pad independently communicates asynchronously with the PBT controller and since each intelligent LED pad generates its own internal time reference for LED playback, the strictly speaking, the disclosed distributed PBT is an asynchronous system. That said, because of the high clock rates, precision time references, and high speed communication network, timing mismatch between the intelligent LED pads is in the range of microseconds, imperceptible in UI control and UX response and having no impact on PBT efficacy.

In distributed PBT systems, one PBT controller controls many intelligent LED pads, e.g. 3, 6 or more. Because of the number of intelligent LED pads required, economic considerations mandate limiting the complexity of intelligent LED pads, specifically the cost and processing power of pad μP 121. Likewise, to manage product costs, the total memory within an intelligent LED pad must also be limited. Limited in computing power and memory, synthesis of waveforms within an intelligent LED pad in a distributed PBT system requires several criteria be met:

The amount of data transferred to or stored in the intelligent LED pad should be limited.

Calculations performed in intelligent LED pad should preferably comprise simple arithmetic calculations such as addition and subtraction, avoiding complex iterative processes such as functions, matrix operations, etc. unless absolutely unavoidable and even then infrequently.

Calculations should be made in real time with minimal power consumption or heating.

Figure 37:
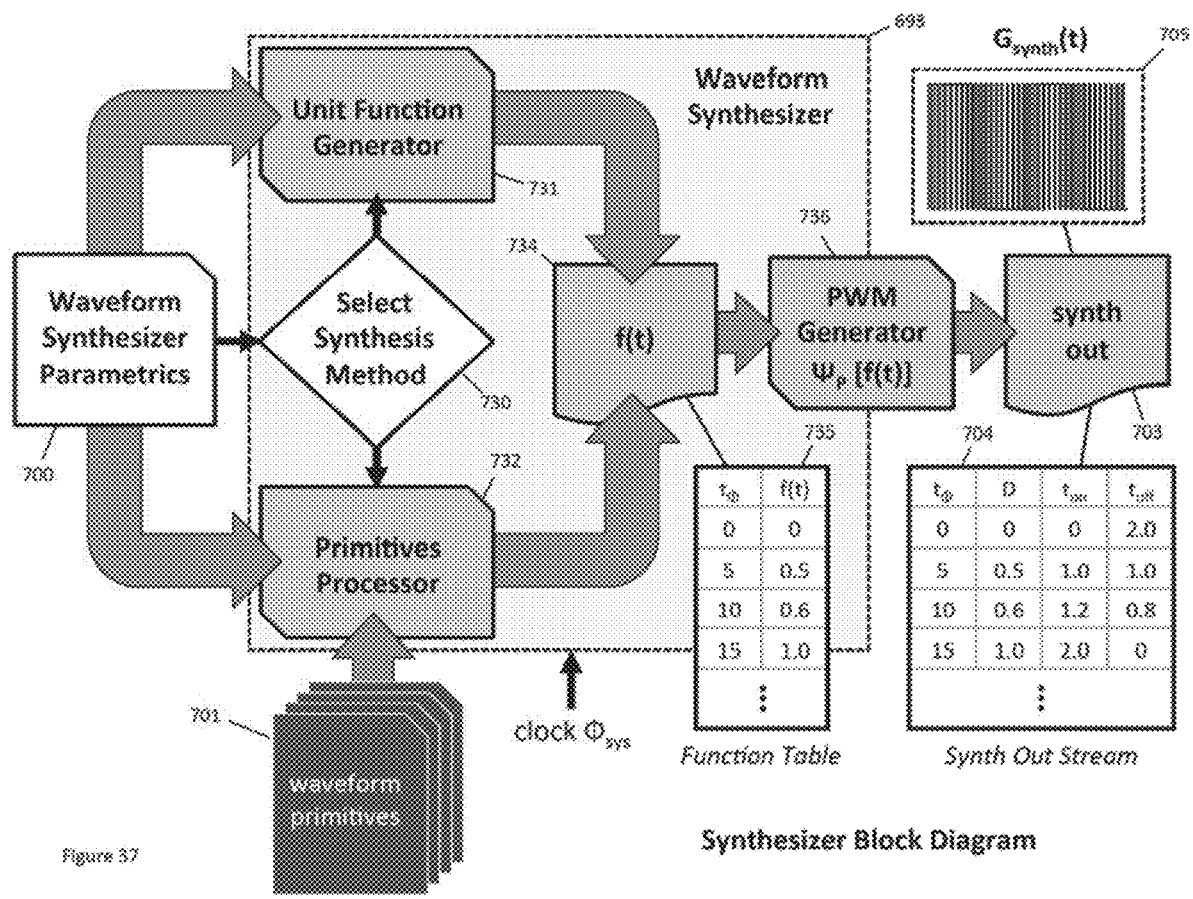
FIG. 37 is a block diagram showing details of waveform synthesizer operation.

Detailed operation of waveform synthesizer 693 is illustrated in FIG. 37 where an input file comprising waveform synthesizer parametrics 700 once loaded into waveform synthesizer 693 selects a synthesis method 730 used to calculate a function f(t) 734, either utilizing unit function generator 731 or primitives processor 732 all performed synchronous to system clock $\Phi_{sys}$. In the case of waveform synthesis, primitives-processor 732 requires access to detailed waveform descriptions, specifically waveform primitives 701. The resulting function f(t) 734 comprises Cartesian pairs of time t versus f(t) illustrated graphically in function table 734. Function table 734 is then converted into time varying digital data by PWM generator 736 using the process [f(t)] to produce synth out file 703. Synth out 703 comprises a digital PWM file numerically equivalent to synth out table 704 represented graphically as $G_{synth}(t)$ 705.

An exemplar communication data packet used in the downloading the LED playback file from PBT controller 110 to the intelligent LED pad 120 is shown in FIG. 34. In step 1, LED player file 740 is sent containing payload 744 with embedded LED playback file 750 comprising payload file 751 containing the playback file version number and files for synthesizer parametrics file, primitives files, PWM player file, and LED driver parametrics file. The packet is identified in packet type 741 as Send File with hex code |03| with a filetype 742 of |13-02| together having an instructional meaning "Send File/LED Playback File/Deliver Playback File." Treatments vary in length and complexity, and as such payload length 743 varies in accordance with size of LED playback files 750. In step 2, LED playback file 750 is installed in unencrypted form into volatile memory 126 where waveform synthesizer parametrics 700 and select waveform primitives 701 are installed to drive waveform synthesizer 693, PWM parametrics 710 is installed to drive PWM player 694, and LED driver parametrics file 720 is installed to control LED driver 695. In general, the download of an LED player file carries with it the LED primitives file needed to support LED playback.

In some instances LED primitives needed to execute a program may be missing from a playback download file component, in which case the intelligent LED pad 120 must request the missing file from PBT controller 110. An exemplar communication data packet used in the downloading a LED primitives file is shown in FIG. 39. In step 1, intelligent LED pad 760 sends a request to download the missing file with packet type 761 of hex value |02| and filetype 762 of |14-01| meaning "Request File/LED Primitives File/Request Specific File #." In the request the payload length 763 is |00-FF-FF| or 2-Bytes accommodating up to 256 different file numbers, e.g. hex file |F0-10| or in decimal file #61,456.

In response to this request, PBT controller 110 sends exemplar communication packet 770 with embedded LED playback file 750 comprising payload data 774 containing the LED primitives file 780 containing payload data 781 with and identifying primitive file # followed by the primitives data file. The reply packet is identified in packet type 771 as Send File with hex code |03| with a filetype 772 of |14-01| together having an instructional meaning "Send File/LED Primitives File/Deliver Primitives File." The primitive file varies in size based on its resolution, and as such payload length 773 varies in accordance with size of LED primitive file 780. In step 2, LED primitive file 780 is installed in unencrypted form into volatile memory 126 whereby waveform primitives file 782 is loaded into waveform synthesizer 693.

Figure 40:
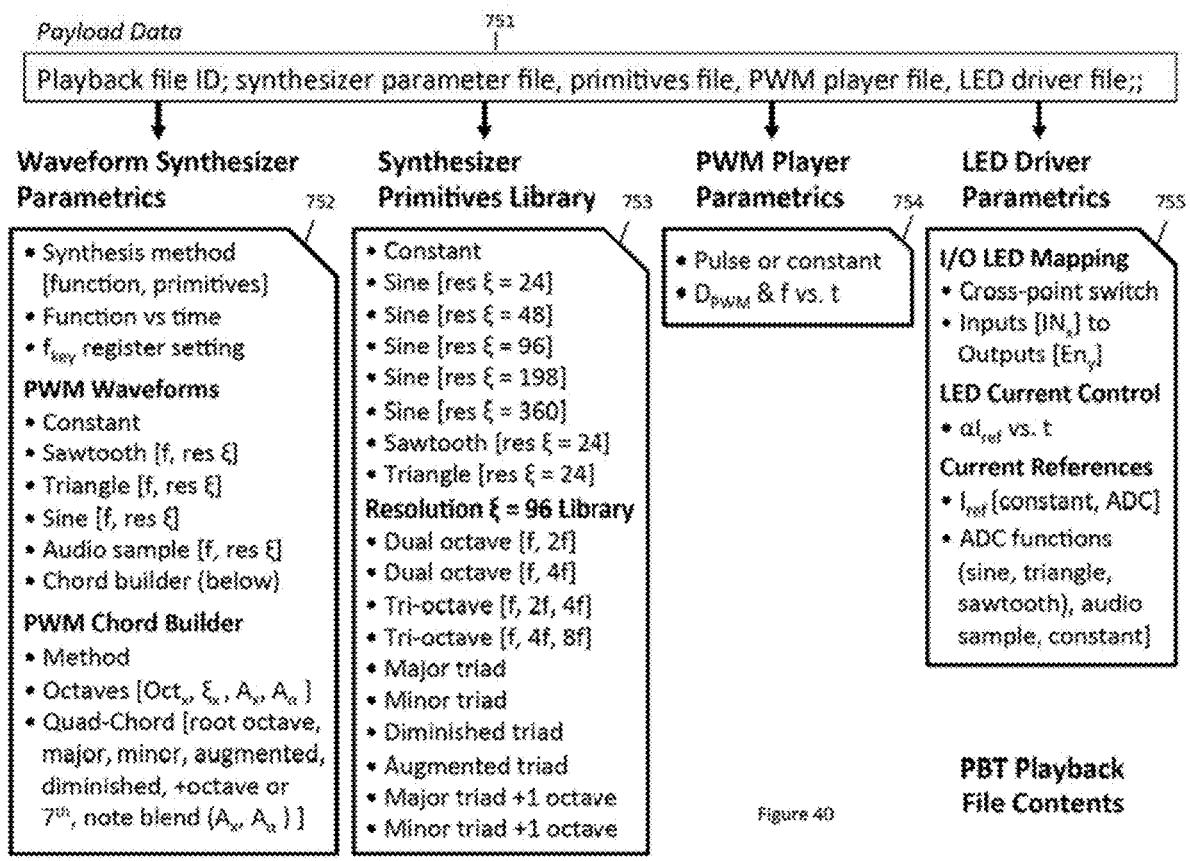
FIG. 40 illustrates a detailed description of a LED playback file including playback file ID, a synthesizer parameter file, waveform "primitives" file or files, a PWM player file, and a LED driver file.

FIG. 40 illustrates an exemplar of library elements for LED player parametric and waveform primitive files, which may be included as payload in playback file 751 or downloaded separately. This library includes waveform synthesizer parametrics 752, synthesizer primitives 753, PWM player parametrics 754, and LED driver parametrics 755. The waveform synthesizer parametrics 752 comprises the information needed to execute a specific treatment or session, i.e. an instruction file. The general instruction file for waveform synthesis includes the following:

The waveform synthesis method employed by the file, i.e. either function synthesis or primitive synthesis.

The tuning (key) of the program, i.e. the $f_{key}$ register setting for the synthesis. Available keys of PBT synthesis comprise predefined binary multiples of a $4^{th}$ octave note, the generated harmonic multiples spanning the audio spectrum from the $9^{th}$ to the $-1^{st}$ octaves. Scales include default, musical, physiological, other and custom. While default, and musical scales are even-tempered; the "other" submenu includes alternate tunings such as Werckmeister, Pythagorean, Just-Major and Mean-Tone scales. The physiological scale "physio" is based on empirically derived scales derived from observation. The "custom" UI/UX allows a user to manually set the value of $f_{key}$ as a $4^{th}$ octave frequency (entered in Hertz rather than by note) and passes this frequency into a $f_{key}$ register.

The waveform sequence to be synthesized, including the duration of each waveform "step" in the synthesis. A termination code is included at the program's terminus to signify the treatment or session has completed.

If function synthesis is used, the mathematical expression of each function and its frequency f. Available periodic waveforms using function synthesis include constant, sawtooth, triangle, and single frequency sine wave.

If primitive synthesis is used, each primitive subroutine-call including the frequency $f_x$ and resolution $\xi_x$ of the primitive's playback subroutine. Available primitive based waveform subroutine calls include constant, sawtooth, triangle, sine waves, or audio samples. Primitives-based synthesis of sinusoidal chords is also available using a "chord builder" subroutine.

Chord builder subroutines include specifying the chord construction method and the octaves and notes present. Chord builder algorithms include "octave" synthesis and "tri/quad" chord synthesis.

In octave synthesis, any chord can be described by its component octave "Oct" numbers (a number from −1 to 9 describing the frequency $f_x$ made in accordance with the $f_{key}$ register setting) along with each octave's corresponding primitive resolution $\xi_x$ and blend A. In a tri/quad chord builder, three or four fixed resolution sine wave notes spanning a single octave can be blended using adjustable amplitude set by gain $A_x$ Available chord triads include major, minor, diminished, augmented, each of which includes an optional fourth note +1 octave above the chord's root note. Alternatively a fourth note can be added to form a $7^{th}$ chord, specifically a quad note chord having a $7^{th}$, major $7^{th}$, and minor $7^{th}$ construction. A "custom" chord allows generation of any three note chord spanning one octave, even in dissonance, with an option for a fourth note +1 octave above the chord's root note.

All chord builder outputs may be scaled to increase the chord's periodic amplitude by digital gain $A_\alpha$ without shifting the 0.5 average value of the unit function.

All outputs of the waveform synthesizer represent unit functions, i.e. having analog values between 0.000 and 1.000 converted into PWM pulse strings with a duty factor between 0% and 100%. Any synthesized waveform outside of this range will be truncated.

In operation only waveform primitives 753 required by a playback file specified by waveform synthesizer parametrics 752 are downloaded into an intelligent LED pad. The downloadable primitives library 753 includes a selection of sine wave primitives at various resolutions for example using 24, 46, 96, 198 or 360-point or 16-bit resolution. In the exemplar library, it also includes 24 point descriptions of triangle and sawtooth waveforms although other resolutions may be included without limitation. Other library components, for example with $\xi=96$, involve chords including dual octave chords comprising two sine waves one octave apart f and 2f, two octaves apart f and 4f, or possibly four octaves apart at f and 16f, or five octaves apart at f and 32f.

Other options include tri-octave chords such as [f, 2f, 4f] spanning two octaves; [f, 2f, 8f] or [f, 4f, 8f] spanning three octaves, or for example spanning four octaves with [f, 2f, 16f], [f, 4f, 16f], or [f, 8f, 16f]. Other triads include major, minor, diminished, and augmented chords, e.g. [f, 1.25f, 1.5f], [f, 1.2f, 1.5f], [f, 1.2f, 1.444f]. The triads may be modified into quad chords by including a note one octave above the root.

PWM player parametrics file 754 includes settings for constant or pulse mode. In pulse mode, the playback file comprises a sequence of PWM frequencies $f_{PWM}$ and a corresponding duty factor $D_{PWM}$ versus playback time, thereby defining a PWM sequence of pulses of varying durations of $t_{on}$ and $t_{off}$. Note that the pulse frequency $f_{PWM}$ of the pulse width modulator is lower in frequency than the PWM clock $\Phi_{PWM}$=20 kHz used to drive the modulator. To conclude, in PWM player operation, the PWM frequency $f_{PWM}$ is not fixed by varies with the playback program specified in PWM parametrics file 491. Although the frequency $f_{PWM}$ can be as high as the clock $\Phi_{PWM}$ in most cases it is lower so that $f_{PWM} \leq \Phi_{PWM}$. Moreover, the frequency $f_{PWM}$ is in the audio spectrum, far below the oversampled clock $\Phi_{sym}$ in the supersonic range used by in the PWM generator $\Psi_P[f(t)]$ in the waveform synthesizer block, i.e. mathematically as $f_{PWM} \leq \Phi_{PWM} << 1/\Phi_{sym}$.

In LED driver parametrics 755, the unit function digital PWM inputs $IN_x$ are mapped against the current sink enable $En_y$. For example, the input $IN_1$ maps to the channel 4 current sink enable $En_4$, the input $IN_2$ maps to current sink enables $En_1$ and $En_5$ (not shown) for channels 1 and 5, etc. LED current control comprises a playback file of $\alpha I_{ref}$ versus time. The value of $I_{ref}$ for each channel is set by the output of each corresponding D/A converter, which may comprise a constant, a periodic function, or an audio sample. Alternatively, one D/A converter may be used to supply the reference current of all output channels with the same function or constant value.

In conclusion, the disclosed distributed PBT system and its communication protocol thereof has uniquely distinct advantages over existing prior art solutions including the following:

A distributed PBT system able to execute algorithmic treatments remotely and autonomously using intelligent LED pads. Present day systems employ passive LED pads where the algorithm is executed in the PBT controller, not in the LED pad A distributed PBT system able where the PBT controller has a user interface that provides a means for selecting a PBT treatment or a succession of treatments (a session), and communicates this selection over a digital serial communication bus to the intelligent pad as a file or a series of files. Present day systems deliver real time signals to passive LED pads, not as files.

A distributed PBT system where the PBT controller delivers playback files for algorithmically driving LEDs in encrypted form, where the intelligent LED pad decrypts the incoming file either all in one step or piecemeal "on-the-fly" just before the instructions are executed, storing the files in volatile memory where removal of power (e.g. in attempts to hack the code) causes a loss in the code. Prior art PBT systems do not employ encrypted code no are they capable of just-in-time decryption for added security.

A distributed PBT system where the PBT controller delivers encrypted LED playback or streaming files to an intelligent LED pad where the encryption used for communication is different than the encryption used for storing the playback library in the PBT controller. In the execution of a multi-treatment session, the PBT controller retrieves and decrypts several treatments reassembles them into a multi-treatment session then encrypts the new file for secure network communication. Prior art PBT systems do not employ secure communication.

A distributed PBT system where the PBT controller is capable of delivering executable code for LED drive as streaming files supplied is pieces ahead of playback. Prior art PBT systems do not deliver executable streaming files over a communication bus to intelligent LED pads.

A distributed PBT system where the PBT controller is capable of delivering a non-executable playback file that when combined with a previously installed LED playback file is able to algorithmically generate LED drive waveforms. Prior art PBT systems do not employ separate player and playback files.

A distributed PBT system where the PBT controller is able to instruct the intelligent LED pad to start, pause, or cancel instructions controlling the otherwise autonomous execution of a LED playback or streaming file, where the intelligent LED pad employs bidirectional communication over the communication bus to inform the PBT controller of its status. LED pads in prior art systems cannot receive remote instructions, cannot execute those instructions autonomously (i.e. without receiving real time signals from the PBT controller), and cannot inform a PBT controller of its operational status.

A distributed PBT system where an LED player file is delivered and installed in a LED pad including a waveform synthesizer, a PWM player, and a programmable LED driver, where the LED player can be used to execute algorithmic playback instructions received as LED playback files.

A distributed PBT system where a waveform synthesizer installed in an intelligent LED pad is controlled to execute LED drive in accordance with a waveform synthesizer parametrics file and optionally using a waveform primitive file both delivered over a communication bus. No prior art PBT system has a waveform synthesizer, nor can waveform synthesis be performed autonomously in an intelligent LED pad A distributed PBT system where a PWM player installed in an intelligent LED pad is controlled to execute LED drive in accordance with a PWM parametric file delivered over a communication bus. No prior art PBT system has a PWM player operated in accordance with a PWM parametric file, nor can PWM playback be performed autonomously in an intelligent LED pad A distributed PBT system where a programmable LED driver installed in an intelligent LED pad is controlled to execute LED drive in accordance with a LED driver parametric file delivered over a communication bus including the ability to dynamically map multiple driver waveforms to different LED strings. No prior art PBT system has a programmable LED driver operated in accordance with a LED driver parametric file, nor can dynamic LED drive be performed autonomously in an intelligent LED pad.

A distributed PBT system where a combination of waveform synthesizer, PWM player, and LED driver work in various combinations within an intelligent LED pad to produce programmable pulses, periodic functions, and pulse-gated periodic functions of varying amplitude and frequency, where periodic functions include sine waves, triangle waves, and sawtooth waves, all in response to parametric files delivered over a communication bus.

Controlling LED Playback

Figure 41:
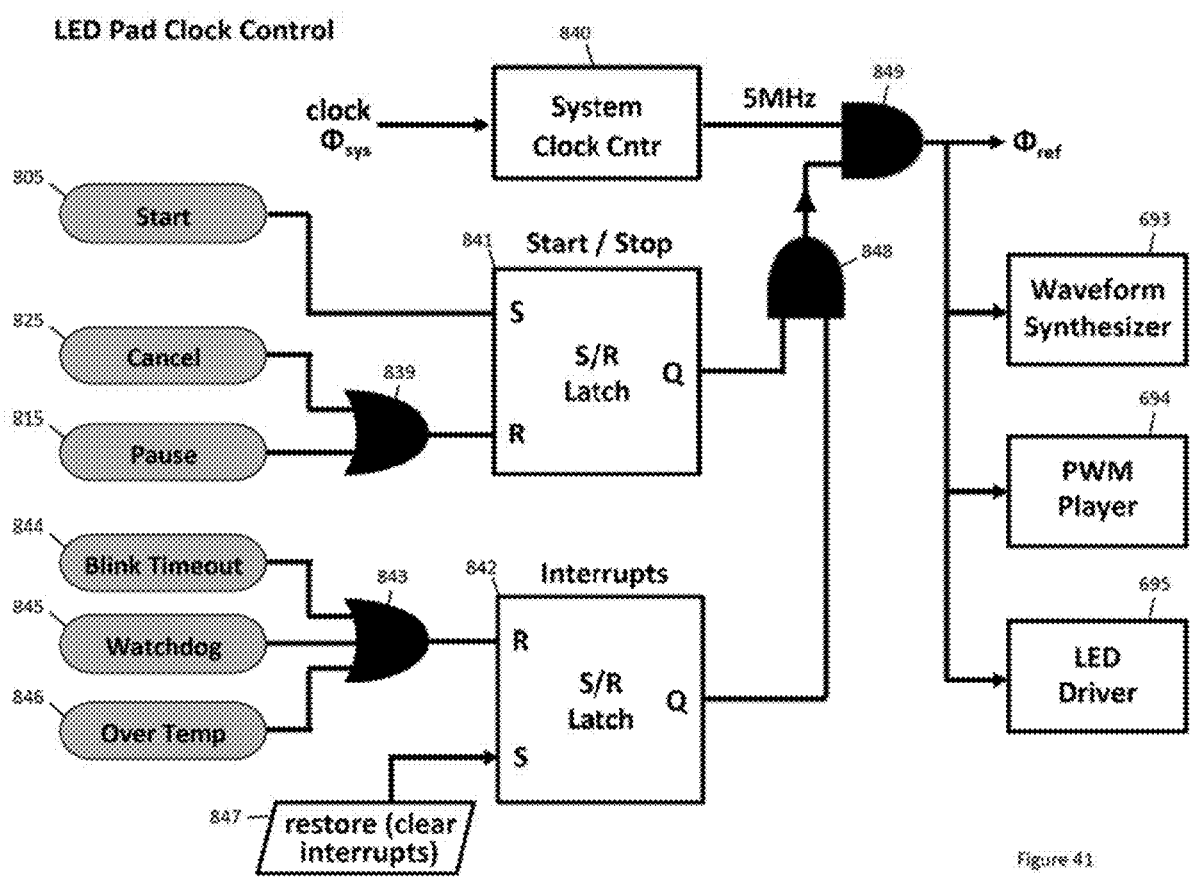
FIG. 41 is a schematic analog of firmware used to control the PWM player clock $\Phi_{ref}$.

After downloading the LED player and LED playback file into an intelligent LED pad, playback is enabled by a start signal 805 and PBT System timing control which may be implemented in software or using the exemplar logic gate circuit of FIG. 41 including start/stop latch 841 comprising a set/reset or S/R type flip flop, interrupts latch 842, PBT system clock counter 840, logical AND gates 848 and 849, and logical OR gates 839 and 843. Two input AND gate 849 acts as a system clock enable of oscillator $\Phi_{sys}$ to the LED player, gated by start, cancel, and pause signals 805, 825, and 815, and from a variety of interrupts, specifically a blink timer timeout 844, a watchdog timer timeout 845, or an over-temperature flag 846. When user input "start" 805 is selected it generates a positive going pulse setting the output Q of start/stop latch 846 to high. With the Q outputs of both start/stop latch 841 and interrupts latch 842 set high, then AND gate 848 is enabled. As such, oscillator $\Phi_{sys}$ divided by counter 840 is delivered to the PWM player as reference clock $\Phi_{ref}$.

Selecting "pause" 815 generates a pulse that resets the output of start/stop latch 841 to zero and suspends playback. Playback remains latched off until "start" 805 is selected cancelling the pause command. As such start/stop latch 841 starts and stops program execution. Selecting "cancel" 825 generates a pulse that resets the output of start/stop latch 841 to zero, suspending playback and disabling the playback file. After a cancel instruction, the entire treatment selection process must be repeated.

In the invent that an interrupt occurs for any reason, i.e. if any one of the inputs to OR gate 643 go high, the PR gate's output will also go high thereby resetting the output Q of interrupts latch 842 to zero. With its Q output low the outputs of AND gates 848 and 849 also go low, disconnecting clock $\Phi_{osc}$ from the LED player function waveform synthesizer 669, PWM player 694, and LED driver 695 and suspending treatment. This situation will persist until the cause of the interrupt is remedied, the inputs to OR gate 843 are reset to low and a system restore pulse 847 is sent to the S input of interrupts latch 842. For example if an over temperature condition occurs, the over temp flag will go high 846 and disable LED pad operation until normal temperatures return and the fault flag is reset.

A unique safety feature of the disclosed distributed PBT system is the blink timer. This timer operates within the intelligent LED pad itself and does not rely on the PBT controller. At regular intervals in the pad e.g. every 20 or 30 seconds, the program counter interrupts operation to execute an interrupt service routine (ISR). During this interval, the blink timeout flag is set to logic 1 while the LightPadOS software executes a safety check regarding intelligent LED pad electrical connections, any priority messages or file updates, file parity checks, etc. Once the blink interrupt routine has been completed the blink timeout is reset to zero, the hardware watchdog timer is reset, and program execution is returned to the main routine. After completing the ISR, the pad generates a system restore pulse to interrupts latch 842 and program operation recommences. If the software has for any reason frozen, the program will not resume operation and the LED strings in the pad will remain off. Otherwise, the intelligent LED pad will resume operation after a defined interval, e.g. 2 seconds.

Another failure mode involves the frozen software while the LEDs are on and emitting light. If the condition persists the LEDs may overheat and present a burn risk to a patient. To prevent a dangerous condition from arising, a hardware watchdog timer (whose operation is not dependent on software) counts down in parallel to the software program counter. Should the software timer become frozen in an on state, the watchdog timer will not be reset, and the watchdog timer will time out generating a blink timeout interrupt 844 and discontinuing operation of the PBT system until the fault condition is resolved.

An exemplar communication data packet used in the controlling intelligent LED pad playback and PBT treatment is shown in FIG. 42A. In step 1, PBT controller 110 sends a start command to intelligent LED pad 120 via communication packet 800 comprising Command packet type 801 having hex code |O5| with a filetype 802 of |13-01| together having an instructional meaning "Command/LED Playback File/Commence Playback." Payload length 803 having a value |00-FF-FF| means payload field 804 can address up to 65,536 different treatments playback ID e.g. treatment |F0-10|. In step 2, execution of the command communication packet 800 triggers the start command, first resetting the playback counters 809 then starting operating by enabling intelligent LED pad reference clock $\Phi_{ref}$.

In the event a user chooses to pause 815 operation, exemplar Command communication packet 810 comprising in concatenated form packet type 811 and filetype 812 having a value |05-13-02| is an instruction meaning "Command/LED Playback/Pause Playback," for the execution of program number identified in payload field 814, for example where payload length 813 is |00-FF-FF| and where the playback ID number may be |F0-10|. Execution of "Pause" 815 in step-4 inhibits LED pad reference clock $\Phi_{ref}$ in operation 807 but does not reset the intelligent LED pad's program counters.

Shown in the exemplar communication packets of FIG. 42B in step 5, treatment is restarted after pause 815 by repeating command 800 in response to "Start 805" comprising |05-13-01| meaning "Command/LED Playback/Commence Playback" with as shown in step 6 starts intelligent LED pad reference clock $\Phi_{ref}$ 806 starting at the time when pause was depressed without resetting the playback counters. The instructions to cancel 815 a PBT treatment is shown in step 7 where exemplar communication packet 820 comprises in concatenated form packet type 811 and filetype 812 having a value |05-13-03| is an instruction meaning "Command/LED Playback/Cancel Playback," for the execution of program playback ID number identified in payload field 824. The Cancel 825 action as implemented in step 8 first inhibits intelligent LED pad reference clock $\Phi_{ref}$ 807 then resets playback counters 809.

As described, in addition to Start 805, Pause 815, and Cancel 825 instructions, program operation can be halted through the action of an interrupt. An interrupt is a fork or subroutine call in a software or firmware program where operation is diverted to an alternate sequence of instructions referred to an interrupt service routine or ISR. Interrupts can occur regularly based on a clock or counter, can occur if a specific condition is met, or can happen is the event of a fault or risk arising. Provided the criteria for returning to normal program execution is met, than at the end of the ISR, the program returns to the main algorithm and resumes program execution. If, however, a fault condition persists the ISR may warn a user, initiate a shutdown, or invoke a hard reboot. As disclosed, two of the time based interrupts in the disclosed PBT system are based on time, specifically a "blink timeout" 844 interrupt based on a software timer, i.e. software counting a constant rate clock, and watchdog 845 interrupt, a hardware timer that continues to count even if the software code execution crashes or gets stuck in an endless loop. Instead base interrupt temporarily halts intelligent LED pad reference clock $\Phi_{ref}$ then executes an interrupt service routine, a routine that matches the cause of the interrupt.

The intent of both the blink counter and hardware watchdog timer is to autonomously confirm proper intelligent LED pad operation and insure safety even if the communication link to the PBT controller is lost permanently or momentarily. This provision, not utilized in prior art PBT systems, while beneficial in passive LED systems, is critical in distributed PBT systems to insure safety in maintained at all times even absent any central controller instructions, signals, or connectivity. The use of autonomous safety systems separate from the PBT controller is therefore a unique feature of a PBT system made in accordance with this disclosure. For example, in a passive PBT system inclusion of a blink counter or watchdog timer in the main PBT controller, while checking if the controller is working, cannot detect if any of the connected LED pads have malfunctioned. Moreover, since passive LED pads are unable to communicate bidirectionally with the PBT controller, they are unable to inform the PBT controller that a problem has occurred. For this reason, the operational sequence of an ISR in an intelligent LED pad is important, namely 1. Detect a fault or time interrupt within the intelligent LED pad.
2. Immediately cease intelligent LED pad operation by inhibiting the clock used for modulating or pulsing the LEDs is stopped and the LEDs are turned off as part of the interrupt.
3. Transfer program control to the ISR checking for the source of the interrupt and remedying its origin if possible.
4. Returning to normal operation, if possible, at the terminus of the interrupt service routine.

Figure 43A:
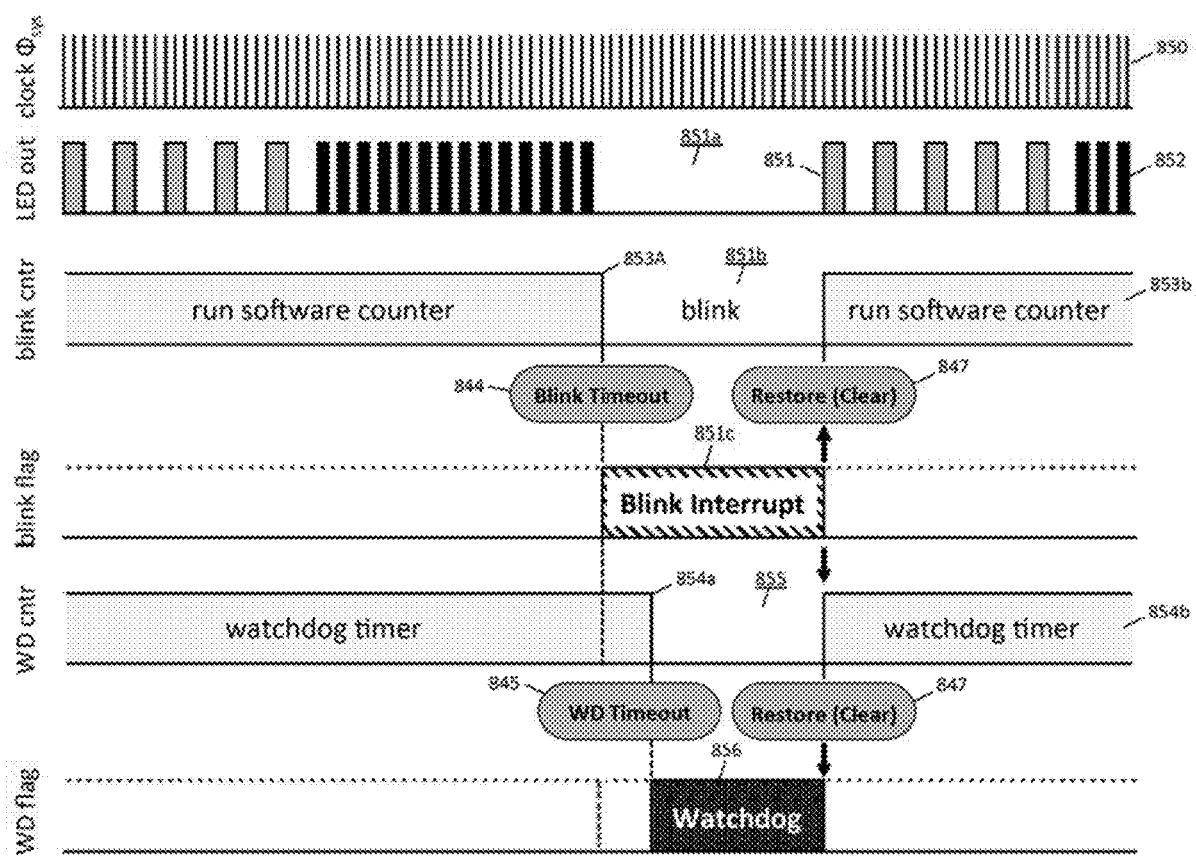
FIG. 43A is a timing diagram representing watchdog and blink timer operation and interrupts.

Operation of time based ISR can be explained by example as shown in the LED pad timing diagrams shown in FIG. 43A. As shown system clock $\Phi_{sys}$ 850, the oscillator frequency used to advance the program counter in a LED pad's microcontroller, continues unabated regardless of any interrupt conditions. The LED output, measured either by LED current or LED light output, as shown alternates driving two different LED wavelengths 851 and 851, the LED drive for each wavelength (color) LED operating at different pulse frequencies and possibly for different durations. A software blink counter counts a fixed duration 853 until when a certain count is reached, e.g. 30 seconds in duration, a blink timeout 844 occurs and a blink interrupt 851c is generated. When blink interrupt 851c occurs at time "Blink Timeout" 844, as shown in FIG. 44A in step 1, concurrently reference clock $\Phi_{ref}$ is halted (even though system clock $\Phi_{sys}$ 850 keeps running), blink counter ceases 851b during the blink interval, and LED light output 851b is temporarily interrupted.

Figure 43B:
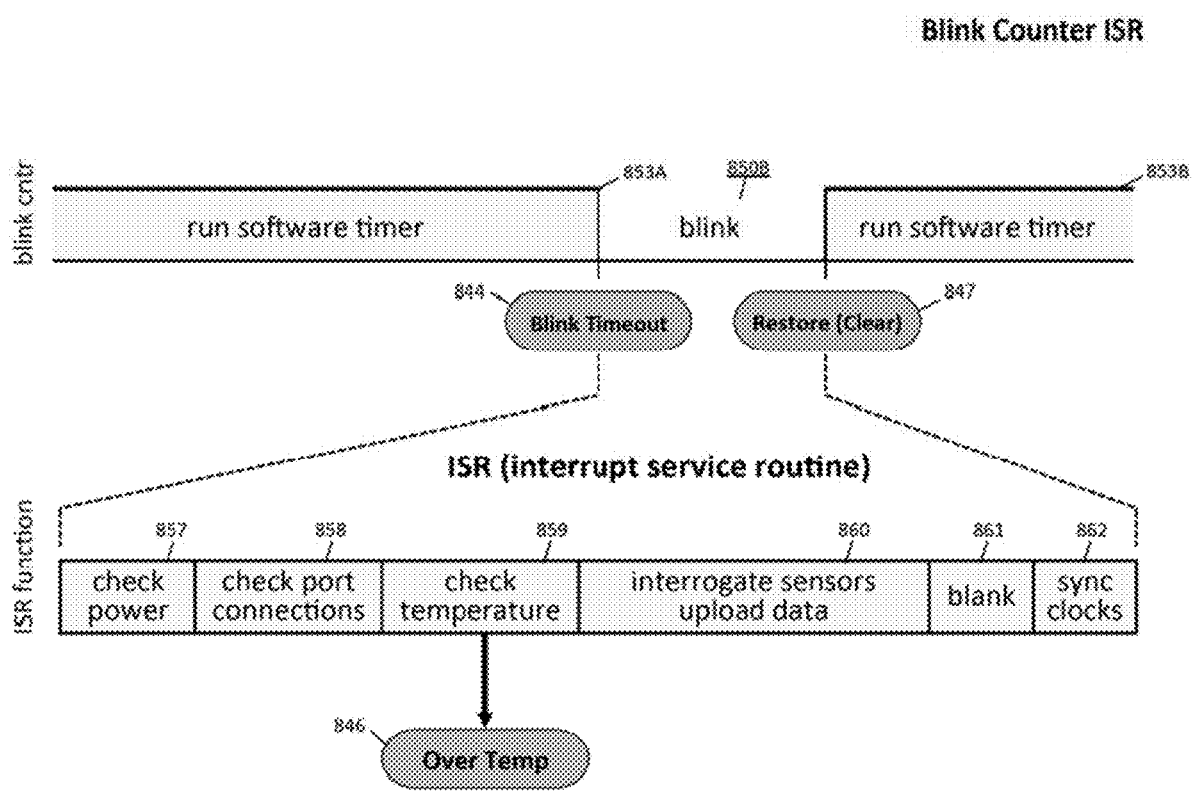
FIG. 43B is a timing diagram illustrating an example of a blink timer interrupt service routine.
Figure 44A:
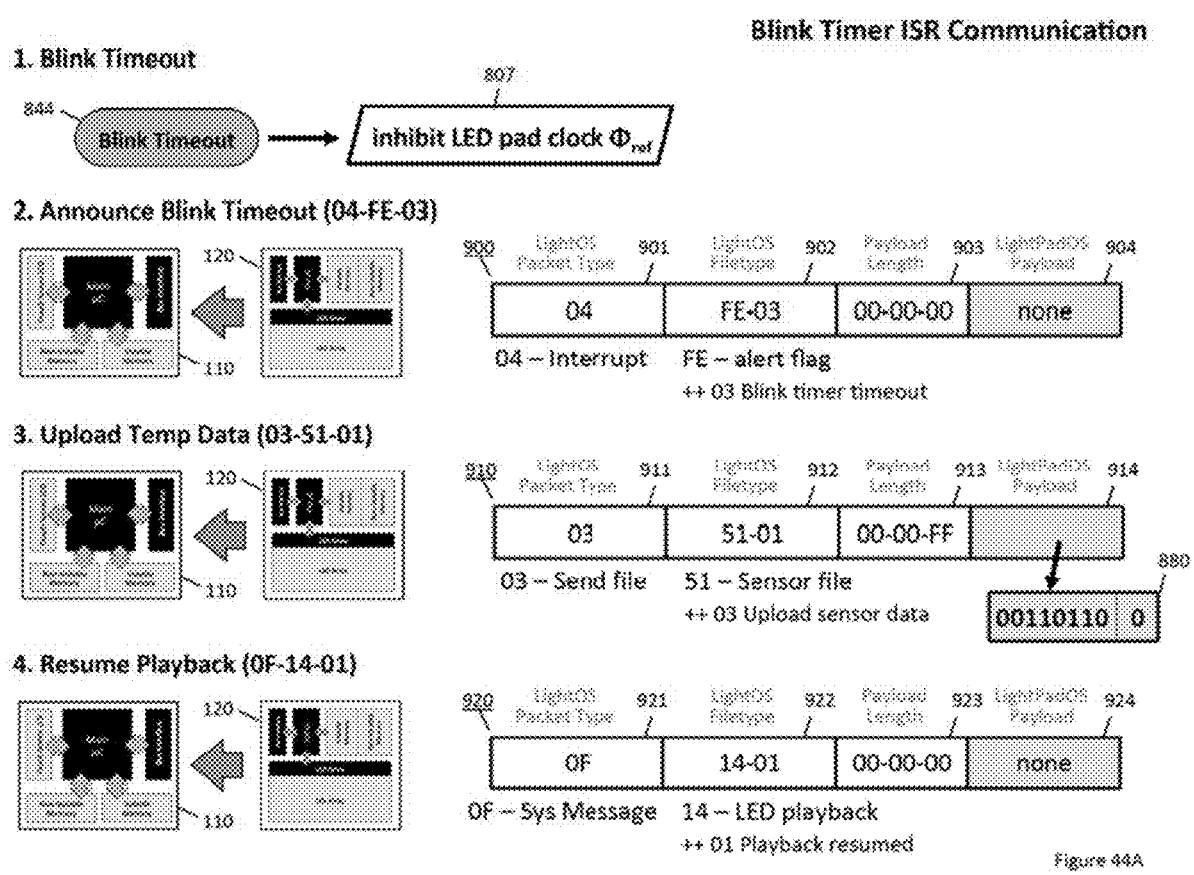
FIG. 44A illustrates data packet communication for a blink timer interrupt service routine with automatic temperature sensor upload.
Figure 44B:
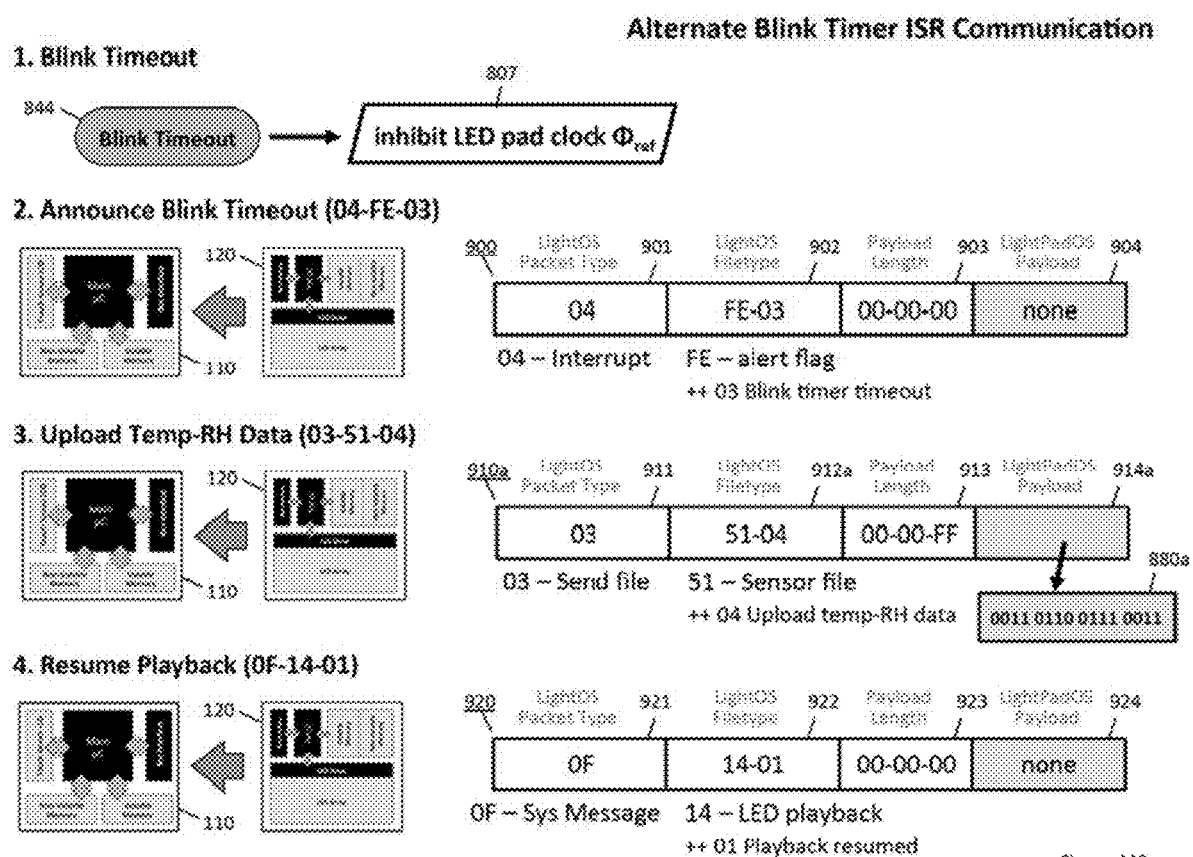
FIG. 44B illustrates data packet communication for a blink timer interrupt service routine with automatic temperature and relative humidity sensor upload.

In step 2 of FIG. 44A, intelligent LED pad 120 interrupt is communicated to the PBT controller 120 using packet 900 comprising packet type 901 and filetype 902 comprising hexadecimal code |04-FE-03| meaning "Interrupt/Alert Flag/Blink Timer Timeout," with a |00-00-00| length and a null payload 904. Consistent with the blink counter ISR shown in in FIG. 43B, in step 3 of FIG. 44A, intelligent LED pad 120 sends communication packet 910 to PBT controller 110 a status file of the LED pad's operating temperature status 880 in communication packet 910 comprising hexadecimal code |03-51-03| meaning "Send File/Sensor File/Upload Temp Data," containing payload 914 with temperature file 880 having a payload length 913 of |00-00-FF1. Unless PBT controller 110 determines there is a problem in the reported temperature file 880, no action will be taken as a result of this information. The LightOS operating system may, if instructed, data log the temperature data. In an alternative embodiment shown in FIG. 44B, step 3 of the blink timer ISR comprises a modified payload 910*a* comprising hexadecimal code |03-51-04| meaning "Send File/Sensor File/Upload Temp-RH Data," containing payload 914 with temperature and relative humidity file 880*a*. The relative humidity data can be data logged for subsequent inspection in the event of an intelligent LED pad failure, primarily to ascertain if the LED was exposed to water or sweat, indicating a protective sanitary barrier was either not used or misapplied.

After uploading the temperature file a similar process and communication packet (not shown) can also be used to upload other sensor data at this time using a packet type and file type instruction |03-22-03| meaning "Send File/Sensor Data/Upload Sensor Data" having a variable payload length depending in the data being uploaded. After the ISR subroutine is completed, normal operation is restored and the intelligent LED pad 120 informs PBT controller 110 with communication packet 920 comprising |0E-14-01| meaning "System Message/LED Playback/Playback Resumed" as shown in step 4 of FIG. 44A and of FIG. 44B with a payload length 923 of |00-00-00| and a null payload 924.

During the blink timeout interval watchdog timer 845*a* continues to count unabated until it times out at WD timeout 845 generating a second interrupt on the WD flag line, i.e. watchdog interrupt 856. Since under normal operation however the system has already been interrupted by the blink timeout 844 interrupting counter 851*c* operation, the watchdog time interrupt 845 is unimportant and has no impact of the intelligent LED pad's operation. Once the blink ISR routine is completed, the blink interrupt 851*c* is terminated and a restore signal 847 is used to clear the blink counter ending the blink interval 851*b* and restarting the blink software time 853*b*. This action terminates the blink duration 851*a* in the LED illumination pattern where pulses 851 and 852 recommence pulsing in accordance with the PBT treatment program or session. At the same, the watchdog timer interrupt flag 856 is cleared ending the timer stop period 855, resetting and restarting the watchdog timer count 854*b* from the beginning.

The functions performed during the blink timer ISR are detailed in the exemplar timing-diagram shown in FIG. 43B, including a test to check proper power connections 857, check port connections 858 for improper pad connections (that might have changed since the last ISR), check for safe pad temperatures 859, as well as providing time to interrogate in-pad sensors and upload data 860 as needed. Blank interval 861 is included to maintain a constant duration for the ISR interrupt period after which the system times are exchanged as sync clocks 862 and the restore (clear) signal 847 occurs. Returning to the timing diagrams of FIG. 43A, the waveforms shown illustrate normal counter operation where after completing the interrupt service routine, the reset (clear) signal 847 restarts the blink software timer 853*b* and watchdog timer 854*b* as well as resuming LED pulsing and PBT therapy. Should everything go as normal, the entire process will repeat again 30 seconds later.

Figure 45A:
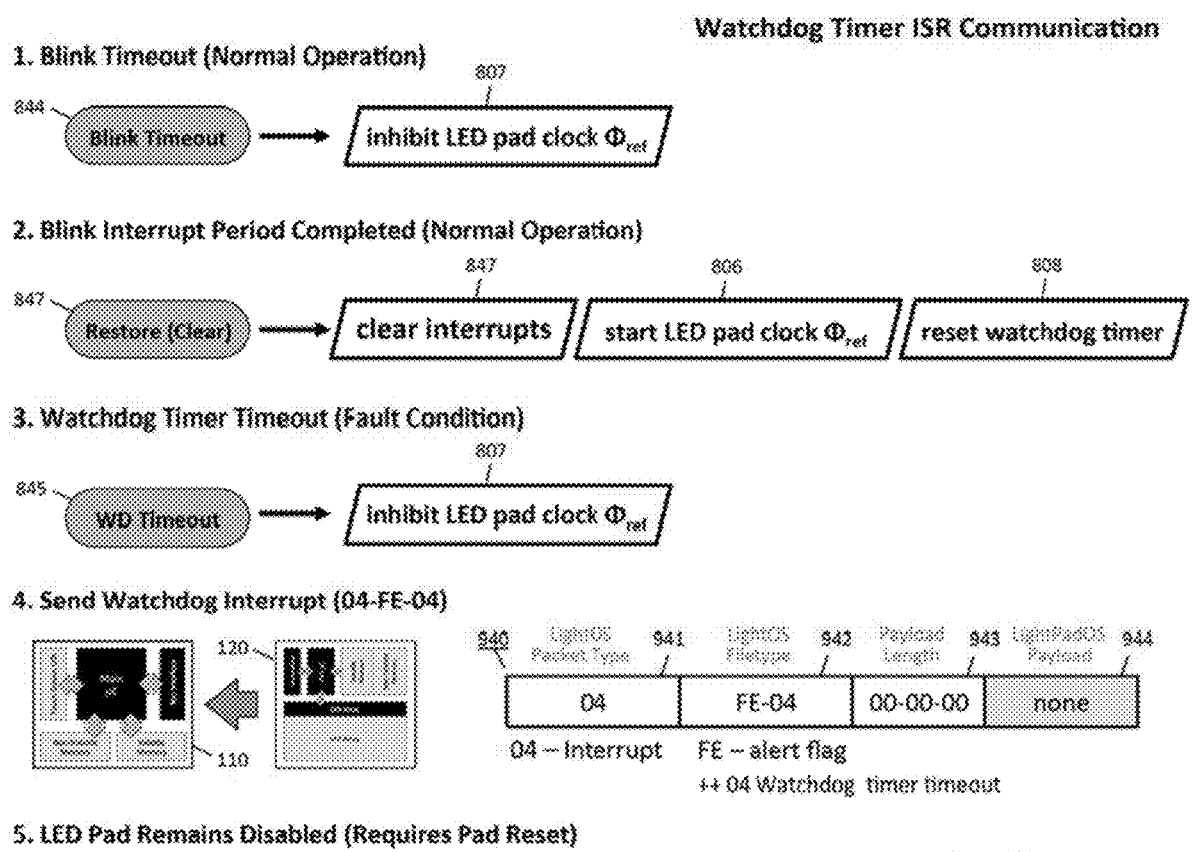
FIG. 45A illustrates data packet communication for watchdog timer interrupt service routine.

If however the software is corrupted, the software based blink counter 853*b* will not restart, in which case hardware watchdog timer 854*b* will time out and generate an interrupt WD timeout 845. Because in this fault scenario, the blink timer is not operational, the software timer is unable to generate restore (clear) command 847. This fault scenario, represented in watchdog timer ISR communication of FIG. 45A, involves the case where the blink counter fails. Starting in step 1, during normal operation, blink timeout 844 inhibits reference clock $\Phi_{ref}$. In step 2, also in normal operation, restore (clear) 947 clears all the interrupts 847, starts reference clock $\Phi_{ref}$ 806, and resets watchdog timer 808.

If however, the blink counter or the executable code malfunctions, the next blink counter timeout will not occur and instead as shown in step 3, the watchdog timeout 845 will occur first. While the immediate action to inhibit reference clock $\Phi_{ref}$ is the same as a blink timeout, the interrupt service routine is different involving a system self check and diagnosis as to why the problem occurred. In step 4, intelligent LED pad 120 communicates the watchdog timeout 845 to the PBT controller 110 using packet 940 comprising packet type 941 and filetype 942 comprising hexadecimal code |04-FE-04| meaning "Interrupt/Alert Flag/Watchdog Timer Timeout," with a |00-00-00| packet length 943 and a null payload 944. Unless the cause of the watchdog interrupt is easily ascertained and remedied, then as shown in step 5 the intelligent LED pad remains disabled, requiring a full system reset to restart the intelligent LED pad.

The watchdog timer fault recovery process is described in FIG. 45B. Starting with the watchdog timer timeout 845*a*, in step 865*a* packet 940 is sent from intelligent LED pad 120 to PBT controller 110. The controller then issue a user dialog popup 831*a* inquiring "An error has occurred. Do you wish to restart the treatment?" If the user confirms "no" to the conditional "Restart?" 830*a* then the treatment is abandoned. Even so, as a precautionary matter the PBT player file is reloaded 932*a* before operation is cancelled 825*a*. If the user confirms yes to the conditional "Restart?" 830*a* then the program tries again executing start 805*a* and commencing treatment from where the error last occurred without reloading the LED player file and the LED playback file (or the LED streaming file for streaming treatments). If a second watchdog timeout 845*b* occurs packet 940 is again sent from intelligent LED pad 120 to PBT controller 110 whereby controller then issue a user dialog popup 831*b* inquiring "An error has occurred. Do you wish to try again?" If the user confirms "no" to the conditional "Restart?" 830*b* then PBT player file is reloaded 932*c*, the PBT playback file is erased, after which the command Cancel 825*b* is issued. In such a case a new treatment must be selected to initiate a treatment. If the user confirms yes to the conditional "Restart?" 830*b* then PBT player file is reloaded 932*b*, the PBT playback or streaming file is reloaded 933, and the program is again started 805*b*. If a watchdog timeout occurs again the treatment is cancelled 825*b*, requiring the PBT to be restarted.

Figure 46A:
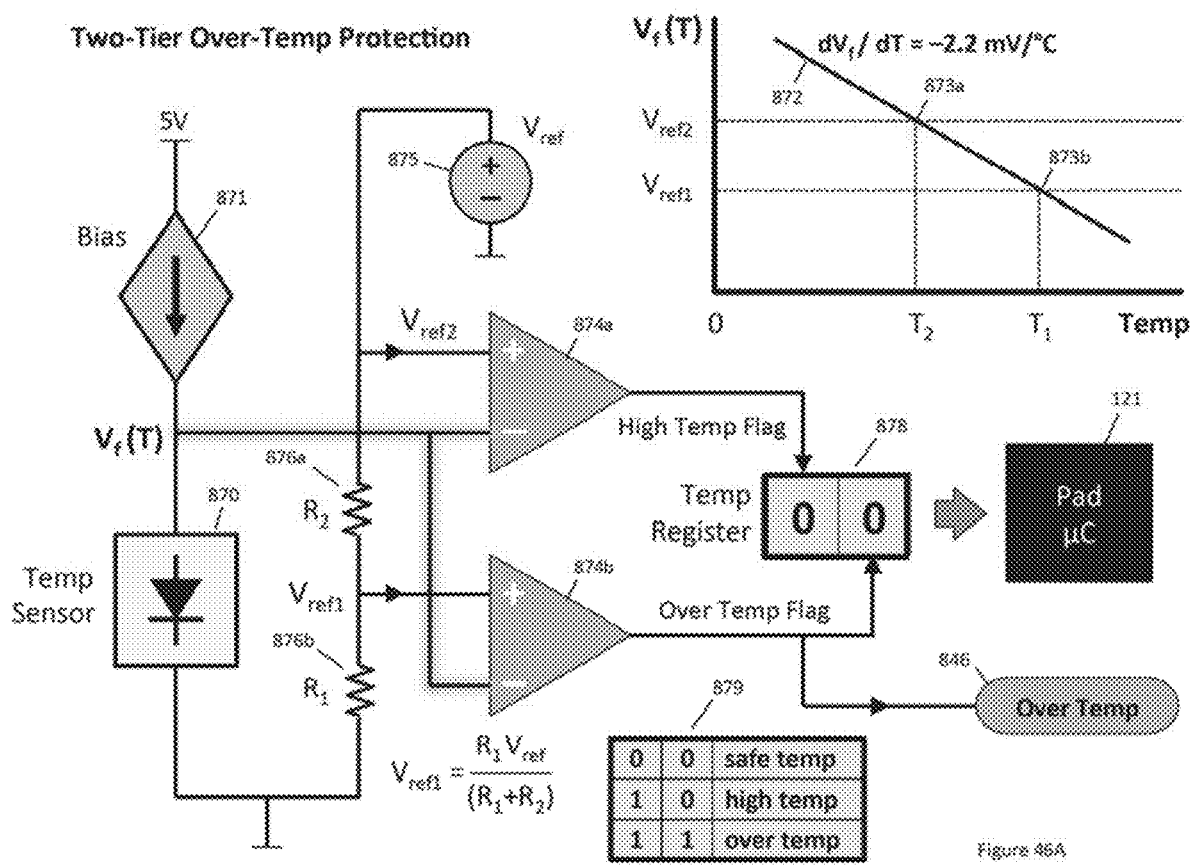
FIG. 46A is a schematic representation of a two-tier over-temperature protected intelligent LED pad.

For temperature measurement or monitoring two different methods are available, each employing a temperature-sensing element such as a forward biased P-N junction semiconductor diode with analog bias and sensing circuitry. One such circuit is illustrated in FIG. 46A comprising forward biased diode temp sensor 870 conducting constant bias current 871 to produce a temperature dependent forward voltage $V_f(T)$. The diode exhibits a negative temperature coefficient. In the case of a silicon diode temperature dependence 872 shown in the graph in the upper right hand corner the forward voltage exhibits a relatively linear slope of $dV_f(T)/dT = -2.2$ mV/° C. The sense voltage $V_f(T)$ is input into the negative input of two analog comparators 874*a* and 874*b*. The positive input to comparator 874*a* is biased at a voltage $V_{ref2} = V_{ref}$ where $V_{ref}$ is determined by a temperature independent reference circuit 875 such as a buffered bandgap reference. The positive input to comparator 874*b* is biased at a lower voltage $V_{ref1} \leq V_{ref2}$ as determined by the resistor divider formed by resistor 876*a* having a resistance $R_2$ and resistor 876b having a value $R_1$ given by the resistive voltage divider equation $V_{ref1}=V_{ref}[R_1/(R_1+R_2)]$. Because resistors $R_1$ and $R_2$ have the same temperature coefficient, the resistor ratio does not change with temperature. In operation under normal LED pad temperatures $T \le T_2 \le T_1$, then $V_f(T) > V_{ref2} > V_{ref1}$ shown graphically as a voltage above point 873a. At this voltage, the negative input to analog comparators 874a and 874b are both larger than their respective positive input reference voltages, i.e. $V_f(T) > V_{ref2}$ and $V_f(T) > V_{ref1}$. As such the outputs of the analog comparators comprise digital bits as logic zero, i.e. the Boolean state "0". The two bits are stored in temperature register 878 as bits |00| and during the blink ISR passed to pad μC 121.

Figure 47:
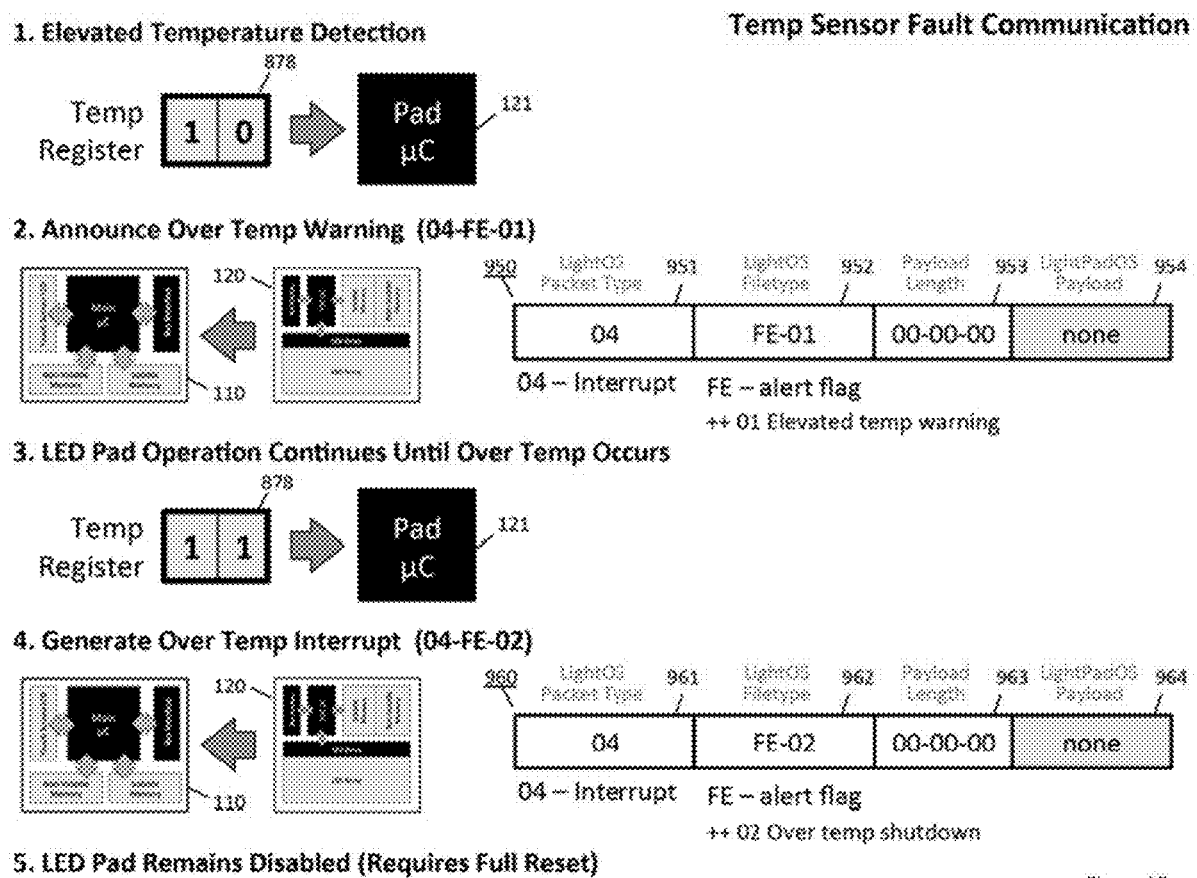
FIG. 47 is a schematic representation of temp sensor communication.

If however, the temperature is elevated so that $T_2 \le T \le T_1$, then accordingly $V_{ref2} > V_f(T) > V_{ref1}$ shown graphically as a point between 873a and 873b. Because $V_{ref2} > V_f(T)$ the positive input of comparator 874a is greater than its negative input, and its output switches to a digital bit comprising logic zero, i.e. the Boolean state "1". Temperature register 878 is then changed to the digital value |10| and as shown in step 1 of FIG. 47, the value of temperature register 878 is passed to a register within pad μC 121. The benefit of protection circuitry operating outside of the μC is that a processor failure will not disable the protection function. Because only the high temperature flag output of comparator 874a is in a high state (but the over-temperature output of comparator 874b is not), then over-temp flag 846 is not triggered and there is no urgency to generate an interrupt. If it is desirable however to more carefully tracking the temperature, e.g. if a patient is sensitive to heat, then packet 950 with interrupt packet type 951 and filetype 952 having a hex code |04-FE-01| meaning "Interrupt/Alert Flag/Elevated Temperature Warning," with a null payload 954 can be sent to inform the host PBT controller the intelligent LED pad is getting warm. The PBT can for example respond by decreasing the duty factor of the PWM pulses in PWM Player 694.

Figure 46B:
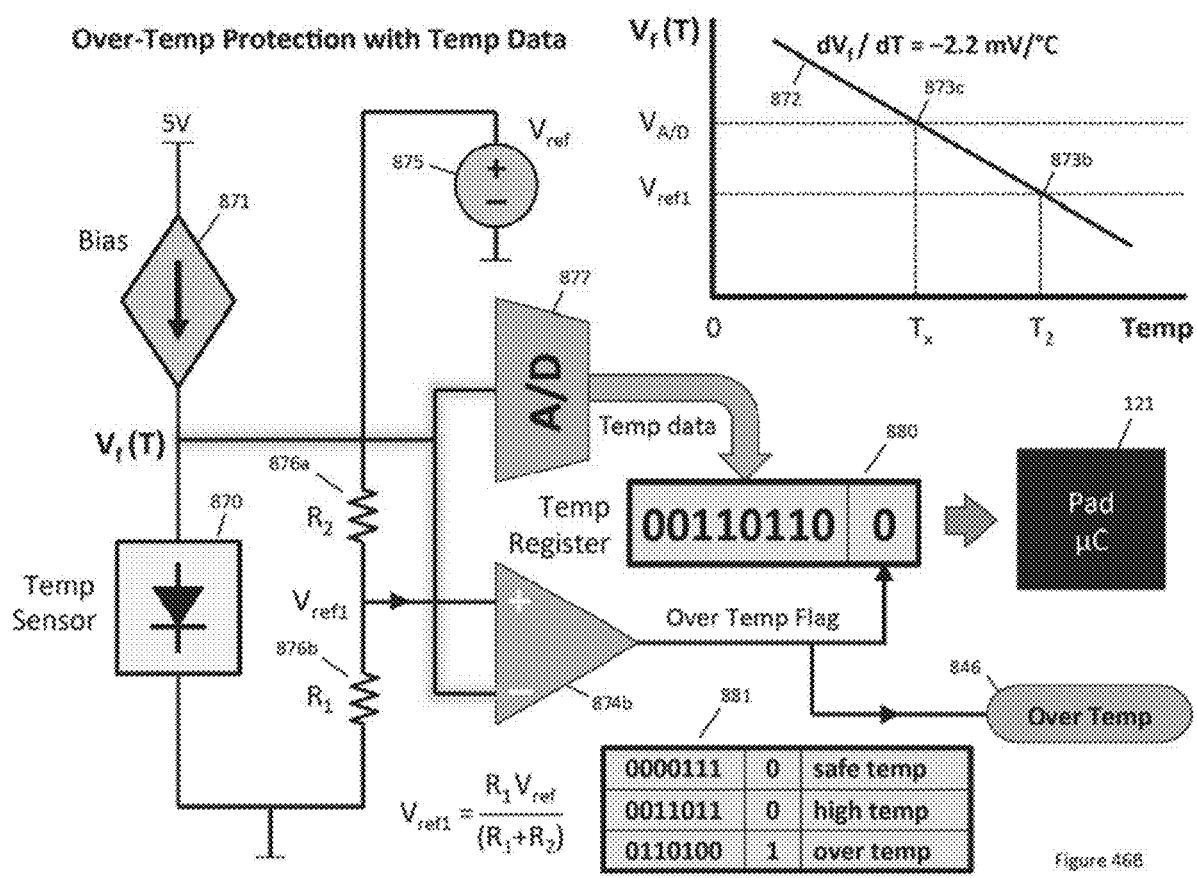
FIG. 46B is a schematic representation of an over-temperature protected intelligent LED pad with real time temperature reporting capability.

Returning to FIG. 46A, at even higher temperatures where $T_2 \le T_1$, $\le T$ then accordingly $V_{ref2} > V_{ref1} > V_f(T)$, i.e. representing a point in the $V_f$ versus T graph beyond 873b. In such an event comparators have positive inputs greater than their negative inputs and the outputs of both have a high logic state where temperature register 878 changes to a digital value |11| and is passed to pad μC 121 as shown in step 3 of FIG. 47. Moreover, because over-temp flag is high, the over-temp interrupt 846 occurs, immediately halting operation, send interrupt communication packet 960 to PBT controller 110. Packet 960 with interrupt packet type 961 and filetype 962 having a hex code |04-FE-02| meaning "Interrupt/Alert Flag/Over Temperature Shutdown," with a null payload 964 is then sent to inform the host PBT controller the intelligent LED pad 120 is overheating and triggering an over-temp interrupt service routine. In an over temp ISR, the LED can be permanently disabled as shown in step 5, or it can be restated after it cools below temperature $T_2$. Options include trying only once, trying multiple times, or repeatedly trying over and over (so called hysteric oscillations). In summary, the result of operation of the temperature sensing circuit is summarized in table 879 of FIG. 46A. In an alternative embodiment shown in FIG. 46B, the high temp comparator 874a is replaced with A/D converter 877, the output of which is stored in temperature register 880. As illustrated in table 881 the digital representation of the temperature increases proportionally with temperature. It is important however to retain over temperature 874b in order to provide autonomous protection for each intelligent LED pad independent from reliance on PBT controller 110 or on software running on pad μC 121. In this manner the disclosed distributed PBT system can be used to control an intelligent LED pad operation remotely. Furthermore, the methods disclosed herein can be adapted to control multiple intelligent LED pads simultaneously from a common PBT controller.

Made in accordance with this invention, sensor data can be automatically and regularly uploaded during every blink timeout and corresponding blink interrupt service routine. While any data set can be uploaded during the blink ISR, it is important to update data files that involve safety or operation-critical functions, i.e. parameters where a timely response is an important factor. For example, images and data files do not need such frequent updating and can be serviced when convenient in operation. Sensors used to detect overheating, electrical failure, and moisture, require a rapid response to prevent device damage and insure safe system operation. For example, detecting a rapid increase in humidity, i.e. moisture detection of water or sweat, indicates that the sanitary barrier has been forgotten or misapplied and is incapable of preventing moisture penetration into the pad through the pad's LED windows. Detecting moisture and rapidly disabling operation can avoid permanent damage to an LED pad.

Figure 46C:
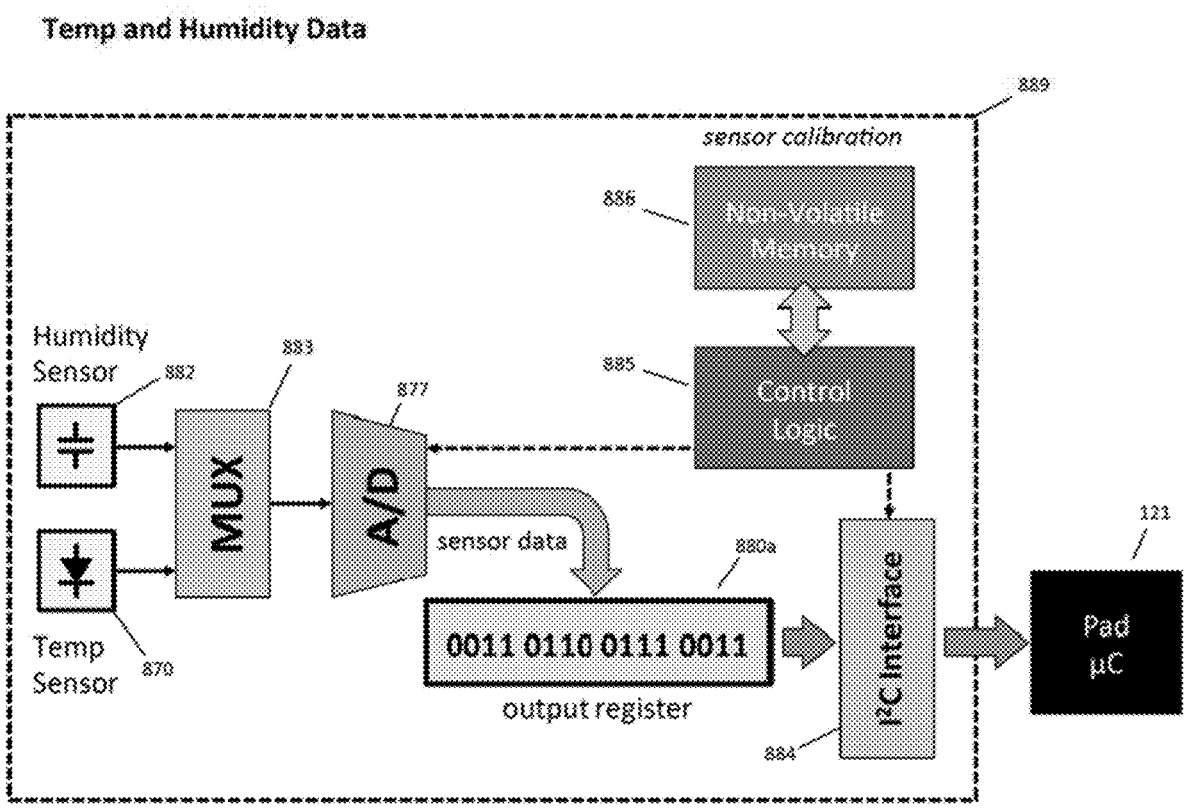
FIG. 46C is a schematic representation of an intelligent LED pad with real time temperature and humidity reporting capability.

For example, sensors exist capable of detecting moisture as relative humidity (RH) and also measuring temperature in a single integrated sensor. As shown in FIG. 46C, integrated sensor 889 for RH and temperature includes temp sensor 870 and humidity sensor 882 whose signals are multiplexed 883 into a single A/D converter 877 creating an output register 880a containing both data types. The data is output vias a bus interface such as $I^2C$ interface 884 to intelligent LED pad μC 121 which is able to interpret the data in order to decide if an over-temperature or high-humidity fault condition has occurred and to take corrective action. The data output from $I^2C$ interface 884 is controlled by integrated control logic 885 and may include sensor calibration data stored in non-volatile memory 886 used to correct for nonlinearities in sensor response and to compensate for stochastic variability arising from the manufacturing process. Other sensor data that may be detected communicated during the blink ISR include:

Stress sensor used to detect to warn against LED pad misuse and excessive bending leading to LED pad breakage
  Force or mechanical pressure detector used to detect and to warn against excessive force or weight being put on the LED pads leading to crushing of the LEDs and lead breakage.
  Air pressure sensor or altimeter used to detect thin air, i.e. low pressure, which may result in unknown physiological effects on a patient undergoing PBT treatments.

In summary, the foregoing control features in the disclosed distributed PBT system uniquely include variety of features not available in any prior art PBT system, including:

A distributed PBT system comprising intelligent LED pads with autonomous operation including interrupt routines including safety provisions against overheating or excessive treatments time due to software malfunction.
  A distributed PBT system where a reference clock local to each intelligent LED pad is paused to suspend treatment due to overheating or software malfunction, and where the intelligent LED pad communicates over a network to PBT controller that a fault condition has occurred. No prior art system offers such local safety and communication feature within an intelligent LED pad.

A distributed PBT system comprising an intelligent LED pad with a blink counter that regularly interrupts operation to check if the pad's software is still executing properly and to inform the system if a fault is detected A distributed PBT system comprising an intelligent LED pad with a blink counter that regularly interrupts operation to check is a pad connection has changed and to insure that the proper power levels are present in the system.

A distributed PBT system comprising an intelligent LED pad with a watchdog timer that disables LED operation, terminating a PBT treatment, if the LEDs stay on for too long (meaning a software execution error has occurred)

A distributed PBT system comprising an intelligent LED pad with an integrated temperature sensor able to distinguish if the pad's temperature is elevated or if the pad is overheating and to take steps to protect the patient and to recover operation if possible, including terminating the treatment, reducing the duty factor of a treatment, or reloading the treatment parametric file while communicating the pad's status to the PBT controller.

A distributed PBT system capable of uploading sensor array data from an intelligent LED pad to the PBT controller during a blink counter ISR (interrupt service routine).

IP Connectivity

As described, the delivery of LightOS data packets in a distributed PBT system can be achieved using a 4-layer communication protocol executed over a wired bus such as USB, I²C, SMBus, FireWire, Lightening and other wired communication mediums. If however distributed PBT system communication is performed over Ethernet, WiFi, telephonically over cellular networks (such as 3G/LTE/4G or 5G), or if data is passed through a public router, communication cannot be performed exclusively through the MAC address, i.e. a Layer-1 and Layer-2 communication stack is not sufficient to execute data routing through the network.

Figure 48:
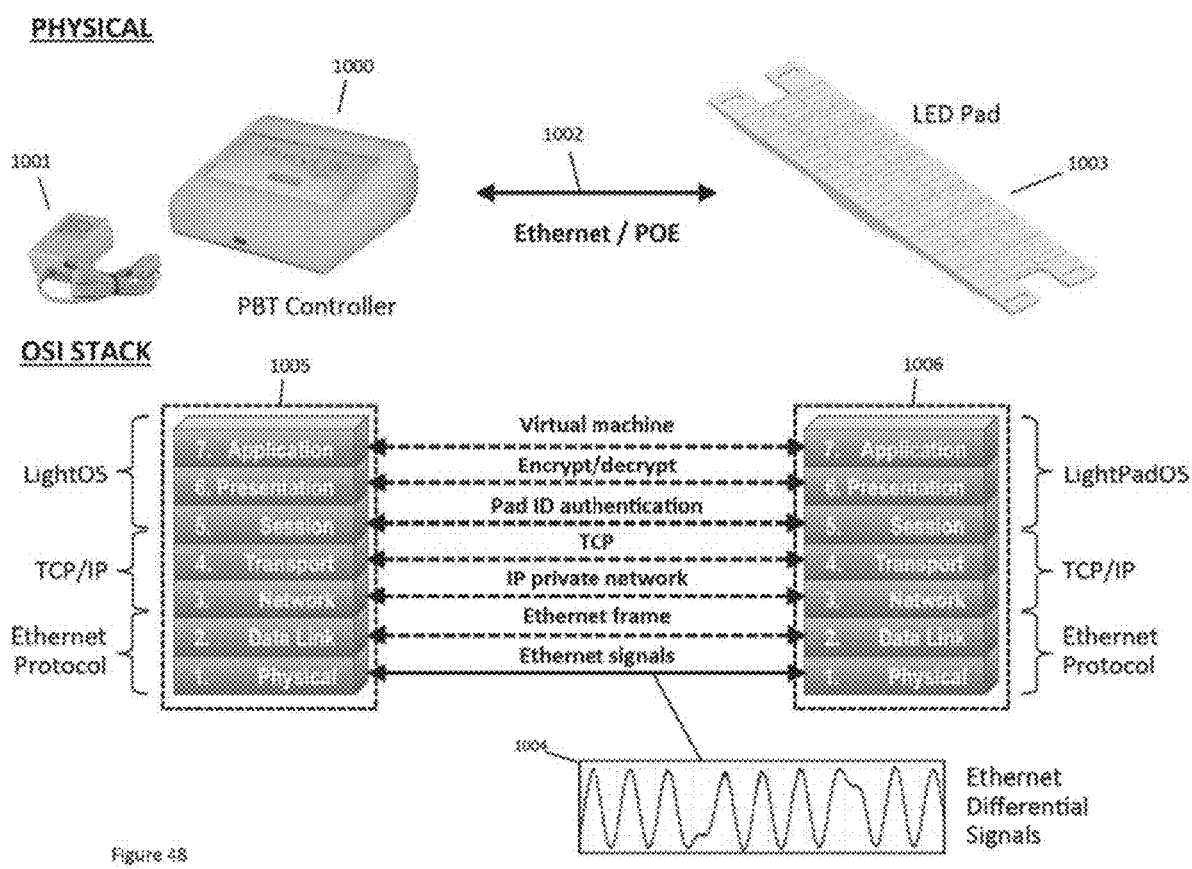
FIG. 48 illustrates a 7-layer Ethernet based PBT system with LightOS communication protocol stack.
Figure 49:
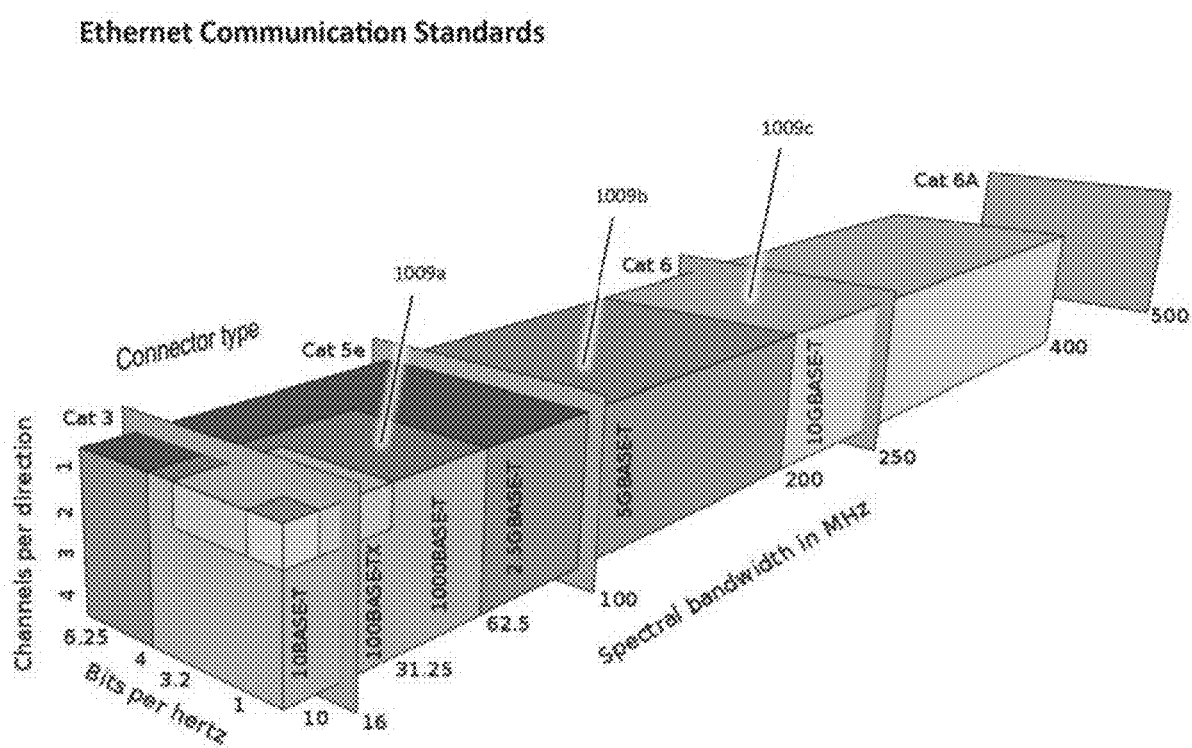
FIG. 49 is a graphical representation of various Ethernet communication performance standards.

For example FIG. 48, PBT controller 1000 communicates over Ethernet 1002 to intelligent LED pad 1003 using a 7-layer OSI compliant communication stack, specifically where communication stack 1005 of PBT controller 1000 includes PHY Layer-1 and Data Link Layer-2 executing the Ethernet communication protocol over Ethernet differential signals 1004; Network Layer-3 and Transport Layer-4 executing network communication in accordance with TCP/IP (transfer communication protocol over Internet protocol network), and LightOS operating system defined applications layers comprising Session Layer-5 for authentication, Presentation Layer-6 for security (encryption/decryption), and Application Layer 7 for PBT system control and therapy. Communication stack 1006 of LED light pad 1006 includes the corresponding Layer-1 and Layer-2 protocols for Ethernet and Layer-3 and Layer-4 for TCP/IP, along with LightPadOS defined layer 5 through 7. In point-to-point communication, i.e. for communication not involving an IP router, Ethernet connection 1002 operates as a private network over network Layer-3. The intelligent LED pad's operating system LightPadOS is a subset of LightOS and therefore is able to communicate with one another as a single virtual machine (VM) despite being physically separated from one another. Using Ethernet as a communication standard FIG. 49 illustrates communication can occur at a variety of bits rates depending on the Ethernet chipset and connector types, spectral bandwidth (in Hertz), channels per direction, and various bits per Hertz (symbol rates). For example, operating up to a spectral bandwidth of 62.5 MHz, Cat-3 connector is used to implement 1000BaseT Ethernet communication 1009*a*, while 5GBaseT Ethernet 1009*b* requires 200-MHz spectral bandwidth and a Cat-5e connector. By extending the bandwidth to 250 MHz, performance can be doubled to 10GBaseT Ethernet communication 1009*c*. Future protocols are planned to extend the spectral bandwidth to 500-MHz.

Figure 50:
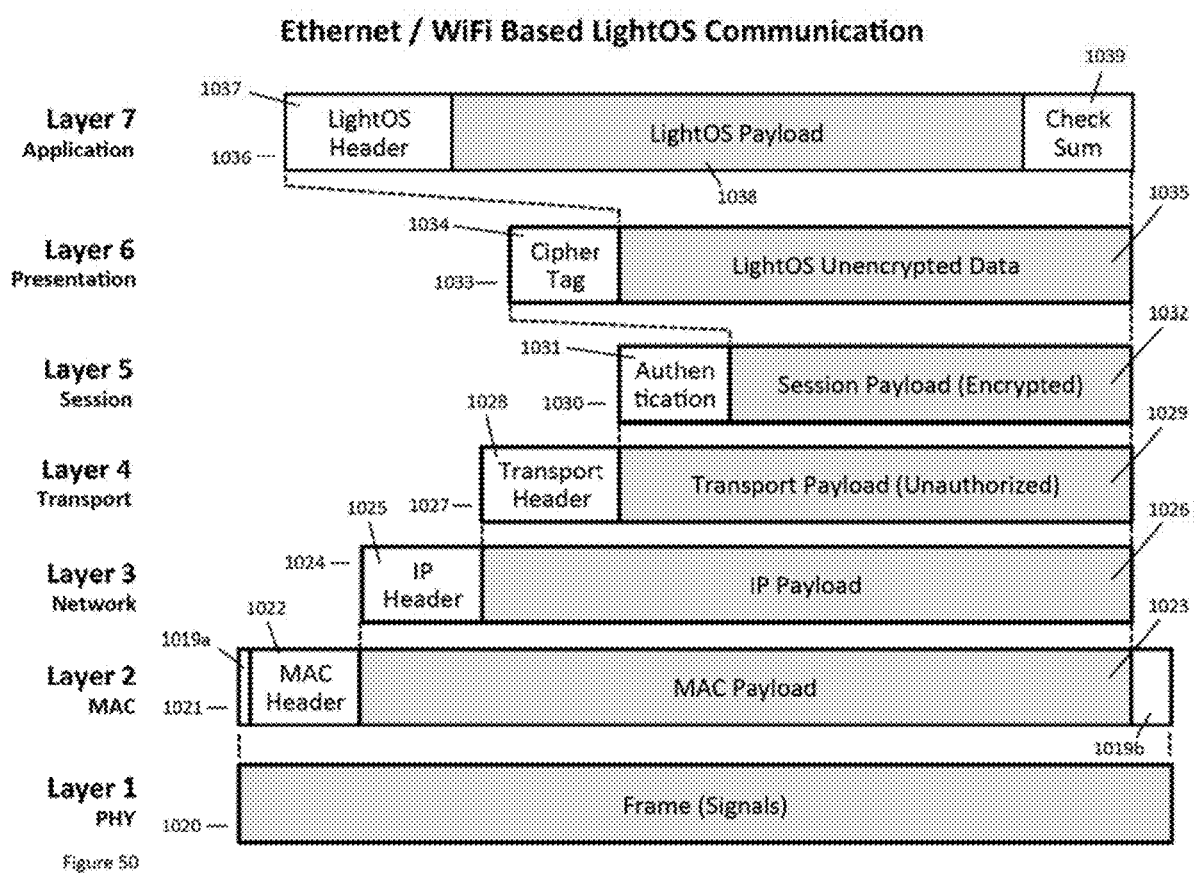
FIG. 50 illustrates a 7-layer Ethernet/WiFi based datagram with LightOS payload.

In a manner similar to the previously described 4-layer communication stack of FIG. 9, the full 7-Layer OSI communication stack comprises nested data packets as shown in FIG. 50 where frame 1020 comprising PHY Layer-1 signals of electrical conduction or electromagnetic waves (radio, microwave, light). These PHY Layer-1 signals are arranged as communication symbols in accordance with specific communication protocols for packet switched networks in MAC Layer-2 packet 1021 comprising MAC header 1022, MAC payload 1023 and padding 1019*a* and 1019*b*. The padding, representing timing and delays for synchronization and error checking is shown here as Layer-2 data, may alternatively be represented as part of the Layer-1 frame. As described previously, the function of MAC header 1022 is to establish a data link between any two directly connected communicating devices such as a PBT controller and the intelligent LED pad, or a PBT controller communicating to an Ethernet or WiFi router.

In the 7-Layer data OSI data packet as shown, MAC payload 1023 contains network routing information in Network Layer-3 data packet 1024 made in accordance with Internet protocol (IP) including IP header 1025 and IP payload 1026. IP header 1025 (described in greater detail later in this application), contains all required routing information for determining network routing using IPv4 or IPv6 protocols including source and destination IP addresses, the length of the IP payload, the longevity of a data packet (to avoid immortal packets clogging the network), provisions for various network messages such as ICMP (ping) and IGMP (group broadcasts), and a variety of error checking vehicles for maintaining packet ordering, detecting packet corruption, and reporting network congestion.

Importantly, IP header 1025 in Network Layer-3 data packet 1024 of FIG. 50 specifies the type of Transport Layer-4 data packet utilized in its IP payload 1026, including the OSI standards transmission control protocol (TCP) and user datagram protocol (UDP) as well as provisions for custom protocols. The details of TCP or UDP are specified in transport header 1028 of Transport Layer-4 datagram 1027, Packet switched network communication using TCP, also referred to as TCP/IP, employs "handshaking" to insure data packet content is delivered with robust data integrity, i.e. error free, utilizing error checking and packet resending until a file's reception is confirmed as error free. TCP therefore offers superior integrity through handshaking but in so doing sacrifices real time performance and propagation delay. UDP comprises a single communication packet with no provision for automatic resending of the data packet, thereby risking data accuracy for the sake of expediency. UDP is therefore beneficial in sending audio and video information where data errors are not detectable by users, but not for program files such as LED streaming files, LED playback files, or software and firmware transfers such as LightPadOS and LED player files.

In general, most 7-layer communication packets employed in a distributed PBT system as disclosed employs TCP used in conjunction with the Internet protocol, shown in FIG. 48 as TCP/IP combining the functions of Network Layer-3 and Transport Layer-4. The value of TCP/IP data packet routing is that packet switched communication between two communicating devices can traverse a network through multiple devices and routers not part of the same local network, i.e. the PBT controller need not be part of the same subnet as the intelligent LED pads being controlled. An example of this situation could occur in any number of hypothetical use scenarios, for example in a hospital ward where a single master PBT controller is used to control multiple channels of intelligent LED pads treating a number of different patients located in different hospital rooms throughout the ward. In such cases, it likely that the patient's rooms may not share the same WiFi subnet as the nurse's station where the PBT controller and monitor is located. Returning to in FIG. 50, transport payload 1029, the payload of Transport Layer-4 is labeled as "unauthorized" because authentication, i.e. the process for confirmation (authentication) that a device or user is not a fraud, and that the device or user is approved (authorized) to connect to the PBT system occurs at Layer-6. For incoming data traversing up the 7-layer communication stack, transport payload 1029 is not authenticated as a valid incoming packet at Layer-4. Instead transport payload 1029 contains Session Layer-5 packet 1030 comprising the session header, labeled as authentication header |O3|, and session payload 1032. Authentication header |O3| plays several roles in its use in the disclosed distributed PBT system. In communication between an intelligent LED pad and the PBT controller, authentication is used to confirm that the intelligent LED pad meets the criteria necessary to connect to one another, i.e. to communicate across a common packet switched network. In communication between the PBT controller and a server, authentication is used to confirm that the user has the authority to access certain menus and files and to download them into the PBT controller. Session Layer-5 authentication protocols include the PAP Password Authentication Protocol, SOCKS5, and other authenticated communications.

The other function of the Session Layer-5 is to facilitate a communication "session" between the PBT controller and either a server or the intelligent LED pad. According to Wikipedia, "In the seven-layer OSI model of computer networking, the session layer is layer 5. The session layer provides the mechanism for opening, closing and managing a session between end-user application processes, i.e., a semi-permanent dialogue. Communication sessions consist of requests and responses that occur between applications. Session-layer services are commonly used in application environments that make use of remote procedure calls (RPCs). Within the service layering semantics of the OSI network architecture, the session layer responds to service requests from the presentation layer and issues service requests to the transport layer." Socket Secure or SOCKS (https://en.wikipedia.org/wiki/SOCKS), a Layer-5 Internet protocol utilizes a proxy server to exchange data packets between a client and server using a TCP connection with an arbitrary, i.e. ad hoc, IP address, or for providing secure forwarding of UDP packets. SOCKS server accepts incoming client connection on TCP port 1080. Its authenticated version SOCKS5, limits access to the proxy server to only authenticated users.

Other available Session Layer-5 protocols include RPC remote call procedure; OSI-SP session-layer protocol (X.225, ISO 8327), PPTP point-to-point tunneling protocol, SCP session control protocol, SDP sockets direct protocol and others. In essence once a session is established between two devices in the distributed PBT system, the session remains open and active (subject to meeting certain activity requirements) where the communicating devices maintain a constant virtual connection with no need to repeat a login or authentication procedure. In essence the devices exchange identifying information to insure an imposter cannot engage in their communication exchange. Other session and security protocols operate at multiple levels, especially comingling security credential exchange and the process of AAA (authentication, authorization, and administration) across OSI Layers-5, 6 and 7.

In FIG. 50 session payload 1032 is labeled as "encrypted" because for incoming data packets, decryption occurs at Presentation Layer-6 (although it can be executed in Layer-7 if desired). Session payload 1032 containing Presentation Layer-6 data packet 1033 may be partially or completely encrypted. In particular, the data used to extract LightOS unencrypted data 1035 is always encrypted. The data in the cypher tag 1034 field may, or may not be, encrypted depending on its use in the LightOS operating (and LightPadOS sub-system). If the cypher tag 1034 is encrypted, the encryption key exchange is executed before the contents of cypher tag 1034 can be known. In such cases its contents are used to determine the context or use of the corresponding LightOS unencrypted data 1035 data field, meaning cypher tag 1034 is used by the operating system to know what to do with file once it is decrypted, e.g. to store it, store it and use it, use it and then delete it, etc. If instead, cypher tag 1034 is unencrypted it can be used in the decryption process. Cipher tag 1034 may comprise:

A partial decryption key (where the remainder of the split key is communicated through another channel or in another packet).

A numeric seed used in a look up table of shared secrets to choose a specific decryption algorithm.

A decryption key provided that the algorithm used to decrypt the packet is not communicated through the same channel or in the same communication packet.

A "state" such as time or location used in a state driven dynamic encryption/decryption system, i.e. where the state must be known to know how to undo the encryption used.

The encryption key to be used in the next packet's encryption of the same communication session.

The encryption algorithms employed by the disclosed distributed PBT system can comprise any number of available methods in various combinations. Although the actual process to secure communication occurs across several OSI layers from Layer-3 to Layer-7, the generic function of encryption and decryption is executed as part of Presentation Layer-6.

Specifically, Presentation Layer-6, also referred to as the syntax-layer, acts as a data translator interface between Session Layer-5 and Application Layer-7, restructuring incoming data packets into a format that the application layer can use for further processing or display. This character mapping function of Presentation Layer-6 involves using public standards needed for syntactic translation, and using shared secrets for security and privacy. Examples of the use of publically adopted standards in Presentation Layer-6 includes mapping an EBCDIC-coded text computer file to an ASCII-coded file, converting a bit file into a BMP image, translating a static picture file into a PNG image, translating a PDF file into a readable document, or translating a time-based file into an MPEG video or audio file. Conversely using shared secrets exchanged in a communiqué or handshaking prior to establishing a session, the Presentation layer-6 can execute character translation of encrypted files. In this context, decryption can be considered a remapping of characters, except it uses a key-based translation table not known to the public.

As mentioned previously, the Presentation Layer-6 does not act alone in insuring security. In many instances the distinction between Layers-5, 6, and 7 are blurred. For example, according to Wikipedia "in many widely used applications and protocols, no distinction is made between the presentation and application layers. For example, Hypertext Transfer Protocol (HTTP), generally regarded as an application-layer protocol, has presentation-layer aspects such as the ability to identify character encoding for proper conversion, which is then done in the application layer." Other Layer-7 security credentials involve the exchange of digital "cookies" to authorize a specific application process. Similarly, encrypted communication may involve the exchange of cryptographic keys or digital-certificates as part of the handshaking process as a Session Layer-5 protocol. Other security protocols involve operations spanning Layer-4 and Layer-5 but also used as part of Layer-7. For example the Internet Engineering Task Force (IETF) responsible for establishing, deploying, and maintaining standards across the Internet, has adopted Transport Layer Security or TLS (https://en.wikipedia.org/wiki/Transport_Layer_Security) along with "forward secrecy" as methods to prevent eavesdropping and tampering in network communication, replacing SSL as a security method, especially for communication between servers and browsers.

Regardless of the protocols used in encryption and decryption and the handshaking procedures employed in authenticating users and devices, in the multilayer communication packet of FIG. 50 the delivery and use of Application Layer-7 data packet 1036 requires secure communication to prevent hacking and intrusion of the distributed PBT system. The process is bidirectional, extracting the LightOS specific payload 1038 from incoming data packets, or obfuscating the payload's contents in outgoing data packets moving down the communications stack in preparation for transmission across the network. For example, for incoming datagrams, Transport Layer-4 datagram 1027 can only be used to extract session payload 1032 after a valid authenticated communication session has been initiated, and encrypted session payload 1032 can only be decrypted to extract LightOS unencrypted data packet 1035 after proper security credentials (such as decryption keys and cipher tag 1034) have been exchanged. Application Layer-7 data packet 1036 comprising LightOS header 1037, LightOS payload 1038, and checksum 1039 although unencrypted, offer further protection, using device ID information to prevent PBT system interoperability with unauthorized devices, copycat manufacturers, or fraudulent components.

Conversely, preparation of outgoing messages, commands, or file transmissions, requires a sequence of steps to prevent unauthorized access to a datagram's contents. In packet preparation, LightOS payload 1038 is first combined with header 1037 describing the contents of the LightOS packet, the device for which the communication is intended, and the size of the payload's data field. Checksum 1039 is appended to the file to create Application Layer-7 data packet 1036. The purpose of checksum 1039 is to insure data integrity of the LightOS communiqué. Unencrypted LightOS data packet 1035 is then encrypted in accordance with cipher tag 1033 or using encryption keys (not included within the data packet) to produce encrypted session payload 1032. Session payload is then combined with authentication criteria stored in authentication header |O3| to create Session Layer-5 data packet 1030. The prepared data packet is then passed down to the TCP/IP layers in preparation for network routing and ultimately down to the data link and PHY Layers-2 and -1 for transmission across the network.

Figure 51:
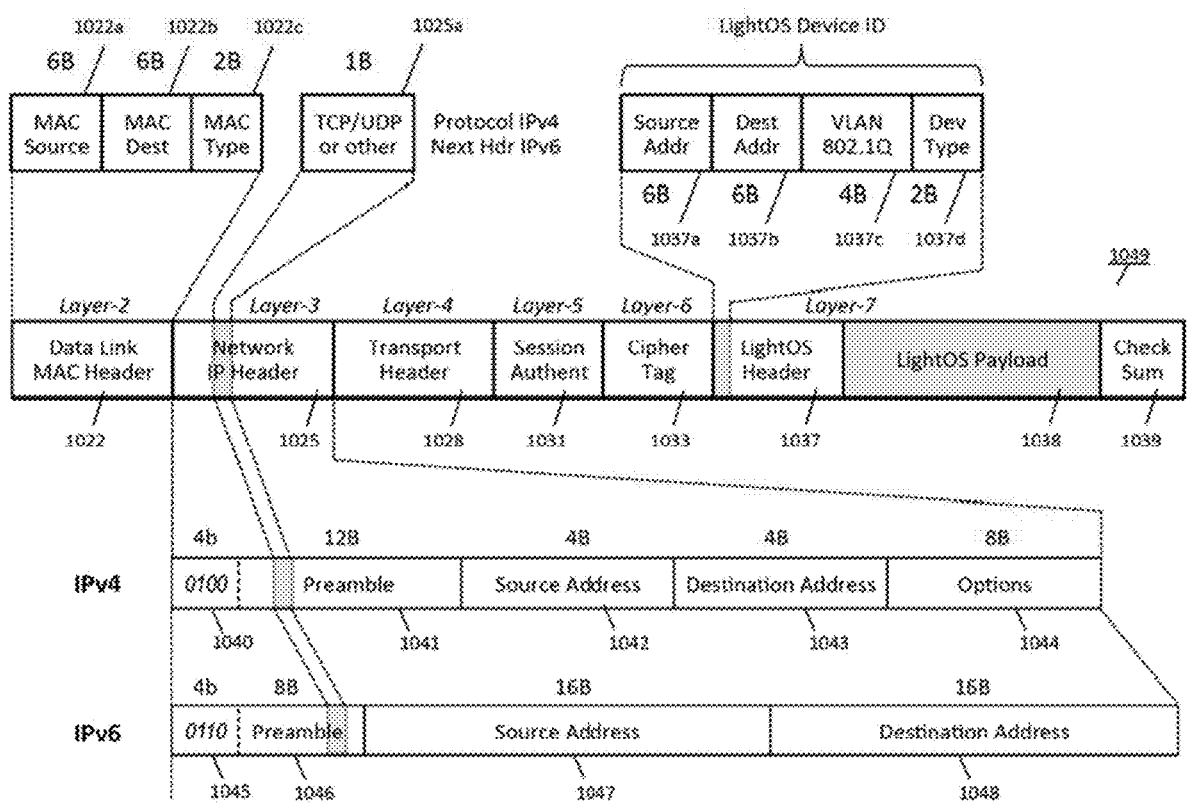
FIG. 51 illustrates an IP datagram with LightOS payload.

To better understand the application of a 7-layer OSI datagram to LightOS communication in the disclosed distributed PBT system, a simplified representation of data frame 1049 is illustrated in FIG. 51 comprising MAC header 1022 for data link Layer-2; IP header 1025 for Network Layer-3; transport header 1028 for Transport Layer-4; session authentication header |O3| for Session Layer-5; cipher tag 1033 for Presentation Layer-6; and LightOS header 1037, LightOS payload 1038, and checksum 1039 for Application Layer-7 contents. The "flattened" format of data frame 1049 replaces the multi-layer embedded format of the OSI model, instead representing each layer as a header and its payload in succession, i.e. as a series of headers preceding LightOS payload 1038. As depicted MAC header 1022 comprises three fields—MAC source address 1022a, MAC destination address 1022b, and MAC type 1022c. The MAC address field is used to facilitate a Layer-2 connection between directly communicating devices, i.e. devices on the same subnet, but not for devices on different subnets where data packets pass through a router.

Figure 52A:
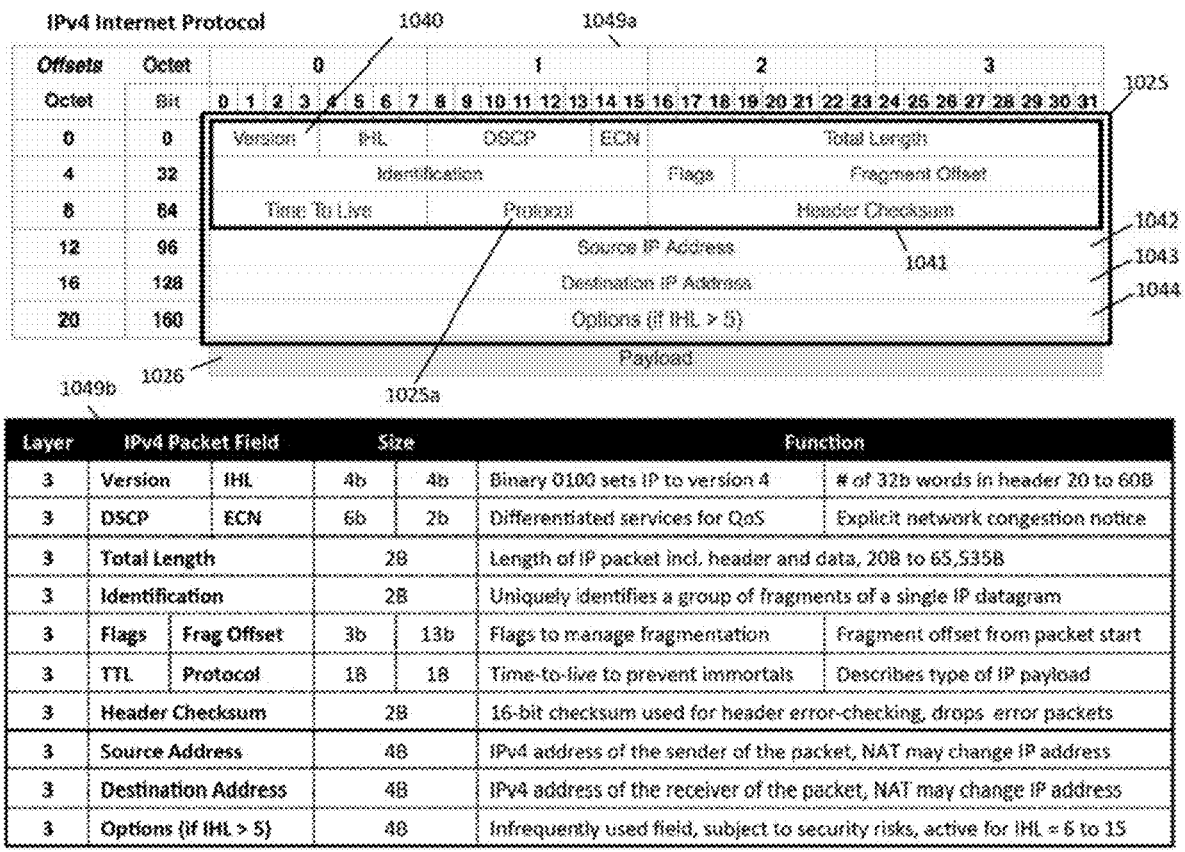
FIG. 52A is a Layer-3 description of IPv4 Internet protocol datagrams.

To facilitate data transmission across a network from one subnet to another (i.e. data packets passing through Ethernet or WiFi router), Network Layer-3 information is included in LightOS data packet 1049 in network IP header 1025. Greater detail of the Layer-3 IPv4 protocol is shown in FIG. 52A as data packet 1049a with explanation table 1049b including network header 1025 and IP payload 1026. The length and content Layer-3 data in network IP header 1025 depends of the first four bits of the field. If the first four bits of the IP header (field 1040 contained within preamble 1041) comprise the binary equivalent of the number 4, i.e. as binary |01-00|, then the IP address is an IPv4 address comprising a 12B preamble 1041, a 4B source IP address 1042, a 4B destination address 1043, and an 8 B options field 1044. Using a 4-B (32 bits) long IP address, IPv4 is able to address $2^{32}$ or 4,294,967,296 unique addresses. These addresses are further subdivided into three classes, namely:

IPv4 class A: 128 ($2^7$) networks of 16,777,216 ($2^{24}$) clients comprising addresses 0.0.0.0 thru 127.255.255.255

IPv4 class B: 16,384 ($2^{14}$) networks of 65,534 ($2^{16}$) clients comprising addresses 128.0.0.0 thru 191.255.255.255

IPv4 class C: 2,097,152 ($2^{21}$) networks of 254 ($2^8$) clients comprising addresses 192.0.0.0 thru 223.255.255.255

With a limited number of addresses, exhaustion of IPv4 addresses is a long-term concern (https://en.wikipedia.org/wiki/IPv4_address_exhaustion), especially with the explosive growth of IoT connected devices. Although the dynamic allocation of IP addresses slows IPv4 address depletion and may postpone address exhaustion, the long-term solution is conversion to IPv6.

Figure 52B:
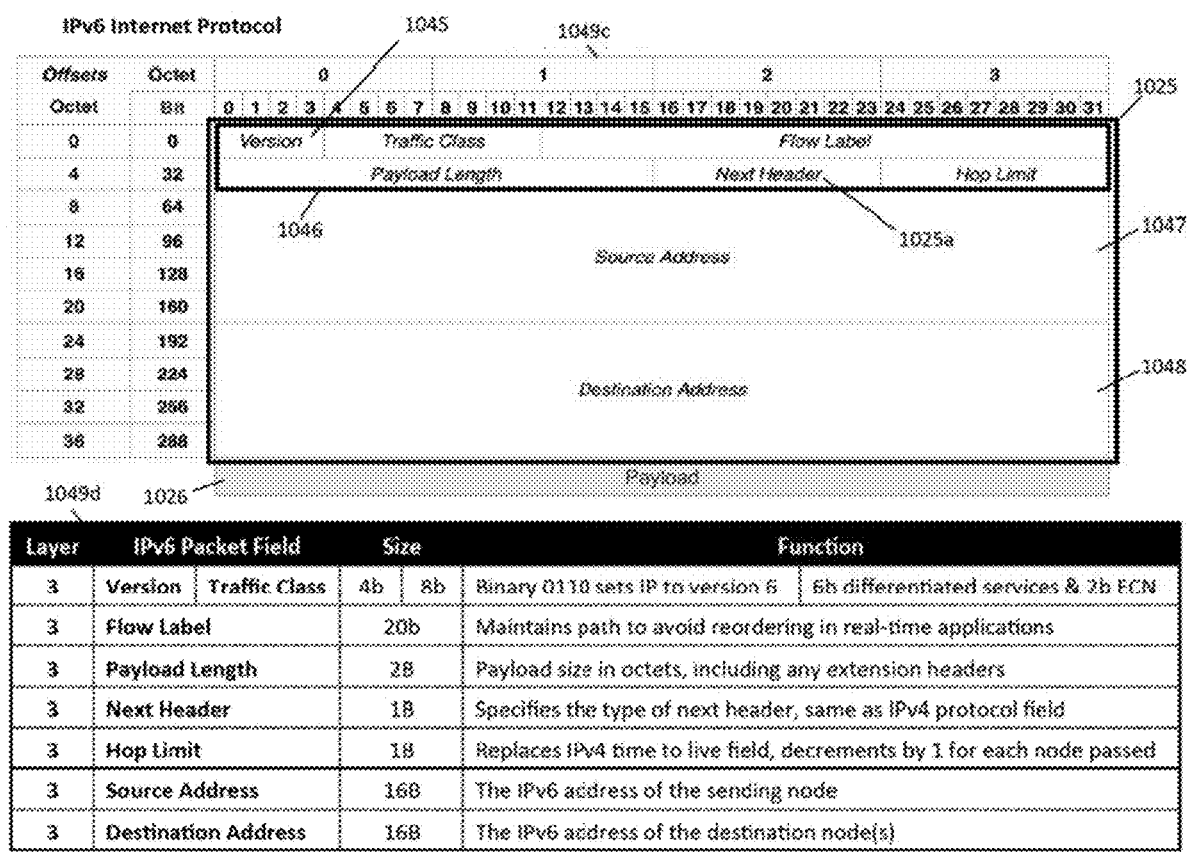
FIG. 52B is a Layer-3 description of IPv6 Internet protocol datagrams.

If the first four bits of the IP header (field 1045 contained within preamble 1046) comprise the binary equivalent of the number 6, i.e. as binary |01-10|, then the IP address is an IPv6 address comprising a 8B preamble 1046, a 16B source IP address 1047, and a 16B destination address 1048. IPv6 does not include an options field. Greater detail of the Layer-3 IPv6 protocol is shown in FIG. 52B as data packet 1049c with explanation table 1049d including network header 1025 and IP payload 1026. Using a 16-B (128 bits) long IP address, IPv6 is able to address $2^{128}$ unique addresses equal to an extraordinarily large number, namely 340,282,366,920,938,463,463,374,607,431,768,211,456 combinations. Unlike IPv4, IPv6 addresses are not divided into subclasses. With so many combinations and with the use of dynamic addressing, IP address exhaustion is not a concern.

As described previously, in 4-layer communication, routing of data packets through an Ethernet or WiFi router is not possible because the MAC address of the communicating devices is lost as the data packet passes through the router. By employing TCP/IP transport and incorporating Layer-3 and Layer-4 data field within an IP datagram, the 7-layer LightOS data packet 1049 as described is capable of data communication across any packet switched network. The need for such network capability in the disclosed distributed PBT system arises in a variety of circumstances, especially in hospitals where WiFi signal distribution throughout various wards, departments, and floors are hosted by different WiFi routers and therefore occupy separate subnets. The need for full 7-layer network communication also arises when a PBT controller contacts a cloud-based server, e.g. when downloading software updates, or uploading biometric data and treatment histories.

Figure 53A:
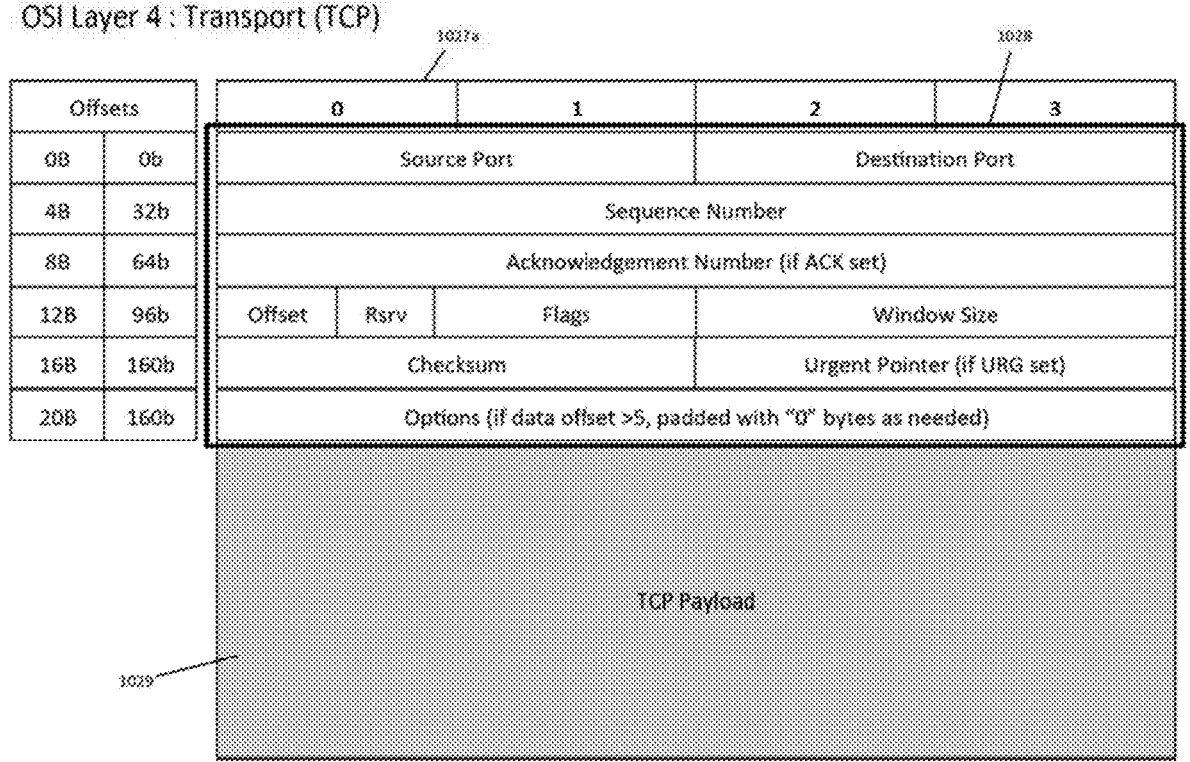
FIG. 53A is a Layer-4 description of TCP based Internet protocol datagrams.
Figure 53C:
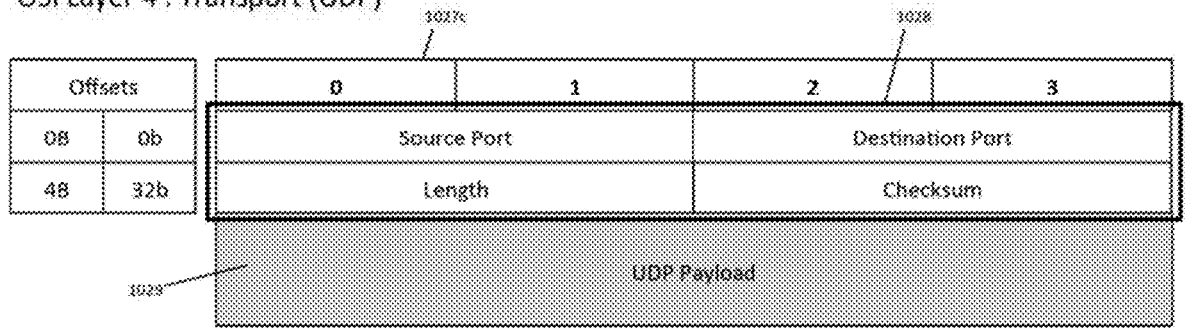
FIG. 53C is a Layer-4 description of UDP based Internet protocol datagrams.

Network IP header 1025 includes a field 1025a specifying the type of transport to be used in datagram routing, e.g. TCP, UDP or other protocols. In IPv4 this field is referred to as the "protocol" field while in IPv6 field 1025a is referred to as the next header field. Although the nomenclature for the 1-B wide field 1025a differs for IPv4 and IPv6, the numeric code and function is identical for both. Common codes include code #1 (hex |01|) for the Layer-3 function ICMP (ping), code #2 (hex |02|) for the Layer-3 function IGMP (group broadcast), code #6 (hex |06|) for the Layer-4 transport protocol TCP, and code #17 (hex |11|) for the Layer-4 transport protocol UDP. If transfer communication protocol (TCP) is selected, the transport header 1028 follows format 1027a with transport payload 1029 shown in FIG. 53A. Table 1027b of FIG. 53B further describes the data fields within TCP format 1027a. If the user datagram protocol (UDP) is selected, the transport header 1028 follows format 1027c with transport payload 1029 as shown in FIG. 53C where table 1027d further describes the data fields within UDP format 1027c.

Aside from the handshaking and error checking features of TCP and the expeditious nature of UDP, both Layer-4 protocols use a feature called a "port" to identify what kind of service is required. In essence, Network Layer-3 determines where (IP address) a datagram is sent, while Transport Layer-4 specifies how it is to be delivered (TCP, UDP) and what function it should perform once it arrives (its port number). According to the table shown in FIG. 53D, port numbers 0 to 1,023 are designated as system ports and generally registered such as those specified in the table shown in FIG. 53E. For example, port 80 refers to an HTTP port in TCP (but not in UDP) while port #20 refers to the FTP file transfer protocol for data transfer in both TCP and UDP. Ports in the range 49,152 to 65,535 comprising open dynamically assigned and reusable ports, as well as private and ephemeral ports are generally not registered. Ports in between, spanning the range of 1,024 to 49,151, are mixed some representing registered ports and others comprising open dynamically assigned reusable ports.

Despite the importance for being able to communicate across open networks and 3rd party routers, 7-layer network routing suffers certain disadvantages compared to the previously described 4-layer network communication, namely that precise pairing of the PBT controller and the specific type LED pad being controlled is not possible using the network packet because the manufacturer's OUI and product serial number contained in its MAC address is irrevocably lost when the Internet datagram packet passes through a router. Without knowing the LED pad's LightOS ID, it is difficult for the PBT controller to insure that it is controlling the right set of intelligent LED pads or to confirm if a particular LED pad might have been listed as part of a manufacturing recall. This situation is especially problematic when independent systems are being used in the same room, ward, or sharing the same router subnet.

Similarly, without knowing the PBT controller's ID, an intelligent LED pad may be unable to confirm commands it receives are intended for it and not for another intelligent LED pad. This scenario represents a very real risk of accidental communication between device components in clinics or hospitals where a large number of PBT systems may coexist and possibly share a communication network. Moreover, without identity pairing as part of the authentication process of initiating a communication session, the possibility exists for PBT system control to suffer interference from other devices, or for control to be usurped or tampered with by hackers or for malevolent purposes. Because an attacker may seek to intentionally defeat safety systems to create mischief or even confer harm to a patient, the authorization process needs to occur securely, immune to hacking or surveillance of security credentials. Because, however, the MAC address does not pass beyond a router, the MAC address cannot be used for device identification by the LightOS operating system.

To circumvent theses identity and security issues, an inventive feature of the LightOS data packet 1049 shown in FIG. 51 includes embedding LightOS device ID information in the encrypted portion of every LightOS communication packet 1049, for example comprising LightOS specific Application Layer-7 data buried within encrypted session payload 1032 of Session Layer-5 packet 1030. Without authentication and decryption, this device information cannot be monitored or extracted from surveillance of ongoing network traffic. In one embodiment LightOS device ID information is embedded within LightOS header 1037 and may include without limitation a 6-B source address 1037a of the device sending the packet, a 6-B destination address 1037b of the device receiving the packet, a 4-B data field 1037c describing if communication is being sent using a Layer-2 VLAN (communication made in accordance with IEEE standard 802.1Q), and a 2B device type field.

In another embodiment the LightOS Device ID data is a copy of the MAC addresses of the communicating devices. As an example, LightOS data packet 1049 may include Source address 1037a of the LightOS device ID may set to MAC source address 1025a of the first sending device, i.e. the message's origin, either the PBT controller or the intelligent LED pad depending on the direction of communication.

Destination address 1037b of the LightOS device ID may set to MAC destination address 1037d of the last receiving device, i.e. the message's terminus, either the intelligent LED pad or the PBT controller depending on the direction of communication.

Device type 1037d of the LightOS device ID may set to the MAC device type 1025c of the final destination of the data packet, i.e. the message's terminus, either the intelligent LED pad or the PBT controller depending on the direction of communication.

In one embodiment of this invention, the LightOS Device ID address for each intelligent LED pad may be obtained from LED pad identity register 207 shown in FIG. 16. Similarly, the LightOS Device ID address for the PBT controller may be obtained from PBT system identity register. As communication packets 1049 travel from PBT controller 110 to the intelligent LED pad 120 and vice versa during a "conversation" among interconnected devices during operation of the disclosed PBT system, the source address 1037a and destination address 1037b continuously swap depending on which device is the message sender or receiver.

Figure 54:
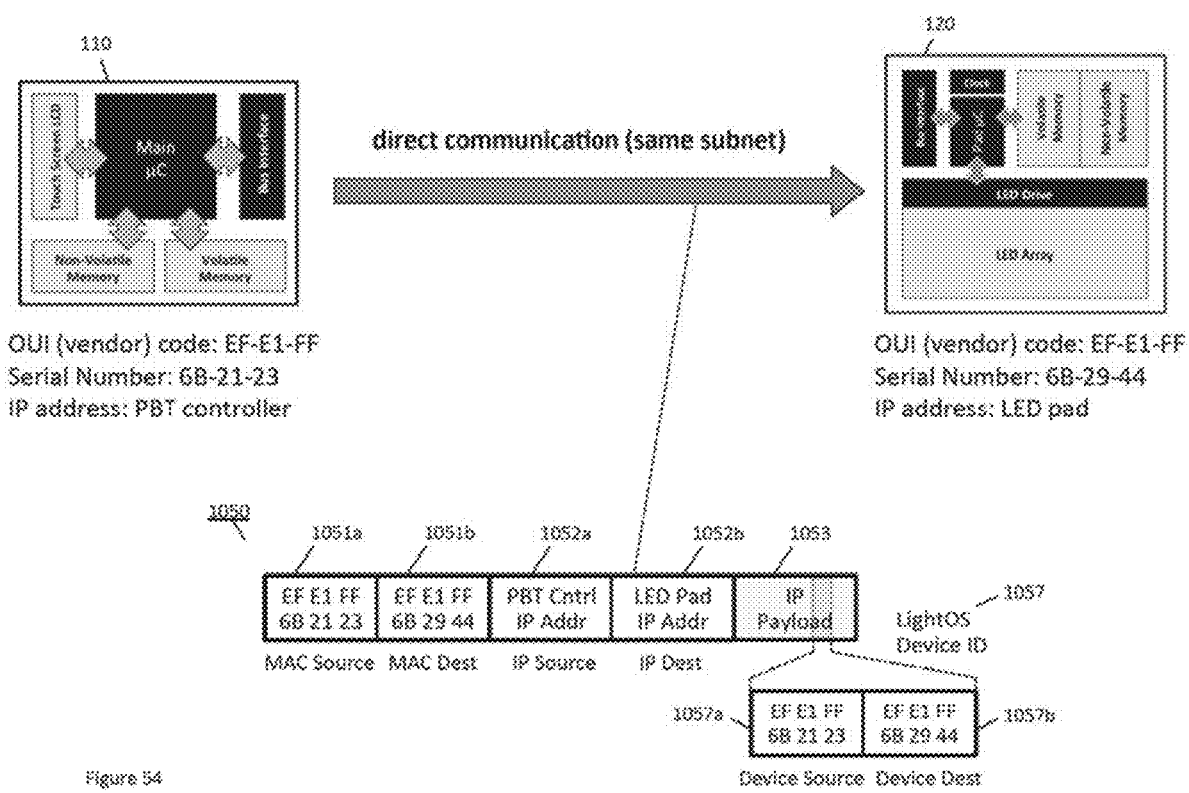
FIG. 54 illustrates an abridged LightOS datagram in direct Ethernet communication between PBT controller and LED pads.

It should be noted that the LightOS device ID contained within LightOS header 1037 and the MAC addresses as in MAC header 1022 are different, they may in some circumstances contain the same address information. For example, as shown in FIG. 54, direct communication between PBT controller 110 and intelligent LED pad 120 comprising exemplar data packet 1050 includes IP payload containing LightOS device ID 1057. In this example of direct communication, device source address 1057a is the same as MAC source address 1051a and device destination address 1057b is the same as MAC source address 1051b. As such, LightOS device ID 1057 is redundant. Similarly, in direct communication IP source address 1052a and IP destination address 1052b are not required to route data packet 1050.

Figure 55:
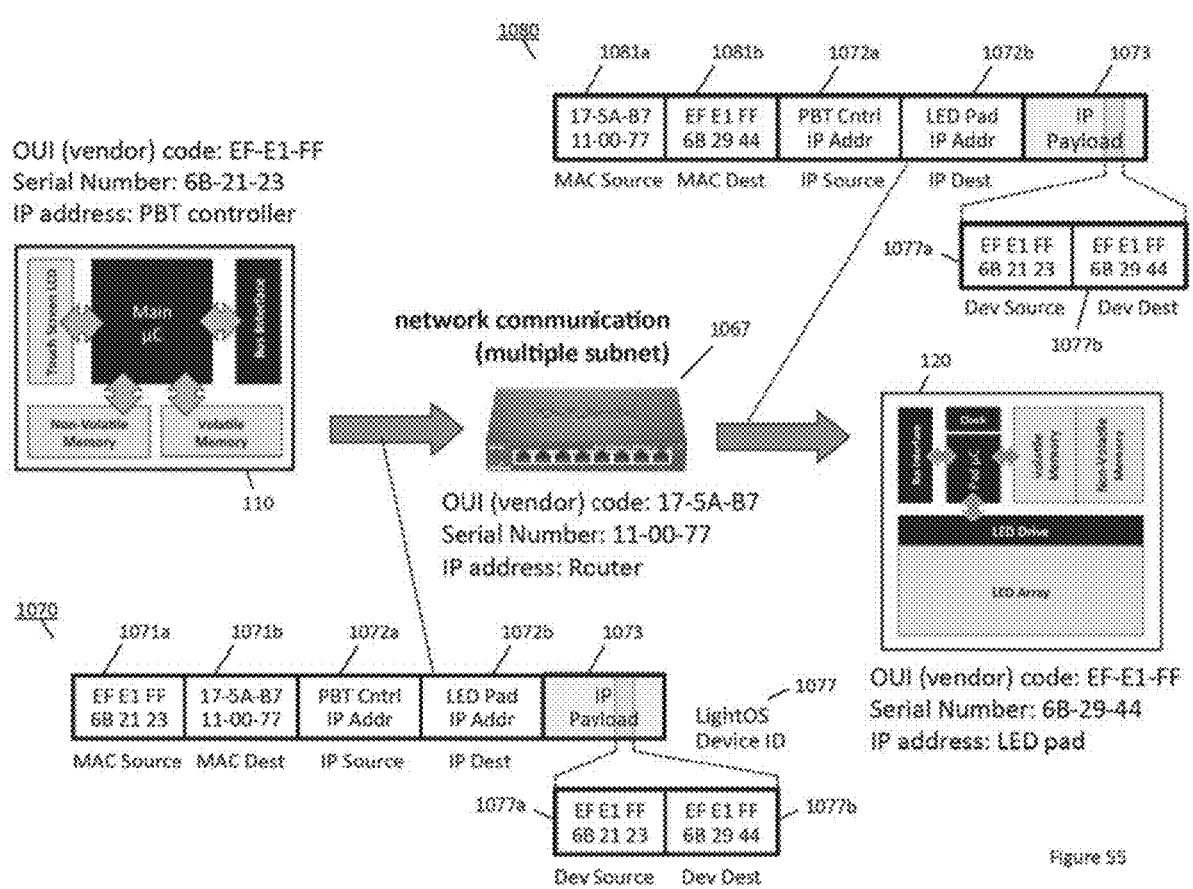
FIG. 55 illustrates an abridged LightOS datagram transport in Ethernet communication between PBT controller and LED pads traversing multiple subnets.

In the event, however, that data routing occurs through a router, across separate subnets having distinct MAC addresses, then the importance of the IP address in routing and the payload embedded LightOS device ID comes into play. This scenario is illustrated in FIG. 55 where communication between PBT controller 110 and intelligent LED pad 120 occurs via Ethernet router 1067 and over multiple subnets. For example in the first subnet between PBT controller 110 and Ethernet router 1067, LightOS communication packet 1070 includes MAC source address 1071A having the exemplar MAC address |EF-E1-FF-6B-21-23| of PBT controller 110 but a MAC destination address 1071b having a MAC address of Ethernet router 1067, namely |17-5A-B7-11-00-77| and not the MAC address of intelligent LED pad 120.

Figure 56:
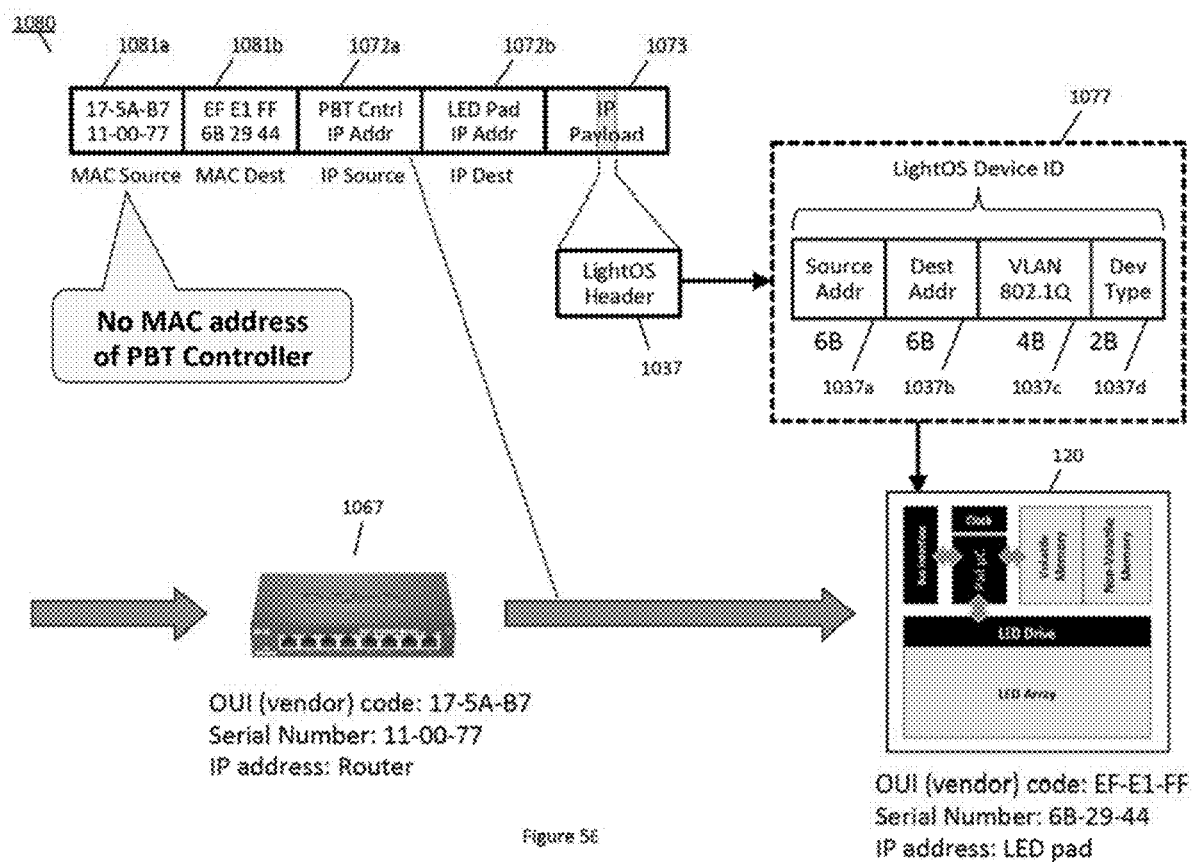
FIG. 56 illustrates extraction of LightOS device ID information from LightOS datagram in PBT controller to LED pads Ethernet communication traversing multiple subnets.

Routing of packet 1070 beyond Ethernet router 1067 to intelligent LED pad 120 occurs not using MAC Layer-2, but by Network Layer-3 having a source IP address 1027a of PBT controller and a destination IP address 1027b of intelligent LED pad 120. During transit, the datagram changes from packet 1070 to packet 1080 by updating the MAC addresses while retaining the same IP source and destination addresses. Specifically source MAC address 1081a is replaced by |17-5A-B7-11-00-77|, the address of PBT controller 110, while the MAC destination address 1081b is replaced by |EF-E1-FF-6B-29-44|, the MAC address of intelligent LED pad 120. As such, the MAC address of the PBT controller 110 is lost as the data packet passes through the Ethernet router 1067 preventing communication authentication between PBT controller 110 and intelligent LED pad 120. Using LightOS data packets made in accordance with this invention, inclusion of device source address 1027a and destination address 1027b in IP payload 1073 allows authentication of incoming data packets even in a network utilizing a router and comprising multiple subnets. In operation, the transfer of LightOS device ID 1077 is further exemplified in FIG. 56, where the contents, once extracted from LightOS header 1037 are loaded into intelligent LED pad 120.

Figure 57:
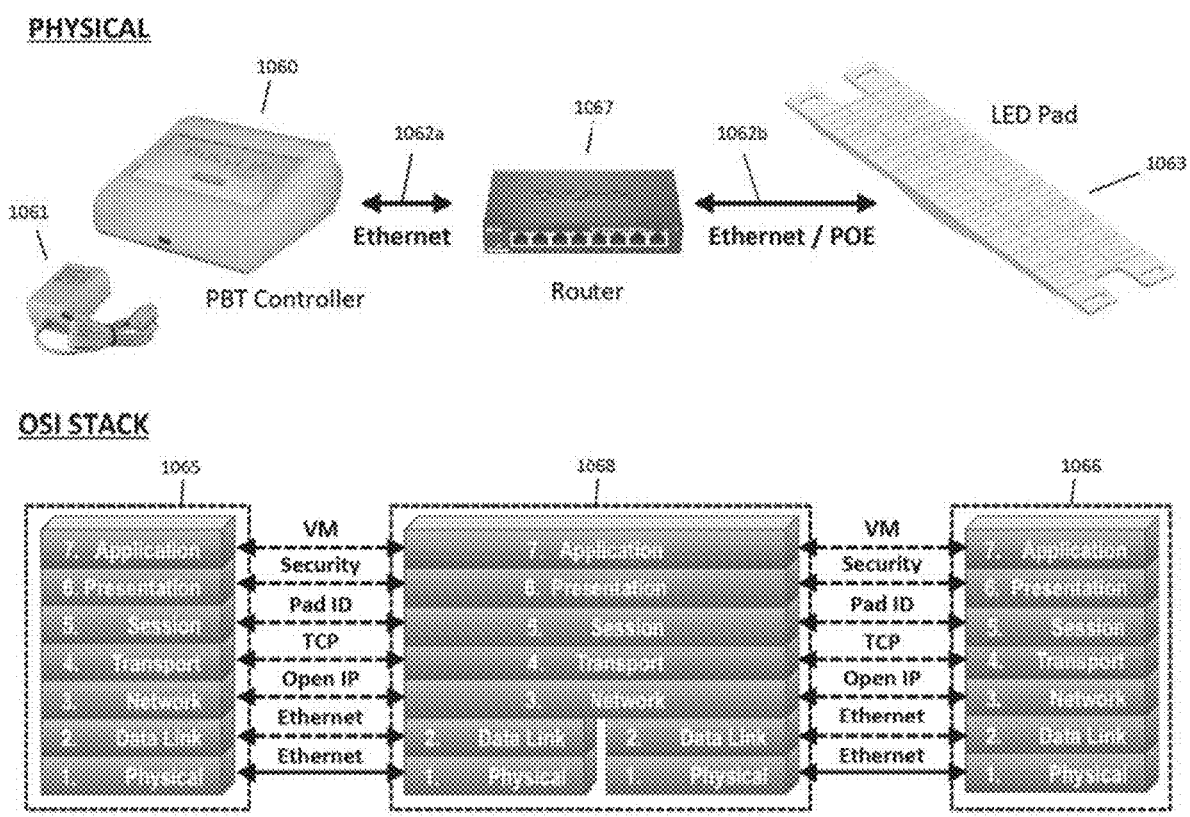
FIG. 57 illustrates 7-layer Ethernet based LightOS PBT system and communication protocol stacks operating across multiple subnets.

The corresponding 7-layer communication is illustrated in FIG. 57, where PBT controller 1060 powered by power supply 1061 connects to router 1067 over Ethernet 1062a, which in turn connects to intelligent LED pad 1063 over Ethernet 1062b including power delivery to the intelligent LED pad using power-over-Ethernet (POE). Network communication is performed using communication stack 1065 of PBT controller 1060 to communication stack 1068 in router 1067 and then onto communication stack 1066 in intelligent LED pad 1063. Although OSI layers-3 to 7 in router communication stack 1068 are shared by both input and output, PHY Layer-1 and Data Link Layer-2 stacks dedicated for each subnet are distinct. Because WiFi network privacy relies on weakly encrypted "WiFi Protected Access" (WPA) methods or even worse on the notoriously porous "Wired Equivalent Privacy" (WEP) protocol, Network Layer-3 communication over WiFi should be considered as an open IP network, and for all practical purposes as an open Internet connection.

WiFi Connectivity

Figure 58:
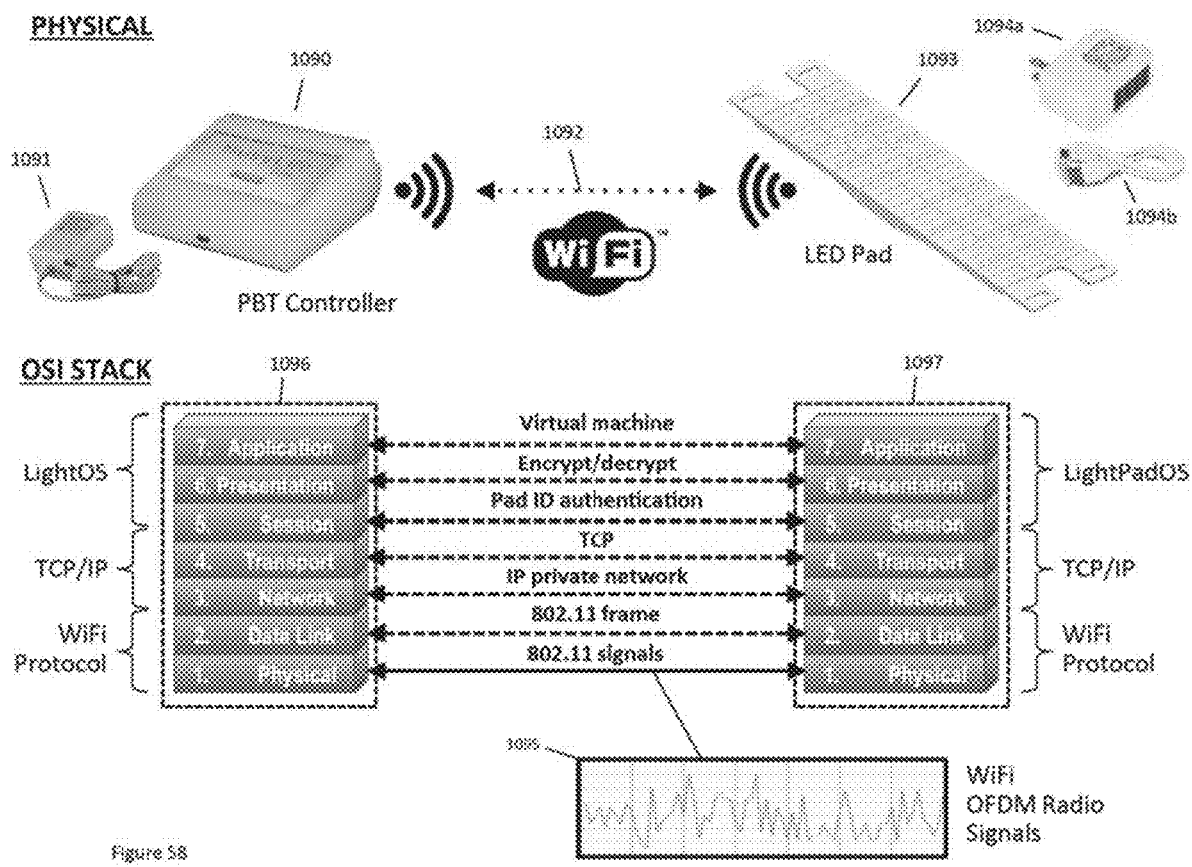
FIG. 58 illustrates a 7-layer WiFi based LightOS PBT system and communication protocol stacks.

Using the described 7-layer OSI communication stack, network communication in the disclosed PBT system can easily be adapted to WiFi wireless communication. In the distributed PBT system shown in FIG. 58, WiFi enabled PBT controller 1090 powered by power supply 1091 communicates by WiFi signal 1092 to intelligent LED pad 1093 using OFDM radio signals 1095 in accordance with the IEEE standards for 802.11. WiFi communication protocols may include 802.11a, 802.1b, 802.11g, 8012.11n, or 802.11ac or other related versions depending on the chip sets employed in intelligent LED pad 1093. PBT controller 1090 can support the superset of all standard WiFi protocols. Because WiFi cannot carry power, intelligent LED pad 1093 must receive power through USB cable 1094b powered either by AC/DC converter and DC power supply (brick) 1094a or a USB storage battery (not shown). WiFi communication occurs over the full 7-layer OSI communication stack 1096 present in PBT controller 1090 connected to communication stack 1097 present in intelligent LED pad 1093.

Figure 59A:
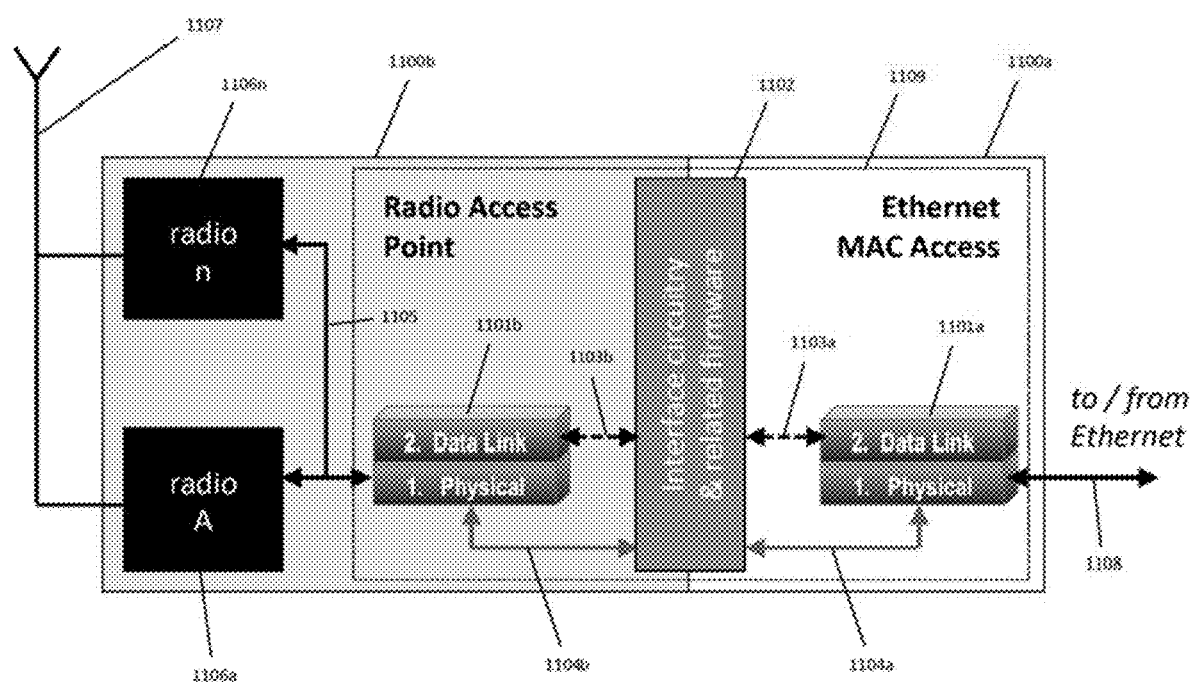
FIG. 59A illustrates a block diagram of a WiFi radio.

In operation, a WiFi radio shown in FIG. 59A converts Ethernet 1108 to radio 1107 converting Ethernet MAC access 1100a to Radio Access Point 1100 using interface circuitry and related firmware 1102. In operation, signals from Ethernet 1108 pass through communication stack 1101a as PHY signals 1104a where the format is converted by interface 1102 to PHY signals 1104b into WiFi communication stack 1101b and on to radios 1106a through 1106n operating over various radio frequencies transmitted over multi-band antenna array 1107. Data Link Layer-2 within communication stack 1101a transfers data 1103a in accordance with Ethernet protocol where interface circuitry and related firmware 1102 converts it into WiFi data 1103b in accordance with Data Link Layer-2 of communication stack 1101b formatted for radios 1106a through 1006n.

Unlike data packets for Ethernet containing two MAC addresses for source and destination devices, a WiFi packets made in accordance with 802.11 shown in FIG. 59B include three (and sometimes four) addresses—two MAC addresses 1115 and 1116 for the radio base stations, and Ethernet address 1117 as source or destination of the data packet's payload 1121, sequencing of split packets 1118, and the packet's direction using frame control 1113. The WiFi packet also includes several accessory fields, namely Frame Control 1113, Duration 1114, and Frame Check 1120 operating in accordance with explanatory command table 1122. The WiFi packet as shown is processed from left to right (as denoted by timeline 1110), starting with the PHY Layer-1 sub-frames Preamble 1111a, start frame delimiter SFD, along with physical layer convergence procedure (PLCP) 1112, a data field operating spanning Layer-1 and Layer-2 functions.

Ethernet address 1119 is optional, used only in radio bridge applications where one network address operates as the source and another network address acts as destination with the radio base station address forming the wireless bridge. The four-address WiFi bridge feature is not specifically required to implement the disclosed PBT system (although it may be used in floor-to-floor routing in a hospital). In contrast, a WiFi "access point" has only one of the two radios connected to the distribution system. Although the term "distribution system" has no real meaning in point-to-point communication over a network with only two components, in general, one PBT controller may connect through a network to a number of intelligent LED pads.

As such, data flow from the PBT controller 110 to the intelligent LED pads such as intelligent LED pad 120 will herein be considered as "To DS" while data flow from intelligent LED pad 120 to PBT controller will be considered as "From DS." The term BSS (base station service) is synonymous with the radio communication module, and distinct from the distribution system the radio services. In addition to the "To/From DS" directional control bits contained inside frame control 1113. the direction of data transfer through a WiFi access point depends on the contents of the MAC address fields 1115, 1116, and 1117 corresponding to the BSS receiving radio address, the BSS transmitting radio address, and a conditional address for distribution system (e.g. an Ethernet address).

Figure 60A:
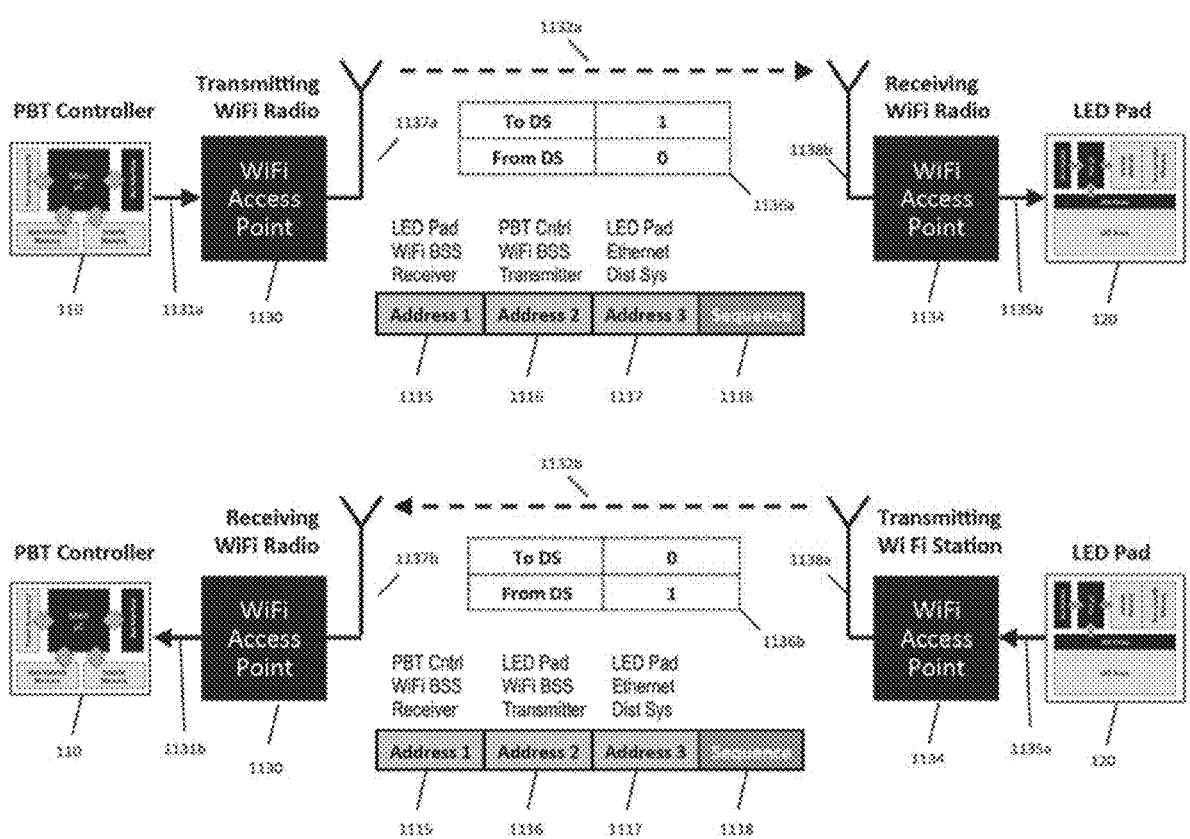
FIG. 60A illustrates bidirectional WiFi data flow in direction communication between PBT controller and LED pad.
Figure 608:
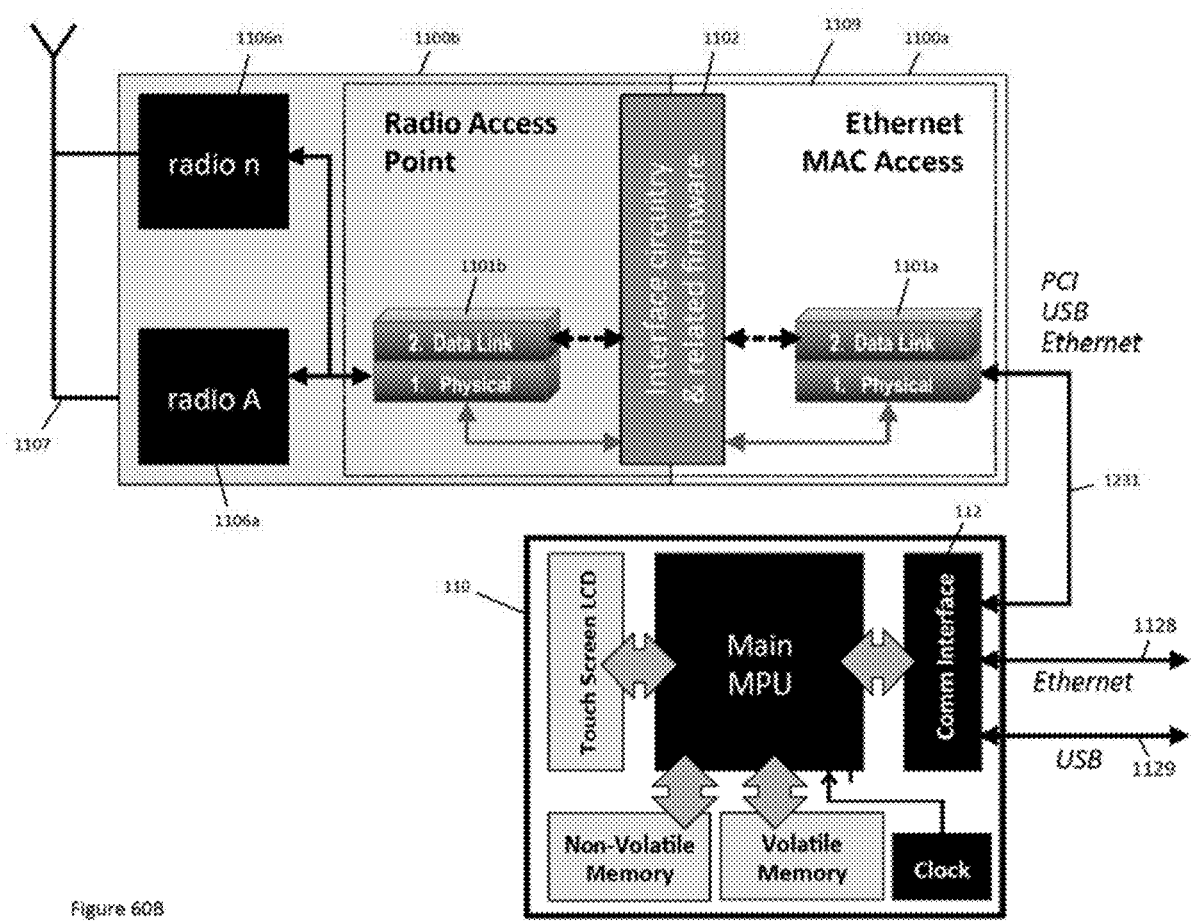

To exemplify data routing, in the topmost illustration of FIG. 60A data packets from PBT controller 110 are sent to intelligent LED pad 120 over WiFi communication 1132a in a direction "To DS", whereby frame control bits in table 1136a are set to the binary values "To DS=111" and "From DS=101". The transmitting radio, specifically WiFi access point 1130, is selected by MAC address 1116 (WiFi address field 2). In operation, signals sent from PBT controller 110 over data bus 1131a to WiFi access point 1130 are broadcast over antenna 1137a using OFDM based modulation techniques. OFDM, an acronym for orthogonal frequency division multiplexing, is a communication method where small amounts of digital data are transmitted across multiple bands of closely packed frequencies. The receiving radio, WiFi access point 1134, is selected by MAC address 1115 (WiFi address field 1) and once received by antenna 1138b, is converted into Ethernet packets. The converted data is then sent over network 1135b to intelligent LED pad 120 as specified by address 1117 (Ethernet address 3). Together, the WiFi radio pair transfers data from base station MAC address 1116 to outgoing Ethernet address 1117 over a radio having a MAC address 1115.

In the lower illustration of FIG. 60A, the direction of radio communication is reversed where intelligent LED pad 120 communicates over WiFi 1132b to PBT controller 110. In this scenario, access point 1130 and antenna 1137b function as the receiving radio, not the transmitter, while WiFi access point 1134 antenna 1138a become the transmitting station. As shown, this task is accomplished by swapping the contents MAC addresses 1115 and 1116, where receiver MAC address 1115 is set to that of PBT controller 110 and where transmitter MAC address 1116 is set to that of intelligent LED pad 120. Concurrently, frame control bits in table 1136b are set to the binary values "To DS=101" and "From DS=111". The content of MAC address 1117, i.e. WiFi address 3, specifies the Ethernet address of the distribution system, in this case the Ethernet address of intelligent LED pad 120 regardless of the direction of WiFi wireless data flow. This means the WiFi radio pair transfers data from WiFi radio MAC address 1116 to Ethernet MAC address 1117 for data packets broadcast from PBT controller 110 and from Ethernet MAC address 1117 to WiFi radio MAC address 1115 for data packets sent from intelligent LED pads 120.

An example of a WiFi connected PBT controller is shown in FIG. 60B where a WiFi radio with radio output 1107 and communication interface 1109 exchanges data packets with communication interface 122 in PBT controller 120 over a wired connection 1231, which may comprise Ethernet, a PCI bus, or USB. The communication protocol of WiFi radio communication interface 1019 and of PBT controller 120 should employ the same protocol. WiFi radio output 1107 may comprise different frequency bands and WiFi protocols 1106a through 1106n as depicted by radios A through N. Radio communication interface 1109 includes radio access point 1110b with OSI communication stack 1101b, interface circuitry 1102, and Ethernet/bus MAC access 1100a with communication stack 1101a supporting Ethernet, PCI bus, or USB protocols. In addition to its WiFi radio link, PBT controller 120 may communicate to upstream servers or Internet connections using Ethernet 1231 or to other peripheral or LED pads via USB connection 1129 or by Ethernet 1128 to servers or the Internet.

Figure 60C:
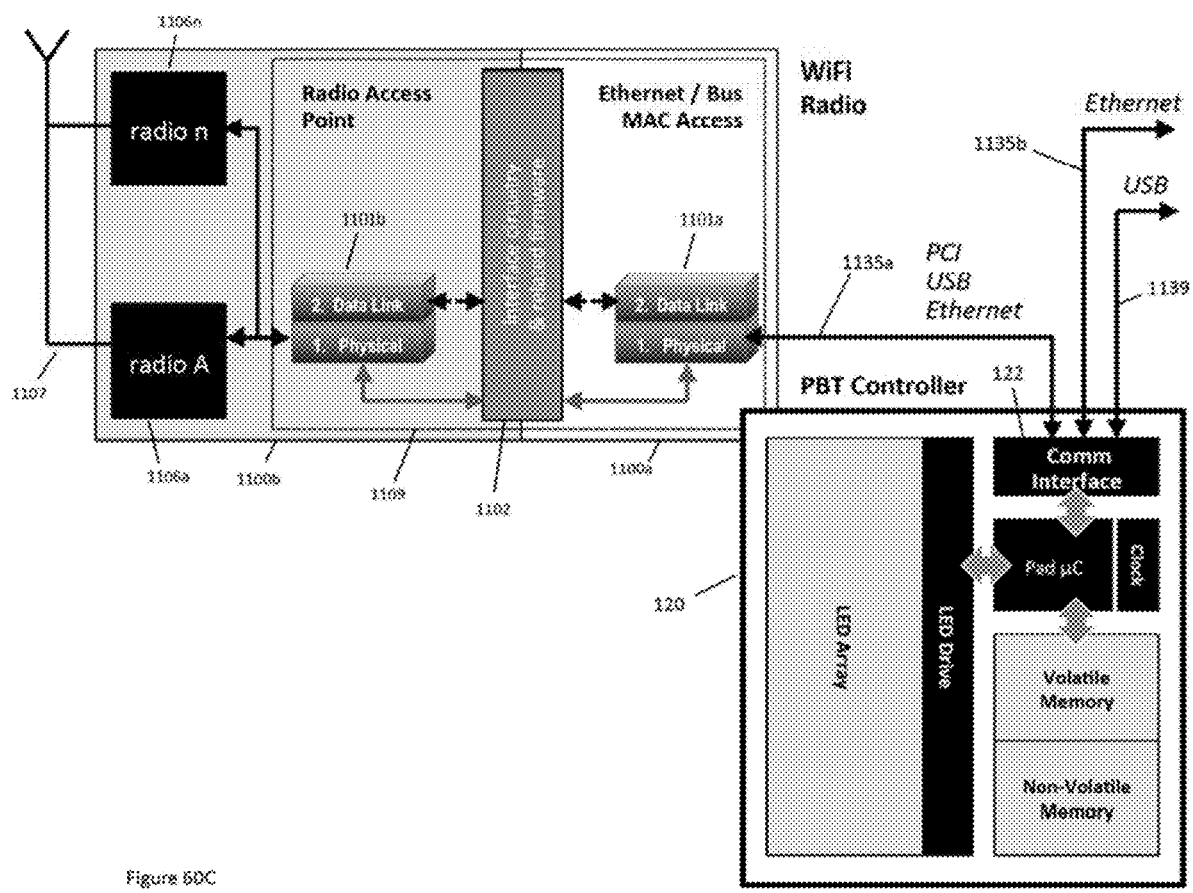
FIG. 60C illustrates block diagram of a WiFi radio enabled intelligent LED pad.

An example of a WiFi connected PBT controller is shown in FIG. 60C where a WiFi radio with radio output 1107 and communication interface 1109 exchanges data packets with communication interface 122 in LED pad 120 circuitry over a wired connection 1135a, which may comprise Ethernet, a PCI bus, or USB. WiFi radio output 1117 may comprise different frequency bands and WiFi protocols 1106a through 1106n as depicted by radios A through N. Communication interface 1019 includes radio access point 1100b with OSI communication stack 1101b, interface circuitry 1102, and Ethernet/bus MAC access 1100a with communication stack 1101a supporting Ethernet, PCI bus, or USB protocols. In addition to its WiFi radio link, PBT controller 120 may communicate to upstream servers or Internet connections using Ethernet 1135b or to other peripheral or LED pads via USB connection 1139.

Figure 61:
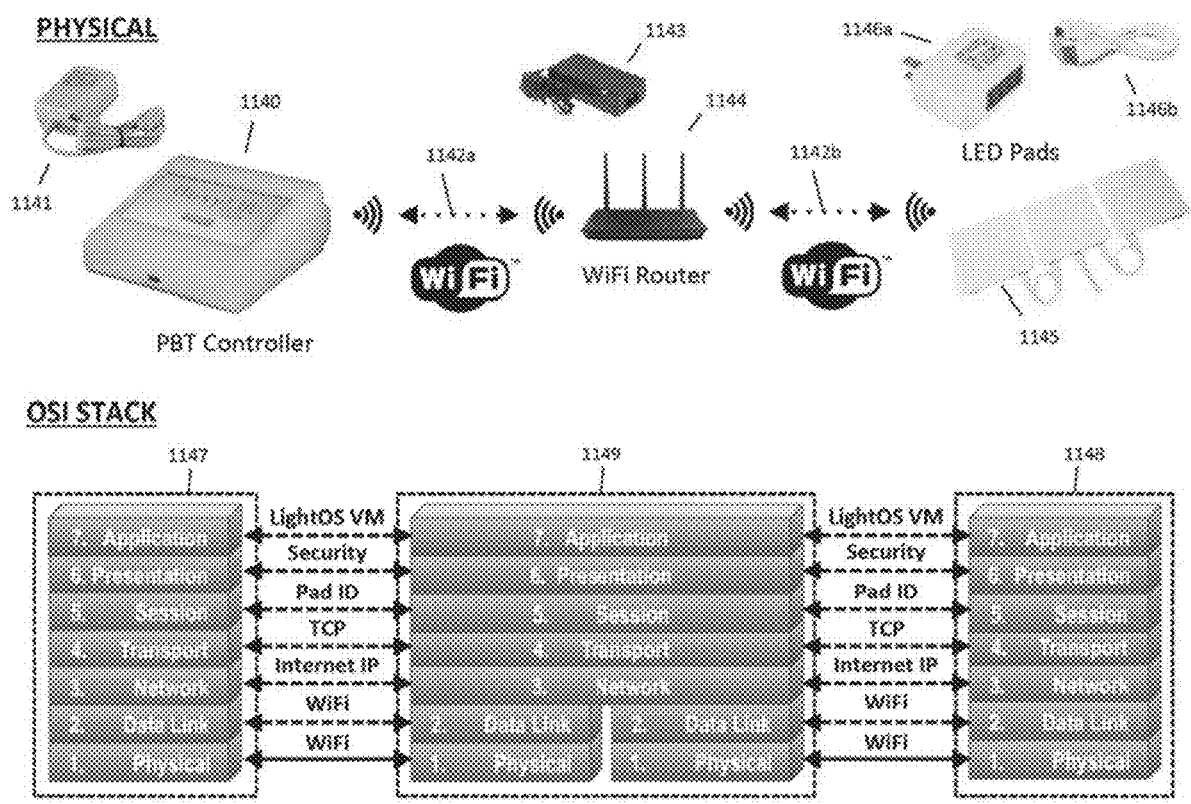
FIG. 61 illustrates 7-layer WiFi-based LightOS communication protocol stacks operating across multiple subnets.

The 7-layer OSI implementation works not only for direct point-to-point communication but also for data packet routing through one or more routers or across the Internet. The application of WiFi network communication to the disclosed distributed PBT system is illustrated in FIG. 61 where PBT controller 1140 uses WiFi communication to wirelessly route signals to intelligent LED pads 1145 through WiFi router 1144 using two separate WiFi links. WiFi communication 1142a between PBT controller 1140 using communication stack 1147 and WiFi router 1144 with communication stack 1149. Separately WiFi communication 1142b occurs between WiFi router 1144, and intelligent LED pads 1145 having communication stack 1148. Although communication stack 1149 of router 1144 shares common layers-3 to layer-7, WiFi specific Layer-1 and Layer-2 operate independently. It should be mentioned that in a purely WiFi connected PBT system such as that shown in FIG. 61, in accordance with FCC regulations, no power is transferred over the microwave link. As such each component must obtain its power locally, e.g. where AC adapter 1141 power PBT controller 1140, AC adapter 1143 powers WiFi router 1144, and AC adapter 1146a and associated USB cable 1146b power intelligent LED pads 1145.

Figure 62:
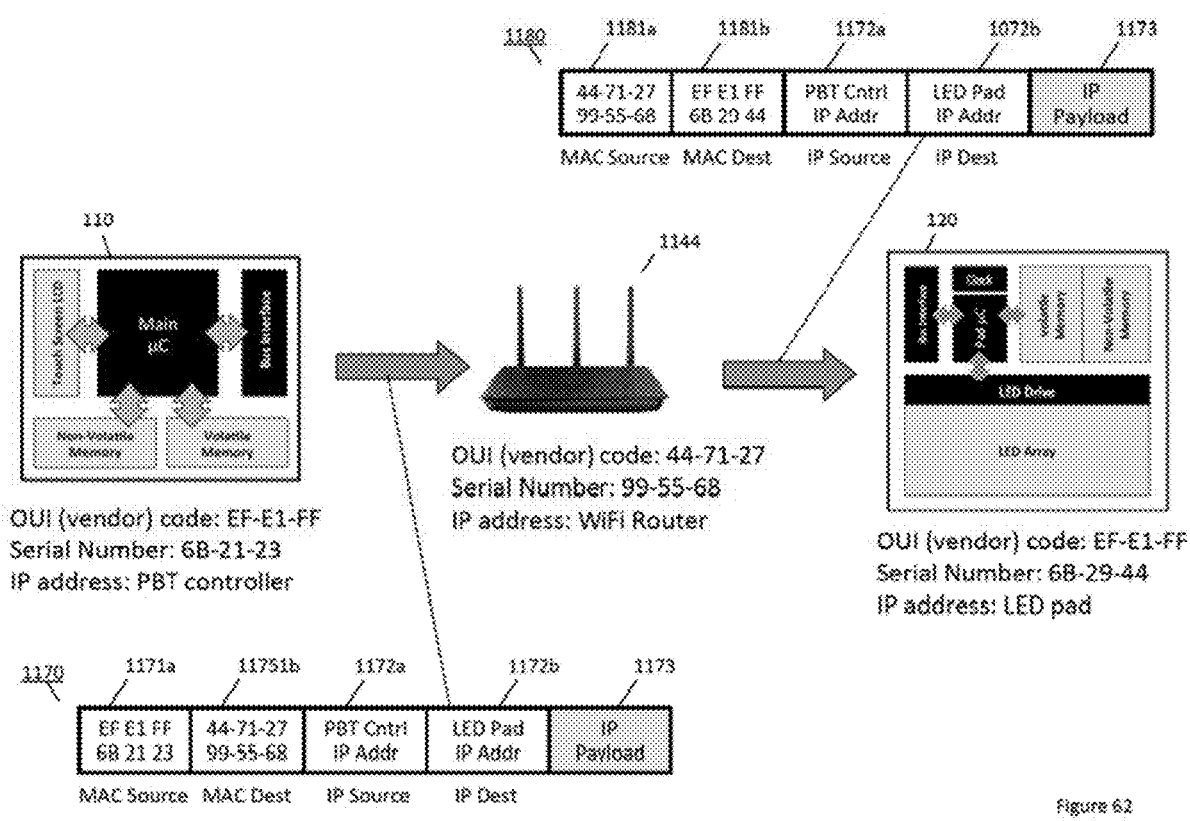
FIG. 62 illustrates an abridged LightOS datagram transport in WiFi communication between PBT controller and LED pads traversing multiple subnets.

FIG. 62 is an example of routing a data packet carrying a LightOS IP payload 1173 through WiFi router 1144 from IP source address 1171a to IP destination address 1171b. In communication of datagram 1170 between PBT controller 110 and WiFi router 1144, MAC source address 1171a is set to |EF-E1-FF-6B-21-23|, the MAC address of PBT controller 110, while MAC destination address 1171*b* is set to |44-71-27-99-55-68|, the MAC address of router 1144. As a data packet passes through WiFi router 1144, datagram 1170 is changed into datagram 1180, during which MAC source address 1171*a* is changed into MAC source address 1181*a*, with a hex value set to |44-71-27-99-55-68|, the MAC address of router 1144. Concurrently, MAC destination address 1171*b* is changed into MAC destination address 1181*b*, with a hex value set to |EF-E1-FF-6B-29-44|, the MAC address of intelligent LED pad 120. Because the MAC addresses are re-written as the datagram traverses WiFi router 1144, PBT controller 110 does not know the MAC address (i.e. the OUI and serial number of LED pad) of intelligent LED pad 120 and vice versa, and as such cannot perform a proper authentication to prevent hacking.

As in the case of datagram routing over Ethernet, an inventive aspect of communication in a distributed PBT system is illustrated FIG. 63, where datagram 1180 includes IP payload 1173 which in turn contains LightOS header 1217. One of the fields of LightOS header 1218 is the LightOS device ID 1227*a*. The LightOS device ID comprises four fields, source address 1237*a*, destination address 1237*b*, VLAN field 1237*c* made in accordance with the IEEE standard 802.1Q, and device type 1237*d*. In one implementation, source address 1237*a* is set to the OUI and serial number of PBT controller 110, data that is used by intelligent LED pad to confirm that PBT controller 110 sent datagram 1180 and not a fraudulent device. Similarly, destination address 1237*b* is set to the OUI and serial number of intelligent LED pad. This data is used by intelligent LED pad 120 to confirm it is the intended recipient of the datagram. The OUI and serial numbers are exchanged between PBT controller 110 and 120 as part of the authentication process when connecting an intelligent LED pad to the PBT controller's network. These addresses 1189 once extracted from datagram 1180 are used by intelligent LED pad 120 to confirm that the conversation between devices is as intended and authorized as an Application Layer-7 packet validation procedure unique to LightOS data packets comprising at least LightOS device IDs 207*a* of PBT controller 110 and LED 120. Additional validation data may include device type 1237*d* and VLAN field 1237*c*, identifying a group of devices authorized to use the content of LightOS payload 1218.

Figure 64:
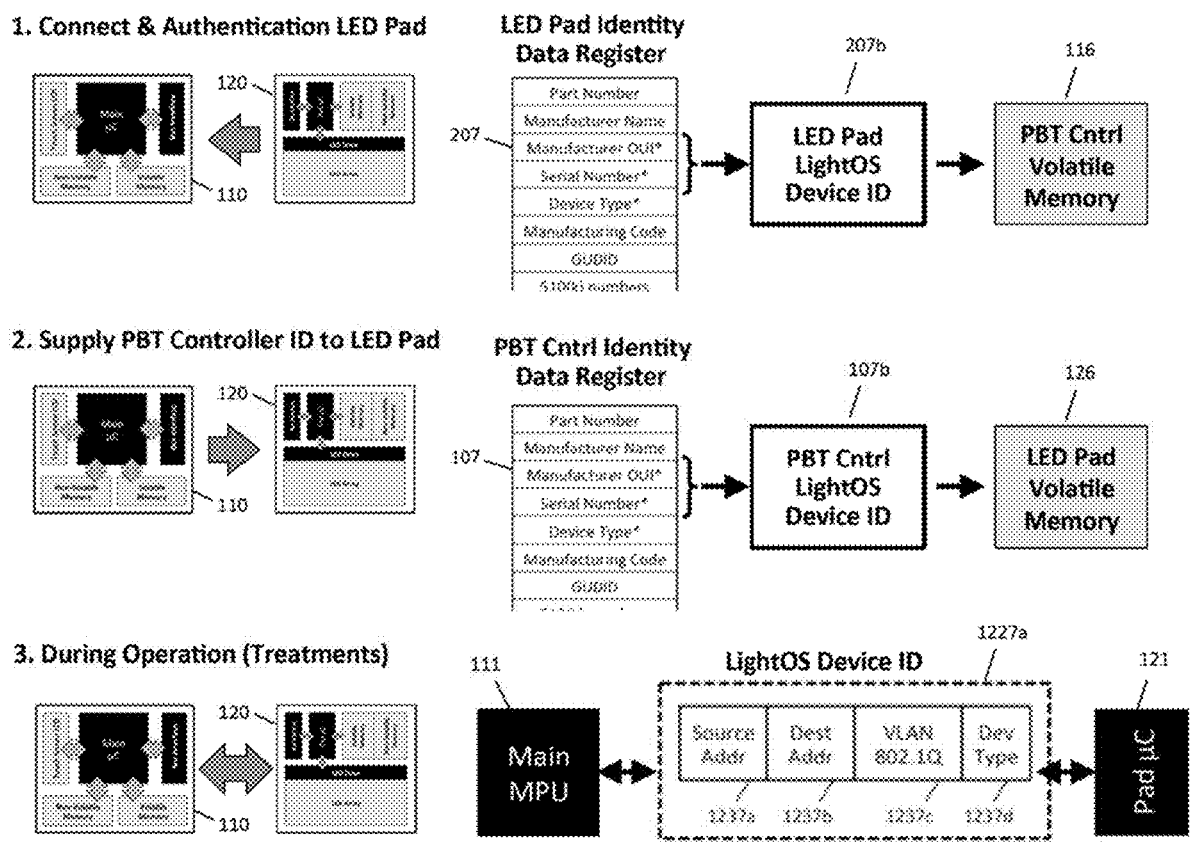
FIG. 64 illustrates the exchanged of LightOS device ID information during authentication prior to initiating an inter-device communication session.
Figure 658:
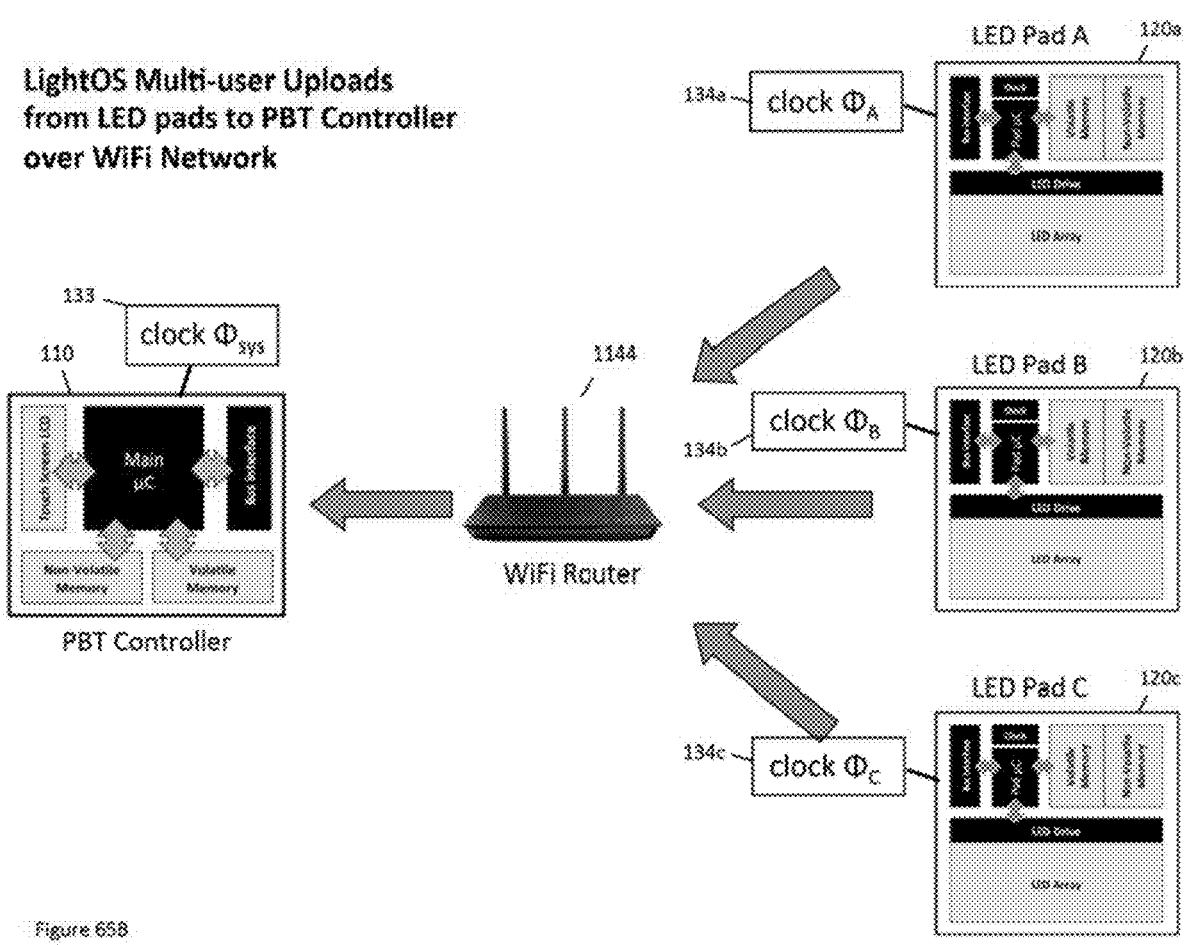

In operation, since communiqués between PBT controller 110 and intelligent LED pad involve both device IDs, this information must change hands before a treatment is performed. While any number of procedures could be used to accomplish this device ID exchange, it is convenient to complete the information exchange as part of the authentication process when a n intelligent is first connected to a PBT system. For example in the flowchart of FIG. 20, device IDs are exchanged as part of the step labeled "authenticate LED pad" 322. This procedure is illustrated in FIG. 64, where upon first connecting an intelligent LED pad (or upon startup), intelligent LED pad extracts from LED pad identity register 207 the LightOS device ID 207*b* for the intelligent LED pad, sending it to PBT controller 120 when it is stored in volatile memory 116 during the entire session. Once the PBT controller confirms intelligent LED pad 120 is a valid device, in step 2 the authentication process is complicated by extracting the LightOS device ID 107*b* for PBT controller 110 from PBT controller identity register 107 and sending it to intelligent LED pad 120 where it is stored temporarily in volatile memory 126. After the handshaking is complete, all subsequent communication between the intelligent LED pad 120 and PBT controller 110 shown in step 3 includes a LightOS device ID file 1227*a* embedded in the LightOS payload. The validity of each payload received is confirmed by main MPU 111 in PBT controller 110 or by pad μC 121 in intelligent LED pad 120 as applicable.

Using the described WiFi wireless communication method with embedded LightOS payloads, operation of the disclosed PBT is able to securely and efficiently control bidirectional communication between a PBT controller and multiple intelligent LED pads. Operation of a distributed PBT system is shown in the example of FIG. 65A, where PBT controller 110 downloads files to a number of intelligent LED pads 120, 120*b*, and 120*c* through a communication network including router 1144. Communication is bidirectional as shown in FIG. 65B where intelligent LED pads 120*a* through 120*c* upload data packets to PBT controller through WiFi router 1144.

Security and performance are insured by the combination of feature comprising LightOS packet communication in a distributed PBT system.

| Layer | LightOS Packet | LightOS Communication Benefit |
|---|---|---|
| 2 | Unique MAC addresses | Supports multiple LED pads within same subnet |
| 2 | Custom MAC type | Supports multiple LED pads within same subnet |
| 2 | Optional VLAN | Supports groups of LED pads within same subnet |
| 2 | WPA privacy | Wi-Fi Protected Access (WPA) discourages WiFi packet sniffing |
| 3 | Dynamic IP addresses | Ad hoc addresses are unknown to remote hacker |
| 4 | TCP based transport | Transfer control protocol handshaking insures integrity |
| 4 | UDP optional transport | Unicode data protocol supports real time packets |
| 4 | Dynamic port number | Ad hoc port numbers unknown to remote hacker |
| 5 | Device authentication | Session based authentication rejects frauds |
| 5 | Device authorization | Session exchange of security credentials confounds surveillance |
| 5 | Device authorization | Session based identity verification limits user privileges and access |
| 6 | Datagram encryption | Encryption of session payload obscures all LightOS functions |
| 6 | Encryption tag | Tag offers added security atop encryption key-based ciphers |

| Layer | LightOS Packet | LightOS Communication Benefit |
| --- | --- | --- |
| 7 | Custom LightOS header | Header contains confidential format specific content descriptions |
| 7 | LightOS device ID | Device ID facilitates secondary authentication of connected devices |
| 7 | LightOS device ID | Device ID supports device verification across multiple subnets |
| 7 | LightOS payload | Payload formatting is dynamic in content and packet length |
| 7 | LightOS continuation | Continuation bit supports sequenced oversized payload transport |
| 7 | LightOS checksum | Application checksum insures integrity, prevents packet fraud |

Because of its ability to distinguish each intelligent LED pad individually, in accordance with this invention multiple PBT controllers and intelligent LED pads can coexist on the same WiFi subnet without confusion. Pairing of the PBT controller with its associated LED pads prevents interference or confusion of a PBT controlling the wrong LED pad. This condition is exemplified in FIG. 65C where by using the LightOS device ID PBT controller A 110*a* communicates exclusively with intelligent LED pad C 120*c* and does not interfere in the operation of intelligent LED pad A 120*a* or intelligent LED pad B 120*b* which instead are both controlled by PBT controller B 110*b*. The pads 120*a* through 120*c* can be completely separate pads, or may comprise portions of a pad set, e.g. LED pad 120*a* might be a facial mask pad covering the face and forehead while LED pad 120*b* might cover the neck. In some cases, the various pads might comprise sections or "zones" of a single multi-zone pad. For example a head cap may be divided unto separate sections for the sides, top, and front of the head for hair treatments, for relaxation, or for recovery from concussion/mTBI.

Figure 65D:
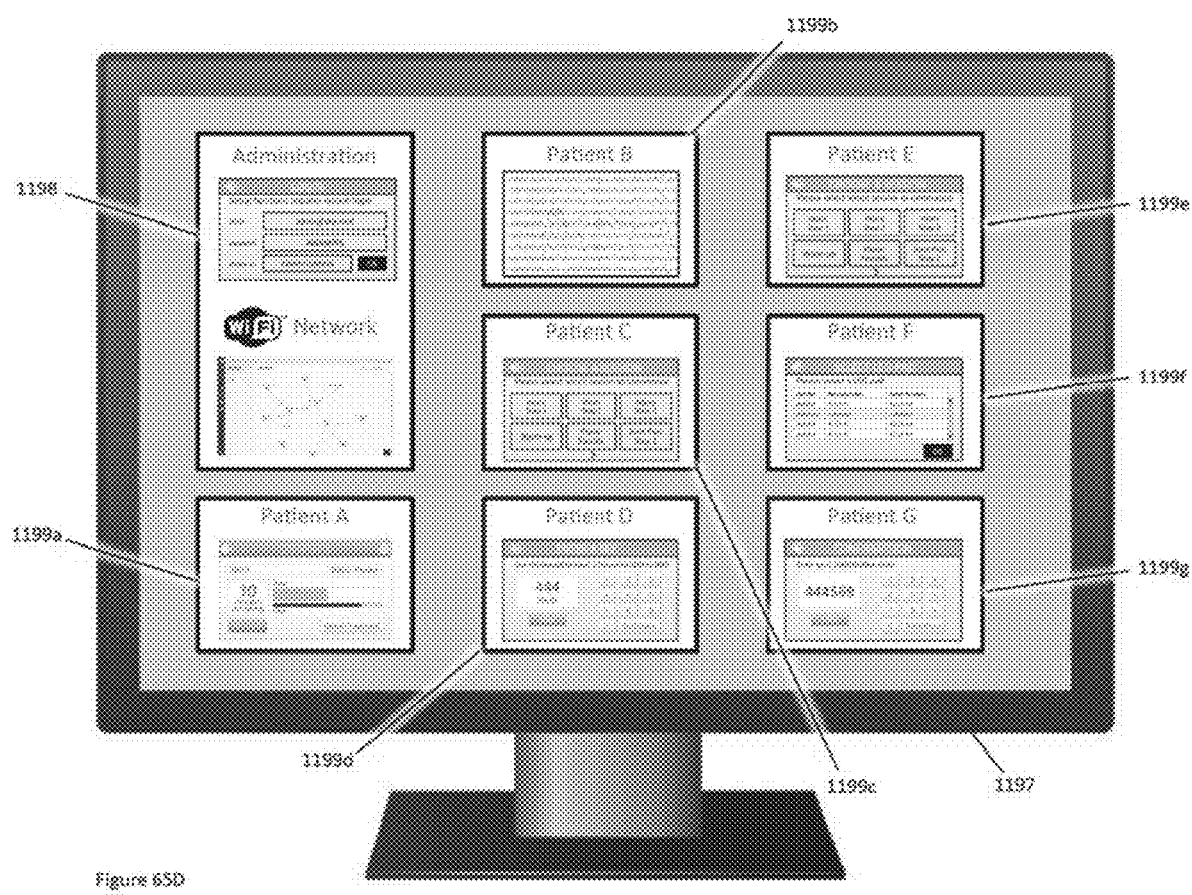
FIG. 65D is an exemplary distributed PBT system comprising a multi-patient workstation and integrated multi-channel PBT controller.

Another application utilizing the multi-user capability of the disclosed PBT system is illustrated PBT control console 1197 of FIG. 65D, where one screen is divided into different windows each wirelessly controlling separate PBT treatments and PBT sessions for different patients, for example patients in separate rooms in a hospital ward or an managed care facility for the aged. The exemplar session windows 1199*a* through 199*g* are not intended to limit the application of the device but simply to represent different activities for different patients. For example patient A in window 1199*a* is undergoing a PBT treatment with 10 minutes remaining in the session, patient B in window 199*b* shows measured EEG data taken as part of the PBT session. In windows 1199*c* and 1199*e*, treatments are being selected for patients C and E respectively. Window 1199*d* shows manual entry of a custom PBT treatment for patient D (in this example at 444 Hz). In window 1199*f* the PBT system for patient F is being setup, specifically to select intelligent LED pads to pair to the PBT system. Window 199*g* shows an authentication process being performed in the room of patient G. System and network administration is managed from window 1198.

Multichannel PBT systems 1197 can be administered with separate controllers, one system for each channel or patient as shown in FIG. 65E. The PBT-controllers 110*a* to 110*g* can be located centrally or within each room. Through one or more routers such as WiFi router 1144, these separate controllers are able to separately control and entire population of intelligent LED pads sharing one or more subnets. As shown PBT controller 110*a* is enabled to control two intelligent LED pads in pad set 120*aa*, while controller 110*b* is enabled to control three intelligent LED pads in pad set 120*bbb*. In a similar manner, PBT-controllers 110*c* through 110*g* are configured in a corresponding manner to control intelligent LED pad sets 120*cc* through 120*gg*, where ranging from single pad 120*f* treatments to triple pads 120*bbb* and 120*eee*. A multichannel PBT controller 1197*a* shown in FIG. 65F can also be implemented using time multiplexing of PBT controller 110 so long that the processing power and memory capacity is sufficient to support the requisite number of channels. In such instances, a WiFi enabled remote control 1196 may be beneficial for nurses to access the PBT central system via WiFi router 1144 without the need to leave a patient's room during setup.

These communication and control features in the disclosed distributed PBT system uniquely includes a variety of unique capabilities not available in any prior art PBT system, including without limitation the following:

Bidirectional communication of PBT command, control, and receipt/action confirmations of data packets routed throughout a packet switched network (including data transport over multiple subnets or traversing $3^{rd}$ party routers).

Communication downloads of LightOS operating system software installations and updates, LED streaming, LED playback, waveform primitives, and LED player files from a PBT controller to one ore more intelligent LED pads over a packet switched network (including data transport over multiple subnets or traversing $3^{rd}$ party routers).

Communication uploads of intelligent LED pad data to a PBT controller including interrupts, data uploads, and confirmation of actions over a packet switched network (including data transport over multiple subnets or traversing 3rd party routers).

Bidirectional multi-channel communication of PBT command, control, receipt/action confirmations, data files, or other data packets over a packet switched network to or from multiple network-connected devices such as intelligent LED pads.

Bidirectional transport of PBT command, control, and sensor data over Ethernet, WiFi, and other packet-switched networks.

Multi-layer security of LightOS communication packets including Layer-7 application identity validation in both uploads and downloads, Layer-6 encryption/decryption and secret cipher tags, Layer-5 user authentications, ad hoc assignment of Layer-4 port numbers and Layer-3 IP addresses, and Layer-2 WPE.

Pair bonding of PBT controller and intelligent LED pads prior to system use using authentication or AAA procedures followed by the exchange of shared secrets (including LightOS device IDs, crypto-keys, cipher tags, and other security credentials).

LightOS payload embedded device IDs for end-to-end application layer validation of communication packets between PBT controller and intelligent LED pads. Unlike MAC addresses, LightOS device-IDs survive transport through $3^{rd}$ party routers and across multiple subnets, as undiscoverable data packets embedded in application layer payloads.

Server and Cloud Connectivity

The same methods used for connecting a PBT controller to one or more intelligent LED pads can be applied to connect a PBT controller to a private computer server or a cloud-connected computer server. The motivations for connecting a PBT controller to a computer server, to a private server cloud, or to the Internet are many. Features available from computers servers including, without limitation, the following purposes:

- Confirm the identity of a PBT controller and its location and as desired match the device ID to a registered owner.
- Remotely check if a PBT controller is running the most current version of the LightOS operating system, executable software, or if has the most current library files.
- Distribute and remotely install software, updates, libraries, and computer code to a large number of PBT controllers and clients.
- If theft is reported, a PBT system can be remotely disabled or wiped of all software.
- Remotely monitor PBT system use and upload user log data.
- Facilitate or control system access and privileges based on online authentication and authorization of a client, super user, or administrator, and record the transaction in an administrator log (AAA).
- Upload sensor and treatment data for further analysis including clinical trial and case study databases. Anonymous data files may also be used in big data applications.

Figure 66:
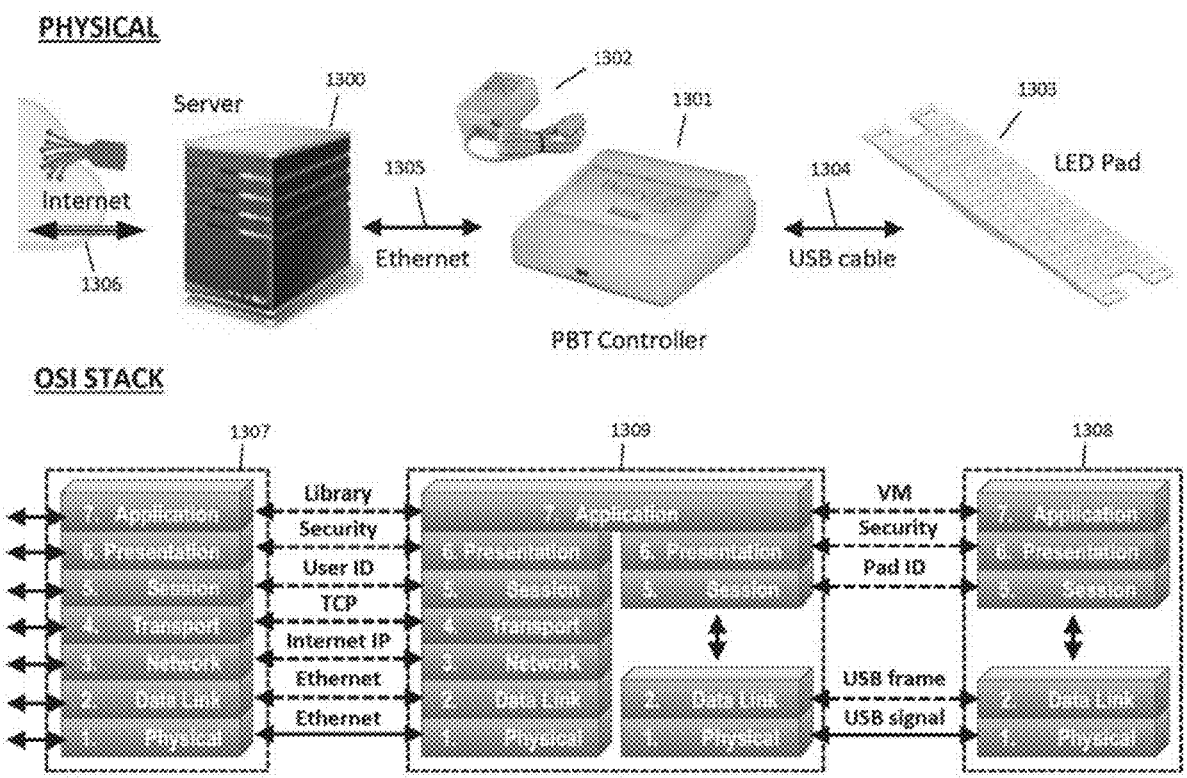
FIG. 66 is an exemplary distributed PBT system comprising a computer-server connected PBT controller using Ethernet based server communication and utilizing USB bus communication to a LED pad.

Server connections can be realized in a variety of implementations. In FIG. 66, computer server 1300 connects to PBT controller 1301 over Ethernet 1305. PBT controller 1301, powered by AC adapter 1302, connects to intelligent LED pad 1303 over USB cable 1304. The 7-layer OSI communication stack 1307 of server 1300 uses Ethernet data packets to connect with communication stack 1309 of PBT controller 1301. In turn, uses only 5-layers of communication stack 1309 to connect to intelligent LED pad 1303 comprising communication stack 1308. As shown, PBT communication stack 1309, mixes two communication stacks, a 7-layer stack for dialog with server 1300, and a 5-layer stack comprising layers-1, 2, 5, 6 and 7 for connecting to intelligent LED pad 1303, where only the LightOS Application Layer-7 bridges the two. In this manner, PBT controller 1301 communicates separately to computer server 1300 and to intelligent LED pad 1303. Because PHY Layer-1 and Data Link Layer-2 are not shared for the Ethernet 1305 and USB 1304 connections, server communication stack 1307 is unable to directly access intelligent LED pad 1303. Moreover, because USB 1304 bus connection is not packet switched, Network Layer-3 and Transport Layer-4 protocols are not included in the USB communication stack. As such, only Application Layer-7 bridges the two communication networks. Aside from its connectivity to PBT controller 1301, server 1300 may also connect to a computer cloud or to the Internet via a high-speed physical link such as fiber 1306.

Figure 67:
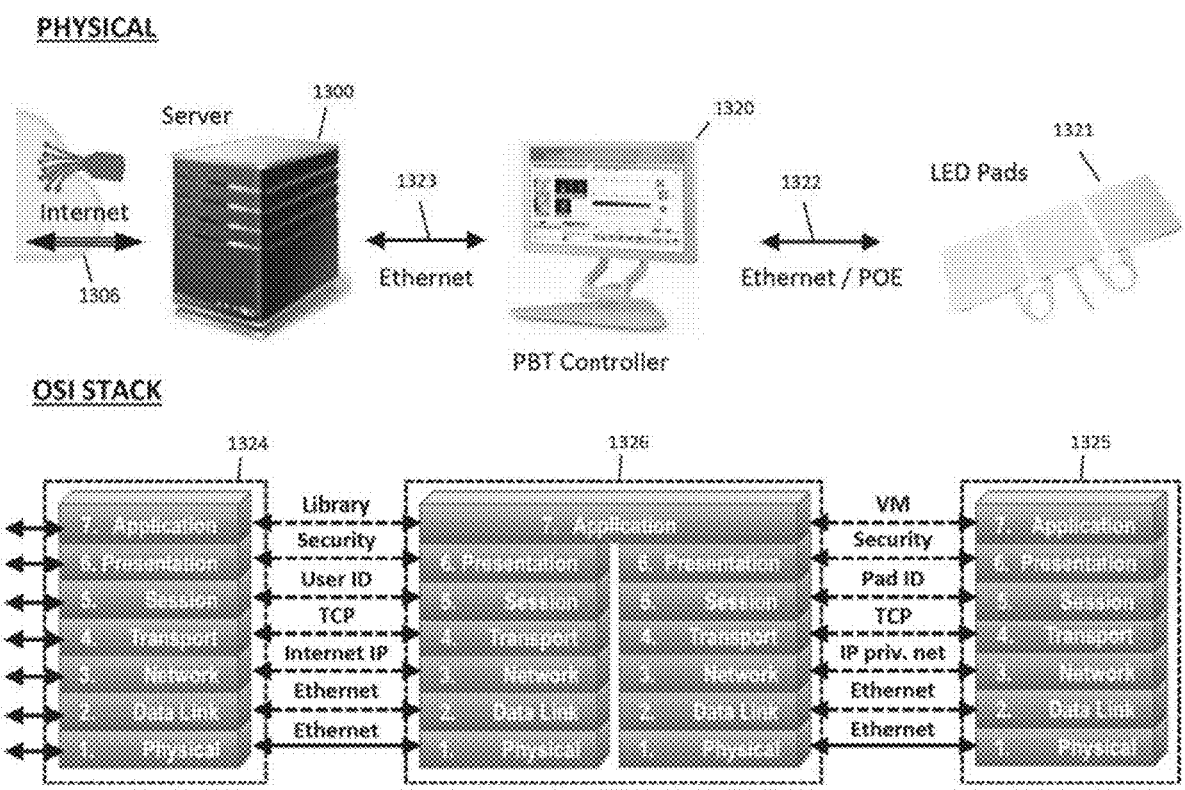
FIG. 67 is an exemplary distributed PBT system comprising a computer-server connected PBT controller using Ethernet based server communication and utilizing POE-powered Ethernet communication to a LED pad.
Figure 68:
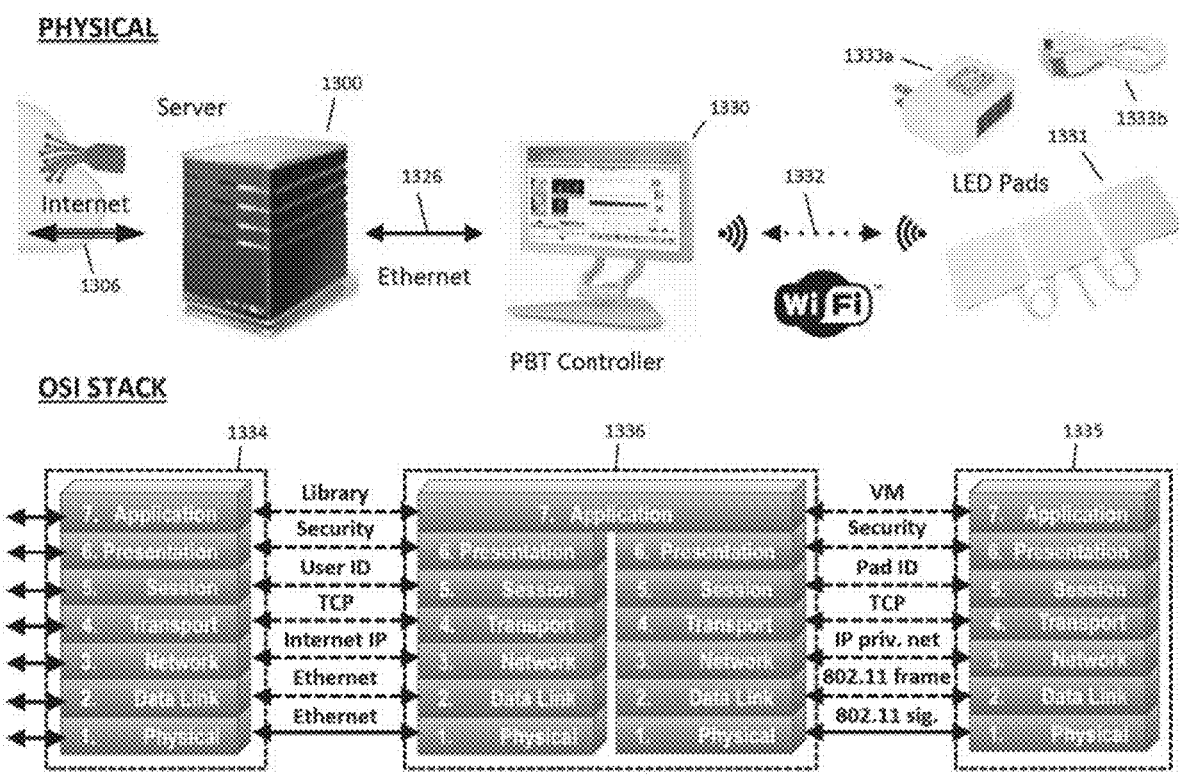

In FIG. 67, computer server 1300 connects to multi-channel capable PBT controller 1320 over Ethernet 1323. AC powered PBT controller 1320 connects to intelligent LED pad 1321 using Ethernet 1322 with POE (power over Ethernet). The 7-layer OSI communication stack 1324 of server 1300 uses Ethernet data packets to connect with communication stack 1326 of PBT controller 1320. In turn, the controller uses 7-layer communication stack 1326 to connect to intelligent LED pad 1321 comprising communication stack 1325. As shown, PBT communication stack 1326, mixes two 7-layer communication stacks, one for dialog with server 1300, and another for connecting to intelligent LED pad communication stack 1325, where only the LightOS Application Layer-7 bridges the two. In this manner, PBT controller 1320 communicates separately to computer server 1300 and to intelligent LED pad 1321. Because PHY Layer-1 and Data Link Layer-2 are not shared for communication across Layers-1 to 6, server 1300, Internet 1306, or communication stack 1324 is unable to directly access intelligent LED pad 1321. Instead, only Application Layer-7 bridges the two communication networks. The value of this two-column communication stack 1326 within disclosed PBT controller 1320 has a number of key benefits, especially in medical devices:

- The server cannot directly access or control the intelligent LED pads. The PBT application software administers all LED pad control instructions, i.e. the LightOS command set prevents executable commands for treatments or sessions from being issued by the server.
- The PBT controller authenticates server identity in a Session Layer-5 transaction before authorizing transactions.
- Communication and data transfers between the server and the intelligent PBT controller use a different encryption process and security credentials than the PBT controllers communication to the intelligent LED pads.
- The driver software is encrypted and sandboxed as a Presentation Layer-6 transaction preventing inspection or analysis of libraries or software by unauthorized parties.
- The LightOS operating system hosted within the PBT controller performs its own Application Layer-7 authentication of the server before granting any privileges or authorizing communications. Imposters are blocked from transactions prohibiting the downloading of spyware, viruses, or usurpation of PBT control functions.
- Subsequent to LightOS Application Layer-7 authentication of an authorized server, all communication between the PBT controller and the server occurs using encrypted file transfer essentially operating a pipelined virtual private network inaccessible to other network users, in essence limiting access over the Internet or by any other cloud to only authorized servers. In this manner a private network server and a cloud-connected server operate in an identical manner with comparable levels of security.
- The PBT controller's two-column communication stack is able to support two completely dissimilar communication protocols for server and intelligent LED pad communication. Typical server access employs Ethernet, WiFi, telephonic (3G/LTE, 4G, 5G), and fiber communication channels while intelligent LED pad communication comprises WiFi, Ethernet, and local bus communication protocols (SMBus, I²C bus, USB, Lightening, etc.).

Security of PBT controller to intelligent LED pad communication employs different methods, protocols, and keys than server to PBT controller communication.

Server downloads of executable code (software, firmware, libraries) require administrator privileges based on two-factor authentication.

No master keys exist for bridging the two-column communication stack, i.e. all file and data transfers require authentication by the LightOS operating system as an Application Layer-7 transaction.

Transfers between a PBT controller and server involving patient specific data are made in accordance with HIPAA privacy and security statutes.

Figure 68:
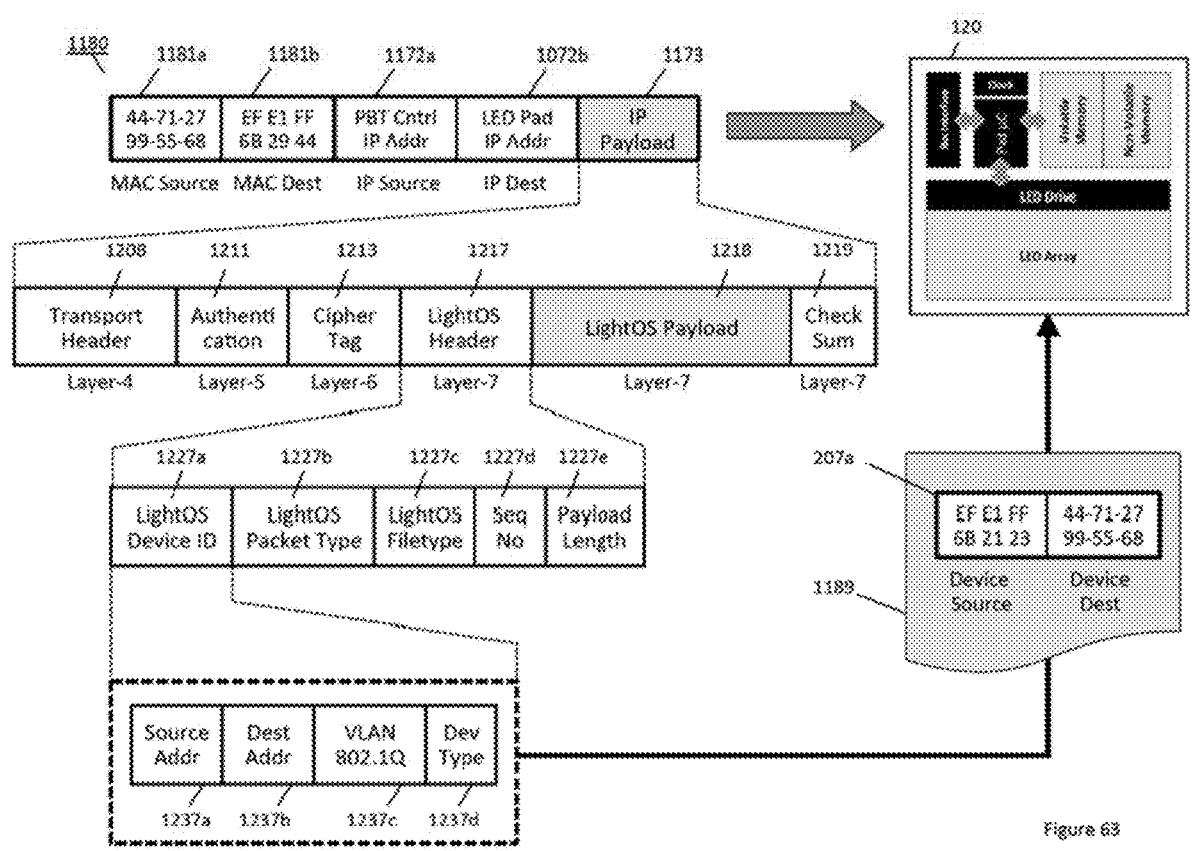
FIG. 68 is an exemplary distributed PBT system comprising a computer-server connected PBT controller using Ethernet based server communication and employing WiFi communication to a LED pad.

The foregoing features of a distributed PBT system comprising a PBT controller hosting a two-column communication stack apply to any number of combinations and permutations of connected devices. For example, in FIG. 68, computer server 1300 connects to multi-channel capable PBT controller 1330 over Ethernet 1326. AC powered PBT controller 1330 connects to intelligent LED pad 1331 using WiFi 1332, where intelligent LED pad 1331 is powered by AC adapter 1333a and cord 1333b. The 7-layer OSI communication stack 1334 of server 1300 uses Ethernet data packets to connect with communication stack 1336 of PBT controller 1330. In turn, the controller uses 7-layer communication stack 1336 to connect to intelligent LED pad 1331 comprising communication stack 1335. As shown, PBT communication stack 1336, mixes two 7-layer communication stacks, one for dialog with server 1300, Internet 1306, and communications stack 1334, and another for connecting to intelligent LED pad communication stack 1331, where only the LightOS Application Layer-7 bridges the two. In this manner, PBT controller 1330 communicates separately to computer server 1300 and to intelligent LED pad 1331. Access to the Internet 1306 and to other cloud-based computer servers is made through server 1300. Because PHY Layer-1 and Data Link Layer-2 are not shared for communication across Layers-1 to 6, server communication stack 1334 is unable to directly access intelligent LED pad communication stack 1335. Instead, only Application Layer-7 bridges the two communication networks.

Figure 69:
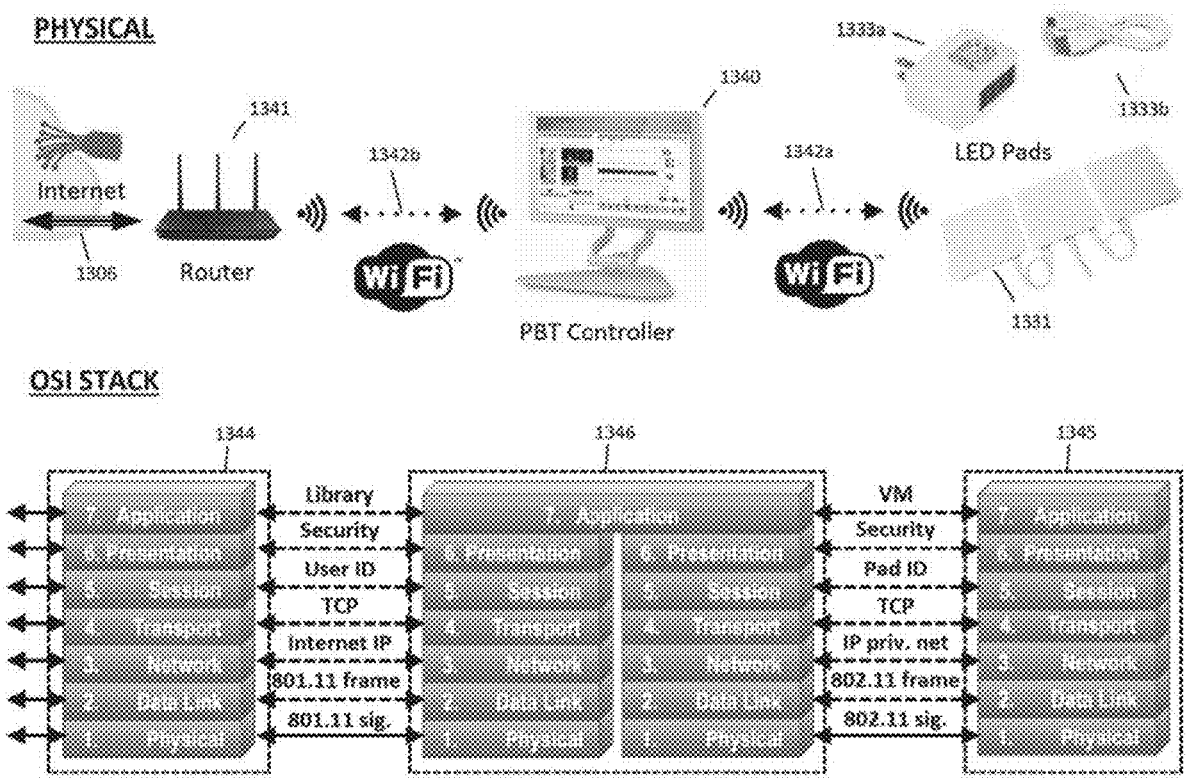
FIG. 69 is an exemplary distributed PBT system comprising a computer-server connected PBT controller using WiFi based communication to a computer server and to a LED pad.

The foregoing discussion also applies to WiFi exclusive networking where in FIG. 69 computer multi-channel capable PBT controller 1340 connects to WiFi router 1341 over Ethernet 1342b. AC powered PBT controller 1340 also connects to intelligent LED pad 1331 using WiFi 1342a, where intelligent LED pad 1331 is powered by AC adapter 1333a and cord 1333b. The 7-layer OSI communication stack 1344 of WiFi router 1341 uses 802.11 compliant data packets to connect with communication stack 1346 of PBT controller 1340. In turn, the controller uses 7-layer communication stack 1346 to connect to intelligent LED pad 1331 comprising communication stack 1345. As shown, PBT communication stack 1346, mixes two 7-layer communication stacks, one for dialog with communication stack 1344 of WiFi router 1341 and through the router to Internet 1306 and to a cloud based server (not shown), and another for connecting to intelligent LED pad 1331 and communication stack 1345, where only the LightOS Application Layer-7 bridges the two.

In this manner, PBT controller 1340 communicates separately to a cloud based computer server (not shown) over Internet 1306 and to intelligent LED pad 1331. Because PHY Layer-1 and Data Link Layer-2 are not shared for communication across Layers-1 to 6, server communication stack 1346 is unable to directly access intelligent LED pad communication stack 1345. Instead, only Application Layer-7 bridges the two communication networks. Regardless of the PHY Layer-1 and Data Link Layer-2 medium employed, communication sessions between a PBT controller and a computer server or cloud-based server can occur in three ways, namely (i) autonomous IoT transactions, (ii) IoT device request transactions, or (iii) server authority based IoT transactions.

Figure 70:
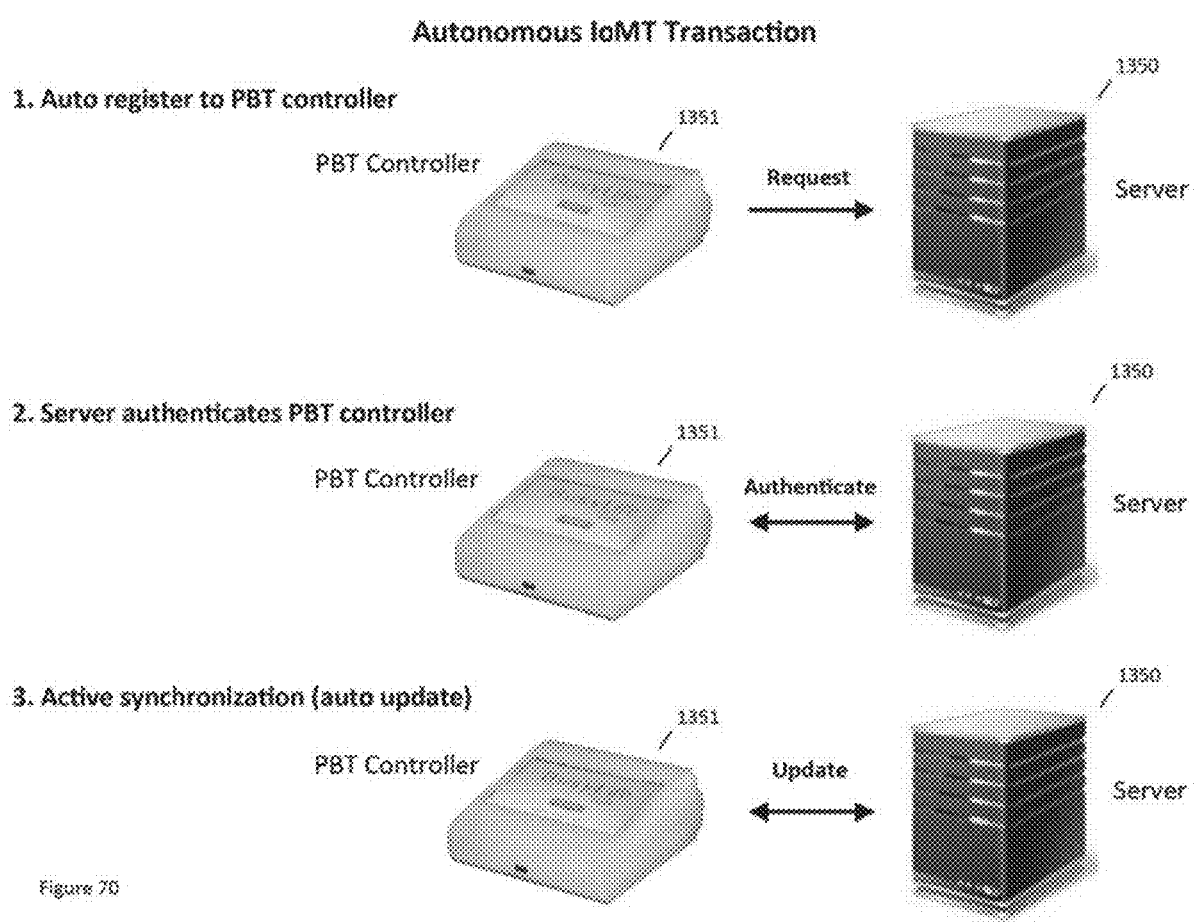
FIG. 70 illustrates a PBT system operation with autonomous IoT transactions.

In autonomous IoT transactions shown in FIG. 70, PBT controller 1351 communicates with server 1350 in an autonomous manner as soon as the device connects to the Internet. Upon startup, the communication interface of PBT controller 1351, whether Ethernet or WiFi based, sends a request as a broadcast packet to a local DHCP server. According to Wikipedia (https://en.wikipedia.org/wiki/Dynamic_Host_Configuration_Protocol), a DHCP server, an acronym for dynamic host configuration protocol, "is a network management protocol used on TCP/IP (packet switched) networks whereby a DHCP server dynamically assigns an IP address and other network configuration parameters to each device on a network so they can communicate with other IP networks". In other words, a DHCP server converts the PBT controller's local Layer-2 MAC address into a Layer-3 IP address by assigning it an ad hoc IP address valid only for the local subnet or region.

The temporarily assigned IP address is not a true IP address recognized by the Internet's DNS servers but in fact is valid only locally. Communication beyond the local subnet onto the Internet involves operation of a NAT (https://en.wikipedia.org/wiki/Network_address_translation) or network address translator, which translates the local Layer-3 IP address, into one-of-many pre-assigned IP addresses owned by the NAT operator and recognizable by the Internet's DNS name servers. The NAT server also maps the sender's local Layer-4 port address to a different dynamic port address used in Internet communications. NAT operation is transparent to the PBT controller, meaning PBT controller 1351 communicates only through sending and receiving data packets involving its locally assigned IP address and port address without any knowledge that its communications traverses the Internet or other private clouds using different IP addresses.

In operation, outgoing communications sent from PBT controller 1351 to Internet-connected server 1350 are translated by the local NAT into datagrams using true DNS-recognizable Internet addresses. In a reciprocal process, communications sent from server 1350 over the Internet to PBT controller 1351 are converted from a DNS-recognizable IP address to the local IP address assigned to the PBT controller. In this manner, IP addresses are dynamic, assigned on an ad hoc basis as needed, and are constantly reused for each new communication session. Server 1350 must however maintain a real DNS-recognizable Internet address (or a proxy thereof) that is preprogrammed into PBT controller 1351, otherwise the controller will have no idea how to establish initial contact with the server. Once contact is established, however, communication can be rerouted to a different server more local to the PBT controller in order to minimize communication latency and network propagation delays.

Figure 71:
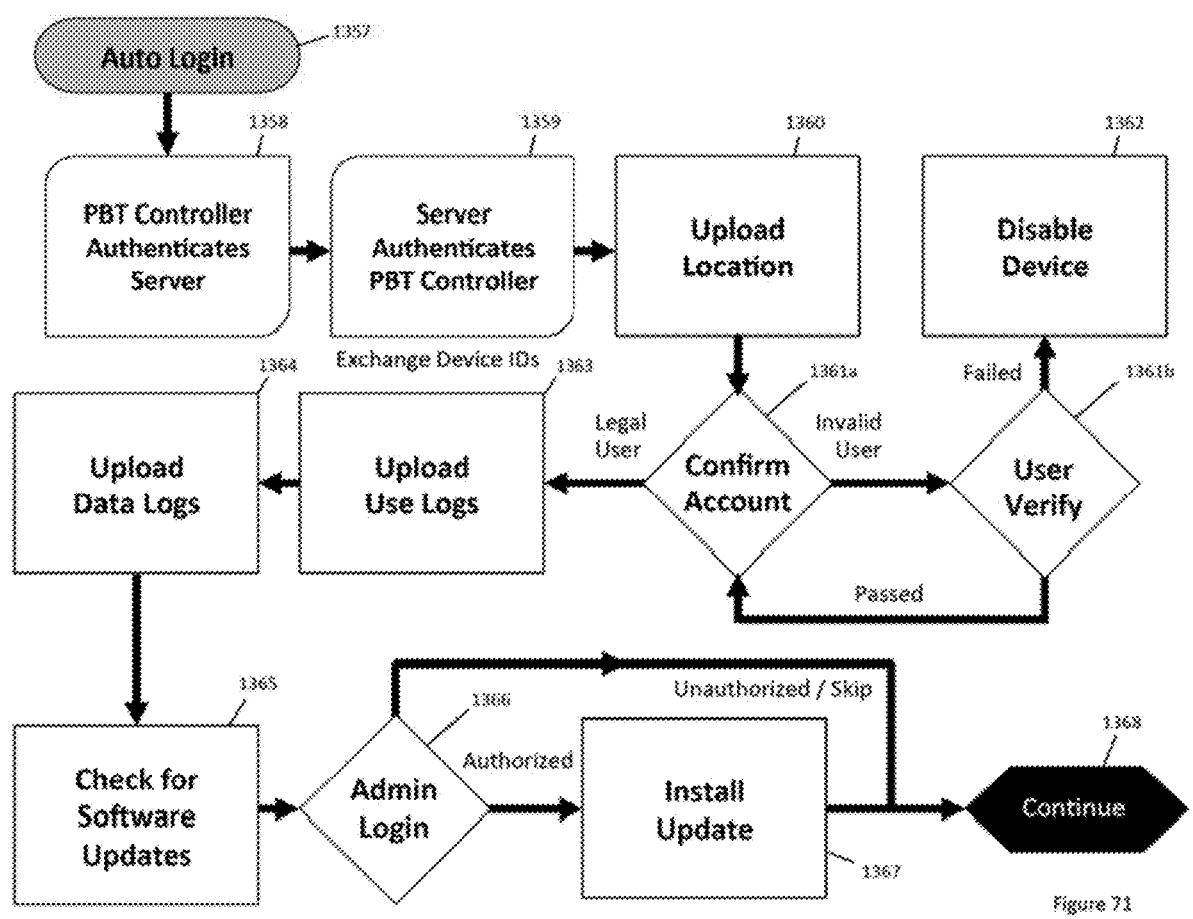
FIG. 71 is a flow chart of a PBT system with autonomous IoT transactions.

Referring again to the autonomous IoT transactions of FIG. 70, upon power up (once communication is established) PBT controller 1351 sends a request to server 1350 to register its connection. The server replies in step 2 by an authentication procedure involving at a minimum Session Layer-5 based authentication and Application Layer-7 validation of the device ID information, but possibly including any combination of Layers-4 through 7. Once the two communicating devices have authenticated one another, active synchronization and automatic updates can commence. This process is represented in greater detail in the exemplar flow chart of FIG. 71 where commencing auto login procedure 1357, after IP addresses are exchanged first the PBT controller authenticates the server in step 1358 followed by the server authentication the PBT controller in step 1359. During the authentication procedure device ID information stored within each device are exchanged, representing a secondary Application Layer-7 method of authentication in accordance with the LightOS operating system. Next, in step 1360, the location of the PBT controller is supplied to the server. The purpose of obtaining the location is two-fold, first in order to optimize communication by optionally transferring session communication to a server closer to the location of the PBT controller, and secondly to track the whereabouts of the PBT controller, both to track its use as well as to detect theft or illegal use (e.g. if the device has been illegally imported).

In step 1361*a*, the device ID and serial number are matched against purchase records. If the device is unable to supply the proper ID and security credentials autonomously, account confirmation fails and the device is referred to a secondary verification process involving more information to complete. For example, this secondary step, represented as user verify 1361*b*, may involve user participation as a dialog of security questions or through email or text messages. In one such method, a random passcode is sent to the registered user, who must in turn enter this code in the system, to pass the test and enable the device. Otherwise the PBT controller is disabled in step 1362. Disabling the device may employ a response comprising several levels of severity depending on the situation. A rudimentary response prevents further use of the PBT controller until the confirmation process is completed. If multiple login attempts fail, the disable device 1362 operation may involve automatically encrypting a portion of the LightOS operating system to prevent possible analysis or hacking. The encrypted portion will stay encrypted until it is restored through a successful user validation process In the extreme case, where the PBT controller has been exported to a banned country or has been reported stolen, disable device 1362 operation may wipe the entire software contents of the PBT controller except for the communications code. By retaining the communications firmware, the device can still be recovered remotely if later the punitive action was found to be in error.

Once the account is confirmed, the server automatically performs some information gathering steps including in the exemplar flow chart uploading use logs 1363, and uploading data logs 1364. Use logs describe what treatments have been performed by the PBT system since the last upload. Use logs may also record the number of use hours of an intelligent LED pad has been employed and to warn the user when an intelligent LED pad is experiencing LED aging and diminishing light output. Data logs may include information from sensors recorded between or during treatments. Each stored data set is time and date stamped with a patient ID number for use in case studies.

After automatic use and data uploads, in the step "check for software update" 1365 the installed LightOS operating system is compared against the newest code updates. If the installed LightOS operating system is not current, the user is requested to login 1366 as an administrator to execute the software update installation 1367 process. If the user does not login in a prescribed time period the installation process is skipped and the PBT controller is ready to continue 1368 in its regular operation.

The sequence of communication packets exchanged between PBT controller 1351 and server 1350 are illustrated in FIG. 72. In step-1, PBT controller 1351 requests to connect to server 1350 by sending data packet 1370 with packet type 1371 and filetype 1372 comprising |0E-02-01| meaning "system message/connection/request to connect to server". Payload length is |00-00-06| where payload 1374 contains PBT controller device ID 1379. The server PBT controller device ID 13879 is passed as part of the LightOS payload in encrypted form so that packet sniffing is not effective in gaining false access. In step-2, server 1350 responds to PBT controller by replying with data packet 1380 that contains packet type 1381 and associated filetype 1382 comprising |0E-02-02| meaning "system message/connection/authentication request". Payload length 1383 is |00-00-06| meaning payload 1384 is six bytes (48 bits) long containing the server's PBT database ID number 1389. This code is useful for the PBT controller to insure in subsequent data packets that it is authorized to communicate to server 1350, i.e. that subsequent communications are not fraudulent devices.

In step-3, PBT controller 1351 requests to connect to server 1350 by sending data packet 1390 with packet type 1391 and filetype 1392 comprising |0E-02-03| meaning "system message/connection/supply authentication code". Payload length 1393 is |00-00-03| so payload 1394 is three bytes long, containing a randomly generated authentication code, e.g. |2F-10-B4| used in an authentication process, either as Session Layer-5 or second authentication as part of Application Layer-7. In step-4, server 1350 confirms the connection to PBT controller 1351 via data packet 1400 containing packet type 1401 and associated filetype 1402 comprising |0E-02-05| meaning "system message/connection/connection confirmed". Payload length 1403 is |00-00-06| so payload 1404 is six bytes (48 bits) long containing either the same of a second authentication code. This code is used to prevent fraud by providing another level of authentication within the LightOS operating system, i.e. as an Application Layer-7 form of validation. If only one code is exchanged, the same authentication code is used in both server 1350 to PBT controller 1351 and in PBT controller 1351 to server 1350 communication. If two authentication codes are exchanged, the code supplied by PBT controller 1351 in field 1394 is to be employed whenever server 1350 communicates with PBT controller 1351, and the code supplied by server 1350 to PBT controller 1351 in field 1404 is to be employed whenever PBT controller 1351 communicates to server 1350.

The disclosed autonomous IoT transaction detailed process continues in FIG. 73 where in step-5, server 1350 responds to PBT controller 1351 with data packet 1420 containing packet type 1421 and filetype 1422 comprising |02-B0-01| meaning "request file/location/request location file". Payload length 1423 is |00-00-00| so payload 1424 is a zero bytes long. In step-6, PBT controller 1351 sends location information to server 1350 via data packet 1430 containing packet type 1431 and associated filetype 1432 comprising |03-A0-01| meaning "send file/location/supply location file". Payload length 1433 is |00-00-06| so payload 1434 is six bytes (48 bits) long containing the PBT controller location file 1439. Location file 1439 contains the PBT controller's GPS location along with its nearest network connections, and optionally contains network trace information. In step-7, the user account is confirmed by a software comparison of active and disabled accounts 1441 against relevant device ID information 1443 containing information such as serial numbers and manufacturing data extracted 1442 from PBT controller device ID 1409, supplied previously during the authentication handshaking process. Not all of the information within PBT controller device ID 1409 is required to confirm the user's account.

Steps 8 through 11 shown in FIG. 74 describe the sequence of communication packets exchanged between PBT controller 1351 and server 1350 during uploading of PBT controller data. In step-8, server 1350 sends PBT controller 1351 data packet 1510 containing packet type 1511 and associated filetype 1512 comprising |02-B4-01| meaning "request file/use logs/upload use log file". Payload length 1513 is |00-00-04| so payload 1514 is four bytes (32 bits) long containing the last upload date 1419. For example, hex payload |02-65-07-E1| represents a hexadecimal equivalent to 06/13/2017. In step-9, PBT controller 1351 uploads user log file to server 1350 via data packet 1520 containing packet type 1521 and associated filetype 1522 comprising |03-A4-01| meaning "send file/use log/upload use file logs". Payload length 1523 varies where payload 1524 contains PBT controller use log files 1529 back till the date described in field 1419. In step-10, server 1350 sends PBT controller 1351 data packet 1530 containing packet type 1531 and associated filetype 1532 comprising |02-B5-01| meaning "request file/data logs/upload data log file". Payload length 1533 is |00-00-04| so payload 1534 is four bytes (32 bits) long containing the last upload date 1439. For example, hex payload |02-65-07-E1| represents a hexadecimal equivalent to 06/13/2017. In step-11, PBT controller 1351 uploads user log file to server 1350 via data packet 1540 containing packet type 1541 and associated filetype 1542 comprising |03-A5-01| meaning "send file/data log/upload data file logs". Payload length 1543 varies where payload 1544 contains PBT controller data log files 1549 back till the date described in field 1439. If however after step 3 in FIG. 72, server 1350 rejects a connection with PBT controller 1351 then as shown in step-4 of FIG. 75, server 1350 sends PBT controller 1351 data packet 1550 containing packet type 1551 and associated filetype 1552 comprising |0E-02-04| meaning "system message/connection/connection rejected". Payload length 1553 is |00-00-00| so payload 1554 is zero bytes length. In step 5 a secondary authentication process is executed. Such steps may involve a user entering information directly into to PBT controller 1351 or by logging directly into server 1350. Should the second login attempt fail and records indicate the particular serial number device has been stolen, carried into unauthorized countries, or for other reasons, the PBT controller 1351 and as shown in step 6, data packet 1560 is sent where packet type 1561 and filetype 1562 comprise |0E-FF-FF| meaning "system message/connection/wipe pad operating system" having a payload length 1563 of zero bytes meaning payload 1564 is a null data.

Figure 76A:
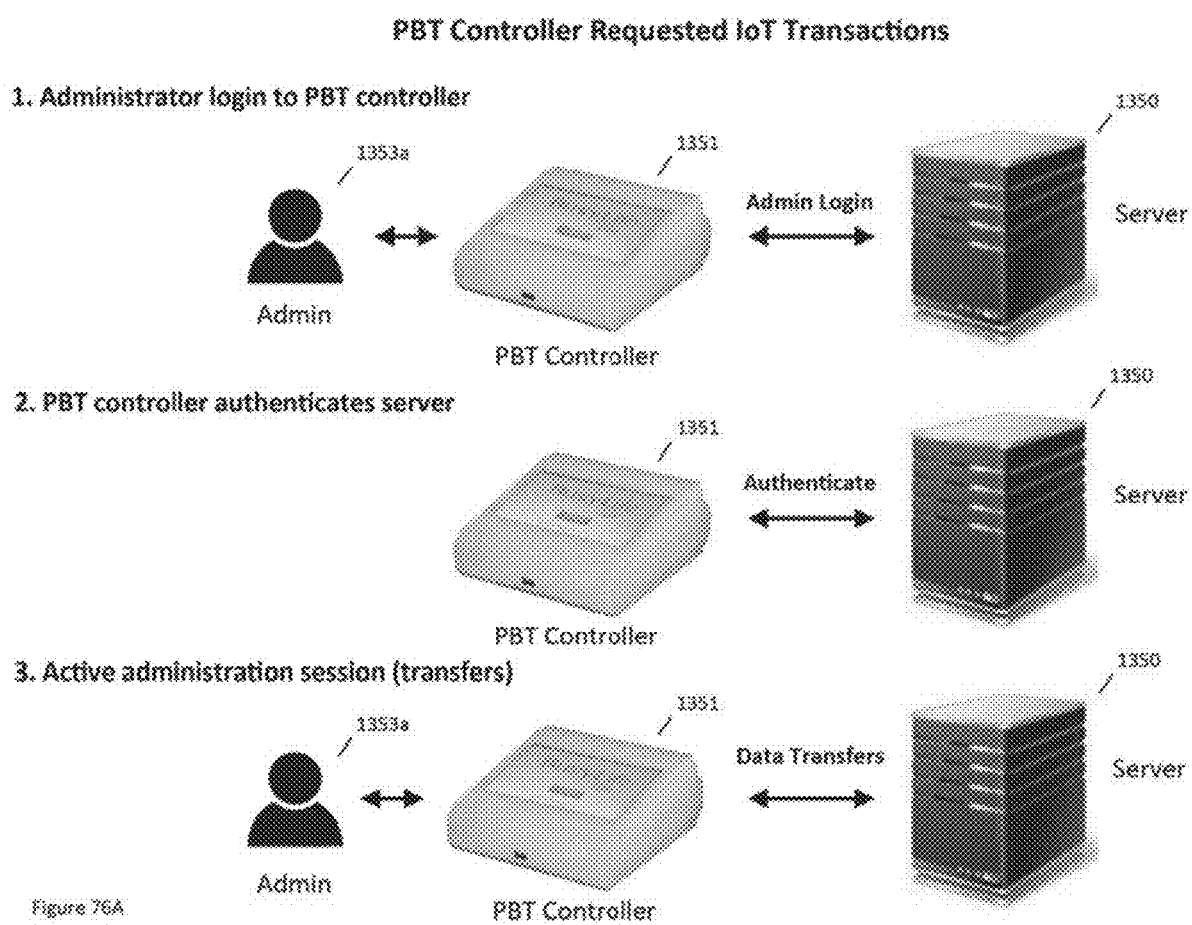
FIG. 76A illustrates a PBT system operation with PBT controller-requested IoT transactions.

In the second category, namely "IoT device requested transactions" represented in FIG. 76A, a user with administrative authority, i.e. admin 1353, logs into to the LightOS operating on PBT controller 1351. The authority of admin 1353 to execute transactions between PBT controller 1351 and server 1350 is then determined by an authorization procedure labeled as admin login. In this manner, admin 1353a is utilizing PBT controller 1351 as a remote terminal. If login fails, PBT controller will prevent the user from any server related access and transactions. Assuming a successful login any system command and transaction between PBT controller 1351 and server 1350 starts with a device-to-device authentication as shown in step-2. Thereafter, as shown in step-3 an active administration is opened and maintained allowing bidirectional file transfers between PBT controller 1351 and server 1350 in response to user commands of admin 1353a. These transfers may include software and firmware downloads to the PBT controller, and any number of data file uploads to the server. Unlike autonomous IoT connections following a prescribed sequence of device-to-device network transactions, in "IoT device requested transactions" a human operator (admin 1353a) controls what transfers are requested. The server responds in turn by executing all transaction within the authority granted admin 1353a.

This file transfer process is illustrated in the flow chart of FIG. 76B, where after login into PBT system 1600 described previously, the server authenticates the network administrator in step 1601 followed by the server authenticating the PBT controller in step 1602 during which device and database IDs are exchanged. This process collectively is referred to as "authentication". In step 1603, the administrator once authenticated requests a file transfer where the server checks the authority granted the admin against the requested transaction. Provided the request doesn't exceed the admin's authority, in step 1604 the transaction is authorized. This step is referred to as "authorization". Thereafter, the data transfer 1605 is executed and the details of the transfer requested and executed are recorded, i.e. chronicled, in the server including the user executing the transaction. This step, referred to as "administration," is required to debug problems, to identify failed or successful attacks, and to identify perpetrators of prohibited transactions. Together the steps of authentication, authorization, and administration, called AAA are used to insure reliable and secure communication. In the event that any patient information is present in the system, the foregoing procedures must also insure the privacy of patient data and prevent unauthorized access of personal information compliant with HIPAA standards.

Figure 76C:
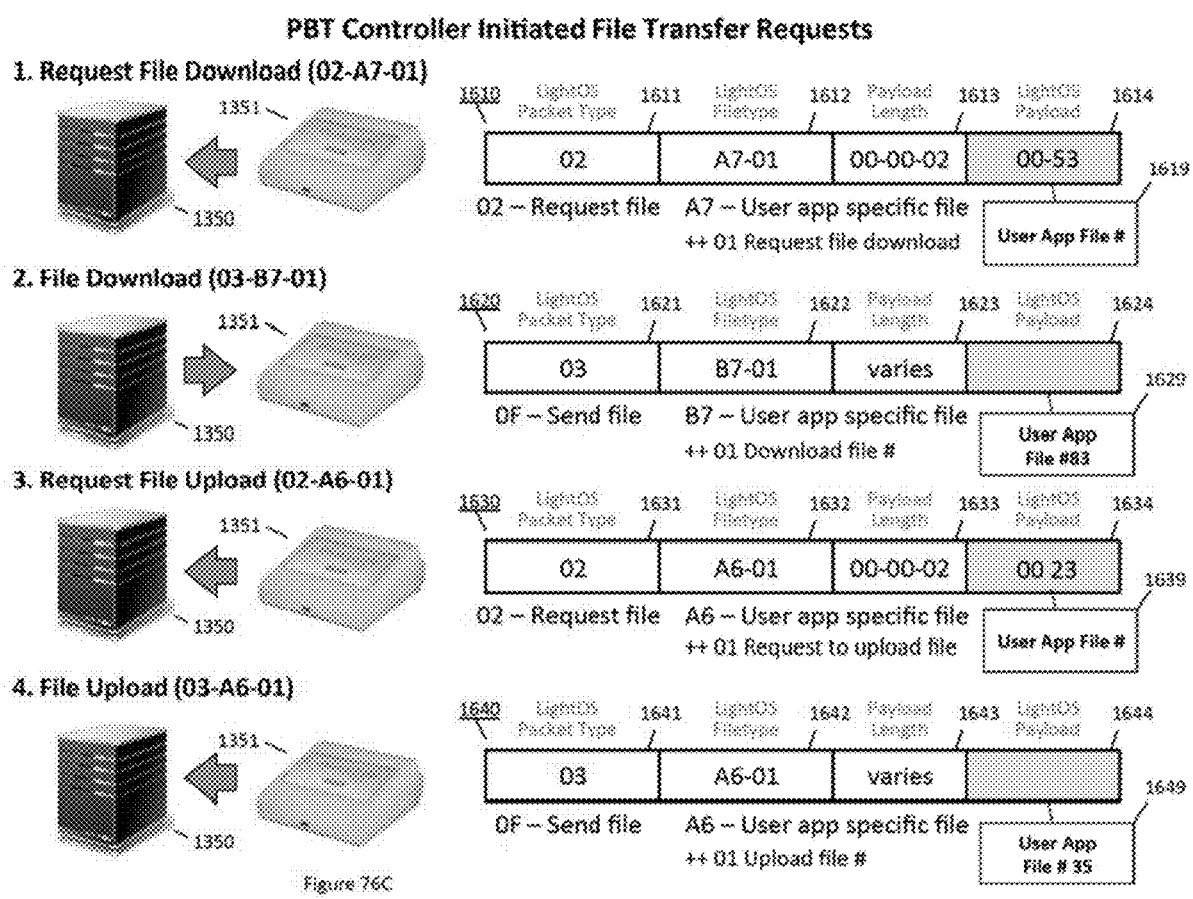
FIG. 76C illustrates communication in a PBT system during PBT controller requested file transfers.

In IoT device requested transactions, the data transfer 1605 operation may involve two types of transfers, namely PBT controller 1351 requesting a download from server 1351, and PBT controller 1351 requesting to upload data to server 1351. In both cases, the administrator is controlling the request from PBT controller 1351. Exemplar LightOS communication packets of these transfers are shown in FIG. 76C. In step-1 PBT controller 1351 request a data download from server 1350 by sending a LightOS compliant communication packet 1610 with packet type 1611 and filetype 1612 comprising hexadecimal instruction |02-A7-01| meaning "request file/user app specific file/request file download". Payload length 1613 has a hex value |00-00-02| meaning payload 1614 is 2-B (16 bits) long describing user app file number 1619. In the example shown, this 16b word is represented by four hexadecimal character |00-53| which is equivalent to the decimal 83, meaning user app file #83. In step-2, server 1350 responds by downloading user app file 1629 as payload 1624 in communication packet 1620 with packet type 1621 and filetype 1622 comprising hexadecimal instruction |03-B7-01| meaning "send file/user app specific file/download file #". Payload length 1623 has a variable length depending on the nature of the file. In the example shown user app file 1619 contains data set #83. In the case of a user app specific file, the user specifies the meaning of the file. In other cases the file may comprise a predefined format for common data types such as temperature files, image files, movie files etc.

In step-3 PBT controller 1351 request a data upload to server 1350 by sending a LightOS compliant communication packet 1630 with packet type 1631 and filetype 1632 comprising hexadecimal instruction |02-A6-01| meaning "request file/user app specific file/request to upload file". Payload length 1633 has a hex value |00-00-02| meaning payload 1624 is 2-B (16 bits) long describing user app file number 1639. In the example shown, this 16-b word is represented by four hexadecimal characters |00-23| which is equivalent to the decimal value 35, meaning user app file #35. Unless the server rejects the request, in step-4 PBT controller 1351 then uploads user app file 1649 as payload 1644 in communication packet 1640 with packet type 1641 and filetype 1642 comprising hexadecimal instruction |03-A6-01| meaning "send file/user app specific file/upload file #". Payload length 1643 has a variable length depending on the nature of the file. In the example shown user app file 1649 contains data set #35. In the case of a user app specific file, the user specifies the meaning of the file. In other cases the file may comprise a predefined format for common data types such as temperature files, image files, movie files etc.

Figure 77A:
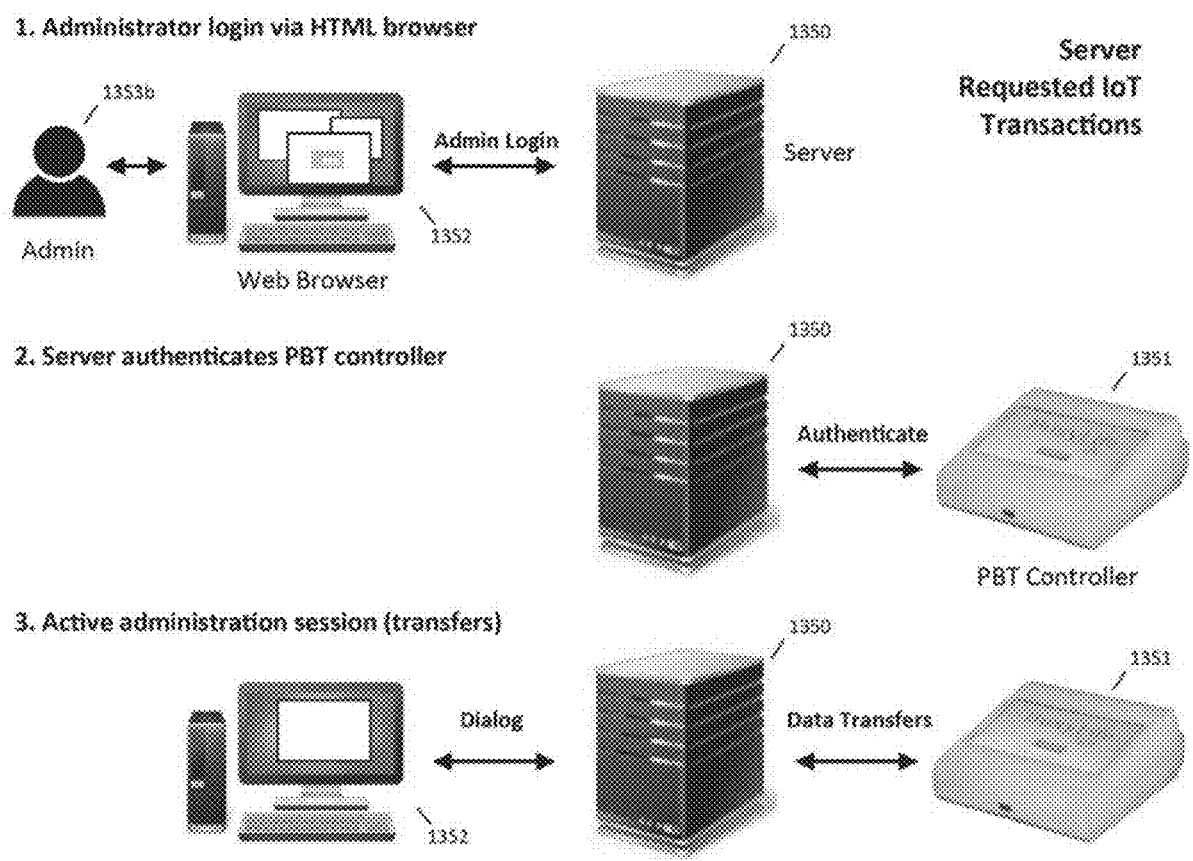
FIG. 77A illustrates a PBT system operation with server-requested IoT transactions.

Alternatively in the third category of transfers, namely "server-authority based IoT transactions" represented in FIG. 77A, a user with administrative authority, i.e. admin 1353*b*, logs directly into server 1352 via a web browser 1352. Web browser 1352 in turn communicates with server 1350 using HTML scripts. The login procedure immediately recognizes the authenticity of admin 1353*b*, determines their system privileges, and establishes their command authority access level. Any attempt to execute a command beyond their authority will be immediately rejected by the server and the illegal request will be logged. Assuming a successful login any system command issued by the administrator 1353*b* initiates a process to establish network communication between server 1350 and PBT controller 1351. For all online PBT controllers, the device's dynamically assigned IP address will appear on the server's contact list whereby authentication shown in step-2 can proceed. If, however, the device is offline there is no way to contact it until the next time the device is Internet connected.

Assuming the PBT controller is online, the server initiates a communication Layer-5 Session between PBT controller 1351 and server 1350 followed by a device-to-device authentication procedure as represented by step-2. Thereafter, as shown in step-3 an active administration is opened and maintained allowing bidirectional file transfers between PBT controller 1351 and server 1350 in response to user commands of admin 1353*b* via a dialog with web browser 1352. These transfers may include software and firmware downloads to the PBT controller, and any number of data file uploads to the server. Unlike autonomous IoT connections following a prescribed sequence of device-to-device network transactions, in "server-authority based IoT transactions" a human operator (admin 1353*b*) controls what transfers are requested. The server responds in turn by executing all transaction within the authority granted admin 1353*b*.

This file transfer process is illustrated in the flow chart of FIG. 77B, where after user server login 1650 occurs, the server authenticates the network administrator in step 1651 followed by the PBT controller and server authenticating one another in step 1652 during which device and database IDs are exchanged. This process collectively is referred to as "authentication". In step 1653, the administrator once authenticated requests a file transfer where the server checks the authority granted the admin against the requested transaction. Provided the request doesn't exceed the admin's authority, in step 1654 the transaction is authorized. This step is referred to as "authorization". Thereafter, the data transfer 1655 is executed and the details of the transfer requested and executed are recorded, i.e. chronicled, in the server including the user executing the transaction. This step, referred to as "administration," is required to debug problems, to identify failed or successful attacks, and to identify perpetrators of prohibited transactions. Collectively the procedure complies with AAA standards for maintaining security and privacy. Additional safeguards may be required in a accordance with HIPAA if patient identity information is retained.

In IoT device requested transactions, the data transfer 1655 operation may involve two types of transfers, namely server 1351 requesting an upload from PBT controller 1351, and server 1350 requesting to download data to PBT controller 1351. In both cases, the administrator is controlling the request from server 1350 via web browser 1352. Exemplar LightOS communication packets of these transfers are shown in FIG. 77C. In step-1 server 1350 request a data upload from PBT controller 1351 by sending a LightOS compliant communication packet 1660 with packet type 1661 and filetype 1662 comprising hexadecimal instruction |02-B6-01| meaning "request file/user app specific file/request file upload". Payload length 1663 has a hex value |00-00-02| meaning payload 1614 is 2-B (16 bits) long describing user app file number 1669. In the example shown, this 16-b word is represented by four hexadecimal character |00-A0| which is equivalent to the decimal 160, meaning user app file #160. In step-2, PBT controller 1351 responds by uploading user app file 1679 as payload 1674 in communication packet 1670 with packet type 1671 and filetype 1672 comprising hexadecimal instruction |03-A6-01| meaning "send file/user app specific file/upload file #". Payload length 1673 has a variable length depending on the nature of the file. In the example shown user app file 1679 contains data set #160. In the case of a user app specific file, the user specifies the meaning of the file. In other cases the file may comprise a predefined format for common data types such as temperature files, image files, movie files etc.

In step-3 server 1350 requests a data download to PBT controller 1351 by sending a LightOS compliant communication packet 1680 with packet type 1681 and filetype 1682 comprising hexadecimal instruction |02-B7-01| meaning "request file/user app specific file/request to download file". Payload length 1683 has a hex value |00-00-02| meaning payload 1684 is 2-B (16 bits) long describing user app file number 1689. In the example shown, this 16-b word is represented by four hexadecimal characters |01-00| which is equivalent to the decimal value 256, meaning user app file #256. Unless the PBT controller experiences a malfunction, in step-4 server 1350 then downloads user app file 1699 as payload 1694 in communication packet 1690 with packet type 1691 and filetype 1692 comprising hexadecimal instruction |03-B7-01| meaning "send file/user app specific file/download file #". Payload length 1693 has a variable length depending on the nature of the file. In the example shown user app file 1699 contains data set #256. In the case of a user app specific file, the user specifies the meaning of the file. In other cases the file may comprise a predefined format for common data types such as temperature files, image files, movie files etc.

A summary of exemplar data transfer codes is shown in the table below including request file packet type |O2| and send file packet type |O3| where filetypes |Bx-xx| comprise packets sent from server 1350 to PBT controller 1351 and filetypes |Ax-xx| comprise packets sent from PBT controller 1351 to server 1350. These payloads comprise non-executable data files such as location, temperature, image, sensor data, use log, data log, and user defined application specific files.

| Transaction | Server File Request | PBT Controller File Request | Send Requested File |
|---|---|---|---|
| PBT Controller to Server Upload | | | |
| Upload location file | \|02-B0-01\| | \|02-A0-01\| | \|03-A0-01\| |
| Upload temperature file | \|02-B1-01\| | \|02-A1-01\| | \|03-A1-01\| |
| Upload image or movie file | \|02-B2-01\| | \|02-A2-01\| | \|03-A2-01\| |
| Upload sensor data file | \|02-B3-01\| | \|02-A3-01\| | \|03-A3-01\| |
| Upload use log file | \|02-B4-01\| | \|02-A4-01\| | \|03-A4-01\| |
| Upload data log file | \|02-B5-01\| | \|02-A5-01\| | \|03-A5-01\| |
| Upload user app specific file | \|02-B6-01\| | \|02-A6-01\| | \|03-A6-01\| |
| Server to PBT Controller Download | | | |
| Download user app specific file | \|02-B7-01\| | \|02-A7-01\| | \|03-B7-01\| |
| Calibration Table | \|02-B8-01\| | \|02-A8-01\| | \|03-B8-01\| |
| Message Display | \|02-B9-01\| | \|02-A9-01\| | \|03-B9-01\| |

Mobile Device Connectivity

Using wireless connectivity, the PBT controller can be replaced an application program running on a mobile device such as a cell phone, tablet, or notebook computer.

Figure 78:
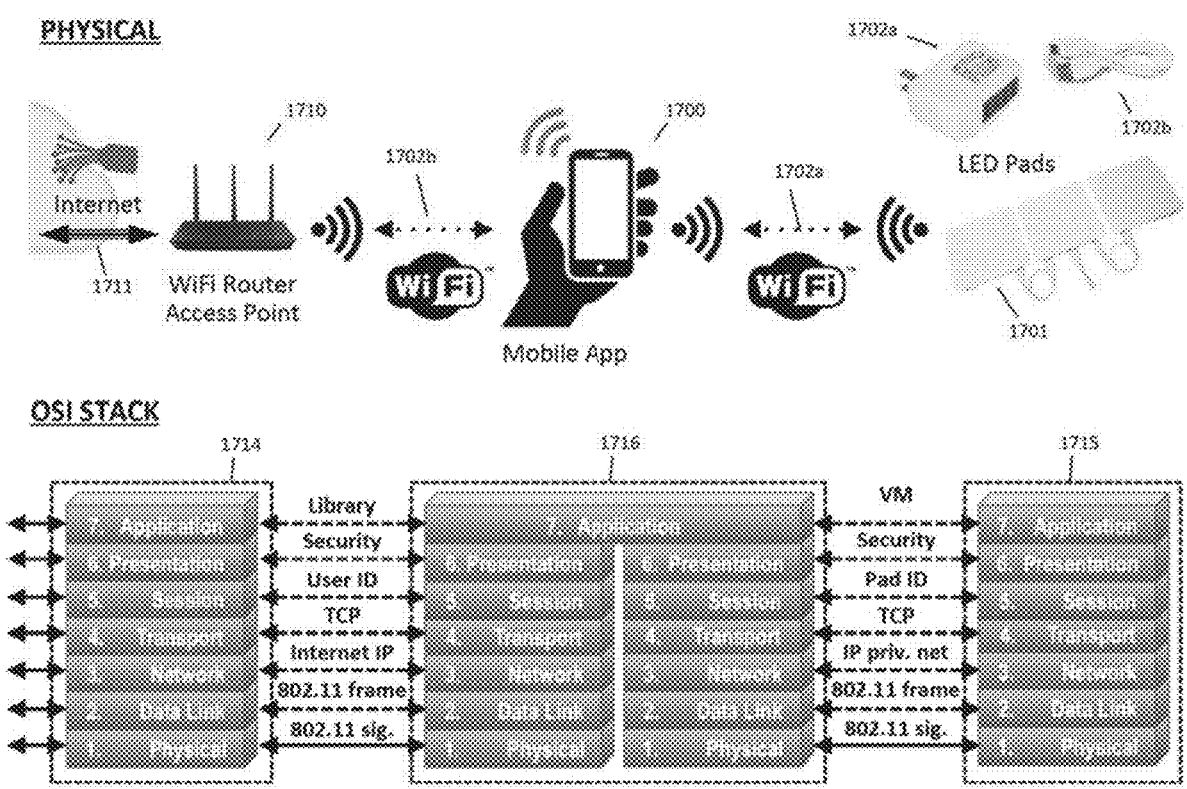
FIG. 78 is an exemplar distributed PBT system comprising a mobile app based PBT controller WiFi based Internet and LED pad connectivity.

For example in FIG. 78 cell phone 1700 running PBT controller application software (herein "Light app") connects to WiFi router 1710 over WiFi 1702*b*. WiFi router 1710 in turn connects to Internet 1711 by Ethernet, fiber, or other means. Cell phone 1700 running the aforementioned Light app also connects to intelligent LED pad 1701 using WiFi 1702*a*, where intelligent LED pad 1701 is powered by AC adapter 1702*a* and cord 1702*b*. The 7-layer OSI communication stack 1714 of WiFi router 1710 uses 802.11 compliant data packets to connect with communication stack 1716 of Light app running on cell phone 1700. In turn, the Light app also uses 7-layer communication stack 1716 to connect to intelligent LED pad 1701 comprising communication stack 1715. As shown, PBT communication stack 1716, mixes two 7-layer communication stacks, one for dialog with communication stack 1714 of WiFi router 1710 and through the router to Internet 1711 and to a cloud based server (not shown), and another for connecting to intelligent LED pad 1701 and communication stack 1715, where only the Light Application Layer-7 bridges the two. In this manner, cell phone 1700 running the aforementioned Light app operates as a PBT controller communicating separately to a cloud based computer server (not shown) over Internet 1711 and to intelligent LED pad 1701.

Figure 79:
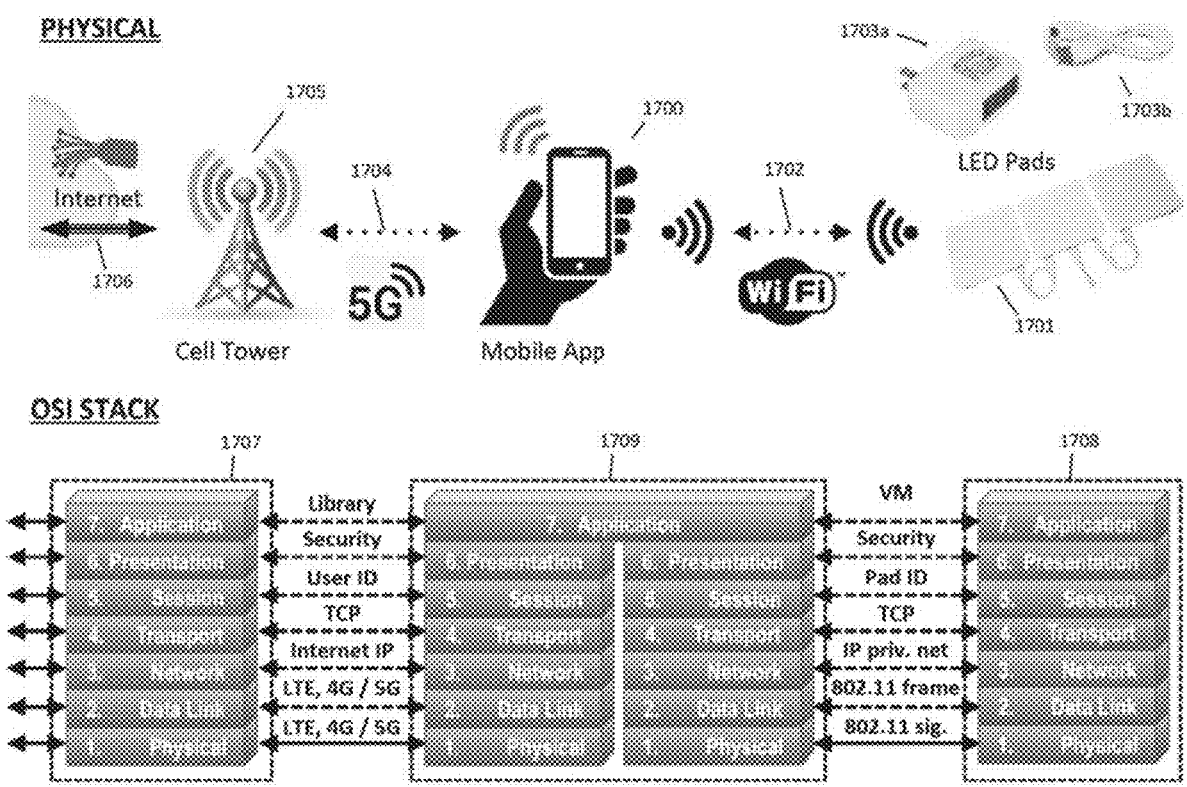
FIG. 79 is an exemplar distributed PBT system comprising a mobile app based PBT controller using 5G telephonic network based Internet communication and WiFi based LED pad connectivity.

Because PHY Layer-1 and Data Link Layer-2 are not shared for communication across Layers-1 to 6, router communication stack 1714 is unable to directly access intelligent LED pad communication stack 1715. Instead, only Application Layer-7 bridges the two communication networks. The application may comprise a dedicated Light app, which like LightPadOS, operates as reduced instruction set version of the LightOS operating system used in dedicated hardware PBT controllers described previously. In essence the Light app emulates the operation of LightOS in facilitating PBT control functionality and its UI/UX touchscreen based control. The Light app is realized as software designed for operating on the operating system used in the corresponding mobile device. For example, in smart phones and tablets, the Light app is created to run atop Android or iOS while in notebooks, the Light app is created to run on MacOS, Windows, Linux, or UNIX. The conversion of the source code, the basic logic and function of the Light app, into executable code adapted to run atop a specific platform is a conversion process referred to as a "compiler". The translation of source code into compiled code is therefore platform-specific meaning multiple versions of the software must be distributed each time a software revision, patch, or new release occurs. The use of mobile devices with telephonic capability including smartphones, tablets, and 3G/4G hotspots also enables another avenue for connecting the Light app and mobile platform to the Internet, namely wireless telephony over 3G/LTE, 4G and 5G wireless networks. This case is illustrated in the exemplar shown in FIG. 79 where cell phone 1700 running the "Light app" PBT controller application software connects to cell tower 1705 using a digital telephonic data network with microwave signals 1554. Cell tower 1705 in turn connects to Internet 1706 by Ethernet, fiber, or other means. Cell phone 1700 running the aforementioned Light app also connects to intelligent LED pad 1701 using WiFi 1702, where intelligent LED pad 1701 is powered by AC adapter 1702*a* and cord 1702*b*. The 7-layer OSI communication stack 1714 of cell tower base station 1707 uses microwave signals to digitally connect with communication stack 1709 of Light app running on cell phone 1700. In turn, the Light app also uses 7-layer communication stack 1709 to connect to intelligent LED pad 1701 comprising communication stack 1708. As shown, PBT communication stack 1709, mixes two 7-layer communication stacks, one for dialog with communication stack 1707 of cell tower 1705 and through Internet 1706 to a cloud based server (not shown), and another for connecting to intelligent LED pad 1701 and communication stack 1708, where only the Light Application Layer-7 bridges the two. In this manner, cell phone 1700 running the aforementioned Light app operates as a PBT controller communicating wirelessly to a cloud based computer server (not shown) over a telephonic network and Internet 1706 and to intelligent LED pad 1701.

In a manner similar to OFDM used for WiFi communication, and Ethernet used in wire-line and fiber communication, modern radiotelephony also uses packet switched communication technology except the each transmitted frame must be subdivided into discrete time slots comprising multiple frequencies and codes to avoid congestion of limited radio bandwidth over large areas. These communication protocols, while the vary for 3G/LTE, 4G, and 5G networks operate exclusively as PHY Layer-1 and Data Link Layer-2 protocols with no influence on Network Layer-3 datagram content or on any of higher OSI layers. As such, the specific radio protocol employed has no impact on the realization of the distributed PBT system. FIG. 80 illustrates a 4G realization of a data packet compatible with OFDM modulation methods to achieve high data rates and communication bandwidth.

As shown PHY Layer-1 comprises OFDM frame 1720 subdivided into time slots 1721. Its MAC Layer-2 equivalent is represented by MAC data packet 1722 comprising MAC header 1723*a*, a single frame MAC payload (also known as a service data unit or SDU) 1724, and padding 1723*b*. The MAC payload in turn contains a sublayer of Layer-2 referred to as radio link control or RLC protocol data unit (or PDU) 1726 comprising RLC header 1727 and its associated single frame RLC SDU payload 1728 ending at time 1722 corresponding to the onset of padding interval 1723*b*. After a time 1731, a new RLC PDU commences comprising RLC header 1729 and payload 1730. Single frame SDU 1728 contains a sequence of multi-frame RLC SDUs 1733, subdivided into segments. The multi-frame SDU segments as shown comprising K segment 1734, (K+1) segment 1735, and (K+2) segment 1736 do not coincide with the PDU intervals, but instead may be longer or shorter than the PDU time slots. For example (K+2) segments 1736 is delivered in part by single payload frame 1728 and part by the next frame 1730. In cases where these (K) segments occupy less than the interval of single frame payload 1728, then the bandwidth is reallocated to another MAC payload. In this manner the PDU intervals and SDU segments dynamically adjust to maximize the data rate, never wasting available bandwidth waiting for more content in the same communication. Ultimately the highest sublayer of Data Link Layer-2 in 4G, the packet data convergence protocol layer (PDCP), identifies the PDCP SDU content 1742, 1743, and 1744 within each of the K segments by their corresponding PDCP headers 1741a, 1741, and 1741c, in order to extract and concatenate data packets 1752, 1753 and 1754 into Layer-3 payload 1750.

Figure 81A:
FIG. 81A illustrates exemplar mobile phone menu for starting Light PBT app program.
Figure 81B:
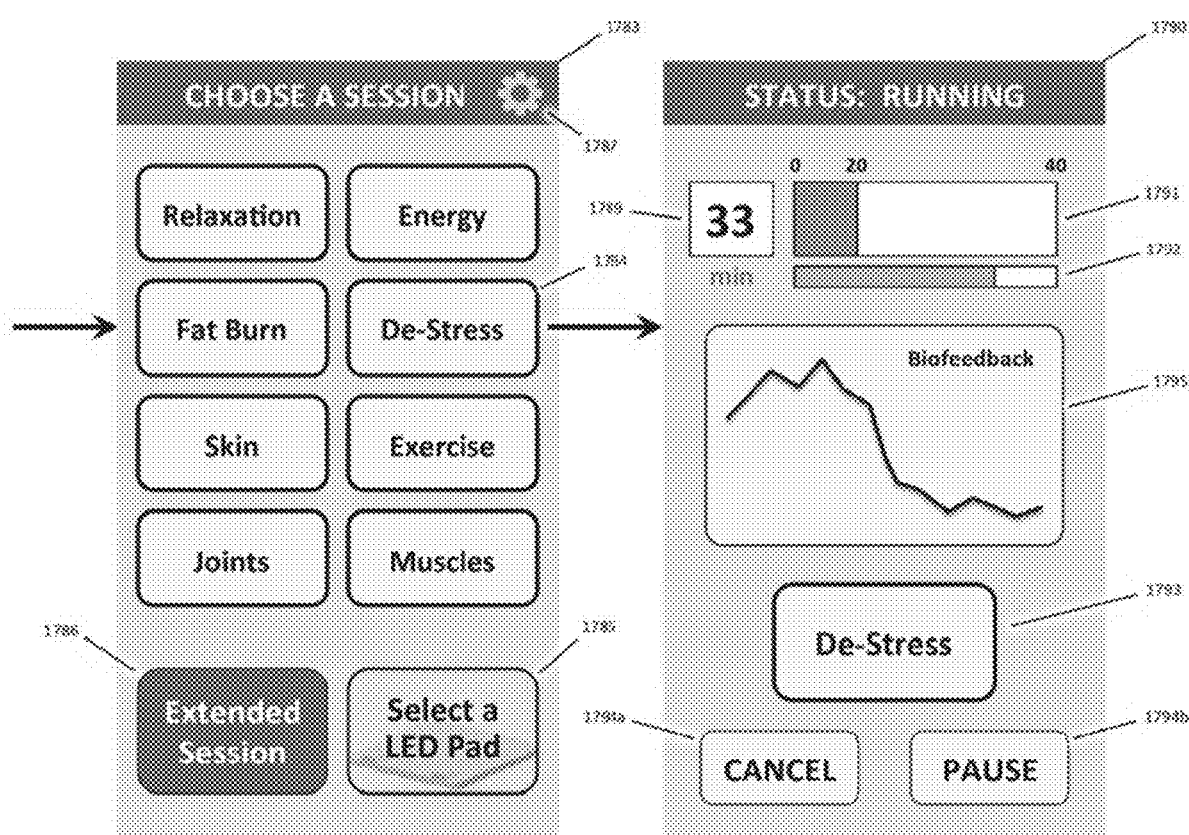

In operation, the Light app emulates the functions of a hardware PBT controller by communicating with the intelligent LED pads to detect their presence, authenticate their connection to the wireless network and LightOS application, control their operation, and to upload data from any in-pad sensors. This sequence is shown in FIG. 81A, where a screen of apps 1780 includes a Light PBT app 1781 that opens a screen 1782 while the app is loading then after a time automatically changes to screen 1783 comprising the menu "choose a session" shown in FIG. 81B. This menu includes buttons such as "de-stress" 1784 to select a therapy session, plus a button to "select a pad" 1785, and also "extended session" 1786 used to choose a longer treatment time, e.g. 50 minutes instead of 20 min. Selecting the gear symbol 1787 opens a settings page used to control default settings such as intelligent LED pad temperature, alarm functions, product information, etc.

Figure 81C:
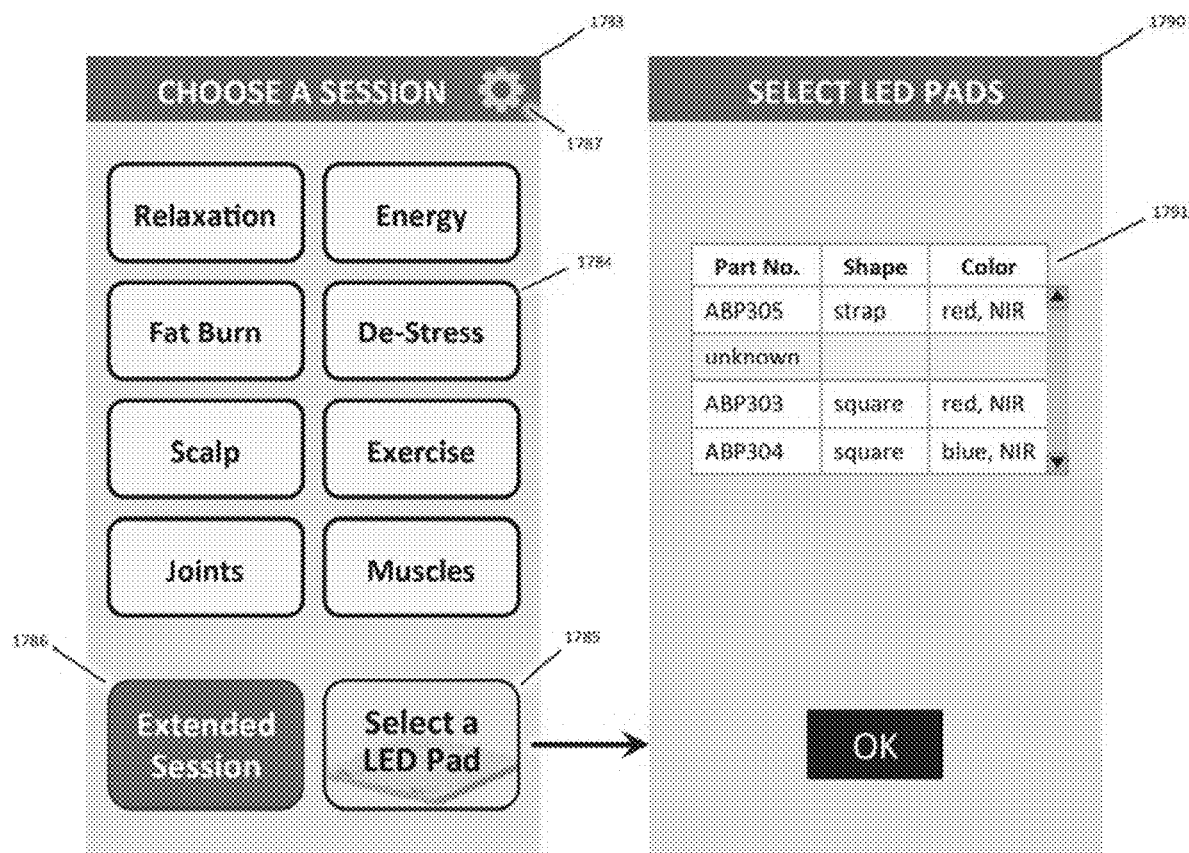

Selecting "de-stress" 1784 opens screen 1790. This screen includes start/pause button 1294b, cancel button 1794a, and also info window 1793 showing the program selected. Depressing the start button 1794b commences the PBT session where step indicator 1792 shows the progress of the current step, session bar 1791 shows the progress of the entire session, and time remaining box 1789 shows how long is left in the treatment. Graphic screen 1795 provides a graph of biofeedback such as heart rate, blood oxygen, blood sugar, brain waves, etc. only if a real time sensor biometric data is available. As shown in FIG. 81C, depressing "select a LED pad" 1785 on screen 1783 opens the "select LED pads" menu screen 1790 which in the exemplar shown illustrates intelligent LED pads recognized by the WiFi network as displayed in menu 1791. Conventional passive LED pads lacking network connectivity and communication network handshaking capability will not register on the selection menu.

Sensor Connectivity and Biofeedback

Sensors play a valuable role in the disclosed distributed PBT system. The sensors may be used in performing static before and after measurements (e.g. blood sugar, blood pressure), or for dynamically monitoring a biometric parameter during a session (e.g. brain waves, heart rate, blood oxygen). Sensors integrated into the pad may also be used to extract a 2-D or 3-D image of the treatment area either as a static image or as a mpg movie file. Sensor measurements can be used in several ways in the disclosed PBT system, either to:

Gather sensor data (electronic data capture or EDC) for upload to a medical database or clinical trial management system (CTMS).

Provide real time display of a patient's biometrics or vital signs to the patient or to a doctor.

Facilitate biofeedback control of PBT therapy conditions.

Figure 82B:
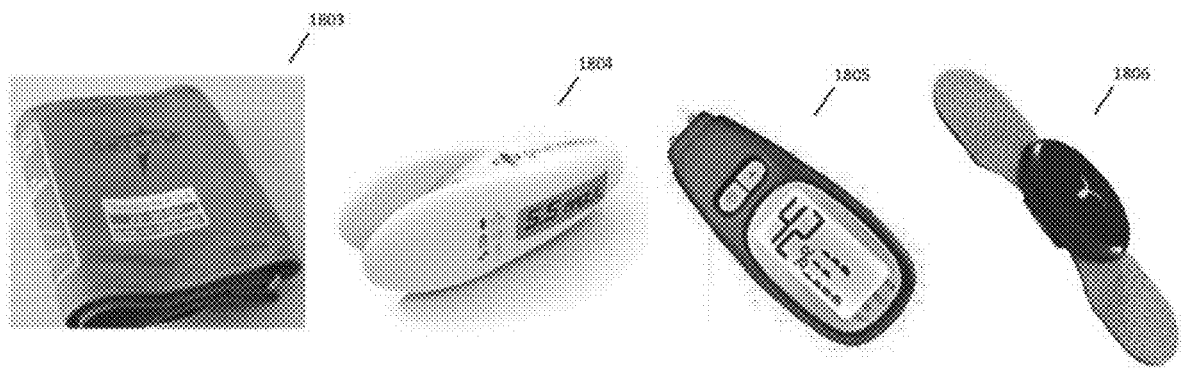

Examples of discrete sensors compatible with the disclosed PBT system are shown in FIG. 82A. Discrete sensors measure one or several parameters from a single sensor possibly over time, but do not support 2-D or 3-D spatial images. Examples include blood oxygen monitor 1800a measuring the blood oxygen concentration (BOC) of the body's circulatory system 1800b and optionally displaying the BOC over time 1800c possibly overlaid with heart rate data. Electroencephalogram or EEG brainwave monitors 1801a may be used to monitor stress and relaxation states of the brain 1801b, The measured results may be tracked over time and displayed in harmonic bands 1801c or may be analyzed to extract additional information, e.g. using non-linear mathematics to detect mild traumatic brain injury electrically using non-linear mathematical analysis (i.e. the Leahy concussive index or LCI). Similarly electrocardiogram heart monitors 1802a, commonly referred to as ECG or EKG, may be employed across the chest, on the arm, across the forehead or even on the ear to detect the health of a patients heart 1802b before and after, or during a PBT treatment. The heart rate can be displayed over time 1802c or may be analyzed for heart rate variability (HRV). Other biosensors shown in FIG. 82B include blood pressure monitor cuffs 1803, non-invasive real time blood sugar monitor 1804, skin moisture monitor 1805, or muscle tension (electromyogram or EMG) 1806.

Most biometric monitors use electrical or optoelectric methods where a biophysical parameter is detected, measured, and reported in real time, avoiding the delay and inconvenience of taking tissue or blood samples and sending the samples to a lab for analysis. Although biophysical parametric measurements (such as blood pressure) may be compared to population norms, stochastic variability in human populations renders most un-calibrated measurements relatively meaningless. Monitoring biophysical parameters over time and tracking relative changes offers greater insight to a patient's condition, especially when correlated to therapeutic regimens as well as lifestyle factors such as food, diet, and exercise. In some cases, such as in the treatment of concussion and mild traumatic brain injury (mTBI) it is also valuable to develop and retain baseline data prior to the risk of an injurious event, e.g. making baseline measurements on team members before football season commences.

Figure 82C:
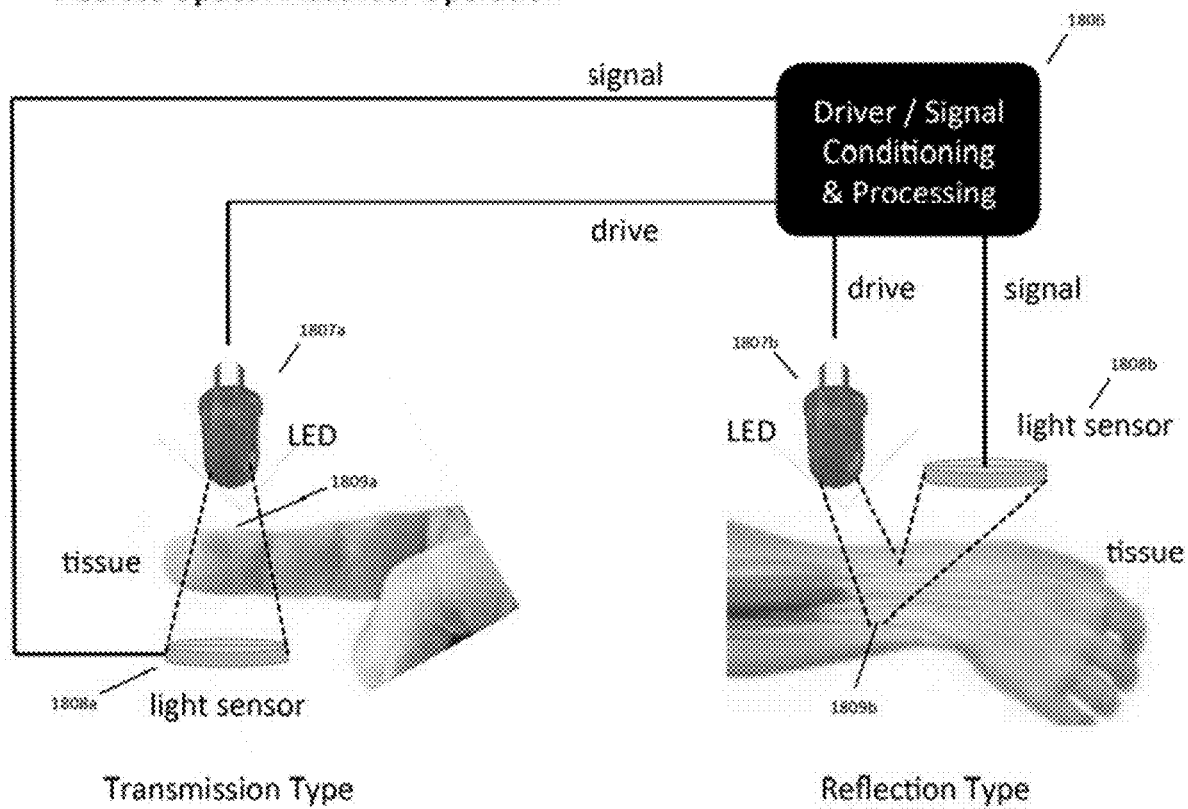

In general, many biometric measurements utilize sensors designed to detect small changes in electrical potential, in electrical resistance affecting micro-current conduction through various tissue type, or in the measurement in the AC or RF impedance of tissue. Such electrical and electromagnetic detectors are especially suitable to the nervous system, which operates using electron, ionic, and electro-chemical conduction. Audio sensors, i.e. microphones, are employed to monitor heart rate and as part of blood pressure detection systems. Another class of biosensor involves subjecting tissue to a source of sound, ultrasound, or light and detecting the interaction of the tissue with the impinging energy. One example shown FIG. 82C employs a LED or laser is used to detect the influence of a biomolecule on light transmission or reflection. The driving waveform and sensor detection signal processing functions are performed by signal conditioning unit 1806. In the transmission type sensor, infrared light from LED 1807a passes through a patient's skin or tissue 1809c and is collected by optical sensor 1808a. Such a method is common for blood oxygen monitoring. In reflection type sensors, visible light from LED 1807*b* reflects off of a patient's skin 1809*b* to be collected by optical sensor 1808*b*. The biometric data once collected can be correlated to the PBT treatment over time.

Figure 82D:
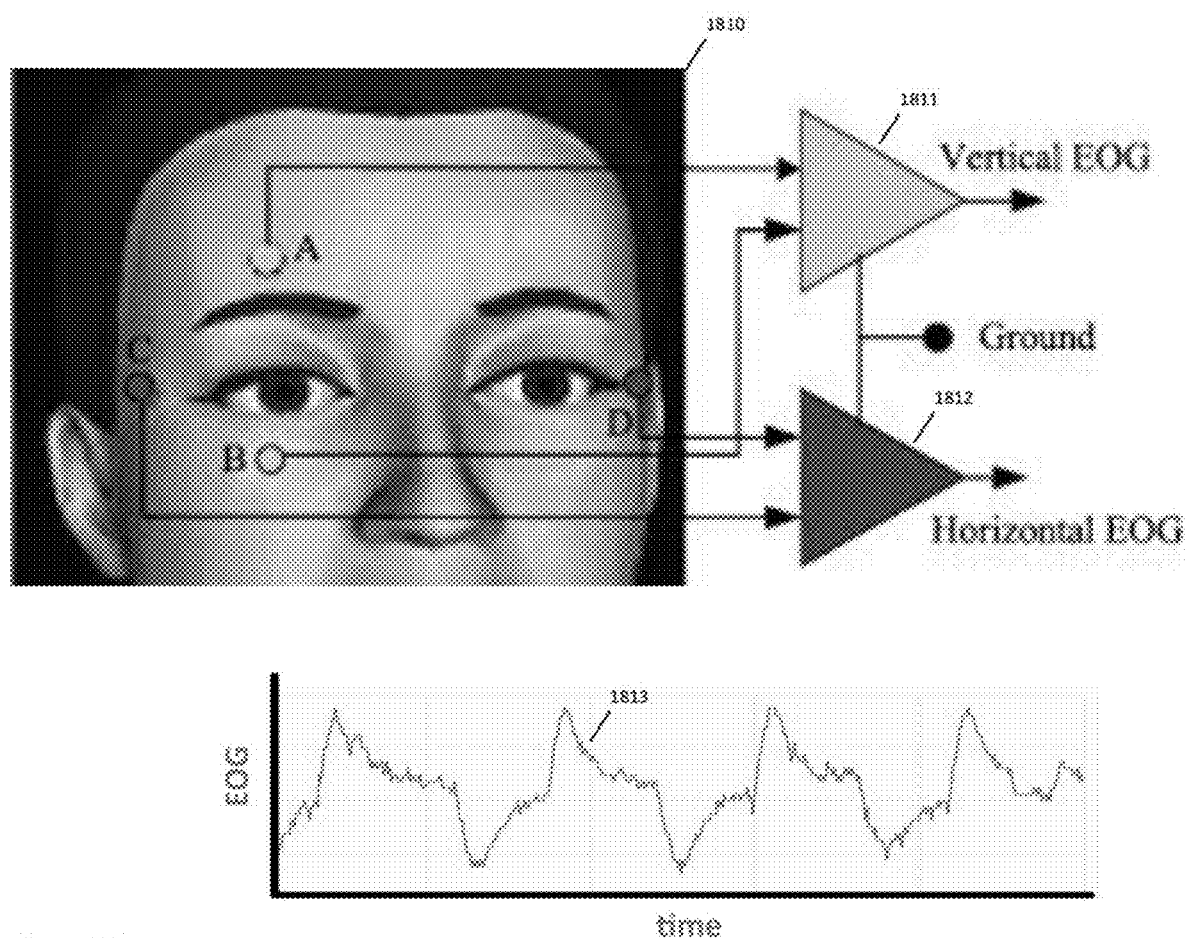

Another class of detector measures movement by detecting electrical signal transduction in muscles. One common application of this type of detector shown in FIG. 82D is used in the monitoring of eye movement, a measurement referred to as a electrooculogram or EOG. Such measurements are useful in detecting and studying REM-sleep in sleep apnea and non-24 (blind) patients. As shown, analysis of eye movement in patient's face 1810 employs four electrical connections—connections A and B positioned vertically located above and below the eye, and connections C and D positioned horizontally located just outside of the left and right eyes. In operation, the electrical potential of the vertical signal detected between electrodes A and B is amplified by op amp 1811 to produce a vertical EOG waveform. Similarly, the electrical potential of the horizontal signal detected between electrodes C and D is amplified by op amp 1812 to produce a horizontal EOG component. Waveform 1813 for example shows the horizontal EOG of a patient repeatedly moving their eyes left to right.

Aside from discrete sensors, integrated sensor arrays can be integrated into the intelligent LED pads, offering the ability for real time monitoring of tissue under treatment. Sensors arrays, i.e. biometric sensors, may detect any number of physical, physiological, chemical, biological, or pathological agents, including temperature, pH, circulation, blood oxygen, leukocyte concentrations, bacterial populations, or inflammatory indicators. Physical and biometric measurements may employ optical, thermal, electrical, electrochemical, ultrasound, or electromagnetic measurements of cells and tissue. Measurements may detect naturally occurring thermal energy, sound and movement, or involve applying energy to the tissue and detecting the effect of the cells or the transmission or reflection of the impinging energy. To develop a 2-D, 3-D or quasi 3-D image, the biometric sensor array must be dispersed over the area of the LED pad. Depending on the parameter being measured, the sensor can sample the data continuously or periodically at any time without regard to LED illumination, or synchronized to blink interrupt intervals.

Figure 83A:
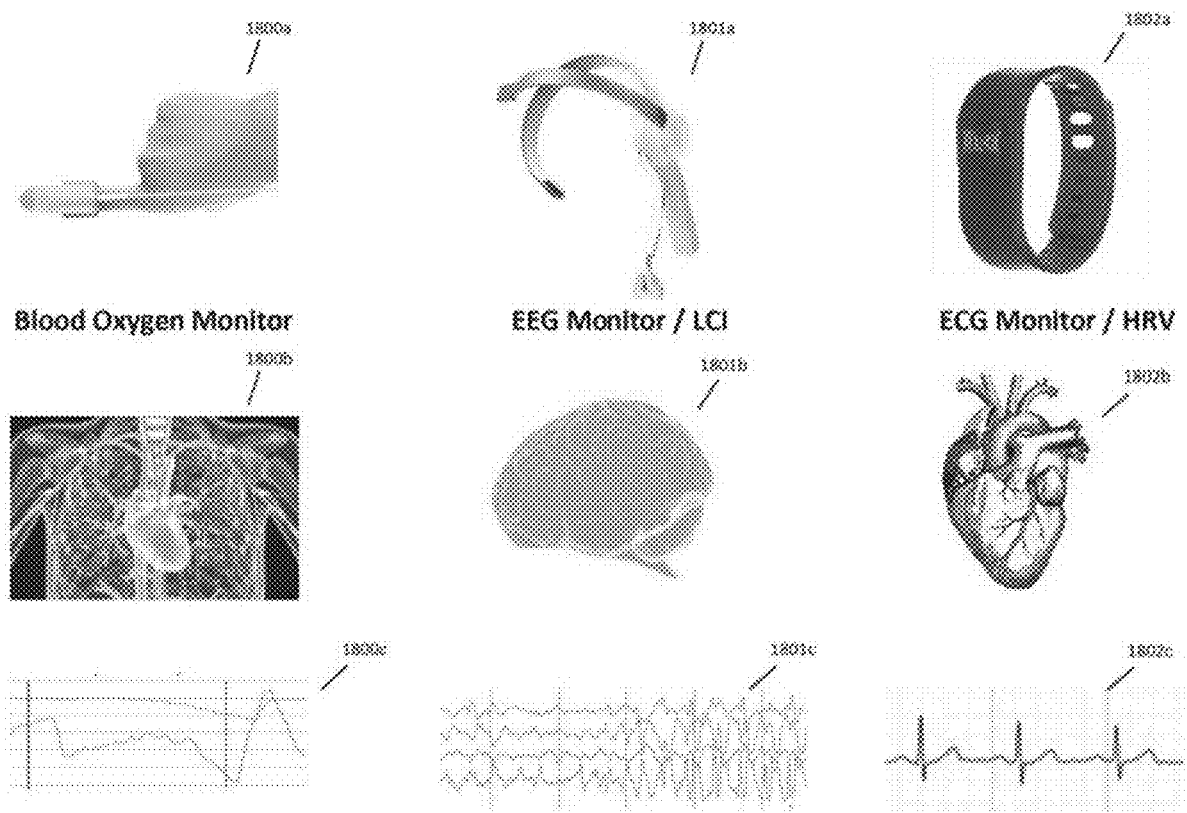

Once such example is shown in intelligent LED pad 1815 of FIG. 83A where the regular periodicity of therapeutic LEDs 1817 is occasionally interrupted to include sensors 1816, arranged in some regular grid pattern to detect special variations in the parameter being measured. Measured data is collected and mapped across a grid pattern, arranged by Cartesian coordinates x, y and time t. In the case of nanosensors, the sensors 1817 are interposed between the LEDs in intelligent LED pad 1818 to achieve a higher resolution. The data can be acquired by repeated measurement and recorded in volatile memory. Although data can be sampled continuously, given the slow rate of change of chemical, biochemical, and physical parameters, these measurements can be acquired by sampling at a prescribed rate using multiplexing to read each sensor's data in succession.

Figure 83A:
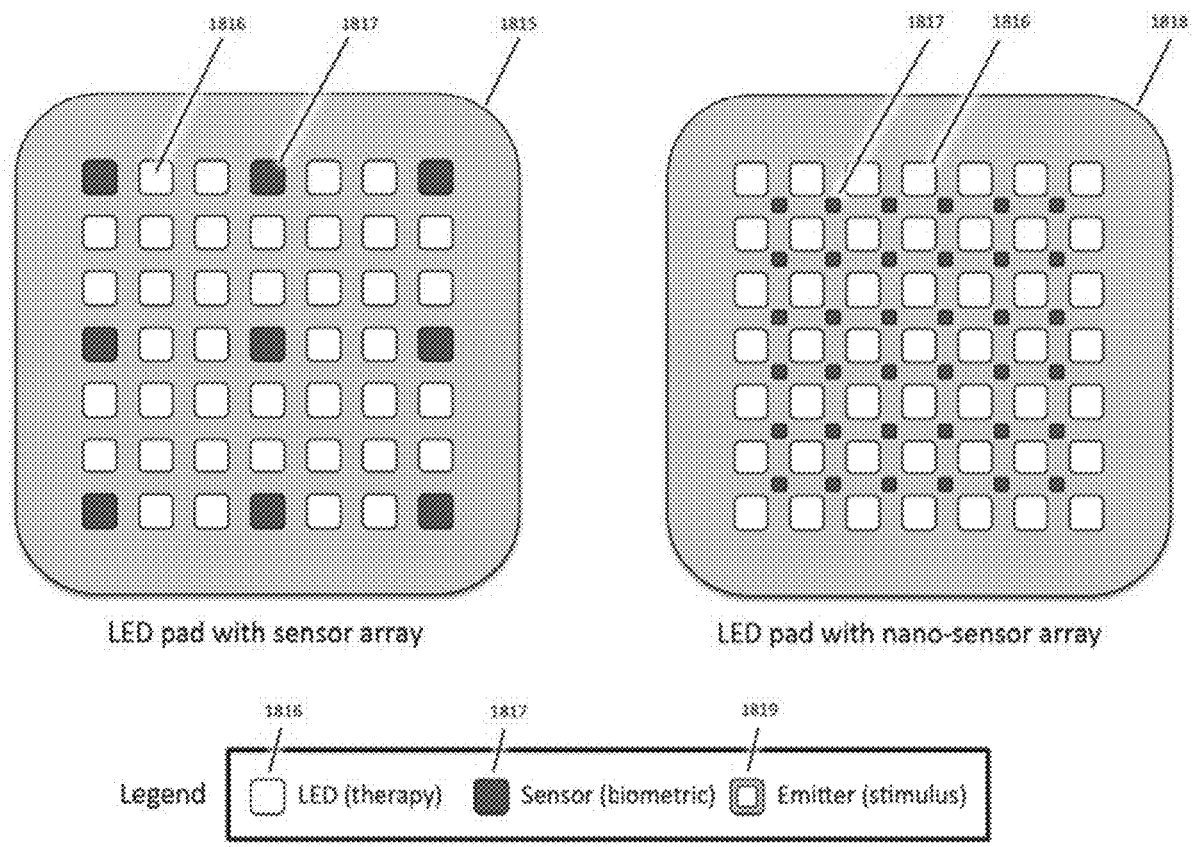
Figure 83B:
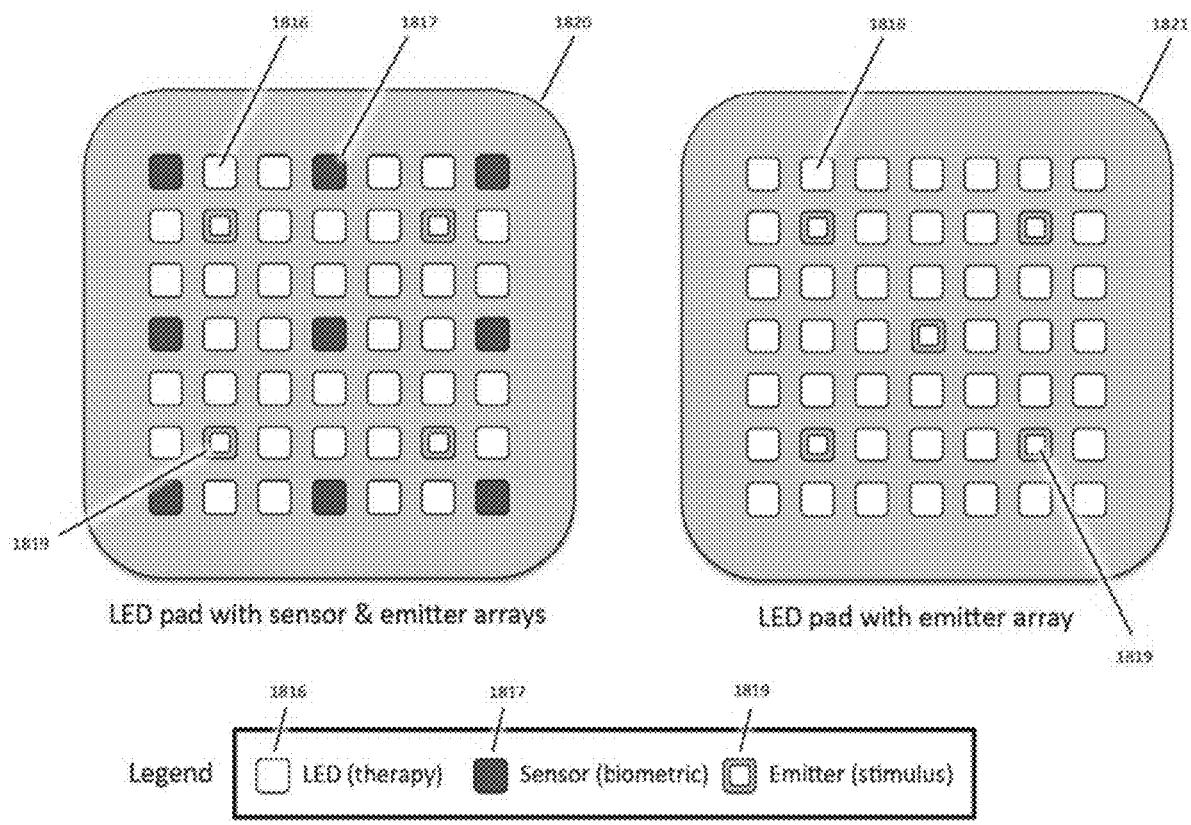
Figure 83C:
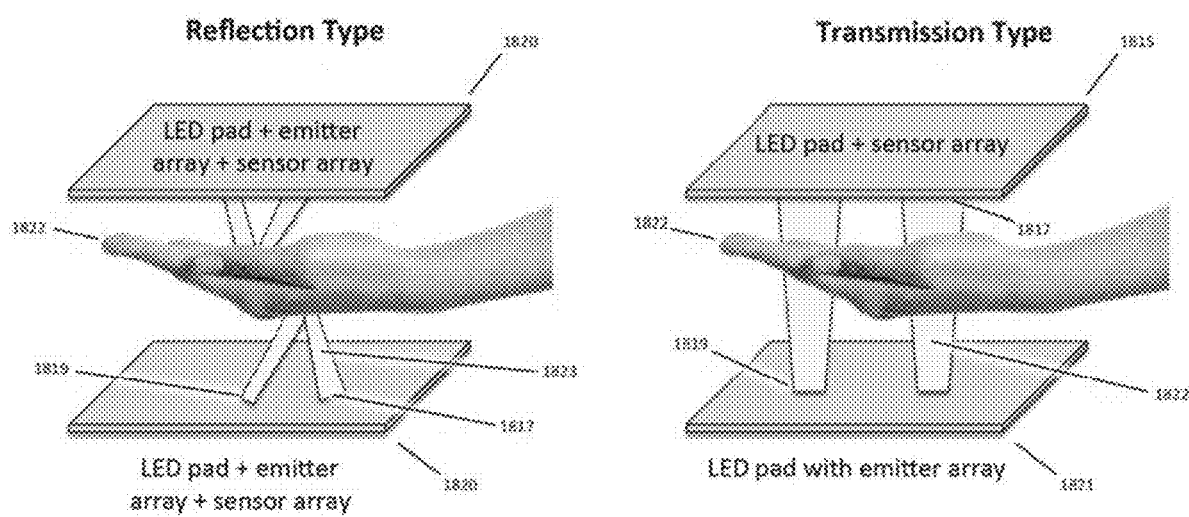

Intelligent LED pad sensor data may be passive or active. While passive sensor data comprises naturally occurring parameters such as temperature, bacteria counts, pH, etc. active sensor arrays rely on using a combination of energy emitters and matching energy sensors. The arrangement of sensors 1817 and emitters 1819 can be integrated into the same LED pad, as shown in LED pad 1820 of FIG. 83B or by pairing an emitter LED pad 1821 with sensor LED pad 1815. Reflection type sensing utilizes LED pads 1820 or 1821 combining sensors 1817 and emitters 1819 into the same pad as shown in the left side illustration of FIG. 83C. Alternatively transmission based sensing shown in the right side of the same figure utilizes LED pad with emitter array 1821 transmitting energy 1822 through tissue 1822 to sensors 1817 in sensor LED pad 1815. In either case energy emitted from emitters 1819 is detected by sensors 1817 and used to reconstruct a 2-D or 3-D image of the treatment area.

Figure 84B:
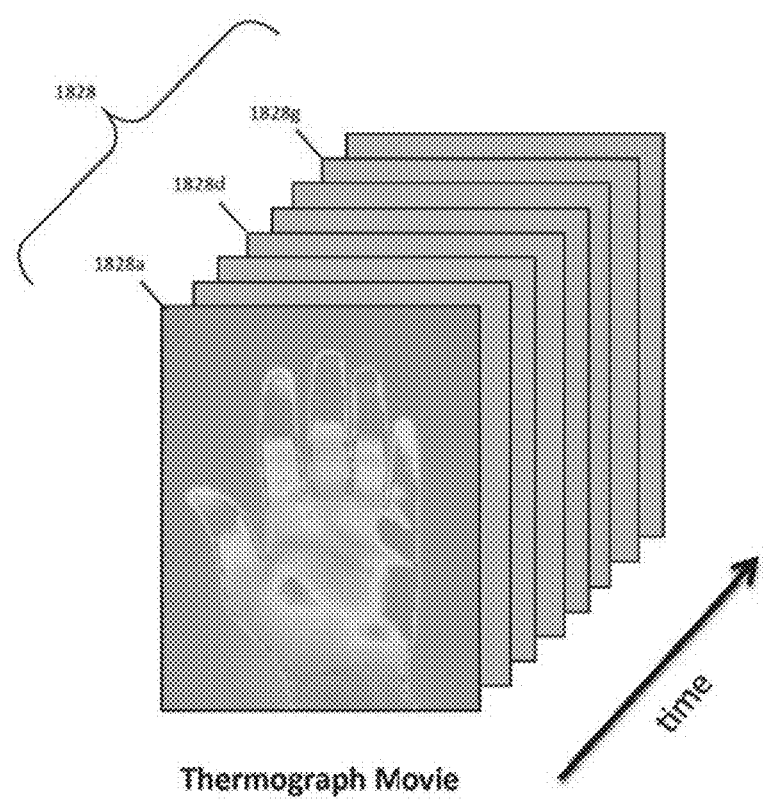

The acquired data is uploaded as part of the PBT treatment records. The images can be obtained using sensors or cameras before and after a PBT session or can be directly integrated into the intelligent LED pads. Image sensor outputs shown in FIG. 84A may include thermographs 1825, ultrasound 1826, and newer form of biosensors 1827. Spatial biosensor imaging may involve an array of moisture or temperature sensors, capacitors, LEDs and photo-sensors, or piezoelectric actuators and microphones that are addressed in a 2-D matrix or array. As shown in FIG. 84B measured data may also be arranged into series of pictures 1828*a*, 1828*b* . . . 1828*n* to form a video 1828.

Sensor operation involves creating one or a series of samples, an array of temperature sensing P-N junction diodes comprises sensor diode 1830 driven by controlled current source 1831. During conduction of a specific element in the array, A/D converter 1832 measures each diode voltage one by one and reports the data to pad µC 1833 to form a data log table of time, voltage and position. Position of the selected diode in pad sensor array is controlled by column scan mux 1835 and row scan mux 1838. In operation scan mux routes the current from current source 1831 to one column, e.g. conductor 1836.

At the same time, row scan mux applies bias voltage 1838 to gate of every selector MOSFET connected to only one row, e.g. row 1840. This bias voltage turns on MOSFET 1841 routing current from current source 1831, through column 1836, through MOSFET 1841 and forward biasing sensor diode 1830 while A/D converter 1832 measures its voltage. In this manner only one sensor conducts at a time. The sensor array 1884 is then scanned to complete a map of the temperature distribution across the intelligent LED pad, i.e. the patient's skin in the area being treated. In practice, this sensing should be performed during the blink interval when the LEDs are off and no noise is present in the intelligent LED pad. In this way a low-resolution image of thermograph 1820 can be obtained in situ, i.e. during the treatment.

An important aspect of sensor connectivity is file management, i.e. creating a file structure that contains all relevant information regarding sensor data and the treatment performed, especially in the event that the biometric data varies during the treatment. In such cases it is important to correlate the sensor data at each time point to the LED excitation conditions comprising LED wavelength, current, duty factor, and pulse frequency. If the data sets are not stored together as the session proceeds, it will be unlikely (if not impossible) to collect and reconstitute the dataset later, especially in aligning multiple sensor data streams and treatment conditions against a single common timeline.

This task is made especially difficult in distributed systems because the LED drive and some sensor data occurs in the intelligent LED pad in response to a LED playback file, while discrete sensor data is not collected by the intelligent LED pad, but instead is directly fed into the PBT controller. Since the intelligent LED pad is controlled by the LED pad µC running atop the previously disclosed LightPadOS operating system while the PBT controller sensor data collection and processing is executed by the main MPU running the LightOS operating system, synchronization of data collection requires reliable communication between the intelligent LED pads, and the PBT controller, especially in correlating LED drive and sensor data to a common "treatment time clock" even though the distributed system itself operates asynchronously. Executing a treatment time clock for synchronizing sensor data inputs to treatment conditions can be accomplished in several ways.

In one method two software counters are run concurrently, one in the main MPU and a second counter, called a "proxy" in the intelligent LED pad. Every time a start 805, pause 815, or cancel command 825 is issued (as depicted in FIGS. 42A and 42B), both the main clock and the proxy clock are operated in identical fashion, starting and stopping simultaneously. Relying on open loop clock operation does not insure microsecond precision concurrence because of the propagation delay of communication between the main clock and the proxy counter. Although the error is small, the proxy clock error is cumulative with each start and stop.

Resynchronizing the counters during each blink timer interrupt can further reduce the treatment time clock error between the main clock and the proxy clock, essentially eliminating the error by loading the main counter to match the proxy clock counter. For example, in the blink interrupt service routine in step 862 of FIG. 43B, the intelligent LED pad and PBT controller can exchange system clock times and measure communication propagation delays to synchronize the main clock and the proxy clock. Otherwise real time clocks can be integrated into both the PBT controller and the intelligent LED pad, thereby synchronizing the treatment time clocks. In practice, however, resynchronizing during the blink interrupt is adequate to avoid any cumulative errors. Assuming a 5-µs error in a 20 second blink interval is equivalent to a precision of 250 ppb (part per billion).

As described throughout this disclosure and illustrated in FIG. 86A, the LightOS payload 1862 comprises an Application Layer-7 payload 1861 embedded in a Network Layer-3 datagram, carried by a PHY Layer-1 frame 1860. In a distributed PBT system with sensor feedback the waveforms driving the LEDs are generated within the intelligent LED pad 1852 either from a LED-playback or LED-streaming file. As such no real time data is carried by PBT communication 1853a or LightOS payload 1862. That said, for illustrative purposes, the LED playback parametric file carried from PBT controller 1851 by LightOS payload 1862 is represented as a sequence of LED pulses 1863 it produces even though it is actually generated within the intelligent LED pad and under the control of start, pause, and cancel commands. The generated LED sequence may include different wavelength LEDs 1864, 1865, and 1866, each pulsed at different frequencies and duty factors. Changes in pulse frequency and LED wavelength occur in accordance with the LED playback or LED-streaming file being executed, i.e. the sequence is known and needn't be measured.

Figure 85:
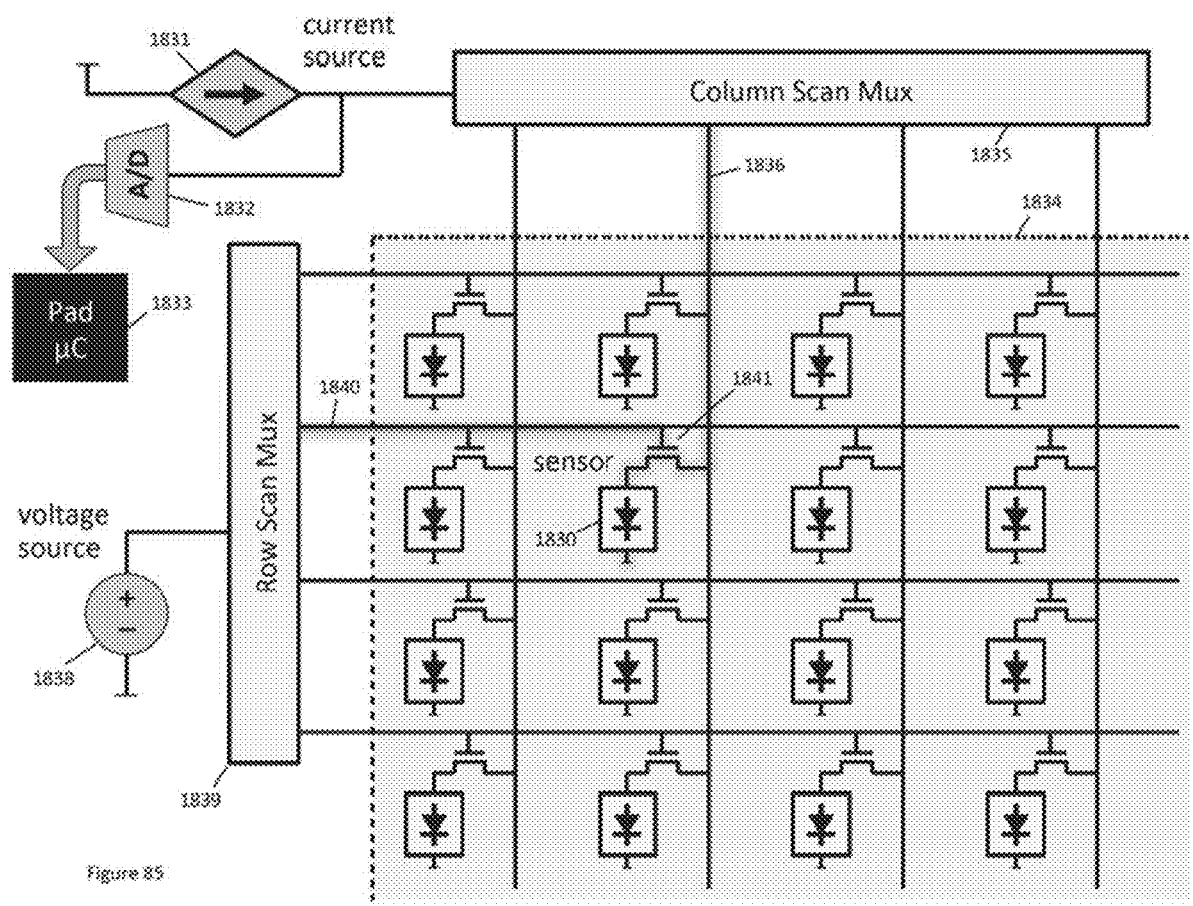

During the PBT session commencing when the start instruction is sent to the intelligent LED pad, integrated sensors within intelligent LED pad begin to collect data and store it in non-volatile memory. At a later time, generally after the end of the PBT session, the sensor data is processed, possibly to remove noise or improve its resolution, match it to the treatment time clock, and the prepare the data set for communication. Although the biometric data exists in tabular form, for illustrative purposes the sensor data 1873 can be represented graphically, e.g. as shown by EEG waveform 1874 in FIG. 86B. This data is packetized as Application Layer-7 LightOS payload 1872, loaded into Network Layer-3 datagram 1871 and sent from intelligent LED pad 1952 to PBT controller 1851 over WiFi 1853b. In this example, intelligent LED pad 1952 is used to gather EEG data if it is used in a transcranial PBT treatment. These transfers are summarized in the diagram FIG. 85C. As shown, PBT controller 1851 sends PHY Layer-1 data frame 1880 over Ethernet 1855 to server 1854, containing Network Layer-3 datagram 1882 containing a concatenated treatment and measurement file 1883 and PBT metadata 1884.

The roll of the PBT controller 110 in coordinating the task of combining treatment and sensor data and uploading it to a server for archiving or analysis is depicted in FIG. 87. As shown, main MPU 1863 prepares the LED playback file for generating waveforms 1863, encapsulates it into LightOS payload 1862 then sends it in encrypted form to the intelligent LED pad using PHY data frame 1860 via communication interface 112. In response a digital table representing EEG measurement file 1873 is encapsulated into LightOS payload 1873 and sent in encrypted form as PHY data frame 1870 to communication interface 112 of PBT controller 110. After processing by main MPU 111 in response to UI/UX commands executed on touch screen LCD 113, PHY data frame 1880 is prepared containing LightOS payload 1882, the contents of which include the data table describing concatenated data file 1883 and PBT metadata header 1884 describing additional details of the PBT session and anonymous patient information (such as patient chart number, age, sex, treatment date, etc.) To persevere privacy and maintain HIPAA compliance, personal data about the patient is not included in the file. Only a confidential patient number or doctor chart number is used.

To complicate matters, biometric sensor data during a treatment may also be input directly to the PBT controller rather than measured by integrated sensors within the intelligent LED pad. An example of this type of feedback is shown in FIG. 88A where wireless pulse oxymeter 1956a by WiFi 1853c sends to PBT controller 1851 delivering PHY Layer-1 1900 containing Network Layer-3 IP datagram 1901 containing LightOS payload 1942. The contents of LightOS payload 1942 are ECG measurement file 1903 comprising a digital table representation of ECG waveform 1904. In an alternative implementation shown in FIG. 88B LightOS payload 1902 comprising ECG measurement file 1903 is carried in PHY data frame 1905 in accordance with a Data Link Layer-2 protocol for Bluetooth data 1901. As such no Network Layer-3 is included in PHY data frame 1905.

The roll of the PBT controller 110 in coordinating the task of combining treatment and both discrete and integrated sensor data and uploading it to a server for archiving or analysis is depicted in FIG. 89. As shown, PBT controller 1851 drives intelligent LED pad 1923 with playback file 1863 and in return gathers real time EEG data 1873 from a sensor integrated within intelligent LED pad 1923 using WiFi 1853a and from pulse oxymeter 1856a providing ECG measurement file 1903 delivered over Bluetooth communication 1857. PBT controller then combines the treatment and sensor into a single concatenated data file 1943, appends a header 1944 comprising PBT metadata. The controller when instructed sends PHY Layer-1 data frame 1940 over Ethernet 1855 to server 1854, containing Network Layer-3 datagram comprising LightOS payload 1942 carrying concatenated treatment and measurement file 1943 and PBT metadata 1944.

This treatment and biometric data acquisition process is depicted in flow chart form in FIG. 90 where upon start 1950 the distributed PBT system executes PBT session 1951 in accordance with LED playback file 1863 followed by acquiring sensor data 1952 comprising sensor data file 1873.

The collected data is then processed to filer sensor noise 1953 resulting in modified data file 1975. In step 1954 additional application specific signal processing of waveforms 1954 may be performed including the mathematical extraction of indexes and statistical data. The original and processed data files are then appended together to form concatenated data file 1943 illustrated here by waveforms rather than by their numerical equivalent. In step 1956, attaching header 1944 comprising PBT metadata appended onto concatenated data file 1943. In step 1957 data frame 1940 followed by an instruction 1958 to transmit the data file from PBT controller 1851 to server 1854 and its execution by send command 1958, a command that may be initiated by an authorized user control from PBT controller 1851 or from server 1854.

The contents of the concatenated data file 1943 comprise time and optionally position based numerical data represented in FIG. 91 is graphical format including LED playback drive waveform 1863, raw EEG data 1874, raw ECG data 1903, algorithmically generated sub-harmonic cardiopulse waveform 1920, and filtered EEG waveforms 1875. Greater detail of PHY frame 1940 is shown in FIG. 92, including Network Layer-3 IP datagram 1941 carrying higher communication layer content. Its Application Layer-7 LightOS payload 1942 includes concatenated data file 1943 and header 1944 comprising PBT metadata, specifically anonymous patient metadata 1946a and session metadata 1946b. In the exemplar PBT metadata header, anonymous patient metadata 1946a may include a system generated PBT patient number, doctor chart number, date the patient metadata sub-file was created, along with the sex and age of the patient. The patient metadata 1946a file remains unchanged throughout multiple treatment sessions. A second sub-data file, session metadata 1946b contains information that may change with each PBT session including the session date, a patient's weight, SP/DP blood pressure, HPR pulse rate, SAO2 blood oxygen, pre- and post-PBT session biometric data taken from discrete sensors or from image sensors, along with optional doctor notes (free form). Aside from the confidential PBT patient number and optional doctor chart number, no patient identification or personal information is included in the file.

Aside from preparing and archiving treatment and sensor data, biometric sensor data may also be used to affect operation of the distributed PBT system. The form of operation, referred to as PBT system "dynamic biofeedback" is shown in FIG. 93 allows an optimum treatment to be achieved by dynamically controlling treatment parameters in response to biometric sensor measurements. As shown in dynamic biofeedback, PBT controller 1851 comprising control system 2000 sends control communication 1863 to intelligent LED pad 2005 emitting photons 2018 absorbed by selected tissue of patient 2019. An integrated sensor or sensor array 2006 contained within intelligent LED pad 2005 send data to intelligent LED pad controller circuit 2020 contained with LED pad 2005 (shown separately for clarification's sake). In response intelligent LED pad controller circuit 2020 executes control and drive of LED drive waveforms using signals 2007 based on its control input communication 1863 and its on biometric sensor feedback data 2008.

Although a copy of intelligent LED pad integrated sensor 2006 and its data 2008 is also sent back to PBT controller (not shown), the dynamic application of this data in affecting LED drive waveforms is executed locally in intelligent LED pad 2005 by intelligent LED pad controller circuit 2020 and therefore represents feedback relating to the tissue being treated, i.e. PBT tissue biofeedback. As such, tissue feedback is local to the intelligent LED pad and does not entail response to changing playback conditions in control communications 2002 and driving data representing waveforms 1863. Other forms of biofeedback include ECG signal 1904 from pulse oxymeter 1856a, EEG signals 1874 from EEG sensor 1801a, and blood glucose levels from BGL monitor 1804. These signals are returned to PBT controller 1851, which after processing may be used to adjust the control signal communication carrying waveform 1863 thereby affecting the PBT treatments. This outer loop of feedback comprising a discrete sensor, PBT controller, and intelligent LED pad in a closed loop represents PBT systemic biofeedback. Regardless of the source of the feedback data, response to biofeedback signal is executed within intelligent LED pad 2005 and not in PBT controller 1851.

One mechanism of biofeedback control is illustrated in FIG. 94 where an LED player file 2009 and LED playback file 2010 installed into intelligent LED pad 2005 comprises waveform synthesizer 2011, PWM player 2012, and LED driver 2013, together generating LED drive signals 2007 driving the LEDs within LED 2005. Operation of the PBT player in response to PBT playback file 2010 is consistent with the prior explanations of the LED player operation, except that dynamically adjusted variables registers influences playback operation. In particular, synth variables registers 2014 affects the operation of waveform synthesizer 2011; PWM variables register 2015 affects the operation of waveform synthesizer 2012; and driver variables register 2016 affects the operation of LED driver 2013. The data contained within the three variables registers 2014, 2015, and 2016, is dynamically loaded by sensor data acquisition and signal processing 2017 in response to local feedback 2018 from in-pad sensor or sensor array 2006 and in response to commands received by communication interface 2003 from PBT controller 2000 via WiFi 2002, comprising commands affected by sensor data received by discrete sensors 2001.

An example of dynamic biometric feedback control of PWM pulse duty factor is illustrated in FIG. 95A where biofeedback parameters w 2040 may include without limitation skin temperature, heart rate, and blood pressure, which are converted into PWM duty factor D for fixed frequency PWM pulse chain, i.e. for a constant $f_{PWM}$ and $T_{PWM}$. The duty factor is then converted into an error term used to modify the original variable, either in an additive or multiplicative manner and stored in the PWM variables register 2015. The PWM variables register increases or decrease the pulse width of pulse 2047 while maintaining a constant period $T_{PWM}$ 2048. For example, if the patient's skin temperature is too cool the pulse width $t_{on}$ time is increased. If, conversely, the patient's skin temperature is too warm the pulse width $t_{on}$ time is automatically decreased.

While a parameter like skin temperature may first appear to be simple physics, in the case of PBT the effect is photochemical and biophysical, not simply physical. For example, the human body regulates its temperature through complex mechanisms such as circulation, respiration, and sweating. Secondly, human physiology includes immune response, which may result into an overall systemic increase in body temperature, i.e. fever, or in some cases localized fever in the vicinity of an injury or infection. Photo-absorption, the energy absorption of tissue also depends on tissue health. PBT delivers energy as light, not heat—heat is the byproduct of photobiomodulation. When a group of cells is inflamed or infected, intercellular pH is affected which in turn modulates its photo-absorption. Biophysically, sick cells tend to be slightly acidic and absorb more light than healthy cells. As the cell's health improves, photo-absorption diminishes and the photon travels through the healthy cell unabsorbed to other less healthy cells, in essence increasing the "healing volume" of the PBT. Because of the complexity of the human anatomy, the physiological benefits of photobiomodulation vary by person.

For example, published data confirms performing PBT over the lungs improves breathing, slows heart rate, lowers blood pressure and improves general circulation. Finding the optimum power level maximizes the physiological benefits without causing the patient discomfort from overheating. In general this involves delivering light at a rate that gradually elevates skin temperature to 43° C. but this may feel too hot for some patients. The disclosed system can perform this optimization automatically using the pad temperature as a biofeedback variable. During a treatment, warming of the intelligent LED pad occurs primarily from heat generated not in the intelligent LED pad, but in the treated tissue. In injured tissue the resulting temperature profile is not uniform, so it is important to detect the hottest portions of the temperature map and use the peak temperature as the biofeedback parameter. The disclosed system is capable of such feedback control despite being executed as a distributed PBT system. Moreover, the disclosed PBT system can employ multiple biofeedback loops concurrently or employ feedback variables derived from multiple sensors, e.g. pulse rate and blood oxygen. The resulting dynamic PBT controlled parameters 2046 include temperature, energy (dose), average power, peak power, and treatment thermal depth. Since these relationships are derived empirically, the disclosed PBT system includes flexible control.

Another example of dynamic biometric feedback control of PWM frequency is illustrated in 594 B where biofeedback parameters w 2050 may include without limitation certain EEG brainwave frequencies, blood pressure, blood oxygen, or muscle tightness, which are converted into PWM pulse frequency with a constant duty factor, e.g. 50%. The pulse frequency $f_{PWM}$ is then converted into an error term used to modify the original variable $T_{PWM}$, either in an additive or multiplicative manner and stored in the PWM variables register 2015. The PWM variables register increases or decrease the period $T_{PWM}$ 2058 and concurrently adjusting the on time $t_{on}$ proportionately so that $D=t_{on}/T_{PWM}$ remains constant, e.g. at 50% duty factor no matter what the frequency or period maybe.

For example, if the patient's muscle is too tight, the pulse frequency can be increased or decreased to search for a relaxing frequency. The resulting PBT controlled parameters 2056 include frequency and thereby tissue type, the nature of certain photochemical reactions and the degree of vasodilation and tissue oxygenation from the therapy. PBT conditions can then be adjusted to maximize physiological benefits such as de-stress and metal relaxation, relaxing muscles, lowering blood pressure, and promoting sleep. Without dynamic biofeedback made possible with this system, finding the optimum excitation frequency is slow and laborious.

Programming Autonomous Intelligent LED Pads

Although the foregoing discussion of a distributed PBT system relies on the combination of a PBT controller (or PBT app program) and a intelligent LED pad, in some applications the intelligent LED pad may need to operate autonomously. Unlike preprogrammed consumer products that utilize fixed hardware implementations and are only capable of performing a single dedicated task, made in accordance with this disclosure, and new form of fully programmable autonomous intelligent LED pad is disclosed. This fully programmable feature means the intelligent LED pads can be adjusted to perform one of a variety of different tasks prior to its sale to match changes in market demand. For example in the summer the market for intelligent LED pads for sunburn treatment is great while in the spring the greatest demand is for treating allergy and hay fever symptoms.

Each dedicated product serves a different market and therefore cannot employ the same PBT treatment software as multi-function devices. Moreover, these devices must work autonomously without the presence of a PBT controller at the time of their use. For example, a LED bandage to stimulate healing and suppress infection of an injury from an explosion or gunshot wound is needed by paramedics or army field doctors during an emergency or battlefield situation. There is no time to program a device or select its features from a menu during its use. That said, to be programmable for different situations, it is economically beneficial (if not mandatory) that the same product is manufactured at low cost and high volume and programmed after the hardware is fully fabricated. In essence the autonomous LED assembly is completed, its basic operating system is installed, and a lite version of the LightOS operating system is preloaded into the device, but the specific treatment programs are not loaded until later, specifically just prior to sale. This just in time or JIT business model is important to scale a factory to support high-volume low-cost products for flexible applications.

At the time of its sale, the product's manufacturer executes final programming, i.e. software download of the autonomous intelligent LED pad (or pads) using a dedicated hardware programmer system. For security's sake this system should operate offline to avoid the risk of hacking, especially in the product of products for the defense market. One example of such a programmer is shown in FIG. 96 comprising a PC based programmer 2070 that employs any powered communication protocol 2072 to program intelligent LED pad 2071. The programmer 2070 operates offline, with an air gap or DMZ 2074 separating it from the Internet cloud 2073. Despite the fact that in use, intelligent LED pad 2071 operates autonomously, during post manufacturing programming the system as shown does in fact constitute a distributed PBT system.

The only difference is the distributed system comprises a programming phase where PC programmer 2070 connects to intelligent LED pad 2071, and a user mode where intelligent LED pad 2071 operates autonomously. Because it is not connected online, communication stacks 2075 and 2075 of the programmer and intelligent LED pad can be customized with proprietary PHY Layer-1 and Data Link Layer-2 programming protocols, and LightOS/LightPadOS operating systems for the upper application Layer-5 through Layer-7. The use of Network Layer-3 and Transport Layer-4 are optional, primarily if a router is used to distribute the program feed to multiple systems across a large factory. Once intelligent LED pad 2071 is programmed, it is disabled from future programming except optionally through the use of a special procedure to unlock the device. The same USB connector can be used to supply battery pack power to the autonomous intelligent LED pad. Even if a USB connector is employed, the LED pad doesn't necessarily need to use the USB communication protocol. In operation, in its simplest form the device turns on immediately as soon as a battery pack or power source is connected. In this way no switch is needed inside intelligent LED pad 2071. Alternatively a membrane switch may be included to turn the pad on or off or to select one of several programs.

Another example of autonomously operated intelligent LED pad is an implanted or "transient" integrated circuit. The integrated circuit comprises a thin membrane based flexible circuit with thin semiconductor components and a power source mounted on it. The transient IC is placed on an organ during surgery and programmed to a specific function, e.g. to stimulate wound healing, to promote improved circulation, or to stimulate the organ to operate more efficiently. Over a period of one to three months the circuit cases to operate and simply dissolves into non-toxic minerals absorbed by the body, hence the nominative "transient integrated circuit" because its presence is only temporary. In such transient implants a PBT system would be programmed probably using a RF link such as WiFi 802.11ah or Bluetooth. After programming either the RF link is disabled, or put into low power mode able only to receive low level commands such as on and off or to select a particular operating mode, e.g. program number 1, 2 or 3.

Other Distributed PBT System Applications

By providing power, bidirectional communication, data acquisition, algorithm implementation, and distributed drive, the foregoing distributed PBT system can be used to drive other medical therapeutic and biometric peripherals including
Laser probes for laser photobiomodulation
Magnetotherapy emitters and detectors
Large area thermography
Thermotherapy
Ultrasound imaging

The invention claimed is:

1. A photobiomodulation therapy (PBT) system comprising:
   a controller, the controller comprising a microprocessing unit (MPU);
   at least one light-emitting diode (LED) pad, the at least one LED pad comprising:
      at least one string of LEDs,
      a pad non-volatile memory, and
      a microcontroller; and
   an input device connected to the controller, the input device allowing the selection of a process sequence suited to the PBT treatment of a condition or disease by the at least one LED pad;
   wherein the controller is connected to the at least one LED pad over a wired or wireless communications network;
   wherein the controller contains a first LED pad identity numeric code and the at least one LED pad contains a second LED pad identity numeric code, the controller also containing a value representative of the second LED pad identity numeric code as a result of the at least one LED pad having previously sent a value representative of the second LED pad identity numeric code to the controller as part of an LED pad authentication process; and
   wherein the pad non-volatile memory holds an LED configuration register, the LED configuration register holding at least one of minimum and maximum voltage specifications, minimum and maximum current specifications, a current source ratio α, and a description of each LED string, including the number of LEDs in the LED string and the respective wavelength of each LED in the LED string.

2. The PBT system of claim 1, wherein the controller comprises a controller clock and the at least one LED pad comprises a pad clock, the controller clock being unsynchronized with the pad clock.

3. The PBT system of claim 2, wherein the communications network contains an asynchronous serial communication, the asynchronous serial communication being unsynchronized with either the controller clock or the pad clock.

4. The PBT system of claim 1, comprising a first LED pad and a second LED pad, the controller comprising a controller clock, the first LED pad comprising a first pad clock and the second LED pad comprising a second pad clock, the controller clock being unsynchronized with either of the first and second pad clocks, and the first pad clock being unsynchronized with the second pad clock.

5. The PBT system of claim 1, wherein the communications network comprises a wired communication link.

6. The PBT system of claim 5, wherein the communications network contains a data packet, the data packet comprising a USB data packet header and a PBT-specific operating system payload.

7. The PBT system of claim 5, wherein the controller comprises controller non-volatile memory.

8. The PBT system of claim 7, wherein the controller non-volatile memory holds a controller identity register, the controller identity register holding at least one of a part number, a manufacturer name, a serial number, an organizationally unique identifier (OUI), a device type, a global unique device identification database (GUDID) number, and a security credential.

9. The PBT system of claim 7, wherein the second LED pad identity numeric code holds at least one of a part number, a manufacturer name, a serial number, an organizationally unique identifier (OUI), a device type, a manufacturing code, a global unique device identification database (GUDID) number, applicable 510 (k) numbers, country-specific import codes, and security credentials.

10. The PBT system of claim 9, wherein the second LED pad identity numeric code in the at least one LED pad is identical to a data table contained in a data packet transferred previously over the network to the at least one LED pad.

11. The PBT system of claim 7, wherein the LED controller contains a security system comprising a login-based system authority for granting or preventing access rights for the purpose of programming the LED pad non-volatile memory.

12. The PBT system of claim 1, wherein the communications network comprises a packet-switched network, the packet-switched network comprising Ethernet, WiFi, or a cellular telephonic network for 2.5G, 3G/LTE, 4G or 5G communication.

13. The PBT system of claim 12, wherein the communications network contains a data packet, the data packet comprising an OSI or TCP/IP compliant packet header and a PBT-specific operating system payload.

14. The PBT system of claim 13, wherein the data packet is compliant with an Ethernet or WiFi data packet format.

15. The PBT system of claim 13, wherein the PBT-specific operating system payload uniquely identifies a LED pad even for data packets that have traversed routers or been transported over more than one subnet.

16. The PBT system of claim 1, wherein the controller comprises a user interface but the at least one LED pad does not comprise a user interface.

17. The PBT system of claim 1, wherein the LED configuration register is identical to a data table contained in a data packet transferred previously over the network to the pad.

18. The PBT system of claim 1, wherein the at least one LED pad comprises a pad non-volatile memory and a pad volatile memory, both the pad non-volatile memory and the pad volatile memory containing files sent over the communications network as data packets to the at least one LED pad.

19. The PBT system of claim 1, wherein the MPU comprises a first operating system and the microcontroller comprises a second operating system different from the first operating system.

20. A photobiomodulation therapy (PBT) system comprising:
- a controller, the controller comprising a microprocessing unit (MPU);
- at least one light-emitting diode (LED) pad, the at least one LED pad comprising at least one string of LEDs and a microcontroller; and
- an input device connected to the controller, the input device allowing the selection of a process sequence suited to the PBT treatment of a condition or disease by the at least one LED pad;
- wherein the controller is connected to the at least one LED pad over a wired or wireless communications network, the communications network comprising an asynchronous communication link, and
- wherein the controller contains a first LED pad identity numeric code and the at least one LED pad contains a second LED pad identity numeric code, the controller also containing a value representative of the second LED pad identity numeric code as a result of the at least one LED pad having previously sent a value representative of the second LED pad identity numeric code to the controller as part of an LED pad authentication process.

21. A photobiomodulation therapy (PBT) system comprising:
- a controller, the controller comprising a microprocessing unit (MPU);
- at least one light-emitting diode (LED) pad, the at least one LED pad comprising at least one string of LEDs and a microcontroller; and
- an input device connected to the controller, the input device allowing the selection of a process sequence suited to the PBT treatment of a condition or disease by the at least one LED pad;
- wherein the controller is connected to the at least one LED pad over a wired or wireless communications network;
- wherein the controller contains a first LED pad identity numeric code and the at least one LED pad contains a second LED pad identity numeric code, the controller also containing a value representative of the second LED pad identity numeric code as a result of the at least one LED pad having previously sent a value representative of the second LED pad identity numeric code to the controller as part of an LED pad authentication process;
- wherein the controller comprises a controller clock and the at least one LED pad comprises a pad clock, the controller clock being unsynchronized with the pad clock; and
- wherein the communications network contains an asynchronous serial communication, the asynchronous serial communication being unsynchronized with either the controller clock or the pad clock.

* * * * *